US011567077B2

(12) United States Patent
Smith

(10) Patent No.: US 11,567,077 B2
(45) Date of Patent: Jan. 31, 2023

(54) **HUMAN *STREPTOCOCCUS PNEUMONIAE* ANTIBODIES AND USES THEREFOR**

(71) Applicant: OKLAHOMA MEDICAL RESEARCH FOUNDATION, Oklahoma City, OK (US)

(72) Inventor: Kenneth Smith, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 332 days.

(21) Appl. No.: 15/058,814

(22) Filed: Mar. 2, 2016

(65) Prior Publication Data

US 2016/0178626 A1 Jun. 23, 2016

Related U.S. Application Data

(62) Division of application No. 13/740,934, filed on Jan. 14, 2013, now Pat. No. 9,279,815.

(60) Provisional application No. 61/593,654, filed on Feb. 1, 2012.

(51) Int. Cl.

| | |
|---|---|
| ***G01N 33/53*** | (2006.01) |
| ***G01N 33/569*** | (2006.01) |
| ***G01N 33/68*** | (2006.01) |
| ***C07K 16/12*** | (2006.01) |

(52) U.S. Cl.
CPC .................. *G01N 33/56944* (2013.01); *C07K 16/1275* (2013.01); *G01N 33/6854* (2013.01); *C07K 2317/21* (2013.01); *C07K 2317/33* (2013.01); *C07K 2317/92* (2013.01); *G01N 2469/10* (2013.01)

(58) Field of Classification Search
CPC ................................................ G01N 33/56944
See application file for complete search history.

(56) References Cited

U.S. PATENT DOCUMENTS

| | | | | |
|---|---|---|---|---|
| 9,279,815 B2 * | 3/2016 | Smith | G01N 33/6854 | |
| 9,568,472 B2 * | 2/2017 | Das | C12Q 1/04 | |
| 2005/0014931 A1 | 1/2005 | Pirofski et al. | | |
| 2011/0053793 A1 | 3/2011 | Monasterio et al. | | |
| 2013/0195876 A1 * | 8/2013 | Smith | C07K 16/1275 | 424/139.1 |
| 2014/0314876 A1 * | 10/2014 | Das | C12Q 1/04 | 424/641 |
| 2016/0178626 A1 * | 6/2016 | Smith | G01N 33/6854 | 506/18 |

FOREIGN PATENT DOCUMENTS

| | | | | |
|---|---|---|---|---|
| CN | 101163499 A | 4/2008 | | |
| CN | 101802198 A | 8/2010 | | |
| JP | 2010-276441 A | 12/2010 | | |
| WO | WO 02/079254 A1 | 10/2002 | | |
| WO | WO-2018222741 A1 * | 12/2018 | | |
| WO | WO-2020070461 A1 * | 4/2020 | G01N 33/56944 | |

OTHER PUBLICATIONS

Rudikoff et al., Proc.Natl. Acad. Sci. USA, 79(6): 1979-1983, Mar. 1982 (Year: 1982).*
Colman P. M., Research in Immunology, 145:33-36, 1994 (Year: 1994).*
Paul, Fundamental Immunology, 3rd Edition, 1993, pp. 292-295, under the heading “Fv Structure and Diversity in Three Dimensions” (Year: 1993).*
MacCallum et al., J. Mol. Biol., 262, 732-745, 1996 (Year: 1996).*
Smith et al, Rapid generation of fully human monoclonal antibodies specific to a vaccinating antigen. 2009, Nature Protocols, 4/3:372-384 published online Feb. 26, 2009 (Year: 2009).*
Smith et al, Fully human monoclonal antibodies from antibody secreting cells after vaccination with Pneumovax® 23 are serotype specific and facilitate opsonophagocytosis, Immunobiology, 218:745-754, 2013, (Year: 2013).*
Sun et al, Avidity, Potency, and Cross-Reactivity of Monoclonal Antibodies to Pneumococcal Capsular Polysaccharide Serotype 6B Infection and Immunity, Jan. 2011, 69/1:336-344 (Year: 2011).*
Lin et al,, Validation of a Multiplex Pneumococcal Serotyping Assay with Clinical Samples Journal of Clinical Microbiology, Feb. 2006, p. 383-388 vol. 44, No. 2 (Year: 2006).*
Kolberg et al, Monoclonal antibodies with specificities for *Streptococcus* for *Streptococcus pneumoniae* group 9 capsular polysaccharides. 1998, 20:249-255 (Year: 1998).*
Wrammert et al, Nature, 2008, 453:667-671 (Year: 2008).*
Smith et al, Nature Protocols, 2009, 4/3:372-384. published online: Feb. 26, 2009 (Year: 2009).*
Yu et al., “A Rapid Pneumococcal Serotyping System Based on Monoclonal Antibodies and PCR,” *Journal of Medical Microbiology*, vol. 57, pp. 171-178 (2008).
Office Action issued in related Japanese Patent Application No. 2014-555559, dated Oct. 20, 2016.
English-language translation of Fifth Office Action, Chinese App. No. 201380017988.6, Oklahoma Medical Research Foundation, 3 pages (dated Feb. 24, 2017).
Antilla, et al. “Contribution of serotype-specific IgG concentration, IgG subclasses and relative antibody avidity to opsonophagocytic activity against *Streptococcus pneumonia*,” vol. 118 No. 3, Clin Exp Immunol., pp. 402-407 (1999).
Baxendale et al., “Correlation of molecular characteristics, isotype, and in vitro functional activity of human antipneumococcal monoclonal antibodies,” vol. 74 No. 2, Infect Immun., pp. 1025-1031 (2006).
Baxendale et al., “Immunogenetic analysis of the immune response to pneumococcal polysaccharide,” vol. 30 No. 3, Eur J Immunol., pp. 1214-1223 (2000).

(Continued)

*Primary Examiner* — Albert M Navarro
(74) *Attorney, Agent, or Firm* — Edwin S. Flores; Chalker Flores, LLP

(57) ABSTRACT

The present invention is directed to particular monoclonal antibodies and fragments thereof that find use in the detection, prevention and treatment of *Streptococcus pneumoniae* infections. In particular, these antibodies may kill *Streptococcus pneumoniae* or limit the replication of *Streptococcus pneumoniae*. Also disclosed are improved methods for producing such monoclonal antibodies.

21 Claims, 7 Drawing Sheets

Specification includes a Sequence Listing.

(56) References Cited

OTHER PUBLICATIONS

Chowdry et al., "Autoantibodies that bind glomeruli: cross-reactivity with bacterial antigen," vol. 52 No. 8, Arthritis Rheum., pp. 2403-2410 (2005).
Clutterbuck et al., "The kinetics and phenotype of the human B-cell response following immunization with a heptavalent pneumococcal-CRM conjugate vaccine," vol. 119 No. 3, Immunology, pp. 328-337 (2006).
Elkayam et al., "Pneumococcal vaccination of patients with systemic lupus erythematosus: effects on generation of autoantibodies," vol. 38 No. 7, Autoimmunity, pp. 493-496 (2005).
Nieminen et al., "Circulating antibody secreting cell response to parenteral pneumococcal vaccines as an indicator of a salivary IgA antibody response," vol. 16 No. 2-3, Vaccine, pp. 313-319 (1998).
Nieminen et al., "Pneumococcal conjugate vaccination in adults: circulating antibody secreting cell response and humoral antibody responses in saliva and in serum," vol. 16 No. 6, Vaccine, pp. 630-636 (1998).
PCT International Search Report and Written Opinion issued in International Application No. PCT/US13/21381, dated Jan. 14, 2013.
Smith et al., "Rapid generation of fully human monoclonal antibodies against influenza virus," vol. 4 No. 3, Nat. Protocol., pp. 372-384; especially abstract p. 18 para 1 (2009).
Wrammert et al., "Rapid cloning of high-affinity human monoclonal antibodies against influenza virus," vol. 453 No. 7195, Nature, pp. 667-671 (2008).
Zhou et al., "Recurrent variable region gene usage and somatic mutation in the human antibody response to the capsular polysaccharise of *Streptococcus pneumonia* type 23F," vol. 70 No. 8, pp. 4083-4091 (2002).
Zhou, et al., "Somatic Hypermutation and Diverse Immunoglobulin Gene Usage in the Human Antibody Response to the Capsular Polysaccharide of *Streptococcus pneumonia* Type 6B," vol. 72, Period 6, Infection and Immunity, pp. 3505-3535 (2004).
Lucas, "Combinatorial Library Cloning of Human Antibodies to *Streptococcus pneumonia* Capsular Polysaccharides: Variable Region Primary Structures and Evidence for Somatic Mutation of Fab Fragments Specific for Capsular Serotypes 6B, 14 and 23F," vol. 69, No. 2, Infection and Immunity, pp. 853-864 (2000).
Marimon, "Antibody microarray typing, a novel technique for *Streptococcus pneumoniae* serotyping," vol. 80, Journal Microbiological Methods, pp. 274-280.
Yu, "A rapid pneumococcal serotyping system based on monoclonal antibodies and PCR," vol. 57, Journal of Medical Microbiology, pp. 171-178 (2008).
Yu, "Development of a multiplexed and automated serotyping assay for *Streptococcus pneumonia*," vol. 18 Clinical and Vaccine Immunology, pp. 1-25 (2011).
Lin, "Validation of a Multiplex Pneumococcal Serotyping Assay with Clinical Samples," vol. 44, No. 2, Journal of Clinical Microbiology, pp. 383-388 (2006).
Meng, "Specificity of antibody response to 23-valent pneumococcal polysaccharide vaccine in patients with chronic pulmonary diseases," vol. 36, No. 17 Jiangsu Medical Journal, pp. 2002-2004 (2010).
Office Action issued in corresponding Chinese Application No. 201380017988.6, dated Jun. 30, 2015.
Office Action issued in corresponding Chinese Application No. 201380017988.6, dated Dec. 10, 2015.
Examination Report issued in corresponding Australian Application No. 2013215630, dated Sep. 4, 2015.
European Search Report issued in corresponding European Application No. 13744086.3, dated Sep. 25, 2015.
Extended European Search Report in corresponding European Application No. 13744086.3, dated Jan. 19, 2016.
Yu et al., "Development of an Automated and Multiplexed Serotyping Assay for *Streptococcus pneumoniae*", Clinical and Vaccine Immunology, vol. 18, No. 11, pp. 1900-1907 (2011).
Examination Report issued in related Australian Patent Application No. 2016219587, dated Aug. 18, 2017.

* cited by examiner

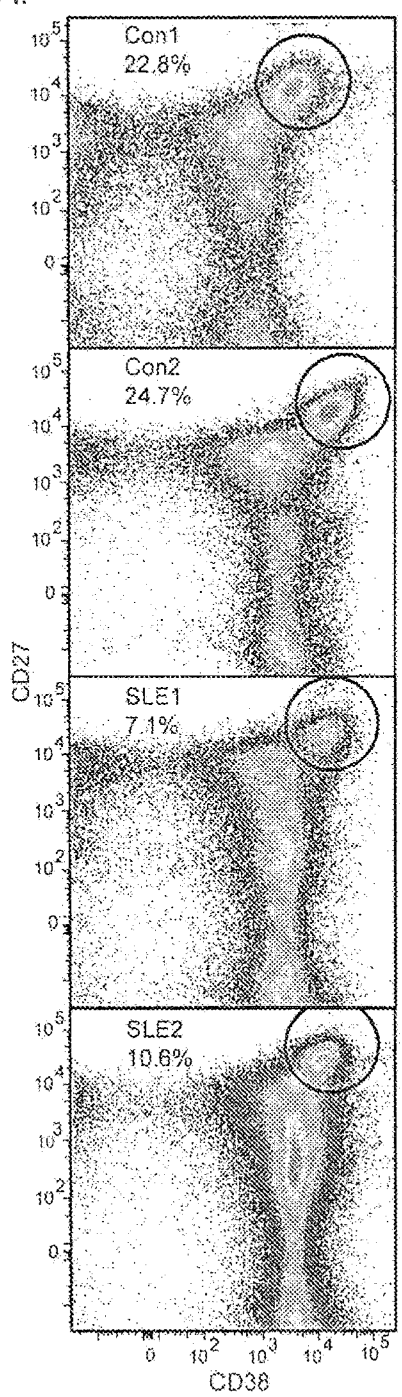
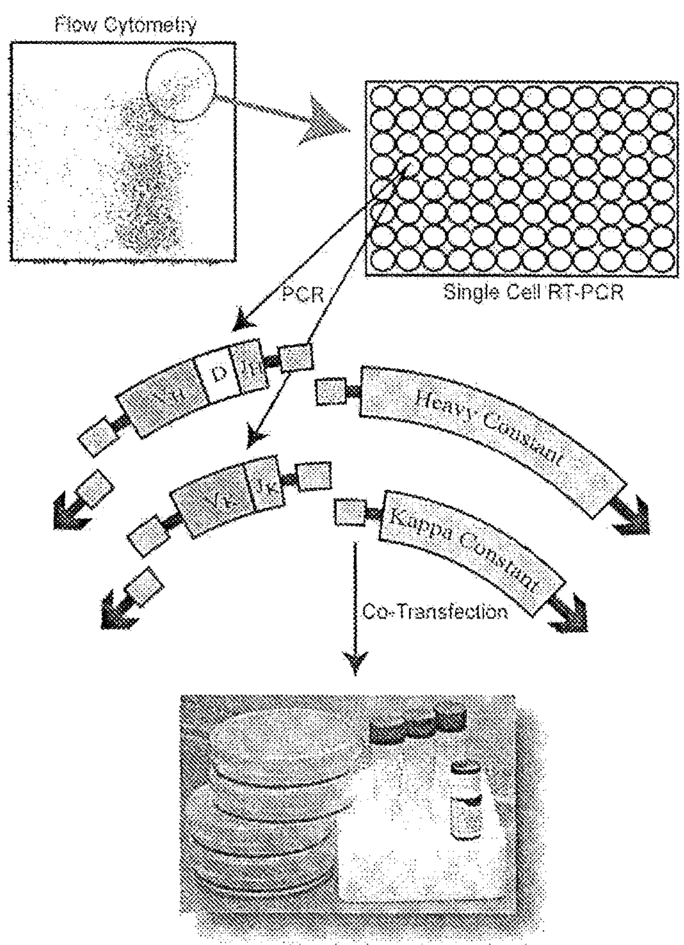
FIG. 1A-B

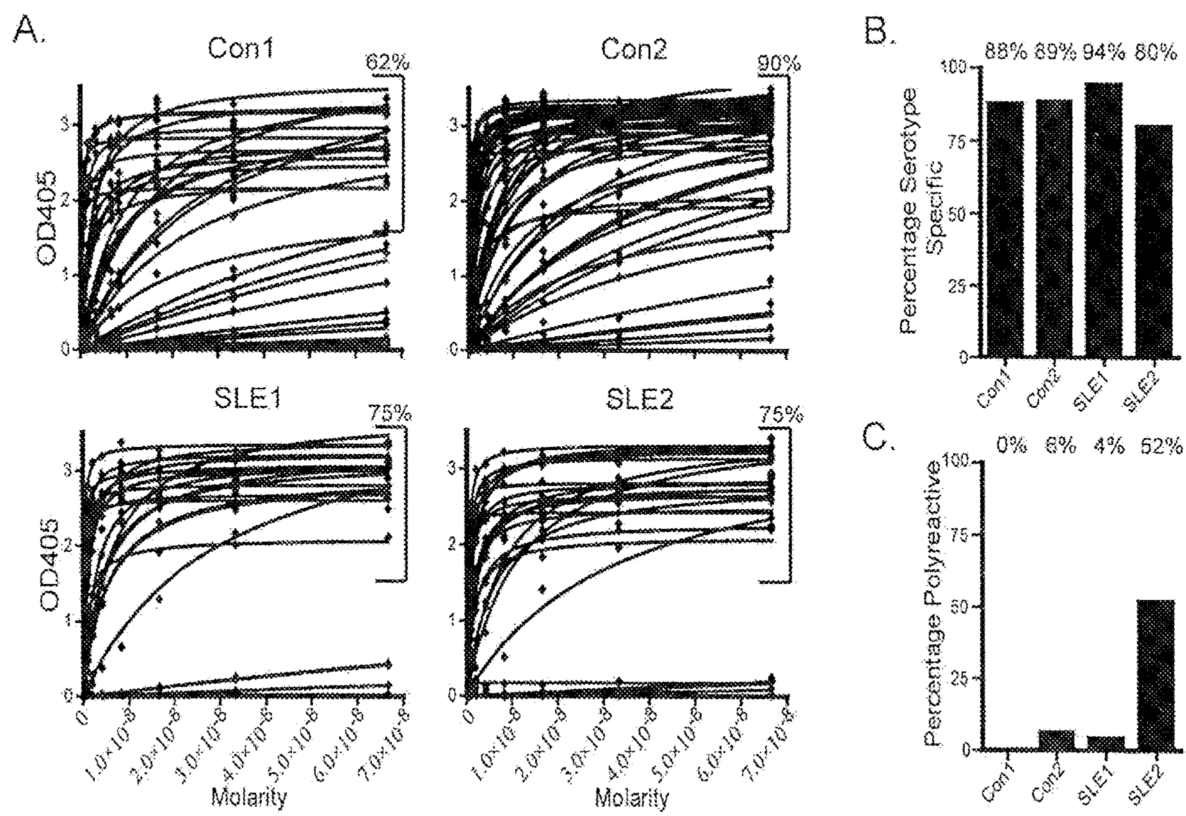
FIG. 2A-C

A.
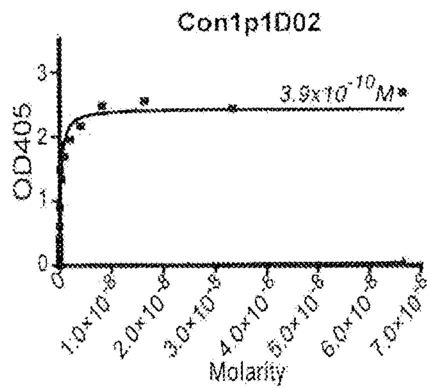
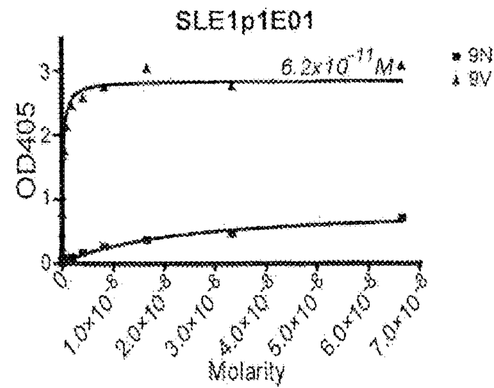
B.
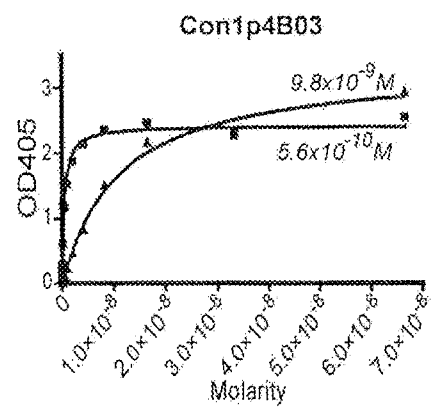
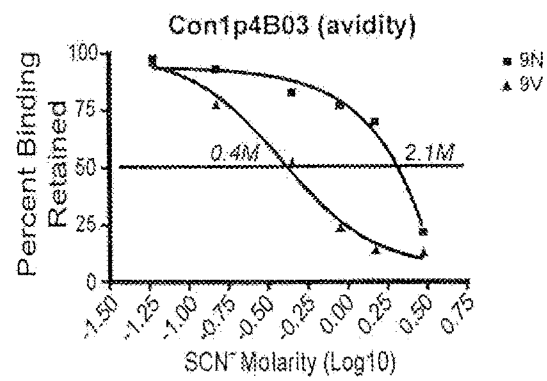
C.
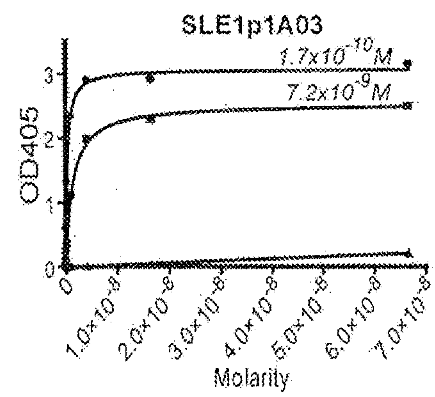
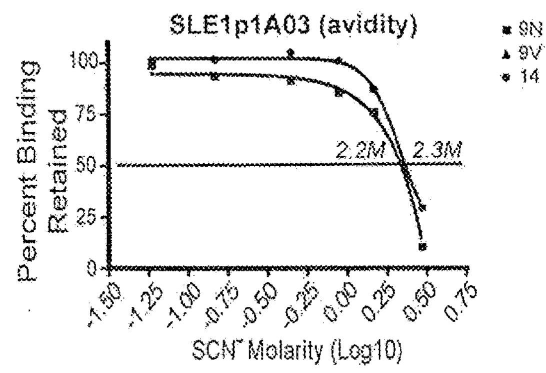
D.
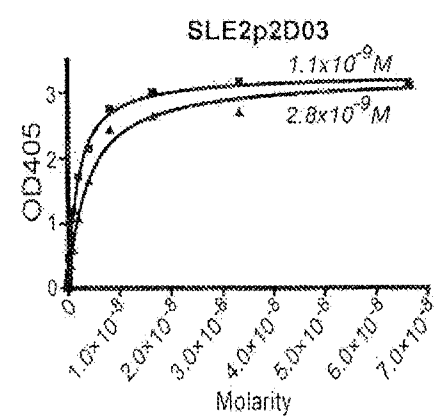
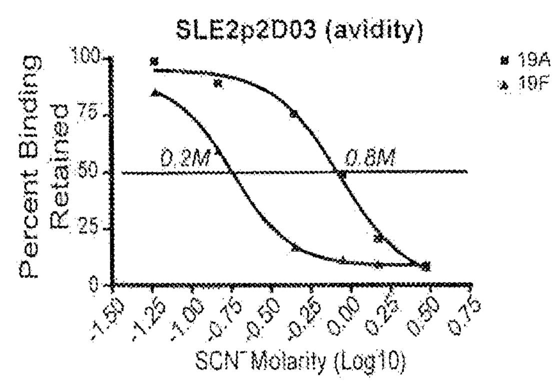
FIG. 3A-D A.
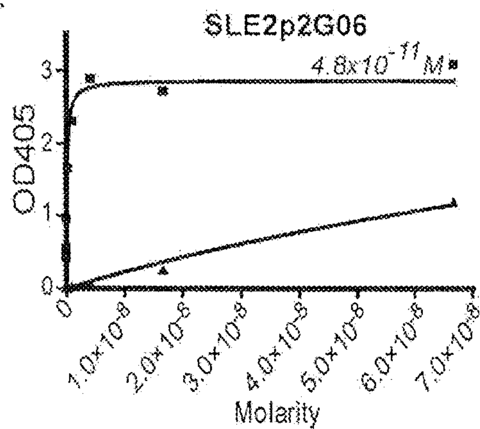
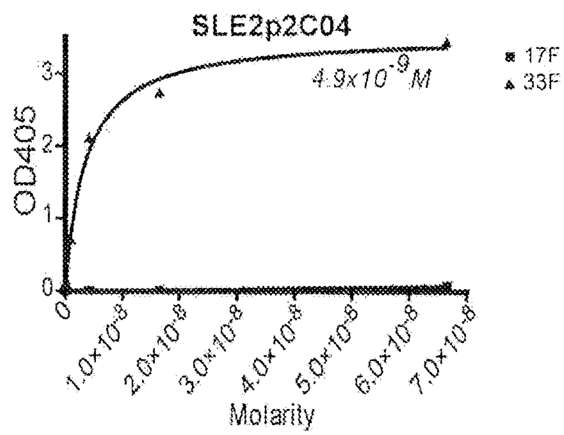
B.
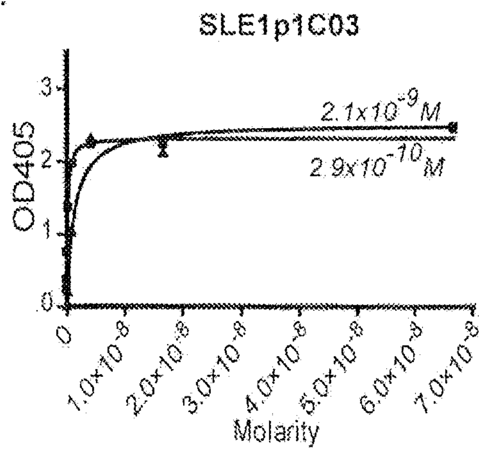
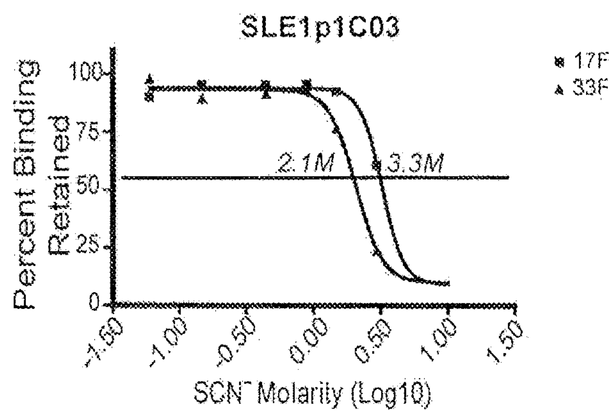
C.
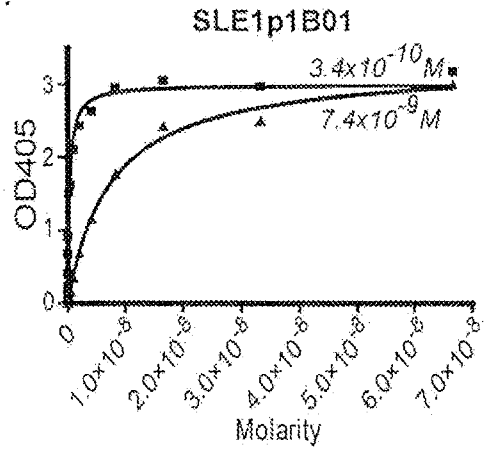
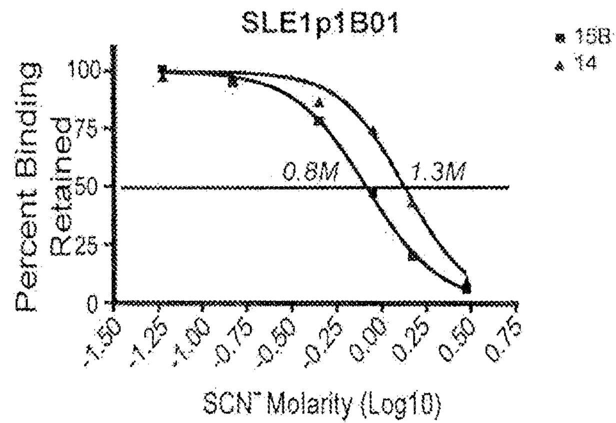
FIG. 4A-C

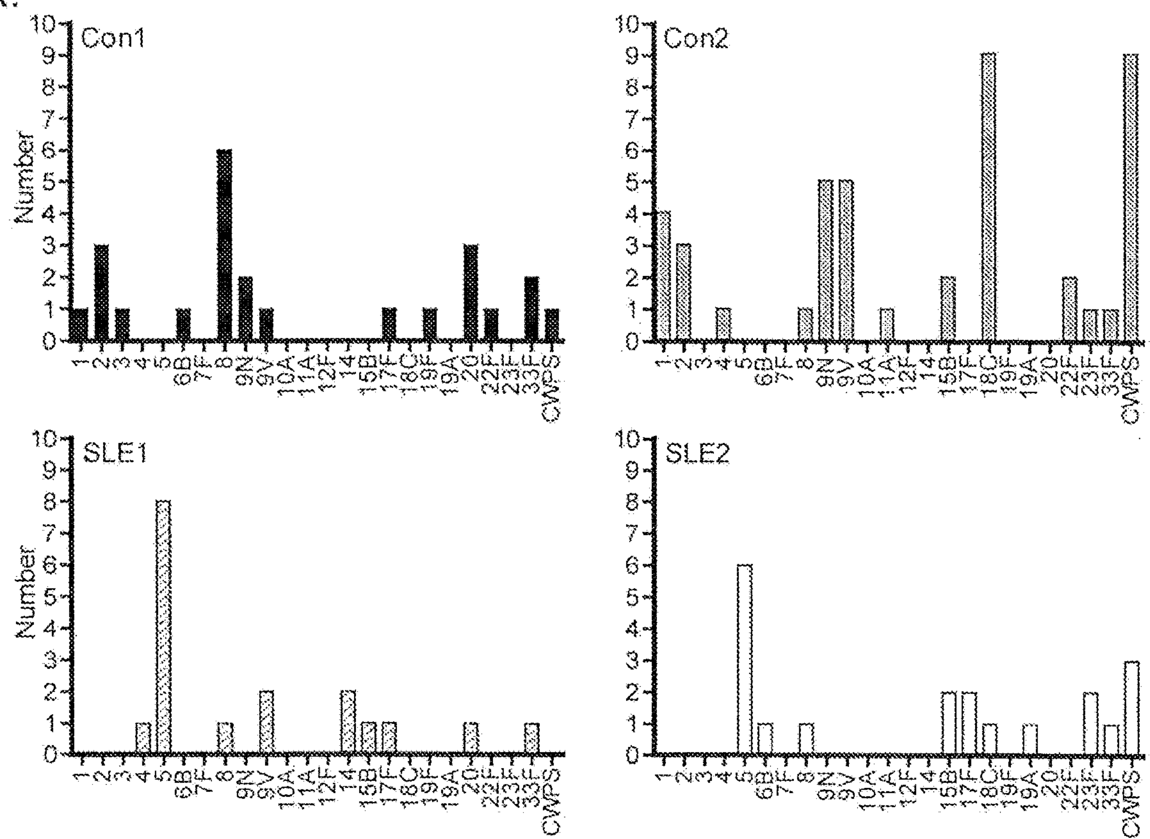
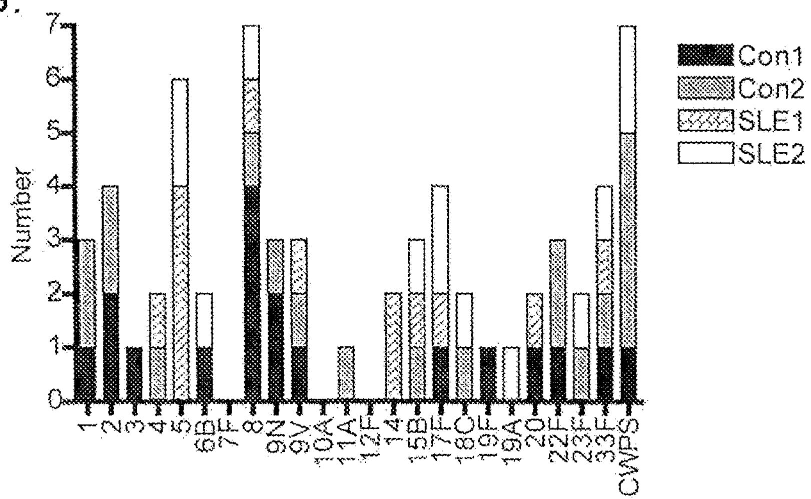
FIG. 6A-B

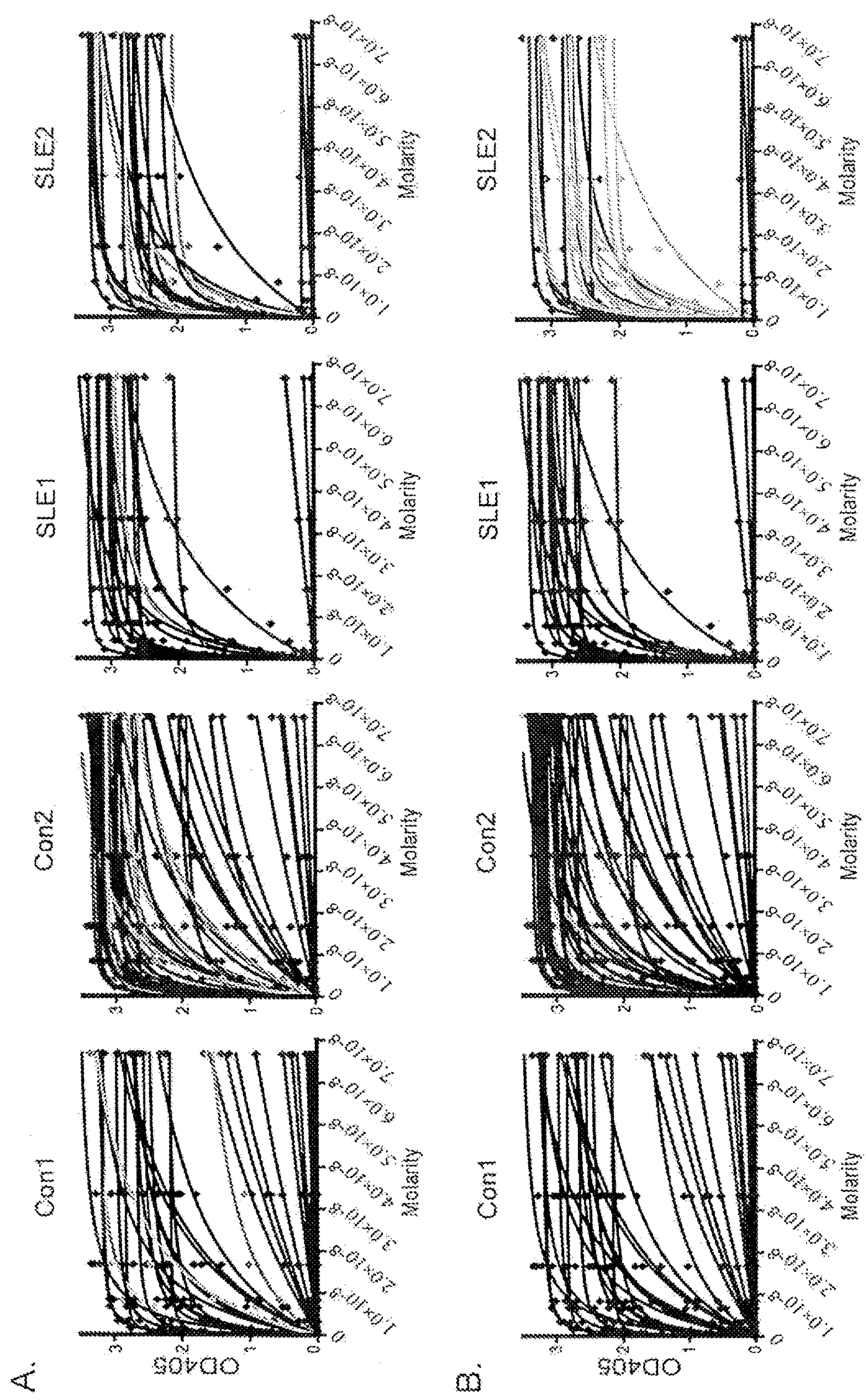
FIG. 7A-B

HUMAN *STREPTOCOCCUS PNEUMONIAE* ANTIBODIES AND USES THEREFOR

This application is a division of U.S. application Ser. No. 13/740,934, filed Jan. 14, 2013, and claims benefit of priority to U.S. Provisional Application Ser. No. 61/593,654, filed Feb. 1, 2012, the entire contents of which are hereby incorporated by reference.

This invention was made with government support under grant numbers P20RR015577, P20RR015577-10S1, P30RR031152, P30AR053483, and U19AI062629, and contract number HHSN266200500026C (N01-AI500026), awarded by the National Institutes of Health. The government has certain rights in the invention.

This application includes an electronically submitted sequence listing in .txt format. The .txt file contains a sequence listing entitled "2022-10-12 OMRF1023DIV_ST25.txt" created on Oct. 12, 2022 and is 224,622 bytes in size. The sequence listing contained in this .txt file is part of the specification and is hereby incorporated by reference herein in its entirety.

BACKGROUND OF THE INVENTION

1. Field of the Invention

The present invention relates generally to the fields of microbiology, immunology and pathology. More particularly, it conceals the development of human monoclonal antibodies for use in the diagnosis, prevention and therapy of *Steptococcus pneumoniae* infections.

2. Background of the Invention

*Streptococcus pneumoniae* is a ubiquitous human pathogen causing a range of clinical infections, such as otitis media, pneumonia, meningitis, and bacteremia. The more serious manifestations are especially virulent in immunocompromised and elderly individuals. Over 90 different *S. pneumoniae* serotypes have been characterized, each having a different capsular polysaccharide structure. These polysaccharides are immunogenic in adults, and the Pneumovax®23 vaccine consists of a cocktail of 23 of the most common and/or virulent *S. pneumoniae* strains. The vaccine is recommended for everyone over the age of sixty, as well as all immunocompromised individuals, to ensure seroprotection against these strains.

The serology of the response to Pneumovax®23, as well as the conjugate vaccine Prevnar® (used to immunize children), has been studied in depth with regard to the humoral polyclonal IgG and IgA responses in both sera and saliva (Anttila et 1999, Nieminen et al., 1998a; Nieminen et al., 1998b). The memory and antibody secreting cell (ASC) response to these vaccines has also been previously explored on a cellular level with B cell ELISpot assays and flow cytometry Nieminen et al., 1998b; Clutterbuck et al., 2006), and the presence of both responses after vaccination is now well established. However, utilizing ASCs to produce human monoclonal antibodies would provide a novel way to fully elucidate the recall response to pathogen serotypes after vaccination, and even provides a window to explore the evolution of past responses.

Antibodies that cross-react to two or more pneumococcal polysaccharides are present in sera both pre and post-immunization (Lee et al., 1984; Soininen et al., 2000); however, whether this is due to single antibody specificities that are capable of cross-reacting or rather due to broad polyclonal antibody specificities is not known. Although it has been reported that immunization with Pneumovax®23 in patients with SLE does not induce new auto-specificities (Elkayam et al., 2005), one report has shown that kidney-binding antibodies in a patient with SLE also cross-reacted with pneumococcal polysaccharide (Chowdhry et al., 2005). Thus, it is possible that antibodies produced from B cells in SLE donors may show increased poly-reactivity or auto-reactivity. It is only possible to determine such per-antibody phenomenon by the characterization of human monoclonal antibodies from SLE donors.

SUMMARY OF THE INVENTION

Thus, in accordance with the present invention, there is provided a human monoclonal antibody panel comprising a plurality of antibodies, wherein antibodies in said panel bind to at least 15 serotypes of *Streptococcus pneumoniae*. The antibodies in said panel may bind to at least 18 *S. pneumoniaee* serotypes or 21 *S. pneumoniaee* serotypes. At least 15 antibodies may be serotype specific, at least 17 antibodies may be serotype specific, or 19 antibodies may be serotype specific. The antibody panel may be attached to a support, such as a bead, a dipstick, a filter, a membrane, a plate, or a chip. The serotypes may be selected from 1, 2, 3, 4, 5, 6B, 8, 9N, 9V, 11B, 14, 15B, 17F, 18C, 19A, 19F, 20, 22F, 23F, 33F and CWPS. The antibody panel may comprise an antibody that reacts with two serotypes.

In another embodiment, there is provided a method of assessing a *Streptococcus pneumoniae* in a subject comprising obtaining a first antibody-containing sample from said subject and assessing binding of antibodies in said sample to a human monoclonal antibody panel comprising a plurality of antibodies, wherein antibodies in said panel bind to at least 15 serotypes of *Streptococcus pneumoniae*. The antibodies in said panel may bind to at least 18 *S. pneumoniaee* serotypes or 21 *S. pneumoniaee* serotypes. At least 15 antibodies may be serotype specific, at least 17 antibodies may be serotype specific, or 19 antibodies may be serotype specific. The antibody panel may be attached to a support, such as a bead, a dipstick, a filter, a membrane, a plate, or a chip. The serotypes may be selected from 1, 2, 3, 4, 5, 6B, 8, 9N, 9V, 11B, 14, 1513, 17F, 18C, 19A, 19F, 20, 22F, 23F, 33F and CWPS. The antibody panel may comprise an antibody that reacts with two serotypes.

The subject may be immunocompromised and/or 60 years old or older. The subject may be suspected of having a *Streptococcus pneumoniae*. The method may further comprise treating said subject with an anti-*Streptococcus pneumoniae* therapy if said first antibody-containing sample is found to be positive for one or more serotypes. The method may further comprise treating said subject with vancomycin or levoflaxin if first said antibody-containing sample is found to be positive for serotype 19A and/or 19F. The first antibody-containing sample may be blood, serum, plasma, sputum, or saliva.

The method may further comprise obtaining a second antibody-containing sample from said subject and assessing binding of antibodies in said second sample to a human monoclonal antibody panel comprising a plurality of antibodies, wherein antibodies in said panel bind to at least 15 serotypes of *Streptococcus pneumoniae*. The second antibody-containing sample may be blood, serum, plasma, sputum, or saliva. The subject may have been treated with an anti-*Streptococcus pneumoniae* therapy after determining that said first antibody-containing sample was positive for one or more serotypes, and a reduction in antibody titer to serotypes from said first sample indicates that said anti-*Streptococcus pneumoniae* therapy is effective at treating *Streptococcus pneumoniae*. The subject may have been treated with an antibiotic after determining that said first antibody-containing sample was positive for one or more serotypes, and the absence of a reduction in antibody titer to serotypes from said first sample indicates that said anti-*Streptococcus pneumoniae* therapy is ineffective at treating *Streptococcus pneumonia*, and optionally the method may further comprise treating said subject with a different anti-*Streptococcus pneumoniae* therapy.

In yet another embodiment, there is provided an antibody that binds selectively to *Streptococcus pneumonia*, wherein said antibody has heavy and light chain CDRs selected from those set forth in Table 2. The antibody may be a single chain antibody, a single domain antibody, a chimeric antibody, a Fab fragment, or an IgG. The antibody may further comprise an antibiotic linked thereto, such as one linked to said antibody through a photolabile linker or through an enzymatically-cleaved linker. The antibody may be conjugated to a nanoparticle or a liposome.

In still yet another embodiment, there is provided a method of treating a *Streptococcus pneumoniae* infection in a subject comprising administering to said subject an antibody as described above. The method may further comprise administering to said subject a second anti-*Streptococcus pneumoniae* treatment, which can be given at the same time as said antibody or given before and/or after said antibody. The antibody may be a single chain antibody, a single domain antibody, a chimeric antibody, a Fab fragment or an IgG.

The antibody may further comprises an antibiotic linked thereto, such one linked to said antibody through a photolabile linker or through an enzymatically-cleaved linker. The antibody may be conjugated to a liposome or nanoparticle. Multiple anti-*Streptococcus pneumonia* antibodies are administered, such as multiple anti-*Streptococcus pneumonia* antibodies that bind to 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or 100 *Streptococcus pneumonia* serotypes.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one" The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-B. Pneumovax®23 causes a massive ASC burst which can be used as a source of high affinity anti-polysaccharide antibodies. (FIG. 1A) PBMCs were harvested from four donors 7 days after vaccination with Pneumovax®23. They were stained and sorted for cells which are CD3 and CD20 negative and CD19 intermediate. The dot plots presented indicate a large ASC burst in all four donors (CD27 high, CD38 high; circular gate). Averaging the percentage of ASCs from these four donors, designated as Con1, Con2, SLE1, and SLE2, 16.3% of total B cells in the peripheral blood are ASCs. (FIG. 1B) The ASCs indicated in A. are sorted into 96-well plates. RT-PCR and several rounds of nested PCR are performed to prepare the V regions for cloning. The DNA is then cloned into expression vectors, amplified, and transfected into the HEK293 human cell line.

FIGS. 2A-C. On average, 77% of antibodies produced after vaccination with Pneumovax®23 bind to a vaccine component. (FIG. 2A) An average of 77% (Con1, 62%; Con2, 90%; SLE1, 75%; SLE2, 75%) of the antibodies expressed bind to *S. pneumoniae* capsule or cell wall polysaccharide by ELISA. (FIG. 2B) While a significant percentage of antibodies are cross-reactive (12%), most of the antibodies produced are specific to a single serotype. (FIG. 2C) 52% of the antibodies from ST are poly-reactive, binding to at least two of the following five antigens: Ro, La, Sm, nRNP, or cardiolipin.

FIGS. 3A-D. An individual can produce multiple antibodies to the same serotype, some of which are specific and others of which cross-react. (FIG. 3A.) Serotypes 9N and 9V have very similar structures, yet Con1p2D02 binds only 9N and SLE1p1E01 binds only 9V. (FIG. 3B) Conversely, Con1p4B03 binds to both 9N and 9V. As shown by both affinity and avidity measurements, the binding to 9N is stronger than to 9V. (FIG. 3C) SLE1p1A03 binds to 9N, but cross-reacts with 14 rather than 9V. Its affinity and avidity for both 9N and 14 are similar. (FIG. 3D) SLE2p2D03 binds to both 19A and 19F, which also share similar structures. The affinity to 19A and 19F is similar, however, the avidity to 19A is 4 times stronger than to 19F. Affinity ELISAs are performed by coating plates with a single purified polysaccharide using serial dilutions of the antibody. Affinities (Kd's) are expressed in molarity. Avidity chaotropic ELISAs are performed in the same manner, but a 15 minute elution step using various dilutions of ammonium, thiocyanate is added. Avidity graphs are presented as percent binding retained ($OD_{405}$ with SCN/$OD_{405}$ without SCN*100) versus the log of the thiocyanate concentration. The avidity is equal to the concentration of ammonium thiocyanate causing a 50% reduction (or retention) of binding.

FIGS. 4A-C. B cells generate cross-reactive antibodies to serotypes 15B and 14, as well as 17F and 33F. (FIG. 4A) Two antibodies, SLE2p2G06 and SLE2p2C04 bind solely to 17F or 33F respectively. (FIG. 4B) SLE2p1C03, however, binds to both serotypes. The affinity for 33F is an order of magnitude better than the affinity for 17F, however, their avidities are similar. (FIG. 4C) SLE2p1B01 binds to both 15B and 14. Although the affinity is almost an order of magnitude higher for 15B, it actually shows two-fold higher avidity for 14.

FIGS. 6A-B. The specificity of ASCs induced by. Pneumovax®23 is determined, by a donor's memory response invoked by the vaccine. (FIG. 6A) The 'anamnestic fingerprint' from the four donors. None had previously received Pneumovax®23, thus the ASC 'recall' antibodies cloned resulted from memory due to previous exposure to *S. pneumoniae*. Each donor has a unique "fingerprint" of serotypes against which they have produced antibodies. (FIG. 6B) After eliminating members of clonal pools and combining all four graphs, the donors have very different 'pneumococcal fingerprints' with only three serotypes (9V, 15B and 17F) being represented from three donors, and only two from all four (8 and 33F).

FIGS. 7A-B, Cross-reactive and poly-reactive antibodies are shown from each donor. The ELISA curves from FIG. 2A are reproduced here also showing antibodies which are (FIG. 7A) cross-reactive in red and (FIG. 7B) poly-reactive in orange. Three of the four cross-reactive antibodies from SLE2 are also poly-reactive (but none from the other donors).

DESCRIPTION OF ILLUSTRATIVE EMBODIMENTS

Figure 5:
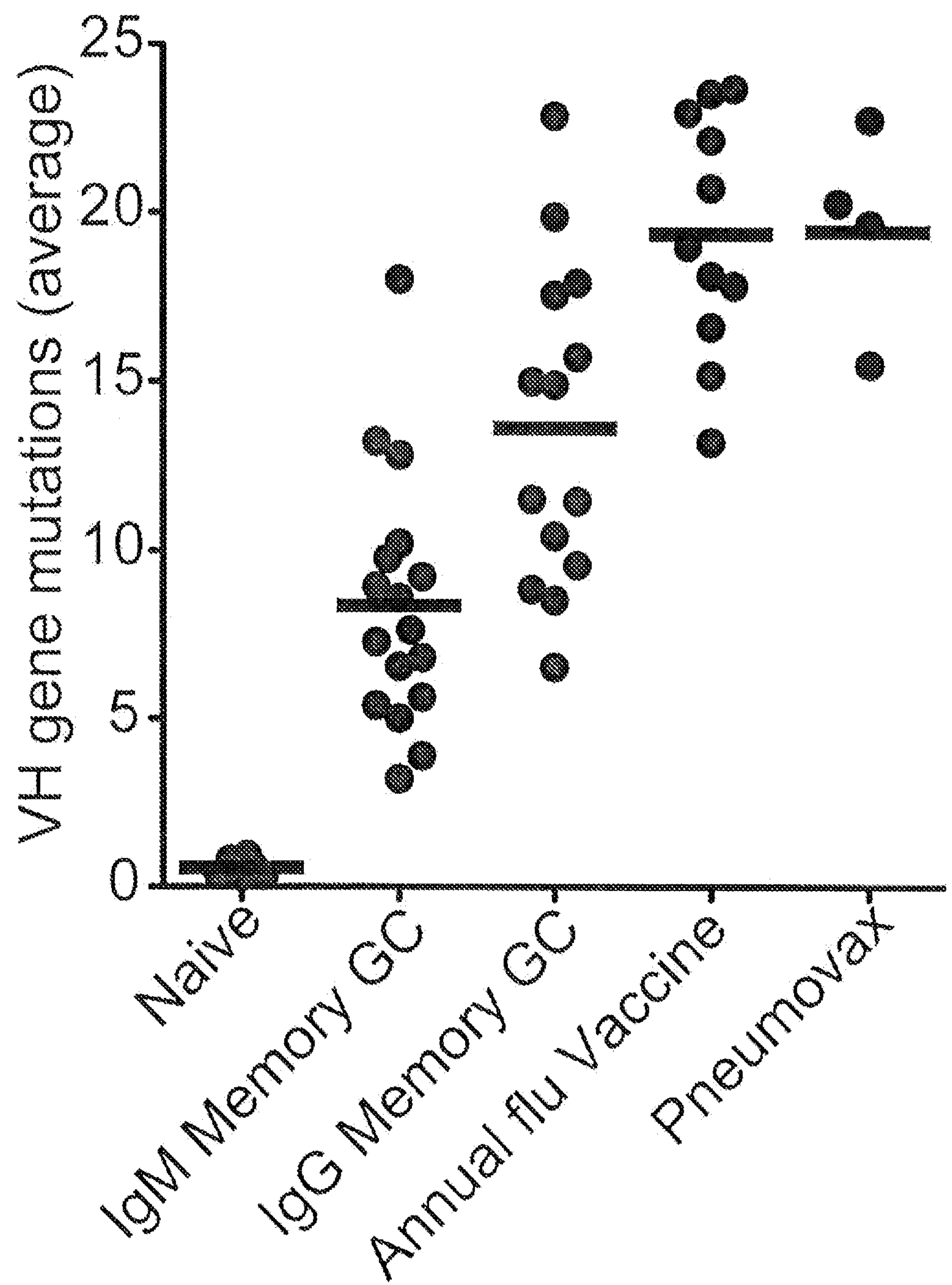
FIG. 5 ASCs resulting from vaccination with Pneumovax®23 produce antibodies which are highly mutated. Each data point is the average frequency of somatic mutations (nucleotide) per sequence from each donor (n values in Methods). On average, the anti-polysaccharide ASCs had accumulated a similar number of mutations as anti-influenza ASCs after seasonal influenza vaccination[14]. GC=germinal center populations.

To explore the antibody response generated by the Pneumovax®23 vaccine, the inventor generated and characterized large numbers of high affinity human monoclonal antibodies to the *S. pneumoniae* serotypes present in the vaccine from SLE patients and healthy controls. Although human monoclonal antibodies to *S. pneumoniae* have been made in the past (Baxendale and Goldblatt, 2006; Baxendale et al., 2000; Zhou et al., 2002; Zhou et al., 2004), these studies have been limited by two factors: one, they employed lab expression library screens and two, they employed random production of hybridomas. In addition, previous studies have either focused on one serotype (6B and 23F) or have utilized vaccination with the conjugate vaccine Prevnar that consists of only seven capsular serotypes. In contrast, the inventor's technique provides cross-sectional characterization of the anti-polysaccharide response at one particular point in time seven days post vaccination; this every cell used to clone an antibody has arisen from a memory response to this particular vaccination. This system will inform on a number of still unanswered questions in the field of polysaccharide immune responses and autoimmunity. In particular, the data here specifically address the percentage of human monoclonal polysaccharide antibodies that cross-react between different serotypes, how an ASC response to Pneumovax®23 is a result of previous exposure to *S. pneumoniae*, and how this response differs in donors with SUE. As a result, there are now available a wide range of fully human monoclonal antibodies to *S. pneumoniae* that can be applied to diagnostic, theranostic and therapeutic applications. These and other aspects of the invention are described in detail below.

II. *Steptococcus pneumoniae*

A. General

*Streptococcus pneumoniae*, or pneumococcus, is Gram-positive, alpha-hemolytic, bile-soluble aerotolerant, anaerobic member of the genus *Streptococcus*. A significant human pathogenic bacterium, *S. pneumoniae* was recognized as a major cause of pneumonia in the late 19th century, and is the subject of many humoral immunity studies.

*S. pneumoniae* can be differentiated from *Streptococcus viridans*, some of which are also alpha-hemolytic, using an optochin test, as *S. pneumoniae* is optochin-sensitive. *S. pneumoniae* can also be distinguished based on its sensitivity to lysis by bile. The encapsulated, Gram-positive coccoid bacteria have a distinctive morphology on Gram stain, the so-called, "lancet-shaped" diplococci. They have a polysaccharide capsule that acts as a virulence factor for the organism; more than 90 different serotypes are known, and these types differ in virulence, prevalence, and extent of drug resistance.

The genuine of *S. pneumoniae* is a closed, circular DNA structure that contains between 2.0 and 2.1 million base-pairs, depending on the strain. It has a core set of 1553 genes, plus 154 genes in its virulome, which contribute to virulence, and 176 genes that maintain a noninvasive phenotype. Genetic information can vary up to 10% between strains.

*S. pneumoniae* is part of the normal upper respiratory tract flora, but, as with many natural flora, it can become pathogenic under the right conditions (e.g., if the immune system of the host is suppressed). Invasins, such as pneumolysin, an antiphagocytic capsule, various adhesins and immunogenic cell wall components are all major virulence factors.

Community-acquired pneumonia (CAP) is becoming more and more common, and represents an important cause of mortality and morbidity worldwide. While a number of different pathogens can give rise to CAP, *Streptococcus pneumoniae* is one of the most common. CAP is often acquired via inhalation or aspiration of pulmonary pathogenic organisms into a lung segment or lobe. Less commonly, CAP results from secondary bacteremia from a distant source.

Severe CAP normally develops in patients with cardiopulmonary disease, diminished splenic function, and/or pathogenic virulence, but even young and/or healthy hosts can develop severe CAP if the causative pathogen is sufficiently virulent. Complications in CAP depend on the infecting pathogen and patient health. Myocardial infarction can be precipitated by fever due to community-acquired pneumonia (CAP). Also, patients with CAP who have impaired splenic function may develop overwhelming pneumococcal sepsis, potentially leading to death within 12-24 hours, regardless of the antimicrobial regimen used.

CAP morbidity and mortality are highest in elderly patients and in immunocompromised hosts. Other factors that predict an increased risk of mortality in patients with CAP include the presence of significant comorbidities, an increased respiratory rate, hypotension, fever, multilobar involvement, anemia, and hypoxia.

B. Related Disease States

Despite the name, *S. pneumoniae* causes many types of pneumococcal infections other than pneumonia, including acute sinusitis, otitis media, meningitis, bacteremia, sepsis, osteomyelitis, septic arthritis, endocarditis, peritonitis, pericarditis, cellulitis, and brain abscess.

C. Multi-Drug Resistance

A growing concern in *S. pneumoniae* therapy is the resistance of strains many to penicillin and other beta-lactams (like amoxicillin), which is increasing worldwide. The major mechanism of resistance involves the introduction of mutations in genes encoding penicillin-binding proteins. This development complicates treatment immensely, and also adds unnecessary cost when therapies fail.

In 2000, Whitney et al. examined data on invasive pneumococcal disease in patients identified from 1995 to 1998 in the Active Bacterial Core Surveillance program of the Centers for Disease Control and Prevention. During 1998, 4013 cases of invasive *Streptococcus pneumoniae* disease were reported, and isolates were available for 3475 (87%). Overall, 24% of isolates from 1998 were resistant to penicillin. Penicillin-resistant isolates were more likely than susceptible isolates to have a high level of resistance to other antimicrobial agents. Serotypes included in the 7-valent conjugate and 23-valent pneumococcal polysaccharide vaccines accounted for 78% and 88% of penicillin-resistant strains, respectively. Between 1995 and 1998, the proportion of isolates that were resistant to three or more classes of drugs increased from 9% to 14%; there also were increases in the proportions of isolates that were resistant to penicillin (from 21% to 25%), cefotaxime (from 10% to 14%), meropenem (from 10% to 16%), erythromycin (from 11% to 15%), and trimethoprim-sulfamethoxazole (from 25% to 29%). These trends are like to continue, putting greater pressure on clinicians to resort to drugs such as vancomycin and levoflaxin.

D. Diagnosis

*S. pneumoniae* can be differentiated from other *Streptococcus* infections based on the alpha-hemolytic test. *Streptococcus viridans*, some of which are also alpha-hemolytic, can be distinguished using an optochin test, as *S. pneumoniae* is optochin-sensitive but *S. viridans* is not. *S. pneumoniae* can also be distinguished based on its sensitivity to lysis by bile. The encapsulated, Gram-positive coccoid bacteria have a distinctive morphology on Gram stain, the so-called, "lancet-shaped" diplococci. They have a polysaccharide capsule that acts as a virulence factor for the organism; more than 90 different serotypes are known, and these types differ in virulence, prevalence, and extent of drug resistance.

In terms of distinguishing serotypes, antibodies are currently available to serotypes 1, 3, 4, 5, 6B, 7F, 8, 9N, 9V, 12F, 14, 18C, 19F and 23F (ARUP Laboratories, Salt Lake City, Utah).

E. Treatments

Antibiotics are the treatment of choice for *S. pneumoniae* infects, with ventilation (oxygen supplement) as supportive therapy of bacterial pneumonia. The antibiotic choice depends on the the microorganisms most commonly causing pneumonia in the geographical region, as well as nature of the specific organism, the immune status and underlying health of the individual, the severity of infection, and prior treatment history. In the United Kingdom, amoxicillin is used as first-line therapy in the vast majority of patients who acquire pneumonia in the community, sometimes with added clarithromycin. In North America, where the "atypical" forms of community-acquired pneumonia are becoming more common, clarithromycin, azithromycin, or fluoroquinolones as single therapy, have displaced the amoxicillin as first-line therapy. Local patterns of antibiotic-resistance should always be considered when initiating pharmacotherapy. In hospitalized individuals or those with immune deficiencies, local guidelines determine the selection of antibiotics. These antibiotics are typically given through an intravenous line. Specifically, *S. pneumoniae* is treated with amoxicillin (or erythromycin in patients allergic to penicillin), and with cefuroxime and erythromycin in severe cases.

III. Producing Monoclonal Antibodies

A. General Methods

It will be understood that monoclonal antibodies binding to *S. pneumoniae* will have utilities in several applications. These include the production of diagnostic kits for use in detecting and diagnosing disease. In these contexts, one may link such antibodies to diagnostic or therapeutic agents, or use them as capture agents or competitors in competitive assays. Means for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a earner. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carder protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

In the case of human monoclonal antibodies, one may instead simply look for an individual already known to have generated an immune response, in this case, to have been exposed to *S. pneumoniae* or immunized with Pneumovax®23. In order to identify subjects with immunity to various *S. pneumoniae* strains, one could generally obtain blood from subjects and test them for *S. pneumoniae* antibodies. Many antibodies described in this invention were generated in this way using peripheral blood from otherwise healthy individuals previously infected with *S. pneumoniae.*

Following immunization or obtaining of cells from previously infected subjects as described above, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1, Ag 4 1, Sp210-Ag14, FO, NSO/U, MPG-11, MPC11-X45-GTG 1.7 and S194/5XX0 Bul; for rats, one may use R210.RCY3, Y3-Ag 1.2.3, IR983F and 4B210; and U-266, GMI500-GRG2, LICR-LON-11My2 and UC729-6 are all useful in connection with human cell fusions. One particular marine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line. More recently, additional fusion partner lines for use with human B cells have been described, including KR12 (ATCC CRL-8658; K6116/135 (ATCC CRL-1823 SHM-D33 (ATCC CRL-1668) and HMMA2.5 (Posner et al., 1987). The antibodies in this invention were generated using the HMMA2.5 line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter el al. (1977). The use of electrically induced fusion methods also is appropriate (Goding, pp. 71-74, 1986). The hybridomas secreting the influenza antibodies in this invention were obtained by electrofusion.

Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in FIAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like.

The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Invention

Antibodies according to the present invention may be defined, in the first instance, by their binding specificity. Those of skill in the art, by assessing the binding affinity of a given antibody using techniques well known to those of skill in the art, can determine whether such antibodies fall within the scope of the instant claims.

In the context of the present invention, the antibody specificity relates to the *S. pneumoniae* serotype. There are 24 different serotypes represented by Pneumovax®23, represented by the following designations: 1, 2, 3, 4, 5, 6B, 7F, 8, 9N, 9V 10A, 11A, 12F, 14, 153, 17F, 18C, 19F, 19A, 20, 22F, 23F, 33F and CWPS. The CDR region sequences for representative antibodies are included in the appended sequence listing.

Another way of categorizing the antibodies of the present invention is by their activity. This could include the ability to neutralize or kill *Streptococcus pneumoniae* in the presence or absence of complement. Finally, the antibody may be defined in particular by reference to heavy/light chain variable region sequences. The present inventor provides the following antibodies that have demonstrated activity against *Streptococcus pneumoniae* in an opsonophagocytosis assay (OPA) that measures antibody mediated uptake of bacteria by a phagocytic cell line. The also can be presented by variable regions as set out in Table 2.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy® vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies can generated by subcloning heavy and light chain Fv DNAs from the cloning vector into a second vector, such as a Lonza pConIgG1 or pConK2 plasmid vector, transfected into 293 Freestyle cells or Lonza CHO cells, and antibodies can then be collected and purified from the cell supernatants.

pCon Vectors™ are an easy way to re-express whole antibodies. The constant region vectors are a set of vectors offering a range of immunoglobulin constant region vectors cloned into the pEE vectors. These vectors offer easy construction of full length antibodies with human constant regions and the convenience of the GS System™.

Antibody molecules will comprise fragments (such as F(ab'), $F(ab')_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric or CDR-grafted antibody). In yet a further embodiment, the antibody is a fully human recombinant antibody. Alternatively, one may wish to make more subtle modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (±3.0), lysine (±3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present invention also contemplates isotype modification. By modifying the Fe region to have a different isotype, different functionalities can be achieved. For example, changing to $IgG_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present invention may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known, cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynezak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with dictators, drugs, enzymes, detectable labels and the like, U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

E. Purification

In certain embodiments, the antibodies of the present invention may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Flaying separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present invention, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens my be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

IV. Passive Immunization and Treatment of *S. pneumoniae* Infections

A. Formulation and Administration

Passive transfer of antibodies, known as artificially acquired passive immunity, generally will involve the use of intravenous or intramuscular injections. Such immunity generally lasts for only a short period of time, but provides immediate protection. The antibodies will be formulated in a carrier suitable for injection, i.e., sterile and syringeable. Thus, the present invention provides pharmaceutical compositions comprising anti-*S. pneumoniae* antibodies and antigens for generating the same. Such compositions comprise a prophylactically or therapeutically effective amount of an antibody or a fragment thereof, and a pharmaceutically acceptable carrier.) In a specific embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Generally, the ingredients of compositions of the invention are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. Combination Therapy

In order to increase the effectiveness of the antibody therapy of the present invention, it may be desirable to combine this treatment with other agents effective at treating or preventing *S. pneumonia* infections, e.g., antibiotics. This process may involve administering to the patient the antibody of the present invention and the other agent(s) at the same time. This may be achieved by use of a single pharmaceutical composition that includes both agents, or by administering two distinct compositions at the same time, wherein one composition includes the antibody of the present invention and the other includes the second agent(s).

The two therapies may be given in either order and may precede or follow the other treatment by intervals ranging from minutes to weeks. In embodiments where the other agents are applied separately, one would generally ensure that a significant period of time did not expire between the time of each delivery, such that the agents would still be able to exert an advantageously combined effect on the patient. In such instances, it is contemplated that one may administer both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, the antibody treatment of the present invention is "A" and the secondary treatment is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

Administration of the secondary agent will follow general protocols for that drug, taking into account the toxicity, if any. It is expected that the treatment cycles would be repeated as necessary.

1. Amoxicillin and Erythromycin

Amoxicillin. Amoxicillin (INN), formerly amoxicillin (BAN), and abbreviated amox, is a moderate-spectrum, bacteriolytic, β-lactam antibiotic used to treat bacterial infections caused by susceptible microorganisms. It is usually the drug of choice within the class because it is better absorbed, following oral administration, than other β-lactam antibiotics. Amoxicillin is one of the most common antibiotics prescribed for children. This drug acts by inhibiting the synthesis of bacterial cell walls. It inhibits cross-linkage between the linear peptidoglycan polymer chains that make up a major component of the cell walls of both Gram-positive and Gram-negative bacteria.

It has two ionizable groups in the physiological range (the amino group in alpha-position to the amide carbonyl group and the carboxyl group). Amoxicillin is susceptible to degradation by β-lactamase-producing bacteria, which are resistant to a broad spectrum of β-lactam antibiotics, such as penicillin. For this reason, it is often combined with clavulanic acid, a β-lactamase inhibitor, and marketed under one name. This increases effectiveness by reducing its susceptibility to β-lactamase resistance.

Amoxicillin is used in the treatment of a number of infections including: acute otitis media, streptococcal pharyngitis, pneumonia, skin infections, urinary tract infections, salmonella, lyme disease, and chlamydia infections. It is used to prevent bacterial endocarditis in high risk people who are having dental work done, to prevent strep pneumococus infections in those without a spleen, and for both the prevention and treatment of anthrax. It is also a treatment for cystic acne. The UK however does not recommend its use for infectious endocarditis prophylaxis. These recommendations have not appeared to have changed the rates of infection.

Side-effects are as those for other beta-lactam antibiotics. Side-effects include nausea, vomiting, rashes, and antibiotic-associated colitis. Loose bowel movements (diarrhea) also may occur. Rarer, but patient-reported, side-effects include mental changes, lightheadedness, insomnia, confusion, anxiety, sensitivity to lights and sounds, and unclear thinking. Immediate medical care is required upon the first signs of these side-effects.

The onset of an allergic reaction to amoxicillin can be very sudden and intense—emergency medical attention must be sought as quickly as possible. The initial onset of such a reaction often starts with a change in mental state, skin rash with intense itching (often beginning in fingertips and around groin area and rapidly spreading), and sensations of fever, nausea, and vomiting. Any other symptoms that seem even remotely suspicious must be taken very seriously. However, more mild allergy symptoms, such as a rash, can occur at any time during treatment, even up to a week after treatment has ceased. For some people who are allergic to amoxicillin the side effects can be deadly. Use of the amoxicillin/clavulanic acid combination for more than one week has caused mild hepatitis in some patients. Young children having ingested acute overdoses of amoxicillin manifested lethargy, vomiting and renal dysfunction.

Amoxicillin in trihydrate form is available as capsules, chewable and dispersible tablets plus syrup and pediatric suspension for oral use, and as the sodium salt for intravenous administration (although the IV formulation is not available in the United States). Amoxicillin is most commonly taken orally. The liquid forms are helpful where the patient might find it difficult to take tablets or capsules.

Erythromycin. Erythromycin is a macrolide antibiotic that has an antimicrobial spectrum similar to or slightly wider than that of penicillin, and is often used for people who have an allergy to penicillins. For respiratory tract infections, it has better coverage of atypical, organisms, including mycoplasma and Legionellosis. It was first marketed by Eli Lilly and Company, and it is today commonly known as EES (erythromycin ethylsuccinate, an ester prodrug that is commonly administered).

In structure, this macrocyclic compound contains a 14-membered lactone ring with ten asymmetric centers and two sugars (L-cladinose and D-desosamine), making it a compound very difficult to produce via synthetic methods. Erythromycin is produced from a strain of the actinomycete *Saccharopolyspora erythraea*.

U.S. Pat. No. 2,653,899, which covers the drug, was granted in 1953. The product was launched commercially in 1952 under the brand name Ilosone (after the Philippine region of Iloilo where it was originally collected from). Erythromycin was formerly also called Ilotycin.

Over the years since the discovery of erythromycin A and its activity as an antimicrobial, many attempts have been made to synthesize it in the laboratory. However, the presence of ten stereospecific carbons and several points of distinct substitution has made the total synthesis of erythromycin A a formidable task. Complete syntheses of erythromycins' related structures and precursors such as 6-deoxyerythronolide B have been accomplished, giving way to possible syntheses of different erythromycins and other macrolide antimicrobials. However, Woodward and colleagues did successfully complete the synthesis of erythromycin A in 1981.

Erythromycin is available in enteric-coated tablets, slow-release capsules, oral suspensions, ophthalmic solutions, ointments, gels, and injections. Brand names include Robimycin, E-Mycin, E.E.S. Granules, E.E.S.-200, E.E.S.-400, E.E.S.-400 Filmtab, Erymax, Pry-Tab, Eryc, Ranbaxy, Erypar, EryPed, Eryped 200, Eryped 400, Erythrocin Stearate Filmtab, Erythrocot, E-Base, Erythroped, Ilosone, MY-E, Pediamycin, Zineryt, Abboticin, Abboticin-ES, Erycin, PCE Dispertab, Stiemycine, Acnasol and Tiloryth.

Gastrointestinal disturbances, such as diarrhea, nausea, abdominal pain, and vomiting, are very common because erythromycin is a motilin agonist. Because of this, erythromycin tends not to be prescribed as a first-line drug. However, erythromycin may be useful in treating gastroparesis due to this pro-motility effect. Intravenous erythromycin may also be used in endoscopy as an adjunct to clear gastric contents. More serious side-effects include arrhythmia with prolonged QTc intervals including Torsades-de-Pointe and reversible deafness. Allergic reactions range from urticaria to anaphylaxis. Cholestasis, Stevens-Johnson syndrome, and toxic epidermal necrolysis are some other rare side-effects that may occur.

Exposure to erythromycin (especially long courses at antimicrobial doses, and also through breastfeeding) has been linked to an increased probability of pyloric stenosis in young infants. Erythromycin used for feeding intolerance in young infants has not been associated with hypertrophic pyloric stenosis.

Erythromycin estolate has been associated with reversible hepatotoxicity in pregnant women in the form of elevated serum glutamic-oxaloacetic transaminase and is not recommended during pregnancy. Some evidence suggests similar hepatotoxicity in other populations.

It can also affect the central nervous system, causing psychotic reactions, nightmares and night sweats. It may also alter the effectiveness of combined oral contraceptive pills because of its effect on the gut flora. Erythromycin is an inhibitor of the cytochrome P450 system, which means that it can have a rapid effect on levels of other drugs metabolised by this system, e.g., warfarin.

Erythromycin displays bacteriocidal activity, especially at higher concentrations, but the mechanism is not fully understood. By binding to the 50S subunit of the bacterial 70s rRNA complex, protein synthesis and subsequent structure and function processes critical for life or replication are inhibited. Erythromycin interferes with aminoacyl translocation, preventing the transfer of the tRNA bound at the A site of the rRNA complex to the P site of the rRNA complex. Without this translocation, the A site remains occupied and, thus, the addition of an incoming tRNA and its attached amino acid to the nascent polypeptide chain is inhibited. This interferes with the production of functionally useful proteins, which is the basis of this antimicrobial action.

2. Clarithromycin, Azithromycin, Fluoroquinolones and Cefuroxime

Clarithromycin. Clarithromycin is a macrolide antibiotic used to treat pharyngitis, tonsillitis, acute maxillary sinusitis, acute bacterial exacerbation of chronic bronchitis, pneumonia (especially atypical pneumonias associated with Chlamydia pneumoniae or TWAR), skin and skin structure infections. In addition, it is sometimes used to treat Legionellosis, *Helicobacter pylori*, and lyme disease. Clarithromycin is available under several brand names, for example Crixan, Clarac, Biaxin, Klaricid, Klacid, Klaram, Klabax, Klacid, Claripeit, Clarem, Claridar, Fromilid, Clacid, Clacee, Vikrol, Infex and Clariwin, Resclar.

Clarithromycin was invented by researchers at the Japanese drug company Taisho Pharmaceutical in the 1970s. The product emerged through efforts to develop a version of the antibiotic erythromycin that did not experience acid instability in the digestive tract, causing side effects, such as nausea and stomach ache. Taisho filed for patent protection for the drug around 1980 and subsequently introduced a branded version of its drug, called Clarith, to the Japanese market in 1991. In 1985 Taisho partnered with the American company Abbott Laboratories for the international rights, and Abbott also gained FDA approval for Biaxin in October 1991. The drug went generic in Europe in 2004 and in the US in mid-2005.

Antibacterial spectrum is the same as erythromycin but it is active against *Mycobacterium avium* complex (MAV), *M. leprae* and atypical mycobacteria.

Clarithromycin prevents bacteria from growing by interfering with their protein synthesis. Clarithromycin binds to the subunit 50S of the bacterial ribosome and thus inhibits the translation of peptides. Clarithromycin has similar antimicrobial spectrum as erythromycin but is more effective against certain gram-negative bacteria, particularly *Legionella pneumophila*. Besides this bacteriostatic effect, clarithromycin also has bactericidal effect on certain strains such as *Haemophilus influenzae, Streptococcus pneumoniae* and *Neisseria gonorrhoeae.*

Unlike erythromycin, clarithromycin is acid-stable and can therefore be taken orally without being protected from gastric acids. It is readily absorbed, and diffused into most tissues and phagocytes. Due to the high concentration in phagocytes, clarithromycin is actively transported to the site of infection. During active phagocytosis, large concentrations of clarithromycin are released. The concentration of clarithromycin in the tissues can be over 10 times higher than in plasma. Highest concentrations were found in liver and lung tissue.

Clarithromycin has a fairly rapid first-pass hepatic metabolism. However, 14-hydroxy clarithromycin, clarithromycin's metabolite, is almost twice as active and has a half life of 7 hours compared to clarithromycin's 5. Clarithromycin and its metabolites main routes of elimination are urinary and biliary excretion. Of all the drugs in its class, clarithromycin has the best bioavailability at 50%, which makes it amenable to oral administration.

Most common side-effects are gastrointestinal, including diarrhea, nausea, extreme irritability, abdominal pain and vomiting, facial swelling. Less common side-effects include headaches, hallucinations (auditory and visual), dizziness/motion sickness, rashes, alteration in senses of smell and taste, including a metallic taste that lasts the entire time one takes it. Dry mouth, panic and/or anxiety attacks and nightmares have also been reported albeit less frequently. In more serious cases it has been known to cause jaundice, cirrhosis, and kidney problems including renal failure. Uneven heartbeats, chest pain, and shortness of breath have also been reported while taking this drug.

Adverse effects of clarithromycin in the central nervous system include dizziness, ototoxicity and headaches, but delirium and mania are also uncommon side effects. When taken along with some statins, drugs used to reduce blood serum cholesterol levels, muscle pain may occur. There is also the risk of oral candidiasis, due to the increased yeast production in the body from the antibiotics.

Azithromycin. Azithromycin is an azalide, a subclass of macrolide antibiotics. Azithromycin is one of the world's best-selling antibiotics, marketed in the United States under the name Zithromax, and under a variety of brand names and generic labels worldwide. It is derived from erythromycin; however, it differs in chemical structure from erythromycin in that a methyl-substituted nitrogen atom is incorporated into the lactone ring, thus making the lactone ring 15-membered.

Azithromycin is used to treat or prevent certain bacterial infections, most often those causing middle ear infections, strep throat, pneumonia, typhoid, and sinusitis. In recent years, it has been used primarily to prevent bacterial infections in infants and those with weaker immune systems. It is also effective against certain sexually transmitted infections, such as non-gonococcal urethritis, chlamydia, and cervicitis. Recent studies have indicated it also to be effective against late-onset asthma, but these findings are controversial and not widely accepted.

Azithromycin is used to treat many different infections including acute otitis media, streptococcal pharyngitis, gastrointestinal infections such as traveler's diarrhea, respiratory tract infections such as pneumonia, cellulitis, babesiosis, bartonella, chancroid, chlamydia, cholera, donovanosis, leptospirosis, lyme disease, malaria, *Mycobacterium avium* complex, *Neisseria* meningitis, pelvic inflammatory disease, pertussis, scrub typhus, syphilis, toxoplasmosis, and salmonella. It is used to prevent bacterial endocarditis and some sexually transmitted illnesses post sexual assault.

It has a similar antimicrobial spectrum as erythromycin, but is more effective against certain Gram-negative bacteria, in particular, *Haemophilus influenzae*. Azithromycin resistance has been described and is endemic in many areas. It is notably ineffective against MRSA. Azithromycin has been shown to be effective against malaria when used in combination with artesunate or quinine; the optimal dose for this is not yet known.

Most common side-effects are gastrointestinal: diarrhea (5%), nausea (3%), abdominal pain (3%), and vomiting. Fewer than 1% of patients stop taking the drug due to side-effects.

Nervousness, dermatologic reactions, and anaphylaxis have been reported. As with all antimicrobial agents, pseudomembranous colitis can occur during and up to several weeks after azithromycin therapy. This drug may interfere with the effectiveness of birth control pills; other forms of contraception may be required during the treatment period. Azithromycin suspension has an objectionable taste, so can be difficult to administer to young children, i.e., 2-5 years, who may spit it out.

Occasional patients have developed cholestatic hepatitis or delirium. Accidental intravenous overdosage in an infant caused severe heart, block, resulting in residual encephalopathy.

Azithromycin prevents bacteria from growing by interfering with their protein synthesis. Azithromycin binds to the 50S subunit of the bacterial ribosome, and thus inhibits translation of mRNA. Nucleic acid synthesis is not affected.

Unlike erythromycin, azithromycin is acid-stable and can therefore be taken orally with no need of protection from gastric acids. It is readily absorbed, but its absorption is greater on an empty stomach. Time to peak concentration in adults is 2.1 to 3.2 hours for oral dosage forms and one to two hours after a dose. Due to the high concentration in phagocytes, azithromycin is actively transported to the site of infection. During active phagocytosis, large concentrations of azithromycin are released. The concentration of azithromycin in the tissues can be over 50 times higher than in plasma. This is due to ion trapping and the high lipid solubility (Volume of distribution is too low).

Azithromycin's half-life allows a large single dose to be administered and yet maintain bacteriostatic levels in the infected tissue for several days. The new extended-release formulation of azithromycin "Zmax," A-Max is a liquid oral suspension that releases the drug in a single 2-g dose. With the macrolide technology of Zmax, this allows the drug to bypass the stomach, reducing gastrointestinal side-effects of high-dose azithromycin.

Azithromycin is commonly administered in tablet or oral suspension (a one-dose version was made available in 2005). It is also available for intravenous injection and in a 1% ophthalmic solution. Tablets come in doses of 250 mg and 500 mg. Oral suspension comes in strengths of 100 mg/5 mL and 200 mg/5 mL. The 250 mg tablets are often dispensed in packages of six and commonly referred to as a "Z-Pak," whereas the 500 mg tablets are commonly available commercially in a pack of three tablets, or "Tri-Pak," intended as a three-day treatment. A common dose of oral azithromycin therapy consists of a "double dose" of medication on the first day of treatment and subsequent treatment for four or five additional days. With the "Z-Pak," this means two 250 mg tablets (a total of 500 mg) on the first day and one 250 mg tablet once daily for the next four days.

Pfizer brand-name, i.e., Zithromax, azithromycin tablets are mottled pink, unscored, film-coated, modified-oval-shaped tablets containing azithromycin monohydrate and the following inactive ingredients: butylated hydroxytoluene, calcium phosphate, carmine, colloidal silicon dioxide. FD&C red #40 lake, FD&C yellow #6 lake, hypromellose (2910, 15 cP), lactose monohydrate, magnesium stearate, pregelatinized starch, sodium lauryl sulfate, talc, titanium dioxide, and triacetin.

Fluoroquinolones. The quinolones are a family of synthetic broad-spectrum antibiotics. The term quinolone(s) refers to potent synthetic chemotherapeutic antibacterials. The first generation of the quinolones begins with the introduction of nalidixic acid in 1962 for treatment of urinary tract infections in humans. Nalidixic acid was discovered by George Lesher and coworkers in a distillate during an attempt at chloroquine synthesis. They prevent bacterial DNA from unwinding and duplicating.

Quinolones, in comparison to other antibiotic classes, have the highest risk of causing colonization with MRSA and *Clostridium difficile*. For this reason, a general avoidance of fluoroquinolones is recommended based on the available evidence and clinical guidelines. The majority of quinolones in clinical use belong to the subset fluoroquinolones, which have a fluorine atom attached to the central ring system, typically at the 6-position or C-7 position. Debates are still taking place as to whether or not the effectiveness of fluoroquinolones for the treatment of respiratory disorders is similar to that of other antibiotic classes.

Fluoroquinolone use for pneumonia is increasing, and with it so is bacterial resistance to fluoroquinolones. The majority of the prescribing of fluoroquinolones is inappropriate, with less than four percent of people prescribed quinolones being appropriate according to clinical guidelines. Clinical guidelines in Canada recommend fluoroquinolones only for outpatient treatment of pneumonia in a small number of patients, such as those with certain comorbid conditions, e.g., patients with a history of COPD, or those with recent use of antibiotics. For severe forms of community-acquired pneumonia, the fluoroquinolones are associated with improved treatment rates, but with no differences found in mortality between other antibiotic classes.

Fluoroquinolones are not recommended as first-line antibiotics for acute sinusitis, as this condition is usually self-limiting, and the risks outweigh the benefits in comparison to other antibiotic classes.

Antibiotics including fluoroquinolones can be effective in some cases of bronchitis. However, only about 5-10% of bronchitis cases are caused by a bacterial infection; most cases of bronchitis are caused by a viral infection and are self-limiting and resolve themselves in a few weeks. It has been recommended that antibiotics are limited in most cases to those whose symptoms fail to resolve on their own.

Fluoroquinolones are often used for genitourinary infections; in general they are recommended only after other antibiotic regimens have failed. However, for serious acute cases of pyelonephritis or bacterial prostatitis where the patient may need to be hospitalised, fluoroquinolones are recommended as first-line therapy. Prostatitis has been termed "the waste basket of clinical ignorance" by prominent Stanford University urologist Dr. Thomas Stamey, Campbell's Urology, the urologist's most authoritative reference text, identifies only about 5% of all patients with prostatitis as having bacterial prostatitis, which can be "cured" at least in the short term by antibiotics. In other words, 95% of men with prostatitis have little hope for a cure with antibiotics alone, since they do not actually have any identifiable bacterial infection.

In general, fluoroquinolones are well tolerated, with most side effects being mild to moderate. On occasion, serious adverse effects occur. Some of the serious adverse effects that occur more commonly with fluoroquinolones than with other antibiotic drug classes include CNS and tendon toxicity. The currently marketed quinolones have safety profiles similar to those of other antimicrobial classes. Fluoroquinolones are sometimes associated with an QTc interval prolongation and cardiac arrhythmias, convulsions, tendon rupture, torsade de pointes and hypoglycemia.

These adverse reactions are a class effect of all quinolones; however, certain quinolones are more strongly associated with increased toxicity to certain organs. For example, moxifloxacin carries a higher risk of QTc prolongation, and gatifloxacin has been most frequently linked to disturbed blood sugar levels, although all quinolones carry these risks. Some quinolones were withdrawn from the market because of these adverse events (for example, sparfloxacin was associated with phototoxicity and QTc prolongation, thrombocytopenia and nephritis were seen with tosufloxacin, and hepatotoxicity with trovafloxacin). Simultaneous use of corticosteroids is present in almost one-third of quinolone-associated tendon rupture. The risk of adverse events is further increased if the dosage is not properly adjusted, for example if there is renal insufficiency.

The serious events may occur during therapeutic use at therapeutic dose levels or with acute overdose. At therapeutic doses, they include: CNS toxicity, cardiovascular toxicity, tendon/articular toxicity, and, rarely, hepatic toxicity. Caution is required in patients with liver disease. Events that may occur in acute overdose are rare, and include renal failure and seizure. Susceptible groups of patients, such as children and the elderly, are at greater risk of adverse reactions during therapeutic use. Adverse reactions may manifest during, as well as after fluoroquinolone therapy has been completed.

The CNS is an important target for fluoroquinolone-mediated neurotoxicity. Adverse event reporting in Italy by doctors showed fluoroquinolones among the top three prescribed drugs for causing adverse neurological and psychiatric effects. These neuropsychiatric effects included tremor, confusion, anxiety, insomnia, agitation, and, in severe cases, psychosis. Moxifloxacin came out worst among the quinolones for causing CNS toxicity.

The basic pharmacophore, or active structure, of the fluoroquinolone class is based upon the quinoline ring system. The addition of the fluorine atom at C6 is what distinguishes the successive-generation fluoroquinolones from the first-generation quinolones. The addition of the C6 fluorine atom has since been demonstrated to not be required for the antibacterial activity of this class (circa 1997).

Various substitutions made to the quinoline ring resulted in the development of numerous fluoroquinolone drugs available, today. Each substitution is associated with a number of specific adverse reactions, as well as increased activity against bacterial infections, whereas the quinoline ring, in and of itself, has been associated with severe and even fatal adverse reactions.

Cefuroxime. Cefuroxime is a second-generation cephalosporin antibiotic that has been widely available in the USA as Ceftin since 1977. GlaxoSmithKline sells the antibiotic in the United Kingdom (and other countries, such as Australia, Turkey, Israel Bangladesh, Thailand, Hungary and Poland) under the name Zinnat.

As for the other cephalosporins, although as a second-generation it is less susceptible to beta-lactamase and so may have greater activity against *Haemophilus influenzae, Neisseria gonorrhoeae* and Lyme disease. Unlike other second generation cephalosporins, cefuroxime can cross the blood-brain-barrier.

Cefuroxime is generally well tolerated and side effects are usually transient. Cefuroxime, if ingested with food, is both better absorbed and less likely to cause its most common side effects of diarrhea, nausea, vomiting, headaches/migraines, dizziness and abdominal pain.

Although there is a widely quoted cross-allergy risk of 10% between cephalosporins and penicillin, recent assessments have shown no increased risk for cross-allergy for cefuroxime and several other $2^{nd}$ generation or later cephalosporins.

3. Vancomycin and Levoflaxin

Vancomycin. Vancomycin (INN) is a glycopeptide antibiotic used in the prophylaxis and treatment of infections caused by Gram-positive bacteria. It has traditionally been reserved as a drug of "last resort," used only after treatment with other antibiotics had failed, although the emergence of vancomycin-resistant organisms means that it is increasingly being displaced from this role by linezolid (Zyvox) available PO and IV and daptomycin (Cubicin) IV and quinupristin/dalfopristin (Synercid) IV.

Vancomycin was first isolated in 1953 by Edmund Kornfeld (working at Eli Lilly) from a soil sample collected from the interior jungles of Borneo by a missionary. The organism that produced it was eventually named *Amycolatopsis orientalis*. The original indication for vancomycin was for the treatment of penicillin-resistant *Staphylococcus aureus*. One advantage that was quickly apparent is that staphylococci did not develop significant resistance despite serial passage in culture media containing vancomycin. The rapid development of penicillin resistance by staphylococci led to the compound's being fast-tracked for approval by the FDA in 1958. Eli Lilly first marketed vancomycin hydrochloride under the trade name Vancocin and as COVANC from Nucleus, India.

Vancomycin never became the first-line treatment for *Staphylococcus aureus* for several reasons. First, it possesses poor oral bioavailability. Also, it must be given intravenously for most infections. In addition, β-Lactamase-resistant semi-synthetic penicillins such as methicillin (and its successors, nafcillin and cloxacillin) were subsequently developed, which have better activity against non-MRSA staphylococci.

An Oral form of vancomycin was originally approved by the FDA in 1986 tar the treatment of *Clostridium difficile*-induced pseudomembranous colitis. It is not orally absorbed into the blood and remains in the gastrointestinal tract to eradicate *C. difficle*. This product is currently marketed by ViroPharma in the USA.

Vancomycin biosynthesis occurs via different nonribosomal protein synthases (NRPSs). The enzymes determine the amino acid sequence during its assembly through its 7 modules. Before Vancomycin is assembled through NRPS, the amino acids are first modified. L-tyrosine is modified to become the β-hydroxychlorotyrosine (β-hTyr) and 4-hydroxyphenylglycine (HPG) residues. On the other hand, acetate is used to derive the 3,5 dihydroxyphenylglycine ring (3,5-DPG).

Nonribosomal peptide synthesis occurs through distinct modules that can load and extend the protein by one amino acid through the amide bond formation at the contact sites of the activating domains. Each module typically consists of an adenylation (A) domain, a peptidyl carrier protein (PCP) domain, and a condensation (C) or elongation domain. In the A domain, the specific amino acid is activated by converting into an aminoacyl adenylate enzyme complex attached to a 4'phosphopantetheine cofactor by thioesterification. The complex is then transferred to the PCP domain with the expulsion of AMP. The PCP domain uses the attached 4'-phosphopantethein prosthetic group to load the growing peptide chain and their precursors. In the biosynthesis of Vancomycin, additional modification domains are present, such as the epimerization (E) domain, which is used isomerizes the amino acid from one stereochemistry to another, and a thioesterase domain (TE) is used as a catalyst for cyclization and releases of the molecule via a thioesterase scission.

After the linear heptapeptide molecule is synthesized, Vancomycin has to undergo further modifications, such as oxidative cross-linking and glycosylation, in trans, by distinct enzymes, referred to as tailoring enzymes, in order to become biologically active. To convert the linear heptapeptide, eight enzymes are used. With the help of these enzymes. β-hydroxyl groups are introduced onto tyrosine residues 2 and 6, and coupling occurs for rings 5 and 7, rings 4 and 6, and rings 4 and 2. In addition, a haloperoxidase is used to attach the chlorine atoms onto rings 2 and 6 via an oxidative process.

Vancomycin acts by inhibiting proper cell wall synthesis in Gram-positive bacteria. Due to the different mechanism by which Gram-negative bacteria produce their cell walls and the various factors related to entering the outer membrane of Gram-negative organisms, vancomycin is not active against Gram-negative bacteria (except some non-gonococcal species of *Neisseria*).

The large hydrophilic molecule is able to form hydrogen bond interactions with the terminal D-alanyl-D-alanine moieties of the NAM/NAG-peptides. Under normal circumstances, this is a five-point interaction. This binding of vancomycin to the D-Ala-D-Ala prevents cell wall synthesis in two ways. It prevents the synthesis of the log polymers of N-acetylmuramic acid (NAM) and N-acetylglucosamine (NAG) that form the backbone strands of the bacterial cell wall, and it prevents the backbone polymers that do manage to form from cross-linking with each other.

Although vancomycin levels are usually monitored, in an effort to reduce adverse events, the value of this is not beyond debate. Peak and trough levels are usually monitored, and, for research purposes, the area under the curve is also sometimes used. Toxicity is best monitored by looking at trough values. Common adverse drug reactions (≥1% of patients) associated with IV vancomycin include: local pain, which may be severe and/or thrombophlebitis.

Damage to the kidneys and to the hearing were a side-effect of the early impure versions of vancomycin, and these were prominent in the clinical trials conducted in the mid-1950s. Later trials using purer forms of vancomycin found that nephrotoxicity is an infrequent adverse effect (0.1-1% of patients), but that this is accentuated in the presence of aminoglycosides.

Rare adverse effects (<0.1% of patients) include: anaphylaxis, toxic epidermal necrolysis, erythema multiforme, red man syndrome (see below), superinfection, thrombocytopenia, neutropenia, leucopenia, tinnitus, dizziness and/or ototoxicity (see below).

It has recently been emphasized that vancomycin can induce platelet-reactive antibodies in the patient, leading to severe thrombocytopenia and bleeding with florid petechial hemorrhages, ecchymoses, and wet purpura.

Vancomycin must be given intravenously (IV) for systemic therapy, since it does not cross through the intestinal lining. It is a large hydrophilic molecule that partitions poorly across the gastrointestinal mucosa. The only indication for oral vancomycin therapy is in the treatment of pseudomembranous colitis, where it must be given orally to reach the site of infection in the colon. Following oral administration, the fecal concentration of vancomycin is around 500 μg/mL (sensitive strains of *C. difficile* have a mean inhibitory concentration of ≤2 μg/mL)

Inhaled vancomycin has also been used (off-label), via nebulizer, for treatment of various infections of the upper and lower respiratory tract.

The caustic nature of vancomycin makes IV therapy using peripheral lines a risk for thrombophlebitis. Ideally, central lines, PICCs, or infusion ports should be used.

Vancomycin has traditionally been considered a nephrotoxic and ototoxic drug, based on observations by early investigators of elevated serum levels in renally impaired patients that had experienced ototoxicity, and subsequently through case reports in the medical literature. However, as the use of vancomycin increased with the spread of MRSA beginning in the 1970s, it was recognised that the previously reported rates of toxicity were not being observed. This was attributed to the removal of the impurities present in the earlier formulation of the drug, although those impurities were not specifically tested for toxicity.

Subsequent reviews of accumulated case reports of vancomycin-related nephrotoxicity found that many of the patients had also received other known nephrotoxins, in particular, aminoglycosides. Most of the rest had other confounding factors, or insufficient data regarding the possibility of such, that prohibited the clear association of vancomycin with the observed renal dysfunction. The most methodologically-sound investigations indicate that the actual incidence of vancomycin-induced nephrotoxicity is around 5-7%. To put this into context, similar rates of renal dysfunction have been reported for cefamandole and benzylpenicillin, two reputedly non-nephrotoxic antibiotics.

In addition, evidence to relate nephrotoxicity to vancomycin serum levels is inconsistent. Some studies have indicated an increased rate of nephrotoxicity when trough levels exceed 10 μg/mL, but others have not reproduced these results. Nephrotoxicity has also been observed with concentrations within the "therapeutic" range as well. In essence, the reputation of vancomycin as a nephrotoxin is over-stated, and it has not been demonstrated that maintaining vancomycin serum levels within certain ranges will prevent its nephrotoxic effects, when they do occur.

Attempts to establish rates of vancomycin-induced ototoxicity are even more difficult due to the scarcity of quality evidence. The current consensus is that clearly related cases of vancomycin ototoxicity are rare. The association between vancomycin serum levels and ototoxicity is also uncertain. While cases of ototoxicity have been reported in patients whose vancomycin serum level exceeded 80 μg/mL, cases have been reported in patients with therapeutic levels as well. Thus, it also remains unproven that therapeutic drug monitoring of vancomycin for the purpose of maintaining "therapeutic" levels will prevent ototoxicity.

Another area of controversy and uncertainty concerns the question of whether, and, if so, to what extent, vancomycin increases the toxicity of other nephrotoxins. Clinical studies have yielded variable results, but animal models indicate that there probably is some increased nephrotoxic effect when vancomycin is added to nephrotoxins such as aminoglycosides. However, a dose- or serum level-effect relationship has not been established.

Levofloxacin. Levofloxacin is a synthetic chemotherapeutic antibiotic of the fluoroquinolone drug class and is used to treat severe or life-threatening bacterial infections or bacterial infections that have failed to respond to other antibiotic classes. It is sold under various brand names, such as Levaquin and Tavanic, the most common. In form of ophthalmic solutions it is known as Oftaquix, Quixin and Iquix.

Levofloxacin is a chiral fluorinated carboxyquinolone. Investigation of ofloxacin, an older drug that is the racemic mixture, found that the l form [the (−)-(S) enantiomer] is more active. This specific component is levofloxacin. Levofloxacin is available in tablet form, injection, oral solution, as well as used in prescription eye and ear drops.

Levofloxacin interacts with a number of other drugs, as well as a number of herbal and natural supplements. Such interactions increase the risk of cardiotoxicity and arrhythmias, anticoagulation, the formation of non-absorbable complexes, as well as increasing the risk of toxicity.

Levofloxacin is associated with a number of serious and life-threatening adverse reactions as well as spontaneous tendon ruptures and irreversible peripheral neuropathy. Such reactions may manifest long after therapy had been completed and in severe cases may result in life-long disabilities. Hepatoxicity has also been reported with the use of levofloxacin.

As of 2011 the FDA has added two Black box warnings for this drug in reference to spontaneous tendon ruptures and the fact that levofloxacin may cause worsening of myasthenia gravis symptoms, including muscle weakness and breathing problems. Such an adverse reaction is a potentially life-threatening event and may require ventilatory support.

Levofloxacin is used to treat a number of infections including: respiratory tract infections, cellulitis, urinary tract infections, prostatitis, anthrax, endocarditis, meningitis, pelvic inflammatory disease, and traveler's diarrhea.

In the adult population Oral and I.V. levofloxacin is limited to the treatment of proven serious and life-threatening bacterial infections such as Urinary Tract Infections, Community-acquired pneumonia, Skin and Skin Structure Infections, Nosocomial Pneumonia, Chronic bacterial prostatitis, Inhalational Anthrax, Acute Bacterial Sinusitis, Acute Bacterial Exacerbation of Chronic Bronchitis, and Acute Pyelonephritis.

Oral and I.V. Levaquin are not licensed by the FDA for use in children other than the exception (inhalational anthrax), due to the risk of reversible or irreversible injury to the musculoskeletal system. Although claimed to be effective, levofloxacin is not to be considered a first line agent for inhalational anthrax in the pediatric population due to severe adverse reactions involving the musculoskeletal system and other serious adverse reactions, including fatalities.

The CDC revoked its recommendation regarding the use of fluoroquinolones (ciprofloxacin) as a first-line agent in treating anthrax (in part) due to the risk of adverse reactions documented within the Antimicrobial Postexposure Prophylaxis for Anthrax study (aka Cipro 60-day study). However, the fluoroquinolones are licensed to treat lower respiratory infections in children with cystic fibrosis in the UK.

Serious adverse events occur more commonly with fluoroquinolones than with any other antibiotic drug classes. In most adverse reactions are mild to moderate; however, on occasion, serious adverse effects occur. There have been a number of regulatory actions taken as a result of such adverse reactions, which included published warnings, additional warnings and safety information added to the package inserts, which includes Black Box Warnings together with the issuance of "Dear Doctor Letters" concerning the recent addition of the Black Box Warnings.

In 2004, the FDA requested new warning labels to be added to all of the Fluoroquinolones, including levofloxacin, regarding peripheral neuropathy (irreversible nerve damage), tendon damage, heart problems (prolonged QT Interval/torsades de pointes), pseudomembranous colitis, rhabdomyolysis (muscle wasting), Stevens-Johnson Syndrome, as well as concurrent usage of NSAIDs contributing to the severity of these reactions. Subsequent to this, on Jun. 25, 2007, the FDA required the manufacturer to add an additional warning to the package inserts that stated that "Other serious and sometimes fatal events, some due to hypersensitivity, and some due to uncertain etiology, have been reported in patients receiving therapy with quinolones, including levofloxacin."

Serious visual complications have also been reported to occur with ophthalmic fluoroquinolone therapy, which may also occur with levofloxacin eye drops, especially corneal perforation, but also evisceration and enucleation. This increased incidents of corneal perforation may be due to fluoroquinolones causing alterations in stromal collagen, leading to a reduction in tectonic strength. As noted previously permanent double vision (diplopia) has also been reported.

Levofloxacin is the L-isomer of the racemate ofloxacin, a quinolone antimicrobial agent. In chemical terms, levofloxacin, a chiral fluorinated carboxyquinolone, is the pure (−)-(S)-enantiomer of the racemic drug substance ofloxacin. The chemical name is (−)-(S)-9fluoro-2,3-dihydro-3-methyl-10-(4-methyl-1-piperazinyl)-7-oxo-7H-pyrido[1,2,3-de]-1,4benzoxazine-6-carboxylic acid hemihydrate. The empirical formula is C18H20FN3O4.½H2O, and the molecular weight is 370.38. Levofloxacin is a light-yellowish-white to yellow-white crystal or crystal line powder.

Levofloxacin pharmacokinetics are linear and predictable after single and multiple oral or IV dosing regimens. Levofloxacin is rapidly and, in essence, completely absorbed after oral administration. Peak plasma concentrations are usually attained one to two hours after oral dosing. The plasma concentration profile of levofloxacin after IV administration is similar and comparable in extent of exposure (AUC) to that observed for LEVAQUIN Tablets when equal doses (mg/mg) are administered. Levofloxacin is excreted largely as unchanged drug in the urine. The mean terminal plasma elimination half-life of levofloxacin ranges from approximately 6 to 8 hours following single or multiple doses of levofloxacin given orally or intravenously. Glucuronidation and hydroxylation have been cited as one of the major metabolic pathways for levotioxacin hydrochloride. However the drug card for levofloxacin (DB01137) states that the biotransformation information is not available. Specific information regarding biotransformation does not appear to be readily available within the package inserts.

Levofloxacin is a broad-spectrum antibiotic that is active against both Gram-positive and Gram-negative bacteria. It functions by inhibiting DNA gyrase, a type II topoisomerase, and topoisomerase iv, which is an enzyme necessary to separate replicated DNA, thereby inhibiting cell division.

The fluoroquinolones interfere with DNA replication by inhibiting an enzyme complex called DNA gyrase. This can also affect mammalian cell replication. In particular, some congeners of this drug family display high activity not only against bacterial topoisomerases but also against eukaryotic topoisomerases, and are toxic to cultured mammalian cells and in vivo tumor models. Although the quinolone is highly toxic to mammalian cells in culture, its mechanism of cytotoxic action is not known. Quinolone-induced DNA damage was first reported in 1986.

V. Antibody Conjugates

Antibodies of the present invention may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, antibiotics, therapeutic enzymes, radionuclides, anti-cancer agents, anti-viral agents, chelating agents, cytokines, growth factors, and oligo- or polynucleotides.

By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$, and/or yttrium$^{90}$, $^{125}$I is often being preferred for use in certain embodiments, and technicium$^{99m}$ and/or indium are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renograph in, ROX, TAM RA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include unease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850, 752, 3,939,350, 3,996,345, 4,277,437, 4,275,149 and 4,366, 241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fe region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

VI. Immunodetection Methods

In still further embodiments, the present invention concerns immunodetection methods for binding, purifying, removing, quantifying and otherwise generally detecting *S. pneumonia*. While such methods can be applied in a traditional detection sense, a more specific use will involve the generation of a antibody panel that is capable of distinguishing a single *S. pneumoniae* serotype from most of the serotypes listed above. By identifying the specific serotype responsible for an infection, one can better assess the need and type of therapy. Also, protective immunity is primarily attributed to serotype-specific IgG. Measurement of specific pneumococcal antibodies are clinically useful in two settings: (1) to determine protective status of a patient, and (2) to assess B-cell functionality in a patient with recurrent infection. Use of antibodies in accordance with the present invention in a competitive format will facilitate this type of assay as well.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of antibodies in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing *S. pneumoniae*, and contacting the sample with a first antibody in accordance with the present invention, as the case may be, under conditions effective to allow the formation of immunocomplexes.

These methods include methods for purifying *S. pneumoniae* or related antigens from a sample. The antibody will preferably be linked to a solid support, such as in the form of a column matrix, and the sample suspected of containing the *S. pneumoniae* or antigenic component will be applied to the immobilized antibody. The unwanted components will be washed from the column, leaving the *S. pneumoniae* antigen immunocomplexed to the immobilized antibody, which is then collected by removing the organism or antigen from the column.

The immunobinding methods also include methods for detecting and quantifying the amount of *S. pneumoniae* or related components in a sample and the detection and quantification of any immune complexes formed during the binding process. Here, one would obtain a sample suspected of containing *S. pneumoniae* or its antigens, and contact the sample with an antibody that binds *S. pneumoniae* or components thereof, followed by detecting and quantifying the amount of immune complexes formed under the specific conditions. In terms of antigen detection, the biological sample analyzed may be any sample that is suspected of containing *S. pneumoniae* or *S. pneumoniae* antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to *S. pneumoniae* or antigens present. After this time, the sample-antibody composition, such as a tissue section, MASA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically hound labeled secondary antibodies or ligands, and the remaining label in the secondary immune complexes is then detected.

Further methods include the detection of primary immune complexes by a two step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the *S. pneumoniae* or *S. pneumoniae* antigen is added to the wells. After binding and washing to remove non-specifically bound immune complexes, the bound antigen may be detected. Detection may be achieved by the addition of another anti-*S. pneumoniae* antibody that is linked to a detectable label. This type of ELISA is a simple "sandwich ELISA." Detection may also be achieved by the addition of a second anti-*S. pneumoniae* antibody, followed by the addition of a third antibody that has binding affinity for the second antibody, with the third antibody being linked to a detectable label.

In another exemplary ELISA, the samples suspected of containing the *S. pneumoniae* or *S. pneumoniae* antigen are immobilized onto the well surface and then contacted with the anti-*S. pneumoniae* antibodies of the invention. After binding and washing to remove non-specifically bound immune complexes, the bound anti-*S. pneumoniae* antibodies are detected. Where the initial anti-*S. pneumoniae* antibodies are linked to a detectable label, the immune complexes may be detected directly. Again, the immune complexes may be detected using a second antibody that has binding affinity for the first anti-*S. pneumoniae* antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours, at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the ease of peroxidase as the enzyme label. Quantification is then achieved by measuring the degree of color generated, e.g., using a visible spectra spectrophotometer.

In another embodiment, the present invention contemplates the use of competitive formats. This is particularly useful in the detection of *S. pneumoniae* antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled *S. pneumoniae* monoclonal antibodies to determine the amount of *S. pneumoniae* antibodies in a sample. The basic format would include contacting a known amount of *S. pneumoniae* monoclonal antibody (linked to a detectable label) with *S. pneumoniae* antigen or particle. The *S. pneumoniae* antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria or environmental samples can be the source of protein and thus Western blotting is not restricted to cellular studies only. Assorted detergents, salts, and butters may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a Very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunodetection Kits

In still further embodiments, the present invention concerns immunodetection kits for use with the immunodetection methods described above. As the *S. pneumoniae* antibodies are generally used to detect *S. pneumoniae* or *S. pneumoniae* antigens, the antibodies will be included in the kit. The immunodetection kits will thus comprise, in suitable container means, a first antibody that binds to *S. pneumoniae* or *S. pneumoniae* antigen, and optionally an immunodetection reagent.

In certain embodiments, the antibody may be pre-bound to a solid support, such as a column matrix, dipstick, membrane, particle (e.g., bead or nanoparticle) or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present invention.

The kits may further comprise a suitably aliquoted composition of the *S. pneumoniae* or *S. pneumoniae* antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present invention will also typically include a means for containing the antibody, antigen, and any other reagent containers in close confinement for commercial sale. Such containers may include injection or blow-molded plastic containers into which the desired vials are retained.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Immunization and donors. Donors received Pneumovax®23 (Merck, Whitehouse Station, N.J.) as standard of care vaccination based upon their age or SLE status. Healthy donors Con1 and Con2 were both Caucasian, age 62 and 61 respectively. Lupus donor SLE1 was an African American, age 47, SLE2 was a Caucasian, age 45. All protocols were approved by the IRB and patients consented to participate in this study. Blood was drawn (~40-60 ml) into ACD tubes (BD, Franklin Lakes, N.J.) by venipuncture seven days post vaccination and were stored no longer than 18 hours before processing.

Cell isolation and flow cytometry. Peripheral blood mononuclear cells (PBMC) were isolated from fresh blood using lymphocyte separation medium (Cellgro, Manassas, Va.) and suspended in 2% inactivated fetal calf serum in PBS. Cells were then counted and stained within two hours of the isolation. Antibodies used for the staining were anti-CD3 and anti-CD20 conjugated to FITC, anti-CD38 conjugated to APC-Cy5.5, anti-CD27 conjugated to PE, anti-CD19 conjugated to PE-Alexa610 (all from Invitrogen/Caltag, Carlsbad, Calif.), anti-IgG conjugated to APC (BD Biosciences, San Jose Calif.), and anti-IgM conjugated to biotin (Southern Biotech, Birmingham, Ala.) followed by streptavidin-PE-Cy7 (Invitrogen/Caltag). The B cells were bulk sorted (CD3/CD20$^{neg}$, CD19$^{low}$, CD38$^{high}$, CD27$^{very\ high}$, IgG$^{positive}$) using a Becton-Dickinson FACS Aria cytometer (BD Biosciences, San Jose, Calif.) and then single cell sorted into 96-well PCR plates with a Cytomation MoFlo cytometer (Dako, Carpinteria, Calif.).

Single cell RT-PCR and PCR of antibody variable region genes. As detailed in prior studies (Smith et al, 2009; Wrammert et al., 2008), the plates receiving the single cells sorted above contain 10 microliters of a hypotonic buffer consisting of 10 mM Tris-HCl with 40 U/μl of RNase inhibitor (Promega, Madison, Wis.) in each well. After the sort, plates were immediately frozen on dry ice and stored at −80° C. A One-Step RT-PCR kit (Qiagen, Valencia, Calif.) was used to amplify $V_H$ and $V_K$ message using a cocktail of sense primers to the leader regions of each of the gene families and antisense primers to the constant regions of the heavy and kappa chains. One microliter of the RT-PCR mixture was then amplified in separate heavy and kappa chain PCR reactions to first obtain sequences, and another microliter was used for the final PCR reactions to incorporate restriction sites for further cloning. The variable regions were then cloned into expression vectors (containing full length $IgG_1$ heavy or kappa constant regions), maxi-prepped (Roche, Indianapolis Ind.), and co-transfected into the HEK293A cell line using polyethyleneimine (PEI) (Polysciences, Warrington, Pa.). The transfected cells were allowed to secrete antibodies into serum-free DMEM supplemented with 1% Nutridoma (Roche, Indianapolis, Ind.) for five days. The antibodies were then purified using protein A-agarose beads (Pierce, Rockford, Ill.). Antibody purity and integrity were verified by SDS-PAGE and concentrations were obtained with a Nanodrop spectrophotometer (Fisher, Pittsburg, Pa.).

Polysaccharide affinity and avidity ELISAs. To screen for binding, ELISAs were first performed by coating plates with cocktails of five or six *S. pneumoniae* polysaccharides, screening all 23 (ATCC, Manassas, Va.) in this manner. Positive binders in this cocktail assay were then re-screened against each of the individual polysaccharides. As cell wall polysaccharide (CWPS) is an impurity in nearly all of the coat polysaccharides (Xu et al., 2005), antibodies that bound to all four groups were further tested on purified cell wall polysaccharide (CWPS) (Miravista Labs, Indianapolis, Ind.) to confirm CWPS binding. Wells were coated with 10 μg of each polysaccharide (or total mixed polysaccharide), blocked with 20% FCS and developed with anti-human IgG-HRP (Jackson ImmunoResearch, West Grove, Pa.) and Super Aqua Blue substrate (EBiosciences, San Diego Calif.). The absorbance was measured at 405 nm on a microplate reader (Molecular Devices, Sunnyvale, Calif.). Antibody affinities (Kd) were calculated by curve fitting analysis of individual ELISA curves plotted from a dilution series of 16 two-fold dilutions of antibody beginning at 10 μg/ml. For avidity ELISAs, one concentration of antibody was used (1 μg/ml) and an elution step was added before the addition of the conjugate. This elution step used varying concentrations of ammonium thiocyanate (3M to 0.046M, 8 total dilutions) in PBS, as well as PBS alone. The percent of binding retained was calculated for each dilution of ammonium thiocyanate. These values were graphed versus thiocyanate concentration and the concentration of thiocyanate which caused 50% retention (or loss) of binding was calculated by fitting the data with a dose-response/sigmoidal curve with hillslope correction.

Autoantigen ELISAs. All antibodies were also tested for binding to five autoantigens, Ro, La, Sm, nRNP, and cardiolipin. For each, except cardiolipin, 1 unit of antigen (ImmunoVision, Springdale, Ark.) was coated per well on high bind plates. Plates were blocked with 0.1% BSA in PBS, antibodies were added at 1 μg/ml and developed as per polysaccharide ELISAs above. For anti-cardiolipin ELISAs, cardiolipin solution at ~5 mg/ml (Sigma, St. Louis, Mo.) was diluted 1 to 1000 in ethanol and 50 was allowed to evaporate in medium bind plates. Plates were blocked with 0.5% adult bovine serum in PBS and antibodies were screened at 10 μg/ml and developed as above.

Analysis of sequences and curve fitting. All curve fitting was performed using the GraphPad Prism software, with background subtraction or percent retention values calculated and averaged using Excel. Variable region sequences were analyzed using the International Immunogenetics Information System (IMGT, Montpellier, France), as well as with in-house software and/or Vector NTT (Invitrogen, Carlsbad, Calif.). Clonally related antibodies were defined as those having the same VDJ/VJ usage in the heavy and light chains respectively, as well as highly related $V_H D_H$, $D_H J_H$, and $V_K J_K$ junctions. Average nucleotide somatic hypermutation values were obtain by analyzing sequences (using IMGT) for the number of nucleotide changes from germline in each antibody sequence. Resulting per-antibody values were then averaged to obtain average mutation rates per donor. The n value for these analyses included: naïve cells from six donors (n=18, 42, 21, 34, 15, 36); IgM germinal center/memory cells from 17 donors (n=56, 158, 18, 91, 17, 10, 16, 30, 19, 28, 11, 36, 29, 13, 22, 20, 64); IgG germinal center/memory cells from 13 donors (n=110, 37, 19, 28, 174, 40, 25, 15, 21, 18, 22, 24, 19, 71); anti-influenza ASCs from 11 donors (n=63, 18, 33, 46, 49, 11, 36, 11, 30, 35, 25). These donors were previously described in (Wrammert et al., 2008). The anti-polysaccharide ASC sequences are from the four donors in this study (Con1, 39; Con2, 49; SLE1, 24; SLE2, 25).

Example 2—Results

Pneumovax®23 induces a strong ASC response which is more robust in healthy controls as compared to SLE patients. Four individuals were immunized with Pneumovax®23. Blood was drawn seven days post vaccination and PBMCs were isolated by Ficoll gradient. The cells were then stained and $CD38^{high}/CD27^{very\ high}$ cells were enumerated. The inventor's previous results using these techniques after influenza vaccination (Wrammert et al., 2008) showed an ASC burst ranging from 1% to 16% of total peripheral blood B cells at day seven (average 6.4%). Pneumovax®23 induces an even more robust ASC response (FIG. 1A), with the two healthy donors having ASCs representing 22.8% to 24.7% of their total peripheral blood B cells, especially as this is a primary vaccination for each donor. Although both SLE donors had half as many ASCs as the healthy donors, the overall percentages (10.6% and 7.1%) are still quite high. This strong anamnestic response is likely due to the fact that *S. pneumoniae* is a ubiquitous organism that causes both clinical and subclinical disease among the general population. FIG. 1B shows a schematic representation of the process for making human monoclonal antibodies from antibody secreting cells. This technique has been previously described in detail (Smith et al., 2009; Wrammert at al., 2008). In total, including non-binding antibodies, 137 antibodies were produced and characterized (Con1, n=39; Con2, n=49; SLE1, n=24; SLE2, n=25).

A large majority of polysaccharide antibodies produced from the ASCs bind to a single serotype. Polysaccharide ELISA curves are shown in FIG. 2A, where each curve represents one antibody. A cutoff of an $OD_{405}$ of 1.5 was used as an arbitrary separation between high to moderate affinity antibodies and low to non-binding antibodies. Percentages were calculated using this cutoff as a means to determine which antibodies had significant binding. Averaged across the four donors. 76% of the antibodies (Cool, 62%; Con2, 90%; SLE1 75%; SLE2, 75%) bound to *S. pneumoniae* serotype polysaccharide or cell wall polysaccharide from the vaccine. Of the hmAbs generated, SLE donors showed no significant difference in the number of high-affinity antibodies isolated. A list of all antibodies with positive binding is shown in Table 1, which details serotype bound, number of total clonal siblings characterized, as well as $V_H$ and $V_K$ usage. Of the antibodies which bound to polysaccharide (76% of the total), an average of 88% of the antibodies characterized from the four donors are serotype specific (FIG. 2B) (Con1, 88%; Con2, 90%; SLE1 94%; SLE2, 80%). The observation that 88% of the antibodies currently in the serum bind to carbohydrate epitopes in a manner specific even among very closely related structures reinforces the well known specificity of the antibody repertoire.

TABLE 1

Summary of anti-*S. pneumoniae* antibodies (SEQ ID NOS: 1 through 126)

| Ab | # of Clones | Sero-type(s) | Kd (M)* | OPA** | VH gene | JH gene | Heavy CDR3 | VK gene | JK gene | Kappa CDR3 |
|---|---|---|---|---|---|---|---|---|---|---|
| Con1p2 C013 | | 20 | 1.1E-08 | 512 | VH3-66 | JH6 | AKGVTSFDY | VK3-20 | JK4 | QQFGSSPPDT |
| Con1p2 C041 | | 1 | 2.2E-10 | none | VH3-23 | JH4 | ARDPGIRNGMGV | VK2-30 | JK1 | MQVTHWPRT |
| Con1p2 D021 | | 9N | 3.9E-10 | 256 | VH3-23 | JH4 | AKAHRGDWNNFFDY | VK3-11 | JH4 | QQSGDWPLT |
| Con1p2 D031 | | 19F/19A | 1.2E-08 | 1024/none | VH4-59 | JH3 | AREWSGFDF | VK3-20 | JK1 | QQYGSLPRT |
| Con1p2 E013 | | 8 | 7.7E-11 | 512 | VH3-7 | JH4 | ARGQWLAF | VK2-30 | JK2 | MQGTHWPYT |
| Con1p3 C021 | | 2 | 1.4E-10 | 4096 | VH3-7 | JH4 | ARGRNNFRH | VK1-33 | JK3 | QQFESFPRT |
| Con1p3 C031 | | 22F | 1.8E-10 | 32 | VH3-66 | JH4 | ARELGVFHSGGDQWLGPLDC | VK3-15 | JK3 | HQYKNWPPMGT |
| Con1p3 G012 | | 2 | 1.4E-10 | 2048 | VH3-49 | JH4 | RWTGGVSFGAY | VK1-5 | JK1 | QQYDIYLT |
| Con1p3 G061 | | 8 | 2.1E-08 | 16 | VH3-74 | JH4 | ARDYYHSVDY | VK2-30 | JK2 | MQGTHWPYT |
| Con1p4 B012 | | 33F | 4.0E-08 | 256 | VH4-59 | JH4 | ARGPDAHKTGY | VK4-1 | JK1 | QQYAATPWT |
| Con1p4 B031 | | 9N/9V | 5.6E-10 | 128/128 | VH3-74 | JH4 | ARDSYTSPDY | VK2-30 | JK4 | MQGSHWPLT |
| Con1p4 C011 | | 8 | 9.5E-10 | 128 | VH3-15 | JH3 | TTDNGVKAFDI | VK4-1 | JK3 | HQYYTTPFA |
| Con1p4 G011 | | 6B | 3.1E-10 | 256 | VH3-74 | JH4 | TRGGSGATINY | VK1-39 | JK4 | QQSHSSPLT |
| Con1p6 C011 | | 9V | 3.0E-08 | 256 | VH4-61 | JH4 | ARDRAGIDGYNYYFDY | VK1-5 | JK2 | QQYYSFYT |
| Con1p6 D041 | | CWPS | 4.2E-08 | none | VH1-46 | JH4 | AREVAAEGKAFDY | VK4-1 | JK4 | QQYYTPPLT |
| Con1p6 E031 | | 3 | 8.9E-10 | 128 | VH3-7 | JH3 | ARGQSYPGI | VK3-15 | JK1 | QQYNNWPRT |
| Con1p6 E061 | | 17F/33F | 9.4E-09 | 8/none | VH4-59 | JH4 | AGRAYSSGYYYLIDY | VK3-15 | JK2 | QHYHNWPPT |
| Con2p3 C043 | | CWPS | 7.9E-11 | none | VH3-30 | JH4 | AKGCSNGGNCFLIDY | VK4-1 | JK4 | QQYYNAPLT |
| Con2p3 C051 | | 4 | 1.8E-10 | 256 | VH3-23 | JH3 | AKGGYYESGTMRAFDI | VK3-11 | JK4 | QQRSNWPAT |
| Con2p3 F032 | | 2 | 1.5E-10 | 4096 | VH3-7 | JH4 | ARGESNFRY | VK1-33 | JK3 | QQFVSFPRT |
| Con2p3 G059 | | 18C | 2.8E-10 | 64 | VH3-7 | JH4 | ARDSTSPARFGY | VK3-20 | JK2 | QHYGTSPPRYT |
| Con2p4 B031 | | 1 | 3.4E-08 | none | VH3-53 | JH4 | ATGGMTSSWYGY | VK4-1 | JK2 | QQYYSTPYT |
| Con2p4 C025 | | 9N/9V | 2.7E-10 | 512/8 | VH1-46 | JH4 | SMGPPYCTGGSCYSACDF | VK3-20 | JK2 | QRYGNSPPYT |
| Con2p4 D065 | | 9V | 2.6E-10 | 2048 | VH3-15 | JH5 | TTDIGKGWYTHYPDL | VK4-1 | JK4 | LQYRSAPFT |
| Con2p5 A062 | | CWPS | 5.1E-10 | none | VH3-30 | JH4 | VKEYSWGYYRTADY | VK1-5 | JK1 | QQYSTYPWT |
| Con2p5 B063 | | 1 | 1.4E-10 | none | VH3-74 | JH4 | ARSPGGYFDY | VK3-15 | JK1 | QQYSTWLWT |
| Con2p5 C041 | | 8 | 2.3E-08 | 32 | VH3-15 | JH4 | TTDDLKN | VK1-39 | JK2 | QQRYRIPYS |
| Con2p5 E051 | | 2 | 2.8E-10 | 2048 | VH3-48 | JH6 | ARGRDCYGGNCVIYFHYYGLDV | VK2-28 | JK2 | MRALQTPYT |
| Con2p6 B033 | | CWPS | 6.4E-11 | none | VH3-30 | JH4 | VKESATGWYRTADY | VK1-5 | JK1 | HQYNKYPWT |
| Con2p6 C051 | | 33F | 3.3E-09 | none | VH3-66 | JH3 | ARDIPTTFGIGEAFDI | VK1-5 | JK1 | QQYYSWGT |
| Con2p6 G041 | | 22F | 4.4E-10 | 128 | VH1-46 | JH4 | ARDDSAFDY | VK2-24 | JK1 | MQASQSTWT |
| Con2p7 D031 | | CWPS | 1.8E-09 | none | VH3-30 | JH6 | AKGCSGENCFYMDD | VK4-1 | JK4 | QQCYNAPLT |

TABLE 1-continued

| Summary of anti-*S. pneumoniae* antibodies (SEQ ID NOS: 1 through 126) | | | | | | | | | | |
|---|---|---|---|---|---|---|---|---|---|---|
| Ab | # of Clones | Sero-type(s) | Kd (M)* | OPA** | VH gene | JH gene | Heavy CDR3 | VK gene | JK gene | Kappa CDR3 |
| Con2p8 B011 | | 22F | 2.3E-08 | none | VH1-46 | JH4 | TREIGAVVVDATSLGWL GYFDY | VK3-15 | JK1 | QQYNNWPPVT |
| Con2p8 B052 | | 15B | 1.7E-10 | none | VH3-7 | JH4 | AGWGRTQD | VK2-30 | JK2 | MQYTFWPHT |
| Con2p8 E031 | | 23F | 3.3E-08 | none | VH3-30 | JH3 | TKEGAPPGKYAFDI | VK3-11 | JK3 | QHRGEWPPGAT |
| Con2p8 F051 | | 11A | 1.8E-10 | none | VK3-72 | JH3 | LKDSSQYSFDA | VK1-9 | JK4 | QQFKGYPLT |
| SLE1p1 A023 | | 5 5. | 1E-10 | 1024 | VH4-59 | JH4 | ARGDGYNFF | VK1-9 | JK2 | QQINSYPRT |
| SLE1p1 A031 | | 14/9N | 1.7E-10 | 512/32 | VH3-30 | JH5 | AKCGAEDSTTVWLNWFDP | VK3-11 | JK4 | QQRADWPLT |
| SLE1p1 B053 | | 5 | 9.5E-10 | none | VH3-23 | JH4 | AKPNYFGSGSPDY | VK3-11 | JK2 | LQCSNWPMYT |
| SLE1p1 C041 | | 5 | 2.8E-10 | 2048 | VH4-59 | JH4 | VKEQDYGYYRTADH | VK1-6 | JK2 | QQYDKYPWT |
| SLE1p1 E012 | | 9V/9N | 6.2E-11 | 512/256 | VH3-20 | JH3 | VRVAVPAATYTRGNDAFDI | VK1-17 | JK1 | LQHSSFPWT |
| SLE1p1 F021 | | 14 | 1.0E-09 | none | VH3-15 | JH4 | TTAHGPVGDH | VK4-1 | JK5 | QQYYTTPSIT |
| SLE1p1 G051 | | 15B | 1.6E-10 | none | VH3-7 | JH4 | ARAGGCSSTRCHTTPGFDY | VK4-1 | JK5 | QQYYTTPPIT |
| SLE1p2 A021 | | 5 | 1.4E-10 | 512 | VH4-39 | JH3 | ASLSGTNAFDI | VK3-11 | JK1 | QQRSSGRT |
| SLE1p2 D041 | | 8 | 7.4E-09 | 256 | VH3-23 | JH4 | AKPRGYSYGYFDY | VK3D-20 | JK2 | QQYGISPRT |
| SLE1p3 A021 | | 17F | 2.7E-09 | none | VH3-7 | JH4 | APPARRLDY | VK2-29 | JK1 | MQGTHHPWT |
| SLE1p3 A041 | | 4 3. | 8E-08 | none | VH3-74 | JH4 | ARSNAGHEA | VK4-1 | JK4 | QQYYSTPLT |
| SLE1p3 B031 | | 20 | 1.5E-09 | none | VH1-46 | JH4 | ARDIPHANLDY | VK1-17 | JK1 | LQHTTFPWT |
| SLE1p3 C031 | | 33F | 1.1E-09 | 128 | VH3-23 | JH4 | VKDRVPPGDVPGDF | VK3-11 | JK5 | QQRRTWPPLT |
| SLE2p1 A012 | | 23F | 2.5E-09 | none | VH3-48 | JH6 | ATLLLRDNQLDV | VK2-30 | JK1 | MQGTHWRT |
| SLE2p1 A061 | | CWPS | 7.9E-10 | none | VH3-33 | JH4 | VKEQGFGYYRTADY | VK1-5 | JK1 | HQYDKYPWT |
| SLE2p1 B012 | | 15B/14 | 2.0E-10 | 256/256 | VH4-59 | JH3 | ARRNDFNI | VK3-20 | JK3 | QQYGSSPFT |
| SLE2p1 C031 | | 17F/33F | 2.9E-10 | none | VH3-23 | JH4 | SIWWGTSVQYPLVLDY | VK3D-15 | JK5 | QQYSKWPPIT |
| SLE2p1 C041 | | CWPS | 2.0E-09 | none | VH3-30 | JH5 | VKEQDYGYYRTADH | VK1-5 | JK1 | QQYDKYPWT |
| SLE2p1 D025 | | 5 | 2.0E-10 | none | VH4-61 | JH4 | ARGHGFNAY | VK3-20 | JK1 | QQYGNSPRT |
| SLE2p1 D041 | | 6B | 8.8E-11 | 512 | VH3-15 | JH4 | TTVRNMADLSLNH | VK3-20 | JK1 | QQYDDSRWT |
| SLE2p2 A011 | | 18C | 4.2E-09 | none | VH3-48 | JK4 | ATGNRGSLPRR | VK2D-28 | JK2 | MQALRSPYT |
| SLE2p2 C041 | | 33F | 4.9E-09 | none | VH3-7 | JH4 | VRDGWDTFFDS | VK2-30 | JK2 | MQGRYWPYT |
| SLE2p2 D031 | | 19A/19F | 1.1E-09 | none/8192 | VH3-74 | JH4 | VNFQLG | VK3-20 | JK1 | QQYGNSPRT |
| SLE2p2 E041 | | 8 | 5.1E-10 | 1024 | VH3-30-3 | JH5 | ARAEYCSPGDCFLIDT | VK2-30 | JK1 | MQGTHWRT |
| SLE2p2 F011 | | CWPS | 9.6E-10 | none | VH3-33 | JH4 | LRGNPPSSPTDY | VK1-16 | JK4 | QQYNSYPLT |
| SLE2p2 G011 | | 5 | 1.4E-09 | none | VH3-23 | JH6 | AKVVYSRPPMDV | VK1D-39 | JK1 | QQSYSTPWT |
| SLE2p2 G061 | | 17F | 4.8E-11 | 128 | VH3-7 | JH4 | ARASRETGEPY | VK2-30 | JK1 | MQATHWPWT |

*Calculated ELISA affinities, averaged for the clonal family. The affinity listed from cross-reactive antibodies is for the serotype which is most strongly bound (the serotype listed first in the serotype column).
**Opsonophagocytosis assay (OPA) measures antibody mediated uptake of bacteria: values 4 or less are considered negative ("none").
The number of clones indicates the total number of members of the clonal family

TABLE 2

Selected Heavy and Light Chain Sequences from Antibodies of Table 1 (SEQ ID NOS. 127-252)

| | Seq ID No: | |
|---|---|---|
| Con1 Heavy | | |
| Con1p2-c01h | 127 | GAGGTGCAGCTGTTGGAGTCGGGGGGAGGCTTGGTACAGCCTGGGGGGTCCCTGAGAGTCTCCTGTGCAGC<br>CTCTGGATTCACCTTTAGCAACTCTGGCATGAGTTGGGTCCGCCAGGCTCCAGGGAAGGGGCTGGACTGGGT<br>CTCAGGTATTGGTGGTGGTGGTGGTAGTGCATACTACGCAGACTCCGTGAAGGGCCGGTTCACCATCTCCAG<br>AGACAATTCCAAGAACACGCTGTATCTACAAATGAACAATTTGAGAGCCGAGGACACGGCCGTATACTACT<br>GTGCGAAAGGAGTTACCAGTTTTGACTACTGGGGCCAGGGAATCCTGGTCACCGTCTCCTCA |
| Con1p2-c04h | 128 | GAGGTGCAGCTGGTGGAGTCTGGGGGAGGCTTGGTCCAGCCTGGGGGGTCCCTGAGACTCTCCTGTGCAGCC<br>TCTGGATTCACCGTCAGTAGCGACTATATGAGTTGGGTCCGCCAGGCTCCAGGGAAGGGGCTGGAGTGGGTC<br>TCAGTTATGTATAGCGGGGGTAGCACATACTACGCAGACGCCGTGAAGGACAGATTCACCATCTCCAGAGA<br>CAATTCCAAGAATATACTGTATCTTCAAATGAACAGCCTGAGAGCCGAGGACACGGCGGTTTATTACTGTGC<br>GAGAGATCCCGGGATAAGGAACGGTATGGGCGTCTGGGGCCAAGGGACCACGGTCACCGTCTCCTCA |
| Con1p2-d02h | 129 | GAGGTGCAGCTGTTGGAGTCTGGGGGAGCCTTGGTACAGCCGGGGGGGTCCCTGAGACTTTCCTGTGCAGCC<br>TCTGGATTCACCTTTACCAGCTTTGCCATGGGCTGGGTCCGCCAGGCTCCAGGGAAGGGGCTGGAGTGGGTC<br>TCAGCTGTGACTGGCAGTGGTTATTACAAAAACTATGCAGACTCCGTGAAGGGCCGGTTCACCATCTCCAGA<br>GACAATTCCGACAATACTCTCTATCTGCAAATGAACAGCCTGAGAGGCGACGACACGGCCCTATATTACTGT<br>GCGAAAGCACATAGAGGTGACTGGAATAACTTCTTTGACTATTGGGGCCAGGGAACCCTGGTCACCGTCTCC<br>TCA |
| Con1p2-d03h | 130 | CAGGTGCAGCTGCAGGAGTCGGGCCCAGGACTAGTGAAGCCTTCGGAGACCCTGTCCCTCACCTGCTCTGTG<br>TCTGCTGACTCCTTCAGTCCTTACAAGTGGAGCTGGATCCGGCAGCCCCCAGGGAAGGGACTGGAATGGATT<br>GGATATATCTATTCCAGTGGGAACACCAACTACAACCCCCCCCTCAAGAGTCGAGTCACCATATCACTGGAC<br>ACGTCCAAGAATCAGGTCTCCCTGAGGCTGAGCTCTGTGGCCGCTGCGGACACGGCCATGTATTACTGTGCG<br>AGAGAGTGGAGTGGTTTTGATTTCTGGGGCCAAGGAACAATGGTCACCGTCTCTTCA |
| Con1p2-e01h | 131 | GAGGTGCAGCTGGTGGAGTCTGGGGGAGGCTTGGTCCAGCCTGGGGGGTCCCTGAGACTCTCCTGTGCAGCC<br>TCTGGATTCACCTTTACTAACTATTGGATGAGCTGGGTCCGCCAGGCTCCAGGGAAGGGGCTGGAGTGGGTG<br>GCCAACATAAAGCAAGATGGACGTGAGACATACTATGTGGACTCTGTGAAGGGCCGATTCACCATCTCCAG<br>AGACAACGCCAAGAACTCAGTGTCTCTACAGATGAGTAGCCTGAGAGCCGAGGACACGGCCGTGTATTACT<br>GTGCGCGAGGGCAGTGGCTGGCCTTCCGGGGCCAGGGAACCCTGGTCACCGTCTCCTCA |
| Con1p3-c02h | 132 | GAGGTGCAGCTGGTGGAGTCTGGGGGAGGCTTGGTCCAGATTGGGGGGTCCCTGAGACTCTCCTGTGCAGCC<br>TCTGGATTCACCTTTAGTACCTATTGGATGAGCTGGGTCCGCCAGGCTCCAGGGAAGGGGCTGGAGTGCGTG<br>GCCAGCATAAAGGAGGATGGAAGTGAGAGATACTATGTGGACTCTGTGAAGGGCCGATTCACCATCTCCAG<br>AGACAACGCCAAGAACTCACTGCATCTGCAGATGGACAGCCTGAGAGCCGCGGACACGGCTGTGTATTTCT<br>GTGCGAGAGGCCGGAACAACTTCCGACACTGGGGCCAGGGAACCCTGGTCACCGTCTCCTCA |
| Con1p3-c03h | 133 | GAGGTGCAGCTGGTGGAGTCTGGGGGAGGCTTGGTCCAGCCTGGGGGGTCCCTGAGACTCTCCTGTGCAGCC<br>TCTGGATTCGCCATCAGTGGTAACTACATGAGTTGGGTCCGCCAGGCTCCAGGGAAGGGCCTGGAGTGGGTC<br>TCACTTATTTATTGGACTGATGACACAGTCTACGCAGACTCCGTGAAGGGCAGATTCACCATCTCCAGGGAC<br>GTCTCCAAGAACATGGTGCATCTTCAAATGAGCAGCCTGAGAGTCGAGGACACGGCTGTTTATTACTGTGCG<br>AGAGAATTAGGTGTTTTTCATTCAGGGGGGGACCAGTGGCTGGGCCCTTTAGACTGCTGGGGCCAGGGAACC<br>CTGGTCACCGTCTCCTCA |
| Con1p3-g01h | 134 | GAGGTGCAGCTGGTGGAGTCTGGGGGAGGCTTGGTGCAGCCAGGGCAGTCCCTGAGACTTTCCTGTACAGTT<br>TCTGGATTCAGCGTAGAAGACCATGGTCTGAACTGGGTCCGCCAGGCTCCAGGGAAGGGGCTGGAGTGGGT<br>AGGGTTCATTAGAAGGAAAAGTTCTGGTGGGACAGAATACGCCGCGTCTGTGAAAGGCCGATTCACCATCTC<br>AAGAGATGATTCCAAGAGCGCCGTCTATCTGCAAATGAACAGCCTGAAGATGGAGGACACAGGCGTATATT<br>ATTGTCTTCGCTGGACGGGTGGAGTGAGTTTTGGTGCCTACTGGGGCCAGGGAACCCTGGTCACCGTCTCCT<br>CA |
| Con1p3-g06h | 135 | GAGGTGCAGCTGGTGGAGTCCGGGGGAGGCTTAGTTCAGCCTGGGGGGTCCCTGAGACTCTCCTGTGCAGCC<br>TCTGGATTCACCTTCACTAGCTGGATGCACTGGGTCCGCCAAGCTCCAGGGAAGGGGCTGGTGTGGGTCTCA<br>CATATTAATACTGATGGGAGTAGCACAAGCTACGCGGACTCCGTGAAGGGCCGATTCACCATCTCCAGAGAC<br>AACGCCAAGAACACGCTGTATCTGCAAATGAACAGTCTGAGAGCCGAGGACACGGCTGTGTATTACTGTGC<br>AAGAGATTATTACCACTCCGTTGACTACTGGGGCCAGGGAACCCTGGTCACCGTCTCCTCA |
| Con1p4-b01h | 136 | CAGGTGCAGCTGCAGGAGTCGGGCCCAGGAATGGTGAAGCCTTCGGAGACCCTGTCCCTCATCTGCAGTGTC<br>TCTGGTGCCTCCGTCAGTCGTGACCACTGGAGCTGGATCCGCCAGTCCCCAGGGAAGGGACTGGAGTGGATT<br>GTCTATATATATAACAGTGAGAGCATCGAATACAATCCCTCCCTCAAGAGTCGAGTCACCATATCCGTAGAC<br>ACGTCCAAGAACCAGGTCTCCCTGACAGTGACTTCTGTGACCGCTGCAGACACGGCCTTCTATTACTGTGCG<br>CGAGGGCCAGATGCCCACAAAACTGGCTACTGGGGCCCGGGAACCCTGGTCACCGTCTCCTCA |
| Con1p4-b03h | 137 | GAGGTGCAGCTGGTGGAGTCCGGGGGAGGCTTAGTTCAGCCTGGGGGGTCGCTGAGACTCTCCTGCGCAGC<br>CTCTGGATTCACCTTCAGTAACTTCTGGATGTACTGGGTCCGCCAAGTTCCAGGGAAGGGGCTGGTGTGCGT<br>CTCACGTATTAATAGAGATGGGAGTATCACATTGTACGCGGACTCCGTGAGGGGCCGATTCACCATCTCCAG<br>AGACAACGCCAAGAACACGCTGTATCTGCAAATGAACAGTCTGAGAGTCGAGGACACGGCTGTGTATTACT<br>GTGCAAGAGATTCCTATACCAGCCCTGACTACTGGGGCCAGGGGACCCTGGTCACCGTCTCCTCA |
| Con1p4-c01h | 138 | GAGGTGCAGCTGGTGGAGTCTGGGGGAGGCTTGGTAAAGCCGGGGGAGTCCCTTAGACTCTCCTGTGCGAC<br>CTCAGGATTAACTTTCAGTAACGTATGGATGAGCTGGGTCCGCCAGGCTCCAGGGAAGGGGCTGGAGTGGG |

TABLE 2-continued

Selected Heavy and Light Chain Sequences from Antibodies of Table 1 (SEQ ID NOS. 127-252)

| | Seq ID No: | |
|---|---|---|
| | | TTGGGCGTCTTAAAAACAAGCCTGATGGTGGAACAACAGACTACGCAGCACCCGTGAAGGGCAGATTCACC ATCTCAAGAGATGATTCAAAAACCACGCTGTATCTGGAAATGAACAGCCTGAAAGTCGAGGACACAGCCGT GTATTACTGTACCACAGATAACGGAGTCAAGGCTTTTGATATCTGGGGCCAAGGGACAATGGTCACCGTCTC TTCA |
| Con1p4-g01h | 139 | GAGGTGCAGCTGGTGGAGTCCGGGGGAGGCTTAGTTCAGCCTGGGGGGTCCCTGAGACTCTCCTGTGCAGCC TCTGGATTCACCTTCAGTACCTACTGGATGCACTGGGTCCGCCAAACTCCGGAGAAGGGGCTGGTATGGGTC TCACGTATTCATCCTGATGGGAGTAACACAGCCTACGCGGACTCCGTGAAGGGCCGATTCACCATCTCCAGA GACAACGCCAAGAACACGCTGTATCTGCAAATGAATAGTCTGAGAGTCGAGGACACGGCTTTTTATTATTGT ACAAGAGGGGGTTCCGGGGCTACGATCAATTACTGGGGCCAGGGAATCCTGGTCACCGTCTCCTCA |
| Con1p6-c01h | 140 | CAGGTGCAGCTGCAGGAGTCGGGCCCAGGGCTGGTGAAGCCTTCACAGACCCTGTCCCTCACCTGCACTGTC TCTGGTGGCTCCATCAGCGGTGGTACTTACTCCTGGACCTGGATCCGGCAGCCCGCCGGGAAGGGACTGGAG TGGATTGGGCGTATTTTTGCTAGTGGGAGCACCAACTACAATTCCTCCCTCAAGAGTCGAGTCACCATTTTAG TAGACACGTCCAAGAACCTGTTCTCCCTGAGCCTGAGCTCTGTGACCGCCGCAGACACGGCCATGTATTACT GTGCGAGAGATCGAGCCGGTATAGATGGCTACAATTACTACTTTGACTACTGGGGCCAGGGAACCCTGGTCA CCGTCTCCTCA |
| Con1p6-f04h | 141 | AGGTGCAGCTGGTGCAGTCTGGGGCTGAGGTGAAGAAGCCTGGGGCCTCAGTGAAGGTTTCCTGCAAGACA TCTGGATACACCCTCACCAGTTACTATATGCACTGGGTGCGACAGGCCCCTGGACAAGGGCTTGAGTGGCTG GGAGTGATCAGGCCTACGGACGCTAGCACAAGGTCCGCACAGAAGTTCCAGGGCAGAATCACCATGACCAG GGACACGTCCACGAGCACACTCTACATGGAGCTGAGTAGCCTGAGATCTGAAGACACGGCCGTGTACTATTG TGCGAGAGAAGTGGCAGCAGAAGGTAAAGCTTTCGACTACTGGGGCCAGGGAACCCTGGTCACCGTCTCCT CA |
| Con1p6-e03h | 142 | GAGGTGCAGCTGGTGGAGTCTGGGGGAGGCTTGGTCCAGCCTGGGGGGTCCCTGAGACTCTCCTGTGCAGCC TCTGGATTCACCTTTAGTAGCTATTGGATGAGCTGGGTCCGCCAGGCTCCAGGGAAGGGACTGGAGTGGGTG GGCAAAATAAAGGAAGACGGAAGTGAGAAATACTATGTGGACTCTGTGAAGGGCCGATTCGCCATCTCCAG AGACAACGCCAAGAACTCCCTGTCTCTGCAAATGAACAGCCTGAGAGCCGAGGACACGGCCGTGTATTACT GTGCGAGAGGTCAATCATATCCGGGAATTTGGGGCCAAGGGACAATGGTCACCGTCTCTTCA |
| Con1p6-e06h | 143 | CAGGTGCAGCTGCAGGAGTCGGGCCCAGGACTGGTGAAGCCTTCGGAGACCCTGTCCCTCACCTGCACTGTC TCTGGTGGCTCCATCACTAATTACTACTGGGGCTGGATCCGGCAGCCCCCAGGGGAGGGACTGGAGTGGATT GGCTATATCTATTACAGTGGAAGCACCAACTACAACCCCTCCCTCAAGAGTCGAGTCACCATATCAGTAGAC ACGTCCAAGAACCAGTTCTCCCTAAAGCTGACCTCTGTAACCGCCGCAGACACGGCCGTGTATTACTGTGCG GGTCGGGCTTACAGTAGTGGTTACTACTACCTAATTGACTACTGGGGCCAGGGAACCCTGGTCACCGTCTCC TCA |
| Con1 Kappa | | |
| Con1p2-c01k | 144 | GAAATTGTGTTGACGCAGTCTCCAGGCACCCTGTCTTTGTCTCCAGGGGAAAGAGCCACCCTCTCCTGCAGG GCCAGTCAGAGTGTTACCTACTTAGCCTGGTACCAGCAGAAACCTGGCCAGGCTCCCAGGCTCCTCTTCTAT GGTACATCCAGCAGGGCCACTGGCATCCCAGACAGGTTCAGTGGCAGTGGGTCTGGGACAGACTTCACTCTC ACCATCAGCAGAGTGGAGCCTGAAGATTTTGCAGTGTATTACTGTCAGCAGTTTGGCAGCTCACCTCCGGAC ACTTTCGGCGGAGGGACCAAGGTGGAAATCAAA |
| Con1p2-c04k2 | 145 | TTGTGATGACTCAGTCTCCACTCTCCCTGCCCGTCACCCTTGGACAGCCGGCCTCCATCTCCTGCAGGGCTAG TCAAGGCCTCGAACACAGTGATGGAAACACCTACTTGAGTTGGTTTCAGCAGAGGCCAGGCCGATCTCCCCG GCGCCTAATTTATAAGGTTTCTAACCGGGACTCTGGGGTCCCAGACAGATTCAGTGGCAGTGGGTCAGGCAC TGATTTCACACTGGAAATCACCAGGGTGGAGGCTGAGGATGTTGGAGTTTATTACTGCATGCAAGTTACACA CTGGCCGAGGACGTTCGGCCAAGGGACCAAGGTGGAAATCAAA |
| Con1p2-d02k | 146 | GAAATTGTGTTGACACAGTCTCCAGGCACCCTGTCGTTGTCTCCAGGGGAAAGAGCCACCCTCTCCTGCAGG GCCAGTCAGAGTATTAGTCCCCACTTGGCCTGGTACCAACAGAAACCTGGCCAGTCTCCCAGGCTCCTCATA TATGATGCATCCAACAGGGCCACTGGCATCCCAGCCAGGTTCAGTGGCAGTGAGTCTGGGACAGACTTCACT CTCAGCATCAGCAGCCTAGAGCCTGAAGATTTTGCAGTTTATTACTGTCAGCAGAGTGGCGACTGGCCTCTC ACTTTCGGCGGAGGGACCAAGGTGGAGATCAAA |
| Con1p2-d03k3 | 147 | GAAATTGTGTTGACGCAGTCTCCAGGCACCCTGTCTTTGTCTCCAGGGGAAAGAGCCACCCTCTCCTGCAGG GCCAGTCAGAGTGTTTACAGCATCTACTTCGCCTGGTACCAGCAGAAACCCGGCCAGGCTCCCAGGCCCCTC ATTTATGGTGTCTCCAACAGGGCCACTGGCATCCCAGACAGGTTCAGTGGCAGTGGGTCTGGGACAGACTTC ACTCTCACCATCAGCAGACTGGAGCCAGAAGATTTTGCAGTGTATTACTGTCAGCAGTATGGTAGTTTACCT CGGACGTTCGGCCAAGGGACCAAGGTGGAAATCAAA |
| Con1p2-e01k | 148 | TTGTGATGACTCAGTCTCCACTCTCCCTGCCCGTCACCCTTGGACAGCCGGCCTCCATCTCCTGCAGGTCTAG TCGAAGCCTCGTATACAGTGATGGAGGCACCTACTTGAATTGGTTTCAGCAGAGGCCAGGCCAATCTCCAAG GCGCCTAATTTGGCACGTTTCTAACCGGGACTCTGGGGTCCCAGACAGATTCAGCGGCAGTGGGTCAGGCAC TGATTTCACACTGAAAATCAGCAGGGTGGAGGCTGAGGATGTTGGGGTTTATTACTGCATGCAAGGTACACA CTGGCCTTACACTTTTGGCCAGGGGACCAAGGTGGAAATCAAA |

TABLE 2-continued

Selected Heavy and Light Chain Sequences from Antibodies of Table 1 (SEQ ID NOS. 127-252)

| | Seq ID No: | |
|---|---|---|
| Con1p3-c02k | 149 | GACATCCAGATGACCCAGTCTCCATCTTCCCTGTCTGCATCTGTAGGAGACAGAGTCACCATCACTTGCCAG<br>GCGAGTCAGGACATTAGGAAGCTTTTAAATTGGTATCAGCAGAGACCAGGGAAAGCCCCTAACCTCCTGATC<br>TACGATGCATCCAATTTGGAAACAGGGGTCCCATCAAGGTTCAGTGGAAGTGGATCTGGGACACATTTTAGT<br>TTCACCATCACCAGCCTGCAGCCTGAAGATATTGCAACATATTACTGTCAACAGTTTGAAAGTTTCCCTCGCA<br>CCTTCGGCCCTGGGACCAAAGTGGATATCAAA |
| Con1p3-c03k | 150 | GAAATAGTGATGACGCAGTCTCCAGCCACCCTGTCTGTGTCTCCAGGGGAAACAGCCACCCTCTCCTGCAGG<br>GCCAGTCAGAGTGTTAACAGCTTCTTAGCCTGGTACCAGCAGAAACCTGGCCAGGCTCCCAGGCTCCTCATC<br>TATGCTGCATCCACCAGGGCCACTGGTGTCCCAGCCAGGTTCAGTGGCAGTGGGTCTGGGACAGAGTTCACT<br>CTCACCATCAGCAGCCTGCAGTCTGAAGATTTTGCAGTTTACTACTGTCACCAGTATAAAAACTGGCCTCCG<br>ATGGGCACTTTCGGCCCTGGGACCAAAGTGGATATCAAA |
| Con1p3-g01k | 151 | GACATCCAGATGACCCAGTCTCCTTCCACCCTGTCTTCTTCTGTCGGAGACAGAGTCACTATCACTTGCCGGG<br>CCAGTCAGAATATTGGTGTCTCCTTGGCCTGGTATCAGCAGAAACCAGGGAAAGCCCCTAACCTCCTGATCT<br>ATAAGGCGTCTTATTTAGAAACGGGGGTCCCATCAAGGTTCAGCGGCAGTGGATCTGGGACAGAATTCACTC<br>TCACCATCAGCAGCCTACAGCCTGATGATTTTGCAACTTATTATTGCCAACAGTATGATATTTATTTGACATT<br>CGGCCAAGGGACCAAGGTGGAAATCAAA |
| Con1p3-g06k | 152 | TTGTGATGACTCAGTCTCCACTCTCCCTGCCCGTCACCCTTGGACAGCCGGCCTCCATCTCCTGCAGGTCTAG<br>TCAAAGTCTCGCACACAGTGATGGAAATACCTACTTGAATTGGTTTCAGCAGAGGCCAGGCCAATCTCCAAG<br>GCGCCTAATTTATAAGGTTTCTAACCGGGACTCTGGGGTCCCAGACAGATTCAGCGGCAGTGGGTCAGGCAC<br>TGATTTCACACTGAAAATCAGCAGGGTGGAGGCTGAGGATGTTGGGGTTTATTACTGCATGCAAGGTACACA<br>CTGGCCGTACACTTTTGGCCAGGGGACCAAGGTGGAAATCAAA |
| Con1p4-b01k | 153 | GACATCGTGATGACCCAGTCTCCAGACTCCCTGGCTGTGTCTCTGGGCGAGAGGGCCACCATCAACTGCAAG<br>TCCAGCCAGAGTGTTTTATACAGCCCCAACAACAAGAATTACTTAGCTTGGTTCCAGCAGAAGCCAGGACAG<br>CCTCCTAAATTACTCATTTACTGGGCATCTATCCGGGACTCCGGGGTCCCTGACCGATTCAGTGGCAGCGGGT<br>CTGGGACAGATTTCACTCTCACCGTCAGCAGTCTGCAGGCTGACGATGTGGCAGTTTATTACTGTCAGCAAT<br>ATGCTGCTACTCCGTGGACGTTCGGCCAAGGGACCAAGGTGGAAATCAAA |
| Con1p4-b03k2 | 154 | TTGTGATGACTCAGTCTCCACTCTCCCTGCCCGTCACCCTTGGACAGCCGGCCTCCATCTCCTGCAGTTCTAG<br>TCAAAGCCTCGTATACAGTGATGGAAACACCTACTTGAGTTGGTTTCAGCAGAGGCCAGGCCAATCTCCCCG<br>GCGCCTAATTTATAAGGTTTCTAACCGGGACTCTGGGGTCCCAGACAGATTCAGCGGCAGTGGGTCAGGCAC<br>TGATTTCACACTGAGAATCAGCAGGGTGGAGGCTGAGGATGTTGGGGTTTATTACTGCATGCAAGGTTCACA<br>CTGGCCGCTCACTTTCGGCGGAGGGACCAAGGTGGAGATCAAA |
| Con1p4-c01k | 155 | GACATCGTGATGACCCAGTCTCCAGACTCCCTGGCTGTGTCTCTGGGCGAGAGGGCCACCATCAACTGCAAG<br>TCCAGCCTGAGTGTTTTATCCAGCTCCAATAATGAGAACTACTTAGCTTGGTACCAGCAGAAACCAGGACAG<br>CCTCCTAAGCTGCTCATTTACTGGGCATCTACCCGGGGATCCGGGGTCCCTGGCCGATTCAGTGGCAGCGGG<br>TCTGGGACAGATTTCACTCTCACCATCAGCAGCCTGCAGGCTGAAGATGTGGCAGTTTATTACTGTCACCAA<br>TATTATACTACTCCCTTCGCTTTCGGCCCTGGGACCAAAGTGGATATCAAA |
| Con1p4-g01k | 156 | GACATCCAGATGACCCAGTCTCCGTCCTCCCTGTCTGCATCTGTGGGAGACAGTGTCACCATCACTTGCCGG<br>GCAAGTCAGAGCATTAGCAGCTATTTAAATTGGTATCACCAAAAACCAGGGAAAGCCCCTAAACTCCTGATC<br>TATGGTGCATCCACTTTGCAAAGTGGGGTCCCATCAAGGTTCGGTGGCAGTGGATCTGGGACAGATTTCACT<br>CTCACCATCAGCAGTCTGCAACCTGACGATTTTGCAACTTACTACTGTCAACAGAGTCACAGTTCCCCTCTCA<br>CTTTCGGCGGAGGGACCAAGGTGGAGATCAAA |
| Con1p6-c01k | 157 | GACATCCAGATGACCCAGTCTCCTTCCACCCTGTCTGCCTCTGTAGGAGACAGAGTCACCATCACTTGTCGG<br>GCCAGTCGGAGTCTTGGTAGCTGGTTGGCCTGGTATCAGCAGAGCCCAGGGAAAGCCCCTAAGCTCCTGATC<br>TATAAGGCGTCTACTTTAGAAAGTGGGGTCCCATCACGGTTCAGCGGCAGTGGATCTGGGACAGAATTCACT<br>CTCACCATCAGCAGCCTGCAGCCTGATGATTTTGCAACTTATTACTGCCAACAGTATTATAGCTTCTACACTT<br>TTGGCCAGGGGACCAAGGTGGAAATCAAA |
| Con1p6-d04k | 158 | GACATCGTGATGACCCAGTCTGCAGACTCCCTGGCTGTGTCTCTGGGCGAGAGGGCCACCATCAACTGCAAG<br>TCCAGCCAGAGTCTTTTCTACAGTTCCAACAAGAAGAACTACTTAGCTTGGTACCAGCAGAAGCCAGGACAG<br>CCTCCTAAACTGATCATTTACTGGGCATCTACCCGGGAATCCGGGGTCCCTGACCGATTCAGTGGCAGCGGG<br>TCTGGGACAGATTTCACTCTCACCATCACCAGCCTGCGGGCTGAAGATGTGGCAGTTTATTACTGTCAGCAA<br>TATTATACTCCTCCTCTCACATTCGGCGGAGGGACCAAGGTGGAAATCAAA |
| Con1p6-e03k | 159 | GAAATAGTGATGACGCAGTCTCCAGCCACCCTGTCTGTGTCTCCAGGGGAAAGAGCCACCCTCTCCTGCAGG<br>GCCAGTCAGAGTGTTAGCGGCGACTTAGTCTGGTACCAGCAGAAACCTGGCCAGGCTCCCAGGCTCCTCATC<br>TATGGTGCCACCACCAGGGCCTCTGGTGTCCCAGCCAGGTTCAGTGGCAGTGGGTCTGGGACAGAGTTCACT<br>CTCACCATCAGCAGCCTGCAGTCTGAAGATTTTGCAATTTATTACTGTCAGCAGTATAATAACTGGCCCCGG<br>ACGTTCGGCCAAGGGACCAAGGTGGAAATCAAA |
| Con1p6-e06k | 160 | GAAATAGTGATGACGCAGTCTCCAGCCACCCTGTCTGTGTCTCCAGGGGAAAGAGCCACCCTCTCCTGCAGG<br>GCCAGTCAGAGTGTTGGCAACAACTTAGCCTGGTTTCAGCAGAAACCTGGCCAGGCTCCCAGGCTCCTCATC<br>TATGGTGCATCCACCAGGGCCACTGGTATCCCAGCCAGGTTCAGTGGCAGTGGGTCTGGGACAGAGTTCACT<br>CTCACCATCAGCAGCCTGCAGTCTGAAGATTTTGCAGTTTATCACTGTCAACACTATCATAACTGGCCTCCCA<br>CTTTTGGCCAGGGGACCAAGGTGGAAATCAAA |

TABLE 2-continued

Selected Heavy and Light Chain Sequences from Antibodies of Table 1 (SEQ ID NOS. 127-252)

| | Seq ID No: | |
|---|---|---|
| Con2 Heavy | | |
| Con2p3-c04h | 161 | CAGGTGCAGCTGGTGGAGTCTGGGGGAGGCGTGGTCCAGCCTGGGAGGTCCCTGAGACTCTCCTGTGCAGCC<br>TCTGGATTCACCTTCAGCAACCATGGCATGCACTGGCTCCGCCAGACTCCAGGCAAGGGGCTGGAGTGGGTG<br>GCAGTCATTTCATATGATGGAAGTACCAAATACTATGCAGACTCCGTGAAGGGCCGATGCACCCTCTCCAGA<br>GACAATTCCAAGGAAACGGTGTTTCTGCAAATGAACAGCCTGAGACCTGAGGACACGGCTGTGTATTATTGT<br>GCGAAAGGGTGTTCTAATGGTGGTAAGGCTTTTTGATTGACTACTGGGGCCCGGGAACCCTGGTCACCGTC<br>TCCTCA |
| Con2p3-c05h | 162 | GAGGTGCAGCTGTTGGAGTCGGGGGGAGACTTGGTGCAGCCTGGGGGGTCCCTGAGACTCTCCTGTGCAGCC<br>TCTGGATTCGACTTCAGTATTTATGGCATGAACTGGGTCCGCCAGGCTCCAGGGAAGGGGCTTGAATGGGTC<br>TCAGTTATTAGTGGTGATGGCACTATCATATACTACGCAGACTCCGTGAAGGGCCGGTTCACTATCTCCAGA<br>GACAATTCCAAGAACACACTGTTTTTGCAAGTGAACAGCGTGAGAGCCGAGGACACGGCCGTATATTACTGT<br>GCGAAGGGGGGCTACTATGAATCGGGGACTATGCGGGCTTTTGATATCTGGGGCCAAGGGACAATGGTCAC<br>CGTCTCTTCA |
| Con2p3-f03h | 163 | GAGGTGCAGCTGGTGGAGGAGTCTGGGGGAGGCTTGGTCCAGCCTGGGGGGTCCCTGAGACTCTCCTGTGC<br>AGCCTCTGGATACACCTTTAGTAGTTATTCAATGAGTTGGGTCCGCCAGGCTCCAGGGAAGGGGCTGGAGTG<br>GGTGGCCAGCATTAAGCCAGAAGGAAGTGAGAAATTCTATGTGGACTCTGTGAAGGGCCGATTCACTATCTC<br>CAGAGACAACGCCAAGAACTCACTGTATCTGCAAATGAACAGCCTGAGAGGCGAGGACACGGCTGTCTACT<br>ACTGTGCGAGAGGGGAATCTAATTTCCGATACTGGCACCAGGGAACCCTGGTCACCGTCTCCTCA |
| Con2p3-g05h | 164 | GAGGTGCAGCTGGTGGAGTCTGGGGGAGCCTTGGTCCAGCCTGGGGGGTCCCTGAGACTCTCCTGTGCAGCC<br>TCTGGATTCATCTTCAGTAACTCTTGGATGGGCTGGTTCCGCCAGGCTCCAGGGAAGCGGCCGGAGTTCGTG<br>GCCAACATAAAACCAGATGGAAGTGAGAAATTCCATGTGGACTCTGTGAAGGGCGATTCACCATCTCCAG<br>AGACAACGCCGAGAACTCACTGTATCTGCTGATGAACAGCCTGAGAGCCGAGGACACGGCTGTCTATTACTG<br>CGCGAGAGATAGCACTTCCCCGGCCCGTTTTGGGTACTGGGGCCAGGGAACCCTGGTCACCGTCTCCTCA |
| Con2p4-b03h | 165 | GAGGTGCAGCTGGTGGAGACTGGAGGAGGCTTGATCCAGCCTGGGGGGTCCCTGAGGCTCTCCTGTGCAGC<br>CTCTGGGTTAAACGTCAATAGTTACTACATGAACTGGGTCCGCCAGGCTCCAGGGAAGGGGCTGGAGTGGGT<br>CTCAGTTATTTATAGCGGTGGTGGCACAAACTACGCAGACTCCGTGAGGGGCCGATTCATCATCTCCAGAGA<br>CAATTCCAGGAACGCGCTTTATCTTCAAATGAACAGCCTGAGAGCCGAGGACACGGCCGTGTATTACTGTGC<br>GACGGGCGGGATGACCAGTAGTTGGTACGGCTACTGGGGCCAGGGAACCCTGGTCACCGTCTCCTCA |
| Con2p4-c02h | 166 | AGGTGCAGCTGGTGCAGTCTGGGGCCGAGGTGAAGAAGCCTGGGGCCTCAGTGAAGGTTTCCTGCAAGGCA<br>TCTGAATACACTTTCATCAACTACCTTGTGTTCTGGGTGCGACAGGCCCCTGGACAAGGGCTTGAGTGGATG<br>GGAGAAATGAACCCCACTCGTGGGAGCACAAGCTACGCACAGAAGTTCCAGGGCAGAGTCACCATGACCAG<br>GGACACGTCCACGAGCACAGTCTACATGGAGTTGAGCAGCCTGAGATCTGACGACACGGCCGTTTATTACTG<br>CTCCATGGGTCCGCCCTATTGTACTGGTGGAAGCTGTTACTCCGCCTGTGATTTCTGGGGCCCGGGAACCCTG<br>GTCACCGTCTCCTCA |
| Con2p4-d06h | 167 | GAGGTGCAGCTGGTGGAGTCTGGGGGAGGCTTGATGAAACCTGGGGGGTCCCTTAGACTCTCCTGTGCAGTC<br>TCTGGGTTCACTTTCACTAACGCCTGGCTGAGCTGGGTCCGCCAGCCTCCAGGGAAGGGGCTGGAGTGGGTT<br>GGCCGTGCTTACAGCAGTTCTGGCGGTTGGACAATGGACTACTCTTCACCCGTGAGGGGCAGATTCACCATC<br>ACAAGAGACGATTCAAAAAACACACTGTATCTGCAAATGAACAACCTGAAAACCGAGGACACAGCCGTGTA<br>TTACTGTACCACAGATATTGGCAAAGGCTGGTACACGCACTATCCTGACCTCTGGGGCCAGGGAACCCTGGT<br>CACCGTCTCCTCA |
| Con2p5-a06h | 168 | CAGGTGCAGCTGGTGGAGTCTGGGGGAGGCGTGGTCCAGCCTGGGAAGTCCCTCAGACTCTCCTGTGTAGCC<br>TCTGGATTCACCTTAAGTACCTGTGGCATGCACTGGGTCCGCCAGGCTCCAGGCAAGGGGCTGGAGTGGGTG<br>GCAGTTACAACATATGATGGAGATCGTAAATATAATGTAGACTCCGTGAAGGGCCGATTCACCATCTCCAGA<br>GACAATTCCAAGAACACGGTGTATCTGCAAATGGACGGCCTCAAAGCCGAGGACACGGCTGTGTATCACTG<br>TGTGAAAGAATATAGTTGGGGTTACTACAGAACTGCGGACTACTGGGGCCAGGGAACCCTGGTCACCGTCTC<br>CTCA |
| Con2p5-b06h | 169 | GAGGTGCAGCTGGTGGAGTCCGGGGGAGGCTTAGTTCAGCCGGGGGGGTCCCTGAGACTCTCCTGTGTAGCC<br>TCTGGATTCACCTTCAGTACTTACTGGATGCACTGGGTCCGCCAACCTCCGGGGAAGGGGCTGGTGTGGGTC<br>TCACGTATTAATCCTGATGGCAGTAGCACAAACTACGCGGACTCCGTGAACGGCCGATTCACCATCTCCAGA<br>GACAACGCCAAGAACACGCTGTATCTTGAAATGAACAGTTTGAGAGTCGAGGACACAGCTCTCTATTACTGT<br>GCAAGAAGTCCTGGGGGTTACTTTGACTACTGGGGCCACAGCACCCTGGTCACCGTCTCCTCA |
| Con2p5-c04h | 170 | GAGGTGCAGCTGGTGGAGTCTGGGGGAGGCTTGGTGAAGCCTGGGGGGTCCCTTACACTCTCCTGTGCAGTC<br>TCTGGATTCACTTTCAGTACCGGCTGGATGAGCTGGGTCCGCCAGGCTCCAGGGAAGGGGCTGGACTGGGTT<br>GGCCGTATTAAAAGCAAAACTGCTGGTGGGACAACAGACTATGCTGCACCCGTGAAAGACAGATTCACCAT<br>CTCAAGAGATGATTCAAAAAACACGCTGTATCTGCAACTGAGCAGCCTTAAAACCGAGGACACAGCCGTGT<br>ATTACTGTACCACAGATGACCTGAAAAACTGGGGCCAGGGAACCCTGGTCACCGTCTCCTCA |
| Con2p5-e05h | 171 | GAGGTGCAGCTGGTGGAGTCTGGGGGAGGCTTGGTGCAGCCGGGGGGGTCCCTGAGACTCTCCTGTGCAGC<br>CTCTGGATTCACCTTCAGTAGTTATAGCATGAACTGGGTCCGCCAGGTCCCGGGAAAGGGGCTGGAGTGGGT<br>CTCATACACAAGTACTAAAAGTGATATCAAATACTACGCGGACTCTGTGGAAGGCCGATTCACCATTTCCAG<br>AGACAATGCCAAGAACTCATTGTATCTGCAAATGAACAGCCTGAGAGACGAAGACACGGCTGTCTATTATTG |

TABLE 2-continued

Selected Heavy and Light Chain Sequences from Antibodies of Table 1 (SEQ ID NOS. 127-252)

| | Seq ID No: | |
|---|---|---|
| | | TGCGAGAGGACGAGATTGTTATGGGGTAACTGCGTCATCTACTTCCACTACTACGGTTTGGACGTCTGGGG CCAAGGGACCACGGTCACCGTCTCCTCA |
| Con2p6-b03h | 172 | CAGGTGCAGCTGGTGGAGTCTGGGGGAGGCGTGGTCCAGCCTGGGGGGTCCCTGAGACTCTCCTGTGTAGTC TCTGGATTCACCCTCAGTTCCTGTGGCATGCATTGGGTCCGCCAGTCTCCAGGCAAGGGGCTGGAGTGGCTG TCAGTTAGCACCTATGATGGAGATGGCAATCAGAAATACTATGCGGCCTCCGTGAAGGGCCGATTCCTCATC TCCAGAGACACTTCGAAGAACACGGTGTATCTCCATATGAACAGCCTGACAGCTGAGGACACGGCTCTATAT TATTGTGTGAAAGAGAGTGCCACTGGCTGGTATCGCACCGCTGATTACTGGGGCCAGGGAACCCTGGTCACC GTCTCCTCA |
| Con2p6-c05h | 173 | GAGGTGCAGCTGGTGGAGTCTGGGGGAGGCTTGGTCCAGCCTGGGGGGTCCTTGAGACTCTCCTGTGCAGCC TCTGGATTCACCGTCAGTAGCATATTCATGAGCTGGGTCCGCCAGGCTCCAGGGCAGGGGCTGGAGTGGGTC TCAGTCATCTATACCGATGGAAAAACATATTATGCACACTCCGTGGAGGGCCGATTCACCATCTCCAGAGAC GATTCCAAGAATATGGTGTATCTTCAATTGAGCAGCCTGAGAACTGAGGACACGGCTGTTTATTACTGTGCG AGAGATATTCCAACGACATTTGGAATAGGTGAAGCTTTTGATATCTGGGGCCAGGGGACAATGGTCACCGTC TCTTCA |
| Con2p6-g04h | 174 | AGGTGCAGCTGGTGCAGTCTGGGGCTGAGGTGAAGAAGCCTGGGGCCTCAGTGAAGCTTTCCTGCAAGACA TCTGGATACTCCTTCACCAGCAACTATTTGCACTGGGTGCGACAGGCCCCTGGACAAGGACTTGAGTGGATG GGAATGGTCTACCCAAATGATGGTACTACAACCTACGCTCAGAAGTTTCAGGGCAGAGTCACCATGACCAGT GAGACGTCCACAACCACAATCTACATGGACCTGAGCGGCCTGACATCTGAGGACACGGCCATATATTACTGT GCTAGAGACGATTCGGCCTTTGACTACTGGGGCCAGGGAACCCTGGTCACCGTCTCCTCA |
| Con2p7-d03h | 175 | CAGGTGCAGCTGGTGGAGTCTGGGGGAGGCGTGGTCCAGCCTGGGAGGTCCCTGAGACTCTCCTGTGAAGC CTCTGGATTCATCTTCAGTAGCAATGGCATGCACTGGGTCCGCCAGGCTCCAGGCAAGGGGCTGGAGTGGGT GGCAGTTATATCATCTGATGGAAGTATTAGATACTATGCAGACTCAATGAAGGGCCGATTCACCATCTCCAG AGACAACTCCAAGAACACGCTGTATCTGCAATTGAACAGCCTGAGAGCTGACGACACGGCTGTCTATTACTG TGCGAAAGGCTGTAGTGGTGAAAATTGCTTCTATATGGACGACTGGGGCAAAGGGACCACGGTCACCGTCTC CTCA |
| Con2p8-b01h | 176 | AGGTGCAGCTGGTGCAGTCTGGGGCTGAGGTGAAGAAGCCTGGGGCCTCACTGAAGGTCTCCTGCAAGGCA TCTGGATACACCTTCAGACAGAACTATTTCCACTGGGTGCGACAGGCCCCTGGACAAGGGCTTGAGTGGATG GGAGTAATCAACCCGAGTGATGGTAGTACAAAGTTCGCACAGAAGTTCCAGGGCAGAGTCAGCATGACCAG GGACACGTCCACGAGCACAGTTTACATGGACCTGAGCAGTCTGACATCTGAGGACACGGCCGTCTATTATTG TACGAGAGAGATCGGCGCAGTGGTAGTAGATGCTACGTCGTTGGGGTGGTTGGGCTACTTTGACTACTGGGG CCAGGGAACCCTGGTCACCGTCTCCTCA |
| Con2p8-b05h | 177 | GAGGTGCAGCTGGTGGAGTCTGGGGGAGGCTTGGTCCAGCCGGGGGGGTCCCTGAGTCTCTCCTGTGAAGCC TCTGGATTAACCTTCAGTGGCTACTGGATGAACTGGGTCCGCCAGGCTCCAGGGAAGGGGCTGGAGTGGGTG GCCAACATAAATCCAGAAGGAAGTGAGAGGAGATACGTGGAGTCTGTGCAGGGCCGATTCACCGTCTCCAG AGACAACCCGAAGAACACCCTGTATTTGCAAATGAACAGCCTGAGAGTCGAGGACACGGCTCTGTATTACT GTGCGGGCTGGGGGAGAACCCAGGACTGGGGCCAGGGAGCCCTGGTCACCGTCTCCTCA |
| Con2p8-e03h | 178 | CAGGTGCAGCTGGTGGAGTCTGGGGGAGGCGTGGTCCAGCCTGGGAGGTCCCTGAGACTCTCCTGTGCAGCC TCTGGACTCACCTTCAGCAATTATGGCATGCACTGGGTCCGCCAGGCTCCAGGGAAGGGGCTGGAGTGGGTT GCAGTTGTGTCGGCAAGGGGAGGAACTACATATTATGCAGACTCCGTGAAGGGCCGATTCACCATCTCCAGA GACAATTCCAAGAACACGATGTCTCTGCAAATGAACGGCCTGAGACCTGACGACACGGCTGTGTATTTTTGT ACGAAAGAAGGAGCACCACCTGGAAAATATGCTTTTGATATCTGGGGCCAAGGGACAATGGTCACCGTCTC TTCA |
| Con2p8-f05h | 179 | GAGGTGCAGCTGGTGGAGTCTGGGGGAGGCTTGGTCCAGCCTGGAGGATCCCTGAGACTCTCCTGCGCAGCC TCCGGATTCACCTTCAGTGACTACCGCATGGACTGGGTCCGCCAGGCTCCAGGGAGGGGGCTGGAGTGGATT GCCCGTATTAGACACAGAGATGCAGGCTATAGCACAGAATACGCCGCGTCTGTGAGGGGCAGATTCACCGT CTCAAGAGATGACTCACAGAGTACACTGTACCTGCAGATGAACAGCTTGAAAGCCGACGACACGGCCGTGT ATATTTGTCTTAAAGATTCTTCGCAATACTCTTTTGATGCGTGGGGCCAAGGGACAATGGTCACCGTCTCTTC A |
| Con2 Kappa | | |
| Con2p3-c04k | 180 | GACATCGTGATGACCCAGTCTCCAGACTCCCTGGCTGTGTCTCTGGGCGAGAGGGCCACCATCAACTGCAAG TCCAGTCAGAGTATTTTATCCAGATCCAACAATAAGAACTACTTAGCCTGGTACCAGCAGAAACCAGGACAG CCTCCTAAATTGCTCCTTTATTGGGCATCTACCCGGGAATCCGGGGTCCCTGACCGATTCAGTGTCAGCGGGT CTGGGTCAGATTTCACTCTCACCATCAGTAGCCTGCAGGCTGAGGATGTGGCAGTTTATTACTGTCAGCAGT ATTATAATGCTCCCCTCACTTTCGGCGGAGGGACCAAGGTGGAGATCAAA |
| Con2p3-c05k | 181 | GAAATTGTGTTGACACAGTCTCCAGCCACCCTGTCTTTGTCTCCAGGGGAAAGGGCCACCCTCTCCTGCAGG GCCAGTCAGACTGTTAGCAGGTACTTAGCCTGGTACCAACAAAAGCCTGGCCAGGCTCCCAGGCTCCTCATC TATGCTGCATCCAACAGGGCCACTGGCATCCCAACCAGGTTCAGTGGCAGTGGGTCTGGGACAGACTTCACT CTCACCATCAGCAGCCTAGAGCCTGAAGATTTTGCATTTTATTACTGTCAGCAGCGTAGCAACTGGCCTGCC ACTTTCGGCGGAGGGACCAAGGTGGAGATCAAA |
| Con2p3-f03k | 182 | GACATCCAGATGACCCAGTCTCCTTCCTCCCTGTCTGCATCTGTAGGAGACAGTGTCACCATCACTTGCCAGG CGAGTCAGGACATTAGAGACCGTTTAAATTGGTATCAGCAGAAGCCAGGGAAAGCCCCTAACCTCCTGATCT |

TABLE 2-continued

Selected Heavy and Light Chain Sequences from Antibodies of Table 1 (SEQ ID NOS. 127-252)

| | Seq ID No: | |
|---|---|---|
| | | ACGATGCATCAAGTTTGGAAACAGGGGTCCCATCAAGGTTCAGAGGAAGTGGATCTGGGACAGATTTTACTT TCACCATCAGCAGCCTGCAGCCTGAAGATATTGCAACATATTACTGTCAACAGTTTGTTAGTTTCCCTCGAAC TTTCGGCCCGGGGACCAAAGTGGATATCAAA |
| Con2p3-g05k | 183 | GAAATTGTGTTGACGCAGTCTCCAGGCATCCTGTCTTTGTCTCCAGGGGAAAGAGCCACCCTCTCCTGCAGG GCCAGTCAGAGTGTTAGCAGCAGGTCCTTGTCCTGGTACCAGCAGAGACCTGGCCTGGCTCCCAGGCTCCTC ATCTATGCTGCATCCAGCAGGGCCGCTGTCACCCCAGACAGGTTCACTGCCAGCGGGTCTGGGACAGACTTC ACTCTCACCATCAGCAGTCTGGAGCCTGAAGATTTTGCAGTGTATTACTGTCAGCACTATGGTACCTCACCTC CGAGGTACACTTTTGGGCAGGGGACCAAGGTGGAGATCAAA |
| Con2p4-b03k | 184 | GACATCGTGATGACCCAGTCCCCAGACTCCCTGGCTGTGTCTCTGGGCGAGAGGGCCACCATCAACTGCAAG TCCAGCCAGAGTGTTTTACACAGCTCCAACAATAAGAACTACTTTGCTTGGTACCAGCAGAAACCAGGACAG CCTCCTAAGCTGCTCATTCACTGGGCATCTACCCGGGCATCCGGGGTCCCTGACCGATTCAGTGGCAGCGGG TCTGGGACAGATTTCACTCTCACCATCAGCAGCCTGCAGGCTGAAGATGTGACAATTTATTACTGTCAGCAA TATTATAGTACTCCGTACACTTTTGGCCAGGGGACCAAGGTGGAAATCAAA |
| Con2p4-c02k | 185 | GAAATTGTGTTGACGCAGTCTCCAGGCACCCTGTCTTTGTCTCCAGGGGAAAGAGCCACCCTCTCCTGCAGG GCCAGTCCGAGTCTTGACAGCGCCTACTTAGCCTGGTACCAGCAGAAGCCTGGCCAGGCTCCCAGGCTCCTC ATCTATGGTGCATCCTCCAGGGTCACTGGCATCCCAGATAGGTTCAGTGGCAGTGCGTCAGGGACAGACTTC ACTCTCACCATCAGCAGACTGGAGCCTGAAGATTTTGCAGTGTACTACTGTCAGCGGTATGGTAACTCACCT CCGTACACTTTTGGCCAGGGGACCAAGGTGGAGATCAAA |
| Con2p4-d06k | 186 | GACATCGTGATGACCCAGTCTCCAGACTCCCTGGCTGTGTCTCTGGGCGAGAGGGCCACCATCAGCTGCAAG TCCAGCCAGAGTCTTTTATACAGTTCCAGCAATAAGAACTACCTAGCTTGGTTCCAGCAGAAACCAGGACAG GCTCCTAAGTTGCTCATTTACTGGGCATCTACCCGGGAATCCGGGGTCCCTGACCGATTCAGTGGCAGCGGG TCTGGGACAGATTTCACTCTCACCATCAGCAGCCTGCAGACTGAAGATGTGGCAGTTTATTATTGTCTGCAAT ATCGTAGTGCTCCGTTCACTTTCGGCGGAGGGACCAAGGTGGAGATCAAA |
| Con2p5-a06k | 187 | GACATCCAGATGACCCAGTCTCCTTCCACCCAGTCTGCATCTGTAGGAGACAGAGTCACCATCACTTGCCGG GCCAGTCAGAGTATTAGTAGTTGGTTGGCCTGGTATCAGCAGAAACCAGGGAAAGCCCCTAAGGTCCTGATC TATGCGGTGTCTAGTTTAGAAAGTGGGGTCCCATCAAGGTTCAGCGGCAGTGGATCTGGGACAGAATTCACT CTCACCATCAGCAGCCTGCAGCCTGAGGATTTTGCAACTTATTACTGCCAACTATATAGTACTTATCCCTGGA CGTTCGGCCCAGGGACCAAGGTGGAAATCAAA |
| Con2p5-b06k | 188 | GAAATAGTGATGACGCAGTCTCCAGCCTCCCTGTCTGTGTCTCCAGGGGAAACAGCCACCCTCTCCTGCAGG GCCAGTCAGAGTGTTGGCAGCACCTTAGCCTGGTACCAGCAGAAGCCCGGCCAGGCTCCCAGGCTCCTCATC TATAATGTATTCACCAGGGCCGCTGGTGTCCCAGCCAGGTTCAGTGGCAGTGGGTCTAGGACGGAGTTCACT CTCACCATCAGCAGCCTGCAGTCTGAAGATTTTGCAGTTTATTACTGTCAGCAGTATAGTACCTGGCTGTGGA CGTTCGGCCAAGGGACCAAGGTGGAAATCAAA |
| Con2p5-c04k | 189 | GACATCCAGATGACCCAGTCTCCATCCTCCCTGTCTGCATCTGTAGGAGACAGAGTCACCATCACTTGCCGG GCAAGTCAGCGCATTAGCAGCTACTTGAATTGGTATCAGCAGAAACCAGGGAAAGCCCCTAACCTCCTGATC TACGCTGCAGCCAGTTTGCATGATGGGGTCCCATCAAGGTTCAGTGGCAGTGGATCTGGGACAGATTTCACT CTCACCATCAGCAGTCTGCAACCTGAAGATTTTGCAACTTATTATTGTCAACAGCGTTACAGAATCCCGTACA GTTTTGGCCCGGGGACCAAGGTGGAGATCAAA |
| Con2p5-e05k | 190 | GATATTGTGATGACTCAGTCTCCACTCTCCCTGTCCGTCACCCCTGGAGAGCCGGCCTCCATCTCCTGCAGGT CTAGTCAGAGCCTCCTTCAGGGTAATGGACACAACTATTTGGATTGGTACCTGCAGAAGCCAGGACAGTCTC CACAACTCCTGATCTATTTGGGTTCTATTCGGGCCTCCGGGGTCCCTGACAGGTTCAGTGGCAGTGGATCAG GCACAGATTTTATACTGAAAATCAGCAGAGTGGAGGCTGAGGATGTTGGGGTTTATTACTGCATGCGAGCTC TACAAACTCCGTACACTTTTGGCCAGGGGACCAAGGTGGAAATCAAA |
| Con2p6-b03k | 191 | GACATCCAGATGACCCAGTCGCCTTCCACCCTGTCTGCATCTGTTGGAGACAGAGTCACCCTCACTTGTCGG GCCAGTGAGACTCTTAATAACTGGTTGGCCTGGTTTCAGCAAAAGCCAGGGAAAGCCCCTACCCTCCTGATC TATGAGGCGTCTAGTTTAGAAAGTGGAGTCCCATCAAGGTTCAGCGGCAGTGGATCTGGGACAGACTTCGCT CTCACCATCAGCAGCCTGCAGCCCGATGATTTTGCAACTTATTATTGCCACCAGTATAATAAATACCCGTGG ACGTTCGGCCAAGGGACCAAGGTGGAGATCAAA |
| Con2p6-c05k | 192 | GACATCCAGATGACCCAGTCTCCTTCCACCTTGTCTGCATCTGTAGGAGACAGAGTCACCATCACTTGTCGG GCCAGTCAGAGTATTAGTGGCTGGTTGGCCTGGTATCAGCAGAAAGCAGGGAAAGCCCCTAAGCTCCTGATC TATAAGGCGTCTAGTTTAGAAAGTGGGGTCCCATCAAGGTTCAGCGGCAGTGGATCTGGGACAGAGTTCACT CTCACCATCAGCAGCCTGCAGCCTGATGATTTTGCAACTTATTACTGCCAGCAGTATTATAGTTGGGGAACGT TCGGCCAAGGGACCAAGGTGGAGATCAAA |
| Con2p6-g04k | 193 | GATATTGTGATGACCCAGACTCCACTCTCCTTACCTGTCACCCTTGGACAGCCGGCCTCCATCTCCTGCATAT CTAGTCAAAGCCTCGTACACAGTGATGGAAACACCTACTTGAGTTGGCTTCAGCAGAGGCCAGGCCAGCCTC CAAGACTCCTGATTTATAAGATTTCTAACCGGTTCTCTGGGGTCCCAGACAGATTCAGTGGCAGTGGGGCAG GGACAGATTTCACACTGAAAATCAGCAGGGTGGAAGCTGAGGATGTCGGGGTTTATTACTGCATGCAAGCTT CACAATCTACGTGGACGCTCGGCCAAGGGACCAAGGTGGAGATCAAA |
| Con2p7-d03k | 194 | GACATCGTGATGACCCAGTCTCCAGACTCCCTGGCTGTGCCTCTGGGCGAGAGGGCCACCATCAACTGCACG TCCAGCCAGACTGTTTTATCCAGTTCCAACAATAAGAACTACTTAGTTTGGTACCAGCAGAAACCAGGACAG CCTCCTAAGTTGCTCCTTTACTGGGCGTCTACCCGGGCATCCGGGGTCCCTGACCGATTCAGTGGGAGCGGG |

TABLE 2-continued

Selected Heavy and Light Chain Sequences from Antibodies of Table 1 (SEQ ID NOS. 127-252)

| | Seq ID No: | |
|---|---|---|
| | | TCTGGGACAGATTTCACTCTCACCATTAGCAGTCTGCAGGCTGAAGATGTGGCAGTTTATTACTGTCAGCAAT<br>GTTATAATGCTCCGCTCACTTTCGGCCGAGGGACCAAGGTGGAGATCAAA |
| Con2p8-b01ka | 195 | GAAATAGTGATGACGCAGTCTCCAGCCACCCTGTCTGTGTTTCCAGGGGAAGGAGTCACCCTCTCCTGCAGG<br>GCCAGTCAGAGTATTAGCAACAACTTGGCCTGGTACCAGCAGAAACCTGGCCAGGCTCCCAGGCTCCTCATG<br>TATGATGCATCCACCAGGGCCACTGGTATCCCAGCCAGGTTCAGTGGCAGTGGGTCTGGGACAGAGTTCACT<br>CTCACCATCAGCAGCCTGCAGTCTGAAGATTTCGCAGTTTATTACTGTCAGCAGTATAATAACTGGCCTCCGG<br>TCACGTTCGGCCAAGGGACCAAGGTGGAAATCAAA |
| Con2p8-b05k | 196 | TTGTGATGACTCAGTCTCCACTCTCCCTGCCCGTCACCCTTGGACAGTCGGCCTCCGTCTCCTGCAGGTCAAG<br>TCAAAGCCTCGGCCCCAGTGACGGAAGCACCCGCTTGGATTGGTTTCAACAGAGGCCAGGCCAATCTCCAAG<br>GCGCCTAATTTATGCGGTTTCTAACCGGGACTCTGGGGTCCCAGACAGATTCAGCGGCAGCGGGTCAGGCAG<br>TGATTTCACACTGAGAATCAGCAGAGTGGAGGCTGAGGATGTTGGGGTTTATTACTGCATGCAATATACATA<br>CTGGCCTCACACTTTTGGCCAGGGGACCAAGGTGGAAATCAAA |
| Con2p8-e03k | 197 | GAAATTGTGTTGACACAGTCTCCAGCCACCCTGTCTTTGTCTCCAGGGGAAAGAGCCACCCTCTCCTGCAGG<br>GCCAGTCAGAGTGTTAGCAGTTCCTTAGCCTGGTACCAACAAAAACCTGGCCAGGCTCCCAGGCTCCTCATC<br>TATGATGCATCCAAGAGGGCCACTGACATCCCAGCCAGGTTCAGTGGCAGTGGGTCTGGGACAGACTTCACT<br>CTCACCATCAGCAGCCTAGAGCCTGAAGATTTTGCGGTTTATTACTGTCAGCACCGGGGGGAGTGGCCTCCG<br>GGGGCCACTTTCGGCCCTGGGACCAAAGTGGATATCAAA |
| Con2p8-f05k | 198 | GACATCCAGTTGACCCAGTCTCCATCCTTCCTGTCTGCATCTGTAGGAGACAGAGTCACCATCACTTGCCGGG<br>CCAGTCAGGGCATTGATACTCGTTTGATCTGGTATCAACAGAAGCCAGGGGAAGCCCCTAAGCTCCTGATCT<br>ATGAAGCATCCACTTTGCAAAGTGGGGCCCCATCAAGGTTCAGCGGCAGTGGATTCGGGACAGAATTCACTC<br>TCACAATCAGCAGTCTGCAGCCTGAAGACTTTGCAACTTATTACTGTCAACAGTTTAAAGGTTACCCGCTCAC<br>TTTCGGCGGGGGGACCAAGGTGGAGATCAAA |
| SLE1 Heavy | | |
| SLE1p1-a0211 | 199 | CAGGTGCAGCTGCAGGAGTCGGGCCCAGGACTGGTGAAGCCTTCGGAGACCCTGTCCCTCACCTGCACTGTC<br>TCTGGTGGCTCCATCAGTAGTCACTACTGGAGCTGGATCCGGCAGCCCCCAGCGAAGGGACTGGAGTGGATT<br>GGGTATATCTATCACAGTGGGATGACCAACTACAACCCCTCCCTCAAGAGTCGAGTCACCATATCAATAGAC<br>ACGTCCAAGAACCAGTTCTCCCTGAAGTTGAGCTCTGTGACCGCTGCGGACACGGCCGTGTATTACTGTGCG<br>AGAGGTGATGGCTACAATTTCTTCTGGGGCCAGGGAACGCTGGTCACCGTCTCCTCA |
| SLE1p1-a03h | 200 | CAGGTGCAGCTGGTGGAGTCTGGGGGAGGCGTGGTCCAGCCTGGGGGGTCCCTGAGACTCTCCTGTGCAGC<br>GTCTGGACTCACGTTCAGTAACCAAGATTTCCACTGGGTCCGCCAGGCTCCAGGCAAGGGGCTGGAATGGGT<br>GGCATTTATACGTTATGATGGAGGTTTTAAAAACTATGCAGACTCCGTGAAGGGCCGATTCACCATCTCCAG<br>AGACAATTCCCAGAAAATGCTGTATCTGCAAATGGACAGCCTGAGAGTTGAAGACACGGCTGTGTATTACTG<br>TGCGAAGTGCGGCGCAGAGGACTCTACTACTGTCTGGCTGAATTGGTTCGACCCCTGGGGCCAGGGAACCCT<br>GGTCACCGTCTCCTCA |
| SLE1p1-b05h | 201 | GAGGTGCAGCTGTTGGAGTCTGGGGGAGGCTTGGTAGAGCCTGGGGGGTCCCTGAGACTCTCCTGTGCAGCC<br>TCTGGATTCACCTTTAGCAGCTATGCCATGAGCTGGGTCCGCCAGGCTCCAGGGAAGGGGCTGGAGTGGGTC<br>TCAGCTATTAGTGACAGTGGTGGTAGCACATACTACGCAGACTCCGTGAAGGGCCGGTTCACCATCTCCAGA<br>GACAAGTCCAAGAACACGCTGTATCTGCAAATGAACAGCCTGAGAGCCGAGGACACGGCCGTATATTACTG<br>TGCGAAACCGAATTACTTTGGTTCGGGGAGTCCCGACTACTGGGGCCAGGGAACGCTGGTCACCGTCTCCTC<br>A |
| SLE1p1-c04h | 202 | CAGGTCCAGCTGCAGGAGTCGGGCCCAGGACTGGTGAAGCCTTCGGAGACCCTGTCCCTCACCTGCACTGTC<br>TCTGGTGCCTCCATCAGTAGTCACTACTGGAGCTGGATCCGGCAGCCCCCAGGGAAGGGACTGGAGTGGATT<br>GGGTATATCTATCACAGTGGGATTACCAACTACAACCCCTCCCTCAAGAGTCGAGTCACCATATCAATAGAC<br>ACGTCCAAGAACCAGTACTCCCTGAAGCTGAGCTCTGTGACCGCTGCGGACACGGCCGTGTATTACTGTGCG<br>AGAGGTGATGGCTACAATTTCTACTGGGGCCAGGGAACGCTGGTCACCGTCTCCTCA |
| SLE1p1-e01h | 203 | GAGGTGCAGCTGGTGGAGTCTGGGGGAGGTGTGGTACGGCCTGGGGGGTCCCTGAGACTCTCCTGTGCAGC<br>CTCTGGATTCACCTTTGATGATTATGGCATGACCTGGGTCCGCCAAGCTCCAGGGAAGGGGCTGGAGTGGAT<br>CTCTGGTATTTGTTGCAACGGTGGTTGCTCAGGTTATGCAGACTCTGTGAAGGGCCGATTCACCATCTCCAGA<br>GACAACGCCAAGAAGTCCCTGTTTCTGGTCATGAACAGTCTGAGAGCCGAGGACACGGCCTTGTATTACTGT<br>GTGAGAGTGGCAGTACCAGCTGCTACATACACCCGAGGGAATGATGCTTTTGATATTTGGGGCCAAGGGAC<br>AATGGTCACCGTCTCTTCA |
| SLE1pl-f02h | 204 | GAGGTGCAGCTGGTGGAGTCTGGGGGAGGCTTGGTAGAGCCTGGGGGGTCCCTCAGACTCTCCTGTGCAGTC<br>TCTGGTTTCACTTTCACTGACGCCTGGATGACCTGGGTCCGCCAGGCTCCAGGGAAGGGGCTAGATTGGGTT<br>GGCCATGTAAAAAGTAAATATGATGGTGCGACAACAGAGTACGCTGCACCCGTGCAAGGCAGATTCACCAT<br>CTCAAGAGATGATTCAAAGAAGACAATATATCTGCAAATGAACAGCCTGAACACCGAGGACACAGGCGTCT<br>ATTTTTGTACCACAGCTCATGGCCCGGTGGGTGACCATTGGGGCCAGGGAACACTGGTCACCGTCTCCTCA |
| SLE1p1-g05h | 205 | GAGGTGCAGCTGGTGGAGTCTGGGGGAGGCTTGGTCCAGCCGGGGGGGTCCCTGAGACTCTCCTGTGCAGC<br>CTCTGGATTCAGCTTTGATACCTCTTGGATGACCTGGGTCCGCCAGGCTCCAGGGAAGGGGCTGGAGTGGGT<br>GGCCACCATAAACCAGGGTGGAAGTGACAAATACTATGGGACTCTGTGAAGGGCCGATTCACCATCTCCA |

TABLE 2-continued

Selected Heavy and Light Chain Sequences from Antibodies of Table 1 (SEQ ID NOS. 127-252)

| | Seq ID No: | |
|---|---|---|
| | | GAGACAACGCCAAGAACTCACTGTATCTGCAAATGAACAGCCTGCGAGCCGAGGACACGGCTGTATATTAC<br>TGTGCGAGAGCGGGCGGGTGTAGCTCTACCAGATGCCATACAACCCCGGGATTTGACTACTGGGGCCAGGG<br>AGCGCTGGTCACCGTCTCCTCA |
| SLE1p2-a02h | 206 | TGCAGCTGCAGGAGTCGGGCCCAGGACTGGTGAAGCCTTCGGAGACCCTGTCCCTCACCTGCACTGTCTCTG<br>GTAGCTCCATCAGCAGTAGTAGTTACTACTGGGGCTGGGTCCGCCAGTCCCCAGGGAAGGGACTGGAGTGG<br>ATTGGGAGTATCTATCACAGTGGGACCATCTACTACAACCCGTCCCTCAGGAGTCGAGTCACCATATCCGTA<br>GACACGTCCAAGAACCAGTTCTCCCTGAAGCTGAACTCTGTGACCGCCGCAGACACGGCTGTTTATTACTGT<br>GCGAGTCTTAGTGGCACAAATGCTTTTGATATCTGGGGCCAAGGGACAATGGTCACCGTCTCTTCA |
| SLE1p2-d04h | 207 | GAGGTGCAGCTGTTGGAGTCTGGGGGGGGCTTGGTACAGCCTGGGGGGTCCCTGAGACTCTCCTGTGCAGCC<br>TCTGGATTCACCTTTAGCAGCCATGACATGAGTTGGGTCCGCCTGGCTCCAGGGAAGGGGCCGGAGTGGGTC<br>TCAGCTCTTGGTGCTGGAGATGCTTGGACACACTACGCAAACTCCGTGAGGGGCCGGTTCACCATCTCCAGA<br>GACGATTCCAAGAACACGCTGTATCTGCAAATGAACAGCCTGAGAGCCGAAGACACGGCCGTGTATTTCTGT<br>GCGAAACCCCGTGGATACTCCTATGGCTACTTTGACTACTGGGGCCAAGGAACGCTGGTCACCGTCTCCTCA |
| sLE1p3-a02h | 208 | GAGGTGCAGCTGGTGGAGTCTGGGGGAGGCTTGGTCCAGCCTGGGGGGTCCCTGAGACTCTCCTGTGGAGCC<br>TCTGGATTCACCTTTAGTACCTATTGGATGACCTGGGTCCGCCAGGCTCCAGGGAAGGGCCTGGAGTGGGTG<br>GCCAATATAAACCAAGATGGAAGTGAGAAACAATATGTGGACTCTGTGAAGGGCCGATTCACCATCTCCAG<br>AGACAACGCCAAGAACTCACTGTATCTGCAGATGAACAGCCTGAGAGTCGAGGATACGGCTATTTATTACTG<br>TGCGAGACCCCCAGCTCGCCGACTTGACTACTGGGGCCAGGGATCGCTGGTCACCGTCTCCTCA |
| SLE1p3-a04h | 209 | GAGGTGCAGCTGGTGGAGTCCGGGGGAGGCTTAGTTCAGCCTGGGGGGTCCCTGAGACTCTCCTGTGCAGCC<br>TCTGAATTCACCTTCAGTGACTACTGGATGCACTGGGTCCGCCAAGCTCCAGGGAAGGGGCTGGTCTGGGTC<br>TCACGTATTAATACTGACGGGAGTACCACAACCTACGCGGACTCCGTGAAGGGCCGATTCACCATCTCCAGA<br>GACAACGCCAAGAACACGCTGTATCTACAAATGAACAGTCTGAGGGCCGAGGACACGGCTGTGTATTACTG<br>TGCAAGATCTAATGCGGGGCACGAAGCGTGGGGCCAGGGAACGCTGGTCACCGTCTCCTCA |
| SLE1p3-b03h | 210 | AGGTGCAGCTGGTGCAGTCTGGGGCTGAGGTGAAGAAGCCTGGGGCCTCAGTGAGGGTTTCCTGCAAGGCA<br>TCTGGATACACCTTCACCAACTACTGGATACACTGGGTGCGACAGGCCCCTGGACAAGGGCTTGAGTGGATG<br>GGAATGATCGCCCCTAAGGAAGGTTACACATTCTACGCACAGCAATTACAGGGCAGAGTCACCGTGACCAG<br>GGACACGTCGACGAGCGCGGTTTACATGGAGCTGAACAGCCTGAGATCTGAGGACACGGCCGTATATTTCTG<br>TGCGAGAGACATTCCCCACGCTAATTTGGACTATTGGGGCCAGGGGACGCTGGTCACCGTCTCCTCA |
| SLE1p3-c03h | 211 | GAGGTGCAGCTGTTGGAGTCTGGGGGAGGATTGGTACAGCCTGGGGGGTCCCTGAGACTCTCCTGTGCAGCC<br>TCTGGATTCACCTTTAGCGATTATACCATGAATTGGGCCCGCCAGGCTCCAGGGAAGGGGCTGGAGTGGGTC<br>TCAGCTATTAGAGAGAGTGGTGACAGCACATACTACGCAGACTCCGTGACGGGCCGGTTCACCATCTCCAGG<br>GACAATTCCAGAAACACACTTTATCTGCACATGAACAGCCTGAGAGCCGAGGACACGGCCATGTATTTTTGT<br>GTGAAAGACAGGGTGCCGCCGGGTGACGTGCCGGGTGACTTCTGGGGCCCGGGAACGCTGGTCACCGTCTC<br>CTCA |
| SLE1 Kappa | | |
| SLE1p1-a02k | 212 | GACATCCAGTTGACCCAGTCTCCATCCTTCCTGTCTGCATCTGTAGGAGACAGAGTCACCATCACTTGCCGGG<br>CCAGTCAGGACATGACCCATTCTTTAGCCTGGTATCAGCAAAAACCAGGGAAAGCCCCTAACCTCCTGATCT<br>ATAATGCATACACTTTGCAAAGTGGGGTCCCATCAAGGTTCAGCGGCAGTGGATCTGGGACAGAATTCACTC<br>TCACAATCAGCAGCCTGCAGCCTGAAGATTTTGCAACTTATTACTGTCAACAGATTAATAGTTACCCTCGAA<br>CTTTTGGCCAGGGGACCAAGGTGGAGATCAAA |
| SLE1p1-a03k | 213 | GAAATTGTGTTGACACAGTCTCCAGGCACCCTGTCTTTGTCTCCAGGGGAAAGAGCCACTCTCTCCTGCAGG<br>GCCAGTCAGAATATTGGCACCGCCTTAGCCTGGTACCAACAGAAACCTGGCCAGGCTCCCAGACTCATCATC<br>TATGAAACATCCAACAGGGCCACTGACGTCCCAGCCAGGTTCAGTGGCAGTGGGTCTGGGACAGACTTCACT<br>CTCACCATCAGCAGCCTGGAGCGTGAAGATTTTGCCCTTTATTACTGTCAACAGCGTGCCGACTGGCCGCTC<br>ACTTTCGGCGGAGGGACCAAGGTGGAGATCAAA |
| SLE1p1-b05k | 214 | GAAATTGTGTTGACACAGTCTCCAGCCACCCTGTCTTTGTCTCCAGGGGAAAGAGCCACCCTCTCCTGCAGG<br>GCCAGTCAGAGTGTTAGCAGCTACTTAGCCTGGTACCAACAGAGACCTGGCCAGGCTCCCAGGCTCGTCATC<br>TATGCTGCATCCAACAGGGCCACTGGCATCCCAGCCAGGTTCAGTGGCAGTGGGTCTGGGACAGACTTCACT<br>CTCACCATCAGCAGCCTAGAGCCTGAAGATTTTGCAGTTTATTACTGTCTGCAGTGTAGCAACTGGCCCATGT<br>ACACTTTTGGCCAGGGGACCAAGGTGGAGATCAAA |
| SLE1p1-c04k | 215 | GACATCCAGTTGACCCAGTCTCCATCCTTCCTGTCTGCATCTGTAGGGGACAGAGTCACCATCACTTGCCGGG<br>CCAGTCAGGACATTACCGATTCTTTAGCCTGGTATCAGCAAAAACCAGGGAAAGCCCCTAACCTCCTGATCT<br>ATACTGCATCCACTTTGCAAAGTGGGGTCCCATCAAGGTTCAGCGGCAGTGGATCTGGGACAGAATTCACTC<br>TCACAATCAGCAGCCTGCAGCCTGAAGATTTTACAACTTATTACTGTCAACAGATTAATAGTTACCCTCGAA<br>CTTTTGGCCAGGGGACCAAGGTGGAGATCAAA |
| SLE1p1-e01k | 216 | GACATCCAGATGACCCAGTCTCCATCCTCCCTGTCTGCATCTGTAGGAGACAGAGTCACCATCACTTGCCGG<br>GCAAGTCAGGGCATTAGAAATGATTTAGGCTGGTATCAGCAGAAACCAGGGAAAGCCCCTAAGCGCCTGAT<br>CTATGCTGCATCCAGTTTGCAAAGTGGGGTCCCATCAAGGTTCAGCGGCAGTGGATCTGGGACAGAATTCAC<br>TCTCACAATCAGCAGCCTGCAGCCTGAAGATTTTGCAAGTTATTACTGTCTACAGCATAGTAGTTTCCCGTGG<br>ACGTTCGGCCAGGGGACCAAGGTGGAAATCAAA |

TABLE 2-continued

| Selected Heavy and Light Chain Sequences from Antibodies of Table 1 (SEQ ID NOS. 127-252) | | |
|---|---|---|
| | Seq ID No: | |
| SLE1p1-f02k | 217 | GACATCGTGATGACCCAGTCTCCAGACTCCCTGGCTGTGTCTCTGGGCGAGAGGGCCGCCATCAACTGCAAG TCCAGCCAGAGTGTCTTAGACAGCTCCAACATGAAGAGGTACTTAGCCTGGTATCAGCTGAAAGCAGGACA GCCTCCTAGGTTGCTCATTTACTTGGCTTCCACCCGGGAATCCGGGGTCCCGGACCGATTCAGTGGCAGCGG GTCCGGGACAGATTTCAATCTCACTATCAGCAGCCTGCAGGCTGAAGATGTGGCAGTTTATTACTGTCAGCA ATATTATACAACCCCTTCGATCACCTTCGGCCAAGGGACACGACTGGAGATTAAA |
| SLE1p1-g05k | 218 | GACATCGTGATGACCCAGTCTCCAGACTCCCTGGCTGTGTCTCTGGGCGAGAGGGCCACCATCAACTGCAAG TCCAGCCAGAGTGTTTTATACAGCTCCAACAATAAGAACTACTTAGCTTGGTACCAGCAGAAACCAGGTCAG CCTCCTAAGATGCTCATTTACTGGGCATCTACCCGGGAGTCCGGGGTCCCTGACCGATTCAGTGGCAGCGGG TCTGGGACAGATTTCACTCTCACCATCAGCAGCCTGCAGGCTGAAGATGTGGCAGTTTATTACTGTCAGCAA TATTATACTACTCCTCCCATCACCTTCGGCCAAGGGACACGACTGGAGATTAAA |
| SLE1p2-a02k | 219 | GAAATTGTGTTGACACAGTCTCCAGCCACCCTGTCTTTGTCTCCAGGGGAAAGAGCCACCCTCTCCTGCAGG GCCAGTCAGAGTGTTAGTATCTACTTAGCCTGGTACCAACAGAAACCTGGCCAGGCTCCCAGGCTCCTCATC TATGATTCATCCAACAGGGCCACTGGCATCCCAGCCAGGTTCAGTGGCAGTGGGTCTGGGACAGACTTCACT CTCACCATCAGCAGCCTAGAGCCCGAAGATTTTGCGGTTTATTACTGTCAGCAGCGTAGCAGCGGGCGAACG TTCGGCCAAGGGACCAAGGTGGAGATCAAA |
| SLE1p2-d04k | 220 | GAAATTGTGTTGACGCAGTCTCCAGGCACCCTGTCTTTGTCTCCAGGGGAAAGAGCCACCCTCTCCTGCAGG GCCAGTCAGACTGTTACCAACAACTACTTAGCCTGGTACCAACACAAACCTGGCCTGGCGCCCAGGCTCCTC ATCTTTGATGCATCCATCAGGGCCACTGGCATCCCAGACAGGTTCAGTGGCAGTGGGTCTGGGGCAGACTTC ACTCTCACCATCAGCAGACTGGAGCCTGAAGATTTTACATTCTATTACTGTCAGCAATATGGTATTTCACCTC GAACTTTTGGCCAGGGGACCAAGGTGGAGATCAAA |
| SLE1p3-a02k | 221 | GATATTGTGATGACCCAGACTCCACTCTCTCTGTCCGTCACCCCTGGACAGCCGGCCTCCATCTCCTGCAAGT CTAGTCAGAGTCTCCTGGATAGTGATGGAAGGACCTATTTCTTTTGGTATTTGCAGAAGCCAGGCCAGTCTCC ACAACTCCTGATCTATGAAGTTTCCAACCGGTTCTCTGGAGTGCCAGATAGGTTCAGTGGCAGCGGGTCAGG GACAGATTTCACACTGAAAATCAGCCGGGTGGAGTCTGAAGATGTTGGGGTTTATTACTGCATGCAAGGTAC ACACCATCCGTGGACGTTCGGCCAAGGGACCAAGGTGGAAATCAAA |
| SLE1p3-a04k | 222 | GACATCGTGATGACCCAGTCTCCAGACTCCCTGGCTGTGTCTCTGGGCGAGAGGGCCACCGTCAACTGCAAG TCCAGCCAGAGTGTTTTATACAGCTCCAACAGTAAGAACTACTTAGCTTGGTACCAGCAGAAACCAGGACAG CCTCCTAAGCTGCTCATTTACTGGGCATCTACCCGGGAATCCGGGGTCCCTGACCGATTCAGTGGCAGCGGG TCTGGGACAGATTTCACTCTCACCATCAGCAGCCTGCAGGCTGAAGATGTGGCAGTGTATTACTGTCAGCAA TATTATAGTACTCCTCTCACTTTCGGCGGAGGGACCAAGGTGGAGATCAAAC |
| SLE1p3-b03k | 223 | GACATCCAGATGACCCAGTCTCCATCCTCCCTGTCTGCATCTGTGGGAGACAGAGTCACCATCACTTGCCGG GCAAGTCAGGGCATTGGGAATGATTTAGGCTGGTATCAGCATGAACCAGGGAAAGCCCCTAAGCGCCTGAT CTATGCAGCATCCAGTTTGCAAAGTGGGGTCCCATCGAGGTTCAGCGGCAGTGCATCTGGGACAGAATTCAC TCTCACAATCACCAGCCTGCAGCCTGAAGATTTTGCAACTTATTACTGTCTACAACATACTACTTTCCCGTGG ACGTTCGGCCAAGGGACCAAGGTGGAAATCAAAC |
| SLE1p3-c03k | 224 | GAAATTGTGTTGACACAGTCTCCAGCCACCCTGTCTTTGTCTCCAGGGGAAAGAGCCACCCTCTCCTGCAGG GCCAGTCAGAGTGTTGGCAGTCACTTCGCCTGGTACCAACAGAAACCTGGCCAGGCTCCCAGGCTCCTCATC TATGGTGCATCCAACAGGGCCCCTGGCATCCCACCTAGGTTCAGTGCCAGTGGATCTGGGACAGACTTCACT CTCACCATCAGCAGCCTAGAGCCTGAAGATTTTGCAATTTATTACTGICAACAGCGTAGGACCTGGCCTCCG CTAACCTTCGGCCAAGGGACACGACTGGAGATTAAAC |
| SLE2 Heavy | | |
| SLE2p1-a01h | 225 | GAGGTGCAGCTGGTGGAGTCTGGGGGAGGCTTGGTACAGCCTGGAGGGTCCCTGAGACTCTCCTGTGTAGCC TCTGGATTCAGTTTCAGTGGTCATGAAATGAACTGGGTCCGCCAGCCTCCAGGGAAGGGGCTGGAGTGGGTT TCACACATTGGCAGTGGTGGTGATTATATAGGTTACGCAGACTCTGTGAAGGGCCGATTCACCGTCTCTAGA GACAACGCCAAGAATTTACTCTATCTGCAAATGAACAGCCTGAGAGCCGACGACACGGCTGTTTATTACTGT GCGACCTTGCTTTTGCGAGACAACCAACTGGACGTCTGGGGCCAAGGGACCACGGTCACCGTCTCCTCA |
| SLE2p1-a06h | 226 | CAGGTGCAGCTGGTGGAGTCTGGGGGAGGCGTGGTCCAGCCAGGGAGGTCCCTAAGACTCTCCTGTGCAGC CTCTGGATTCACCCTCAGTAGTTGTGGCATGCACTGGATCCGCCAGGCTCCAGGCAAGGGGCTGGAGTGGGT GGCAGTTATAACATATGATGGACGAAGTCACTTCAACGCAGACGCCGTGAAGGGCCGATTCACCATCTCCAG AGACAGATCCATGAACACGGTGTCTCTGCAAATGGACAGCCTGAGACCCGAGGACACGGCTGTTTATTACTG TGTCAAAGAACAAGGCTTTGGTTACTACCGGACCGCCGACTACTGGGGCCAGGGAACCCTGGTCACCGTCTC CTCA |
| SLE2p1-b01h | 227 | CAGGTGCAGCTGCAGGAGTCGGGCCCAGGACTGGTGAGGCCTTCGGAGACCCTGTCCCTCACCTGCACTGTC TCTGGTGGCTCCATCAGTAGTGACCACTGGAGTTGGATCCGGCAGCCCCCAGGCAAGGGACTGGAGTGGATT GGGAATGTCTATTACAGTGGGCGCACCTACTACAACCCCTCCTTCAAGAGTCGAGTCACCATATCAGTAGCC ACGTCCAAGAACCAGTTCTCCCTGAAGGTGACCTCTGTGACCGCCGCAGACACGGCCATTTATTACTGTGCG AGGCGAAATGATTTTAATATCTGGGGCCAGGGGACAATGGTCACCGTCTCTTCA |
| SLE2p1-c03h | 228 | GAGGTGCAGCTGTTGGAGTCTGGGGGAGGCTTGGTACAGCCTGGGGGGTCCCTGAGACTCTCCTGTGCAGCC TCTGGATTCACCTTTAGTAAATATGCCGTGAGCTGGGTCCGCCAGGCTCCAGGGAAGGGGCTGGAGTGGGTC TCAGCTGTCAGTGGTAATGGTGACTCCACATACTACGCAGACCCCGTGAGGGGCCGGTTCACCATCTCCAGA |

TABLE 2-continued

Selected Heavy and Light Chain Sequences from Antibodies of Table 1 (SEQ ID NOS. 127-252)

| | Seq ID No: | |
|---|---|---|
| | | GACAATTCCAAGAACACCCTGTATCTGCAAATGAACAGCCTGAGAGCCGAGGACACGGCCCTATATTACTGT<br>TCGATCTGGTGGGGACTTCAGTACAGTACCCATTGGTGCTCGACTACTGGGGCCTGGGAACCCTGGTCACC<br>GTCTCCTCA |
| SLE2p1-c04h | 229 | CAGGTGCAGCTGGTGGAGTCGGGGGGAGGCGTGGTCCAGCCTGGGAGGTCCCTAAGACTCCTGTGTGCAGC<br>CTCTGGATTCACCCTCAGTACTTGTGGCATGCACTGGATCCGCCAGACTCCTGGCAAGGGGCTGGAGTGGGT<br>GGCAGTTAAAACATATGACGGAAGAGAGGAGTTCTACGCAGACTCCGTGAAGGGCCGATTCACCATTTCCA<br>GAGACGAGTCCATGAACACGCTGTCTTTGCAGATGAACAGCCTGAGACCTGAAGACACGGCTGTATATTACT<br>GTGTCAAAGAACAAGACTACGGTTACTACCGGACCGCCGACCACTGGGGCCAGGGAACCCTGGTCACCGTC<br>TCCTCA |
| SLE2p1-d02h | 230 | CAGGTGCAGCTGCAGGAGGCGGGCCCAGGACTGGTGAAGCCTTCACAGACCCTGTCCCTCACCTGCACTGTC<br>TCTGGTGGCTCCATCAGCAGTGGTGGTTACTACTGGAGCTGGATCCGCCAGCACCCAGGGAAGGGCCTGGAG<br>TGGATTGGGTACATCTATTACAGTGGGAGCACCTACTACAACCCGTCCCTCAAGAGTCGAGTCACCATATCA<br>GTAGACACGTCCAAGAACCAGTATTCCCTGAAGCTGAGTTCTGTGACCGCCGCAGACACGGCCGTATATTAC<br>TGTGCGAGAGGGCATGGCTTCAACGCCTACTGGGGCCAGGGAACCCTGGTCACCGTCTCCTCA |
| SLE2p1-d04h | 231 | GAGGTGCAGCTGGTGGAGTCCGGGGGAGGCTTGGTAAAGCCGGGGGAGTCCCTTAGACTCTCGTGTGCAAC<br>CTCTGGAGTCAACTTCAACATCGCCTGGATGACCTGGGTCCGCCAGGCTCCAGGGAAGGGACTGGAGTGGGT<br>TGGCCGTATTAAAAGCAAAATTGGTGGTGGGACAACAGACTATGCTGCACCCGTGAAAGGCAGATTCACCA<br>TGTCAATAGATGATTCAAAAAATACCCTATATCTGCAAATGAACAGCCTGAAAACCGAGGACACAGCCGTG<br>TATTATTGTACCACAGTCCGCAATATGGCCGACTTGTCCCTTAATCACTGGGGCCAGGGAACCCTGGTCACC<br>GTCTCCTCA |
| SLE2p2-a01h | 232 | GAGGTGCAGCTGGTGGAGTCTGGGGGAGGCTTGGTACAGCCTGGAGCGTCCCTGACACTGTCATGTGTAGTC<br>TCTGGATTCACCTTCATTGGCACTGAAATGACCTGGATTCGCCAGGCTCCAGGGAAGGGGCTGGAGGGACTT<br>TCGTACATCAGTGGGAGTGGCGGGACAACATACTACGCAGAGTCTGTGAGGGGCCGATTCACCATCTCCAG<br>AGACAACGCCAAGAAGTCACTGTTTCTGCAAATGACCAGCCTGACAGCCGAGGACACGGCTGTTTACTACTG<br>TGCGACAGGCAACCGGGGATCACTTCCTCGCCGCTGGGGCCAGGGAACCCTGGTCACCGTCTCCTCA |
| SLE2p2-c04h | 233 | GAGGTGCAGCTGGTGGAGTTTGGGGGAGGCTTGGTCCAGCCTGGGGGGTCCCTGAGACTCTCCTGTGTAGCC<br>TCTGGATTCACCTTTAGTTCCTCTTGGATGAGTTGGGTCCGCCAGGCTCCAGGGAAGGGGCTGGAGTGCGTG<br>GGCAACATAAAGCCGGATGCAAGTTTGGTGTCCTATGTGGACTCTGTGAAGGGCCGAGTCACCATCTCCAGA<br>GACAACGCCAAGAATTCACTGTTTCTGGATATGAGCAGCCTGAGAGTCGAGGACACGGCCGTCTACTACTGT<br>GTGAGAGACGGGTGGGACACCTTCTTTGACTCCTGGGGCCAGGGAACCCTGGTCACCGTCTCCTCA |
| SLE2p2-d03h | 234 | GAGGTGCAGCTGGTGGAGTCCGGGGGAGGCTTAGTTCAGCCGGGGGGGTCCCTGAGACTCTCCTGTGCAGC<br>CTCTGGATTCACCTTTAGTAACTACTGGATGAGGTGGGTCCGCCAATCTCCAGGGAAGGGGCTGGTGTGGGT<br>CTCACACATTAACCCTGATGGGAGTTTTACAAACTACGCGGACTCCGTGAAGGGCCGATTCACCATCTCCAG<br>AGACAACACCAAGAACACACTGTATCTGCAAATGAACAGTCTGAGAGCCGAGGACACGGCTGTGTATTACT<br>GTGTGAATTTTCAACTGGGGTGGGGCCAGGGAACCCTGGTCACCGTCTCCTCA |
| SLE2p2-e04h | 235 | CAGGTGCAGCTGGTGGAGTCTGGGGGAGGCGTAGTCCAGCCTGGGAGGTCCCTGAAACTCTCCTGTGCAGTC<br>GCTGGATTCACCTTCAGGACCTATGCTATGCACTGGGTCCGCCAGGCTCCAGGCAGGGGGCTGGAGTGGGTG<br>GCACTTATATCAAATGATGGAACCAAAAAATACTCCGCAGACTCCGTGAGGGGCCACTTCACCATCTCCAGA<br>GACAATTCCAAGGACACGCTGTATCTGCAAATGAACAGCCTGCGACCTGACGACACGGCTGTCTATTACTGT<br>GCGAGAGCGGAGTATTGTAGTCCTGGTGACTGCTTCCTTATTGACACCTGGGGCCAGGGAACCCTGGTCACC<br>GTCTCCTCA |
| SLE2p2-f01h | 236 | CAGGTGCAGCTGGTGGAGTCTGGGGGAGGCGTGGTCCAGCCTGGGAGGTCCCTGAGACTCTCCTGTGCAGTG<br>TCTGGATTCACCTTCAGTAGATACGGCATGCACTGGGTCCGCCAGGCTCCAGGCAAGGGGCTGGAGTGGGTG<br>GTAGTTATATGGCATGATGGAAGTAATACATACTATGCAGACTCCGTGAAGGGCCGATTCACCATCTCCAGA<br>GACGACTCCAAGAACACGGTGTATCTGCAAATGAACAGCCTCAGAGTCGAGGACACGGCTATGTATTACTGT<br>CTGAGAGGCAACCCACCTAGCAGCCCCACCGACTACTGGGGCCAGGGAACCCTGGTCACCGTCTCCTCA |
| SLE2p2-g01h | 237 | GAGGTGCAGCTGTTGGAGTCTGGGGGAGGCTTGGTACAGCCTGGGGGGTCCCTGAGACTCTCCTGTGAAGTC<br>TCTGGATTCATCTTTAGCAACTATGCCATGACCTGGGTCCGCCAGGCTCCAGGGAAGGGGCTGCAGTGGGTC<br>TCAGCTATTGGCACTAGTGGTGGTGACACACACTACGCAGACTCCGTGAAGGGCCGGTTCACCATCTCCAGA<br>CACAATTCCCAGAACACCCTGTATCTGCAGATGAACAGCCTGAGAGCCGAGGACACGGCCATATATTACTGT<br>GCGAAAGTCGTTTATAGCAGGCCTCCTATGGACGTCTGGGGCCAAGGGACCACGGTCACCGTCTCCTCA |
| SLE2p2-g06h | 238 | GAGGTGCAGCTGGTGGAGTCTGGGGGAGGCTTGGTCCAGCCTGGGGGGTCCCTGAGACTCTCCTGTGCAGCC<br>TCTGGATTCACCTTTAGTAATCGTTGGATGAGTTGGGTCCGCCAGGCTCCAGGGAAGGGGCTGGAATGGGTG<br>GCCAACATAAACGAAGATGGAAGTCAGAAACACTATGTGGACTCTGTGAGGGGCCGATTCACCATCTCCAG<br>AGACAACGCCAAGAACTCACTGTCTCTGCAAATGGACAGCCTGAGAGTCGAGGATACGGCCGTGTATTATTG<br>CGCGAGAGCATCGAGGGAGACCGGTGAACCTTACTGGGGCCAGGGAACCCTGGTCACCGTCTCCTCA |
| SLE2 Kappa | | |
| SLE2p1-a01k | 239 | TTGTGATGACTCAGTCTCCACTCTCCCTGCCCGTCACCCTTGGACAGTCGGCCTCCATCTCCTGCAGGTCTAG<br>TCGAAGCCTCGTATTCAGTGAIGGAAACACCTACTTGAATTGGTTTCAGCAGAGGCCAGGCCGATCTCCAAG<br>GCGCCTAATTTATAAGGTTTCTAAGCGGGACTCTGGGGTCCCAGACAGATTCAGCGGCAGTGGGTCAGACAC |

TABLE 2-continued

| Selected Heavy and Light Chain Sequences from Antibodies of Table 1 (SEQ ID NOS. 127-252) | | |
|---|---|---|
| | Seq ID No: | |
| | | TGATTTCACACTGAAAATCAGCAGGGTGGAGGCTGAGGATGTTGGGGTTTATTACTGCATGCAAGGTACACA CTGGCGGACGTTCGGCCAAGGGACCAAGGTGGAGATCAAA |
| SLE2p1-a06k | 240 | GACATCCAGATGACCCAGTCTCCTTCCACACTGTCTGCATCTGTGGGAGACAGAGTCACCATCACTTGCCGG GCCAGTCAGAGTATTAATTCCTGGTTGGCCTGGTATCAGCGGAAACCAGGGAAAACCCCTAAACTCCTCATC TATGAGGCGTCCAGTTTAGAAAGTGGGGTCCCATCAAGGTTCAGCGGCAGTAGATCTGGGACAGAGTTCACC CTCACCATCAGCAGCCTGCAGGCTGATGATTTTGCAACTTATTACTGCCACCAGTATGATAAATATCCGTGG ACGTTCGGCCAAGGGACCAAGGTGGAGATCAAA |
| SLE2p1-b01k | 241 | GAAATTGTGTTGACGCAGTCTCCAGGCACCCTGTCTTTGTCTCCAGGGGAAAGAGCCACCCTCTCCTGCAGG GCCAGTCAGAGTGTGACCAACAACTATTTGGTCTGGCACCAGCAGAAACCTGGCCAGGCTCCCAGGCTCCTC ATTTCTGATGCATCCAACAGGGCCACTGGCATCCCAGACAGGTTCAGTGGCAGTGGGTCTGGGACAGACTTC ACTCTCACCATCAACAGACTGGAGCCTGAAGATTTCGCAGTGTATTACTGTCAGCAATACGGTAGCTCACCT TTCACTTTCGGCCCTGGGACCAAAGTGGATATCAAA |
| SLE2p1-c03k | 242 | GAAATAGTGATGACGCAGTCTCCAGCCACCCTGTCTGTGTCTCCAGGGGAAAGAGTCACCCTCTCCTGCAGG GCCAGTCAGAGTATTGGCAGCAGCTTAGCCTGGTACCTGCAGAAACCTGGCCAGGCTCCCAGAGTCCTCATC TATGGTGCATCCACCAGGACCCCTGGCACCCCAGCCAGGTTCAGTGGCAGTGGGTCTGGGACAGAGTTCACT CTCACCATCAGCAGCCTGCAGTCTGAAGATCTTGAGATTTATTATTGTCAACAGTATAGTAAGTGGCCTCCGA TCACCTTCGGCCAAGGGACACGACTGGAGATTAAA |
| SLE2p1-c04k | 243 | GACATCCAGATGACCCAGTCTCCCTCCATCCTGTCTGCATCTGTAGGAGACAGAGTCACCATCAATTGCCGG GCCAGTCAGAGTATTAATGCCTGGTTGGCCTGGTATCAGCAGAAACCAGGGAAAGCCCCTAAATTCCTAATT TATAAGGCGTCTAGTTTAGAAAGTGGGGTCTCGTCAAGGTTCAGCGGCAGTGGATCTGGGACAGAATTCACC CTCATCATCAGCAGCCTGCAGCCTGATGATTTTGCAACTTATTACTGCCAACAGTATGATAAATATCCGTGGA CGTTCGGCCGGGGGACCAAGGTGGAGATCAAA |
| SLE2p1-d02k | 244 | GAAATTGTGTTGACGCAGTCTCCAGGCACCCTGTCTTTCTCTCCAGGGGATAGAGCCACCCTCTCCTGCAGG GCCAGTCAGAGTGTTAGCAGCAGCTCCTTAGCCTGGTACCAGCAGAGACCTGGCCAGGCTCCCAGCCTCCTC ATCTATGGTGCATCCAGCAGGGCCACTGGCATCCCAGACAGGTTCAGTGGCAGTGGGTCTGGGACAGACTTC ACTCTCACCATCAGCAGACTGGAGCCTGAAGATTTTGCAGTGTATTACTGTCAGCAGTATGGTAACTCACCT CGGACGTTCGGCCAAGGGACCAAGGTGGAGATCAAA |
| SLE2p1-d04k | 245 | GAAATTGTGTTGACGCAGTCTCCAGGCACCCTGTCTTTGTCTCCAGGGGAAAGAGCCACCCTCTCCTGCAGG GCCAGTCAGAGTGTCAGCAGCACCTACTTAAACTGGTACCAGCAGAAGCCTGGCCAGGCTCCCAGGCTCCTC ATCTATGGTGCGTCCACCAGGGCCACTGGCATCCCAGACAGGTTCAGTGGCAGTGGGTCTGGGGCAGACTTC ACTCTAACCATCAGCAGACTGGAGCCTGAAGACTTTGCAGTGTACTACTGTCAGCAATATGATGACTCACGG TGGACGTTCGGCCAAGGGACCAAGGTGGAAATCAAA |
| SLE2p2-a01kb | 246 | GATATTGTGATGACTCAGTCTCCACTCTCCCTGCCCGTCACCCCTGGAGAGCCGGCCTCCATCTCCTGCAGGT CTGGTCAGAGCCTCCTGTATAGTGATGGAAACAACTATTTGGATTGGTATCTGCAGAAGCCAGGGCAGTCTC CACAGCTCCTGATCTATTTGGGTTCTAATCGGGCCTCCGGGGTCCCTGACAGGTTCAGTGGCAGTGAATCAG GCACAGATTTTACACTGAAAATCAGCAGAGTGGAGGCTGGGGATGTTGGGATTTATTACTGCATGCAAGCTC TACGAAGTCCGTACACTTTTGGCCAGGGGACCAAGGTGGAGATCAAA |
| SLE2p2-c04k | 247 | TTGTGATGACTCAGTCTCCACTCTCCCTGCCCGTCACCCTTGGACAGCCGGCCTCCATCTCCTGCAGGTCTAG TCAAAGCCCCGTATACAGTGATGGAAACACCTACCTGAATTGGTTTCAGCAGAGGCCAGGCCAATCTCCAAG GCGCCTAATTTATAAGGTTTCTAACCGGGACTCCGGGGTCCCAGACAGATTCAGCGGCAGTGGGTCAGGCAC TGATTTCACACTGAATATCAGCGGGGTGGAGGCTGAGGACGTTGGGGTTTATTACTGCATGCAAGGTAGATA CTGGCCGTACACTTTTGGCCAGGGGACCAAGGTGGAGATCAAA |
| STE2p2-d03k | 248 | GAAATTGTGTTGACGCAGTCTCCAGGCACCCTGTCTTTCTCTCCAGGGGATAGAGCCACCCTCTCCTGCAGG GCCAGTCAGAGTGTAAGCAGCAGCGCCTTAGCCTGGTACCAGCAGAAACCTGGCCAGGCTCCCAGCCTCCTC ATCTATGGTGCATCCAGCAGGGCCACTGGCATCCCAGACAGGTTCAGTGGCAGTGGGTCTGGGACAGACTTC ACTCTCACCATCAGCAGACTGGAGCCTGAAGATTTTGCAGTGTATTACTGTCAGCAGTATGGTAACTCACCT CGGACGTTCGGCCAAGGGACCAAGGTGGAAATCAAA |
| SLE2p2-e04k | 249 | TTGTGATGACTCAGTCTCCACTCTCCCTGCCCGTCACCCTTGGACAGTCGGCCTCCATCTCCTGCAGGTCTAG TCGAAGCCTCGTATTCAGTGATGGAAACACCTACTTGAATTGGTTTCAGCAGAGGCCAGGCCGATCTCCAAG GCGCCTAATTTATAAGGTTTCTAAGCGGGACTCTGGGGTCCCAGACAGATTCAGCGGCAGTGGGTCAGACAC TGATTTCACACTGAAAATCAGCAGGGTGGAGGCTGAGGATGTTGGGGTTTATTACTGCATGCAAGGTACACA CTGGCGGACGTTCGGCCAAGGGACCAAGGTGGAAATCAAAC |
| SLE2p2-f01k | 250 | GACATCCAGATGACCCAGTCTCCTTCCTCACTGTCTGCATCTGTAGGGGACAGAATCACCATCACTTGTCGG GCGAGTCAGGGCATTAACAATTATTTAGCCTGGTTTCAGCAGAAGCCAGGGAAAGCCCCTAAGACCCTGATC TACTCTACATCCACTTTGCAAAGTGGGGTCCCATCAAAGTTCAGCGGCAGTGGATCTGGGACAGTTTTCACT CTCACCATCAGCAACCTGCAGCCTGAAGATTTTGCAACTTATTACTGTCAACAATATAATAGTTACCCGCTCA CTTTCGGCGGAGGGACCAAGGTGGAGATCAAA |
| SLE2p2-g01k | 251 | GACATCCAGATGACCCAGTCTCCATCCTCCCTGTCTGCATCTGTAGGAGACAGAGTCACCATCACTTGCCGG GCAAGTCAGACCATTAGCAACTATTTAAATTGGTTTCAGCAGAAACCAGGGAAAGCCCCTAGGCTCCTGATC TATGCTGCATCGAGTTTGCAAAGTGGGGTCCCATCAAGGTTCAGTGGCAGTGGATCTGTGACAGATTTCACT |

TABLE 2-continued

| Selected Heavy and Light Chain Sequences from Antibodies of Table 1 (SEQ ID NOS. 127-252) | | |
|---|---|---|
| | Seq ID No: | |
| | | CTCACCATCAGCAGTCTGCAACCTGAAGATTTTGCAACTTACTTCTGTCAACAGAGTTACAGCACCCCGTGG ACGTTCGGCCAAGGGACCAAGGTGGAAATCAAA |
| SLE2p2-g06k | 252 | TTGTGATGACTCAGTCTCCATTCTCCCTGCCCGTCACCCTTGGACAGCCGGCCTCCATCTCCTGCAGGTCTAG TCAAAGCCTCGTATACAGTGATGGAAACACCTACTTGAATTGGTTTCAGCAGAGGCCAGGCCAATCTCCAAG GCGCCTGATTTATAAGCTTTCTAACCGGGACTCTGGGGTCCCAGACAGATTCAGCGGCAGTGGGTCAGGCAC TGATTTCACACTGAAAATCAGCAGGGTGGAGGCTGAGGATGTTGGGGTTTATTACTGCATGCAAGCTACACA CTGGCCTTGGACGTTCGGCCAAGGGACCAAGGTGGAAATCAAA |

Antibodies were also tested for binding against five common lupus autoantigens: Ro, La, Sm, nRNP, and cardiolipin. Antibodies which bound to at least two of these five antigens were classified as poly-reactive (whether or not they bind polysaccharide). FIG. 2C shows the percentage of poly-reactive antibodies from each donor. SLE2 shows a remarkable 52% of antibodies showing polyreactivity. Graphs similar to those in FIG. 2A, but highlighting cross-reactive or poly-reactive antibodies from each donor are shown in FIGS. 7A-B.

A small but significant percentage of anti-polysaccharide antibodies produced from ASCs bind to the polysaccharides of two distinct serotypes. Although most of the antibodies are serotype specific, 12% of the antibodies characterized bind two serotypes. Of the antibodies that bind two serotypes, one pair of polysaccharides, 9N and 9V, were dually bound by several antibodies. These two carbohydrates have very similar non-branched structures with one of four D-Glc in a 9N chain repeat being replaced by a D-Gal m 9V. Thus, it is not unexpected that some antibodies will cross-react with both serotypes. However, the inventor observed a wide variety of 9N and 9V binding antibodies, some of which cross-react and some that do not. For example, Con1p2D02 and SLE1p1E01 antibodies are mono-specific to 9N and 9V respectively (FIG. 3A), showing little to no cross-reactivity. Con1p4B03, however, binds to both serotypes, favoring 9N by an order of magnitude in affinity and by 5-times in avidity (FIG. 3B). One antibody to 9N, SLE1p1A03, does not bind to 9V, but rather cross-reacts to serotype 14 polysaccharide (FIG. 3C), with similar affinity and avidity, an observation which is difficult to explain examining only the carbohydrate sequence. Several of these cross-reacting antibodies are from the same donor, demonstrating a variety of antibodies to a certain serotype within a single individual. Serotypes 19A and 19F also have very similar structures with 19F having a D-Glc with a 1-2 linkage and 19A having a 1-3 linkage. The antibody SLE2p2D03 binds to both 19A and 19F with nearly equivalent affinities (FIG. 3D), although four-fold different avidities (favoring 19A).

The inventor also detected cross-reactivity between serotypes 15B and 14 (FIG. 4C), as well as 17F and 33F (FIGS. 4A and 4B). The antibody SLE2p1B01 slightly favors serotype 14 over serotype 15B in avidity, although not in affinity. While SLE2p2G06 and SLE2p2C04 are mono-specific for 17F and 33F respectively (FIG. 4A), SLE2p1C03 (from the same donor; FIG. 4B) cross-reacts to both serotypes with similar avidity. Overall, it is evident that although serum may cross-react between two serotypes, 85% of the actual antibodies making up this response are specific to only one polysaccharide. The inventor encountered no antibodies that reacted with more than two serotypes with a measureable affinity/avidity.

A high frequency of somatic hypermutation in these antibodies indicates frequent anamnestic anti-polysaccharide responses. As previously reported, the ASC recall response to the influenza vaccine is highly mutated, even more so than in the typical IgG germinal center memory cell. The inventor hypothesized that this was due to the repeated nature of the annual vaccine, as well as frequent exposure to various influenza strains. The antibodies obtained in this study have a similar mutation frequency (see FIG. 5). This is particularly interesting because for each donor, this was a primary vaccination. If the donors were truly nave to these polysaccharide antigens, the ASC response would have been smaller and the sequences of the antibodies would show less mutation. Thus, this vaccine is producing an anamnestic response which can only arise from previous infection or exposure to *S. pneumoniae* strains.

Each donor displays a unique anamnestic fingerprint of antibody serotype specificities. Each of the four donors showed a remarkably different antibody response, as demonstrated by the number of antibodies produced against each serotype or cell wall polysaccharide (FIG. 6A, non-binding antibodies not shown; antibodies that cross-react are counted in the bin of the serotype with the strongest affinity). A response to certain serotypes seems to predominate in each donor. Donor Con1 shows a strong response to serotype 8 (six total antibodies, three of which are clonal), Con2 shows a strong response to serotype 18C (nine antibodies, all clonal), SLE1 and SLE2 both exhibit a strong response to serotype S (six antibodies, two of which are clonal and six antibodies, four of which are clonal, respectively). The inventor hypothesizes that this is due to an infection (clinically evident or not) by that serotype at some point in that donor's lifetime.

The inventor's previous study of the immune response to influenza vaccination (Wrammert et al., 2008) highlighted, the strong clonality of the ASC response to that vaccine, and this is also the case after immunization with Pneumovax®23. Thus, several of the antibodies the inventor characterized are clonally related, but show very similar binding characteristics (see Table 1 to compare affinities). When displaying all four donors on a single histogram graph and reducing clonally related antibodies to a count of 1 (FIG. 6B), it is quite evident that the hmAbs isolated from each donor create a unique fingerprint with three donors binding 9V, 15B, 17F, and only serotypes 8 and 33F being bound by all four donors. Also, no subject in the study produced an antibody that bound to serotypes 7F, 10A, or 12F. Although it is difficult to mathematically show that the histograms from each donor are unique, the inventor is confident that producing 44 antibodies from Con2 gives a representative distribution of the serotypes to which this individual is having an anamnestic response and that this differs from donor to donor.

Example 3—Discussion

This is the first comprehensive analysis of the human immune response to Pneumovax®23 immunization, on a per antibody basis, utilizing antibody secreting cells (ASCs) that emerge seven days post vaccination as a source for the production of monoclonal antibodies. An analysis of these polysaccharide specific monoclonal antibodies allowed a detailed study of the human antibody repertoire to this vaccine. It also provided insight into the specificities of each antibody and surprisingly revealed an "anamnestic fingerprint" that the inventor interprets to reflect the prior infection history of each participant.

In an earlier study (Wrammert et al., 2008), the inventor found that the magnitude of the anamnestic response after influenza vaccination was such that an average of 6% of total B cells were ASCs, yet some donors made poor to non-existent responses. Using these same techniques, some vaccines (notably Anthrax AVA) routinely result in a very poor induction of a protective response (Crowe et al., 2010). Here, the inventor reports that Pneumovax®23 invoked a two- to four-fold more robust response than the strongest responses induced in some of the influenza donors, suggesting that these polysaccharides are exceptionally efficient at triggering a memory response. Earlier studies (2-4) also detected antibody secreting cells seven days post vaccination with both the polysaccharide and conjugate vaccines, averaging over 100 serotype specific cells per million PBMCs. The inventor's own ELISpot results were similar to these previous reports (data not shown), but the overall magnitude of the IgG ASC response as determined by flow cytometry was still surprising. Interestingly, one of the SLE donors, SLE2 also participated in the previous influenza study and did not make a response to the influenza vaccine, yet produced an impressive ASC response to the polysaccharide vaccine. This provides a direct comparison, albeit with a small sample size, of the vast difference in potential immune response to vaccines, especially in immunocompromised individuals.

There are several interesting differences in this study between the SLE donors and healthy controls. As discussed above, the percentage of ASCs that arose from the vaccination was considerably smaller in SLE1 and SLE2 (8.8% on average, as compared to 23.8% for Con1 and Con2). Although the percentage of high affinity antibodies generated from these donors was not different, the antibodies generated from SLE2 do appear to be quite poly-reactive against non-carbohydrate antigens. It is also important to note that three of the four cross-reactive antibodies from SLE2 are also poly-reactive (see FIGS. 7A-B). It is remarkable that although they bind to multiple self-antigens, they are still specific for only one or two polysaccharide structures. These results likely indicate a defect in B cell tolerance in this donor which is allowing cross- and poly-reactive B cells, which would otherwise be deleted or anergized, to mature and secrete antibody. Although it is unknown if this manner of poly-reactive antibody has physiological effects, it is likely that any vaccination in this individual will result such poly-reactive antibodies.

This study has greatly increased the number of reported human monoclonal antibodies to *S. pneumoniae* that have been characterized both in terms of binding and repertoire usage. These anti-polysaccharide antibodies are as highly mutated as antibodies which arise from repeated seasonal influenza vaccination. In comparing V gene usage in these antibodies to the previous reports, the inventor observes similar trends. For example, Baxendale (Baxendale and Goldblatt, 2006; Baxendale et al., 2000) suggests that VH3-48 likely contributes to an antigen binding domain that prefers epitopes from serotypes 23F and 18C, as the two VH3-48 family antibodies they characterized bound those two serotypes and Zhou found VH3-48 in the 23F study (Zhou et al., 2002), but not the 6B study (Zhou et al., 2004). Similarly, three of four VH3-48 antibodies (Table 1) characterized in this study also bind these two serotypes. The inventor have also characterized a VH3-48 which binds serotype 2 (Con2p5E05), a case of a VH3-48 binding a different serotype. They have also observed remarkable similarity in the antibodies characterized which bind cell wall polysaccharide (CWPS). Comparing two unique donors, these antibodies use either VH3-30 or closely related VH3-33. The CDR3s even show remarkable similarity, (Con2p6B03, VKESATGWYRTADY (SEQ ID NO:57); Con2p5A06, VKEYSWGYYRTADY (SEQ ID NO:49); SLE2p1A06, VKEQGFGYYRTADY (SEQ ID NO:101); SLE2p1C04, VKEQDYGYYRTADH (SEQ ID NO:107)). Thus, the chemical simplicity of repeated polysaccharide sequences seems to induce similar V gene firmly usage even in distinct individuals.

Although avidity has been shown to be an important correlate with protection (Anttila et al., 1999; Harris et al., 2007; Usinger and Lucas, 1999), thiocyanate ELISA is not commonly performed on monoclonal antibodies. The inventor utilizes it here because there are several complications in determining affinity by fitting simple ELISA curves. These include the magnified effects of small antibody concentration errors on affinities, uncertainty whether or not the antigen binding interaction is univalent or bivalent, and coating plates with large units of repeating epitopes. It is also possible that poly-reactive antibodies from SLE donors (and occasionally healthy controls) may interact with antigens outside of the binding site. All of these effects are minimized in the thiocyanate avidity ELISA system, FIGS. 3D and 4C both represent an antibody for which affinity and avidity ELISA binding measurements do not correlate. Both of these antibodies are from SLE2 and both antibodies are poly-reactive. The inventor is currently exploring interesting antibodies such as these in more detail, but in these cases, thiocyanate avidity is a more reliable measure of the antibody-carbohydrate interaction.

Serum cross-reactivity is typically determined by depleting the serum with a particular serotype carbohydrate and then observing binding of the serotypes still present in the serum. Soininen et al. (2000), for example, found remarkable cross-reactivity in the serum, especially in unvaccinated individuals. However, these assays require careful calibration, as well as pre-adsorption of CWPS and other polysaccharides to remove nonspecific reactivity, especially common in unvaccinated individuals (Marchese et al., 2006). Modern updates to this method, using microarray printing and reading technology (Pickering et al., 2007), for example, have greatly improved the reliability of these assays; yet until this study, one could not be definite whether observed cross-reactivity is due to actual cross-reactive individual antibodies, or the polyclonal nature of serum antibodies.

This study, focusing on cross-reactivity in monoclonal antibodies, has addressed such ambiguities. Park et al. (2009) describes cross-serotype monoclonal antibodies, deducing the common linear carbohydrate structure to which the antibodies were binding. Other reports (Baxendale et al., 2006; Baxendale et al., 2000; Zhou et al., 2004) do not specify cross-reactive antibodies, although those produced from Fab libraries were only panned with the serotype of interest. These experiments are the first, however, that characterize a large number of anti-pneumococcal human monoclonal antibodies, and although most of the antibodies are serotype specific, 15% were not. Unlike the above report, explaining the cross-reactivity of several of the monoclonal antibodies the inventor characterized is clearly not as simple as finding similar primary polysaccharide structures. While 9N/9V and 19A/19F are quite similar, 17F and 33F, and 14 and 15B do not have similar primary structures. Pickering et al. (2007), found that 9V could inhibit 9N binding, 15B inhibited 14 binding, 19F strongly inhibited 19A binding and 33F strongly inhibited 17F binding, all matching the observed results (FIGS. 3A-D and 4A-C). Interestingly, the converse is not typically the case (14 does not inhibit 15B and 17F does not inhibit 33F), but this is likely an affinity issue. Using these results to illustrate this, it is unlikely that Con1p4B03 binding to 9N could be inhibited by adding 9V polysaccharide because its affinity for 9N is over an order of magnitude higher. Overall, the inventor can say with confidence that the serum cross-reactivity observed in these studies is indeed due to individual monoclonal antibodies that bind to at least two different serotypes.

The observation that each of the donors produced a unique panel of antibodies to each of the serotypes is quite interesting. One explanation of this phenomenon is that one is seeing an "anamnestic fingerprint," or that the memory response being observed is a product of the serotypes that each of the subjects had been exposed to in the past. It is difficult to approximate how many of the 23 strains someone has been exposed to up to the time when they receive the Pneumovax®23 vaccine. The four donors whose serum was carefully examined by Pickering et al. (2007) had appreciable IgG concentrations (higher than 1 μg/ml) for 5-12 of the 22 serotypes (the samples were depleted with CWPS and 22F) indicating active plasma cells and subsequently previous exposure to those serotypes. The donors here showed antibodies to just over an average of 11 (13, 13, 9, and 10) serotypes, matching the serology in this previous study. Thus, one is observing that antibodies from the reactivation of memory cells seven days after vaccination is similar to those observed in the sera, likely from long-lived plasma cells.

While the generation of these human monoclonal antibodies elucidates basic anamnestic response, it may also serve a therapeutic purpose. As many current treatments can become ineffective due to antibiotic resistance, it is important to consider passive immunotherapeutics that can safely target pathogens. Several previous reports (Casal et al., 2002; Yuste et al., 2002) have explored the effects of specific antibodies in a mouse sepsis model. Remarkably, administering hyperimmune serum after infection was able to reduce the amount of antibiotic required for the mouse to recover by eight-fold. In addition, this synergistic effect might be effectively used in treating difficult or invasive infections, such as empyema, as well as bacteremia in immunocompromised individuals. In addition to the myriad of treatment options of fully human monoclonal antibodies, the drastically decreased risk of anaphylactic shock and of anti-treatment immune responses suggests that they will become as important in infectious diseases as they are currently in autoimmune settings.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. References

The following references, to the extent that they provide exemplary procedural or other details supplementary to those set forth herein, are specifically incorporated herein by reference.

U.S. Pat. No. 2,653,899

U.S. Pat. No. 3,817,837

U.S. Pat. No. 3,850,752

U.S. Pat. No. 3,939,350

U.S. Pat. No. 3,996,345

U.S. Pat. No. 4,196,265

U.S. Pat. No. 4,275,149

U.S. Pat. No. 4,277,437

U.S. Pat. No. 4,366,241

U.S. Pat. No. 4,472,509

U.S. Pat. No. 4,554,101

U.S. Pat. No. 4,680,338

U.S. Pat. No. 4,816,567

U.S. Pat. No. 4,867,973

U.S. Pat. No. 4,938,948

U.S. Pat. No. 5,021,236

U.S. Pat. No. 5,141,648

U.S. Pat. No. 5,196,066

U.S. Pat. No. 5,563,250

U.S. Pat. No. 5,565,332

U.S. Pat. No. 5,856,456

U.S. Pat. No. 5,880,270

"Antibodies: A Laboratory Manual," Cold Spring Harbor Press, Cold Spring Harbor, N.Y., 1988.

Anttila et al., *Clin. Exp. Immunol.,* 118402-407, 1999.

Atherton et al., *Biol. of Reproduction,* 32:155-171, 1985,

Baxendale et al., *Eur. J. Immunol.,* 30:1214-1223, 2000.

Baxendale et al., *Infect. Immun.,* 74:1025-1031, 2006.

Campbell, *In: Monoclonal Antibody Technology, Laboratory Techniques in Biochemistry and Molecular Biology,* Vol. 13, Burden and Von Knippenberg, Eds. pp. 75-83, Amsterdam, Elsevier, 1984.

Capaldi et al., *Biochem. Biophys. Res. Comm.,* 74(2):425-433, 1977.

Casal et al., *Antimicrob. Agents Chemother.,* 46:1340-1344, 2002.

Chowdhry et al. *Arthritis Rheum.,* 52:2403-10, 2005.

Clutterbuck et al., *Immunol.,* 119:328-337, 2006,

Crowe et al., *J. Infect. Dis.,* 202:251-60, 2010.

De Jager et al., *Semin. Nucl. Med.* 23(2):165-179, 1993.

Dholakia et al., *J. Biol. Chem.,* 264:20638-20642, 1989.

Doolittle and Ben-Zeev, *Methods Mol. Biol.,* 109:215-237, 1999.

Elkayarn et al., *Autoimmunity,* 38:493-496, 2005.

Gefter et al., *Somatic Cell Genet.,* 3:231-236, 1977.
Goding, *In: Monoclonal Antibodies: Principles and Practice,* 2d ed., Orlando, Fla., Academic Press, 60-61, 65-66, 71-74, 1986.
Gulbis and Galand, *Hum. Pathol.* 24(12):1271-1285, 1993.
Harris et al., *Clin. Vacc. Immunol.,* 14:397-403, 2007.
Khatoon et al., *Ann. of Neuroloy,* 26:210-219, 1989.
King et al., *J. Biol. Chem.,* 269:10210-10218, 1989.
Kobasa et al, *Nature,* 445:319-323, 2007.
Kohler and Milstein, *Eur. J. Immunol.,* 6:511-519, 1976.
Kohler and Milstein, *Nature,* 256:495-497, 1975.
Kyte and Doolittle, *J. Mol. Biol.,* 157(1):105-132, 1982.
Lee et al., *J. Immunol.,* 133:2706-2711, 1984.
Marchese et al., *Clin. Vacc. Immunol.,* 13:905-912, 2006.
Morrison, *Science,* 229(4719):1202-1207, 1985.
Nakamura et al., *In: Enzyme Immunoassays: Heterogeneous and Homogeneous Systems*, Chapter 27, 1987.
Nieminen et al., *Vaccine,* 16:313-319, 1998.
Nieminen et al., *Vaccine,* 16:630-636, 1998.
O'Shannessy et al., *J. Immun. Meth.,* 99:153-161, 1987.
Owens and Haley, *J. Biol. Chem.,* 259:14843-14848, 1987.
Park et al., *Infect. Immun.,* 77:3374-3379, 2009.
Persic et al., *Gene,* 187(1):1-8, 1997.
Pickering et al., *Am. J. Clin. Pathol.,* 128:23-31, 2007.
Posner et al., *Hybridoma,* 6:611-625, 1987.
Potter and Haley, *Meth. Enzymol.,* 91:613-633, 1983.
Smith et al., *Nat. Probe.,* 4:372-384, 2009.
Soininen et al., *Clin. Diagn. Lab. Immunol.,* 7:468-476, 2000.
Tang et al., *J. Biol. Chem.,* 271:28324-28330, 1996.
Usinger et al., *Infect. Immun.,* 67:2366-2370, 1999,
Wawrzynczak & Thorpe, In: *Immunoconjugates, Antibody Conjugates In Radioimaging And Therapy Of Cancer*, Vogel (Ed.), New York, Oxford University Press, 28, 1987.
Wrammert et al., *Nature,* 453:667-671, 2008.
Xu et al., *Anal. Biochem.,* 336:262-272, 2005.
Yuste et al., *Clin. Exp. Immunol.,* 128:411-415, 2002.
Zhou et al., *Infect. Immun.,* 70:4083-4091, 2002.
Zhou et al., *Infect. Immun.,* 72:3505-3514, 2004.

SEQUENCE LISTING

```
<160> NUMBER OF SEQ ID NOS: 378

<210> SEQ ID NO 1
<211> LENGTH: 9
<212> TYPE: PRT
<213> ORGANISM: Streptococcus pneumoniae

<400> SEQUENCE: 1

Ala Lys Gly Val Thr Ser Phe Asp Tyr
1               5


<210> SEQ ID NO 2
<211> LENGTH: 10
<212> TYPE: PRT
<213> ORGANISM: Streptococcus pneumoniae

<400> SEQUENCE: 2

Gln Gln Phe Gly Ser Ser Pro Pro Asp Thr
1               5                   10


<210> SEQ ID NO 3
<211> LENGTH: 12
<212> TYPE: PRT
<213> ORGANISM: Streptococcus pneumoniae

<400> SEQUENCE: 3

Ala Arg Asp Pro Gly Ile Arg Asn Gly Met Gly Val
1               5                   10


<210> SEQ ID NO 4
<211> LENGTH: 9
<212> TYPE: PRT
<213> ORGANISM: Streptococcus pneumoniae

<400> SEQUENCE: 4

Met Gln Val Thr His Trp Pro Arg Thr
1               5


<210> SEQ ID NO 5
<211> LENGTH: 14
<212> TYPE: PRT
<213> ORGANISM: Streptococcus pneumoniae
```

<400> SEQUENCE: 5

Ala Lys Ala His Arg Gly Asp Trp Asn Asn Phe Phe Asp Tyr
1 5 10

<210> SEQ ID NO 6
<211> LENGTH: 9
<212> TYPE: PRT
<213> ORGANISM: Streptococcus pneumoniae

<400> SEQUENCE: 6

Gln Gln Ser Gly Asp Trp Pro Leu Thr
1 5

<210> SEQ ID NO 7
<211> LENGTH: 9
<212> TYPE: PRT
<213> ORGANISM: Streptococcus pneumoniae

<400> SEQUENCE: 7

Ala Arg Glu Trp Ser Gly Phe Asp Phe
1 5

<210> SEQ ID NO 8
<211> LENGTH: 9
<212> TYPE: PRT
<213> ORGANISM: Streptococcus pneumoniae

<400> SEQUENCE: 8

Gln Gln Tyr Gly Ser Leu Pro Arg Thr
1 5

<210> SEQ ID NO 9
<211> LENGTH: 8
<212> TYPE: PRT
<213> ORGANISM: Streptococcus pneumoniae

<400> SEQUENCE: 9

Ala Arg Gly Gln Trp Leu Ala Phe
1 5

<210> SEQ ID NO 10
<211> LENGTH: 9
<212> TYPE: PRT
<213> ORGANISM: Streptococcus pneumoniae

<400> SEQUENCE: 10

Met Gln Gly Thr His Trp Pro Tyr Thr
1 5

<210> SEQ ID NO 11
<211> LENGTH: 9
<212> TYPE: PRT
<213> ORGANISM: Streptococcus pneumoniae

<400> SEQUENCE: 11

Ala Arg Gly Arg Asn Asn Phe Arg His
1 5

<210> SEQ ID NO 12
<211> LENGTH: 9
<212> TYPE: PRT
<213> ORGANISM: Streptococcus pneumoniae

<400> SEQUENCE: 12

Gln Gln Phe Glu Ser Phe Pro Arg Thr
1 5

<210> SEQ ID NO 13
<211> LENGTH: 20
<212> TYPE: PRT
<213> ORGANISM: Streptococcus pneumoniae

<400> SEQUENCE: 13

Ala Arg Glu Leu Gly Val Phe His Ser Gly Gly Asp Gln Trp Leu Gly
1 5 10 15

Pro Leu Asp Cys
20

<210> SEQ ID NO 14
<211> LENGTH: 11
<212> TYPE: PRT
<213> ORGANISM: Streptococcus pneumoniae

<400> SEQUENCE: 14

His Gln Tyr Lys Asn Trp Pro Pro Met Gly Thr
1 5 10

<210> SEQ ID NO 15
<211> LENGTH: 11
<212> TYPE: PRT
<213> ORGANISM: Streptococcus pneumoniae

<400> SEQUENCE: 15

Arg Trp Thr Gly Gly Val Ser Phe Gly Ala Tyr
1 5 10

<210> SEQ ID NO 16
<211> LENGTH: 8
<212> TYPE: PRT
<213> ORGANISM: Streptococcus pneumoniae

<400> SEQUENCE: 16

Gln Gln Tyr Asp Ile Tyr Leu Thr
1 5

<210> SEQ ID NO 17
<211> LENGTH: 10
<212> TYPE: PRT
<213> ORGANISM: Streptococcus pneumoniae

<400> SEQUENCE: 17

Ala Arg Asp Tyr Tyr His Ser Val Asp Tyr
1 5 10

<210> SEQ ID NO 18
<211> LENGTH: 9
<212> TYPE: PRT
<213> ORGANISM: Streptococcus pneumoniae

<400> SEQUENCE: 18

Met Gln Gly Thr His Trp Pro Tyr Thr
1 5

<210> SEQ ID NO 19
<211> LENGTH: 11
<212> TYPE: PRT

<213> ORGANISM: Streptococcus pneumoniae

<400> SEQUENCE: 19

Ala Arg Gly Pro Asp Ala His Lys Thr Gly Tyr
1 5 10

<210> SEQ ID NO 20
<211> LENGTH: 9
<212> TYPE: PRT
<213> ORGANISM: Streptococcus pneumoniae

<400> SEQUENCE: 20

Gln Gln Tyr Ala Ala Thr Pro Trp Thr
1 5

<210> SEQ ID NO 21
<211> LENGTH: 10
<212> TYPE: PRT
<213> ORGANISM: Streptococcus pneumoniae

<400> SEQUENCE: 21

Ala Arg Asp Ser Tyr Thr Ser Pro Asp Tyr
1 5 10

<210> SEQ ID NO 22
<211> LENGTH: 9
<212> TYPE: PRT
<213> ORGANISM: Streptococcus pneumoniae

<400> SEQUENCE: 22

Met Gln Gly Ser His Trp Pro Leu Thr
1 5

<210> SEQ ID NO 23
<211> LENGTH: 11
<212> TYPE: PRT
<213> ORGANISM: Streptococcus pneumoniae

<400> SEQUENCE: 23

Thr Thr Asp Asn Gly Val Lys Ala Phe Asp Ile
1 5 10

<210> SEQ ID NO 24
<211> LENGTH: 9
<212> TYPE: PRT
<213> ORGANISM: Streptococcus pneumoniae

<400> SEQUENCE: 24

His Gln Tyr Tyr Thr Thr Pro Phe Ala
1 5

<210> SEQ ID NO 25
<211> LENGTH: 11
<212> TYPE: PRT
<213> ORGANISM: Streptococcus pneumoniae

<400> SEQUENCE: 25

Thr Arg Gly Gly Ser Gly Ala Thr Ile Asn Tyr
1 5 10

<210> SEQ ID NO 26
<211> LENGTH: 9
<212> TYPE: PRT
<213> ORGANISM: Streptococcus pneumoniae

<400> SEQUENCE: 26

Gln Gln Ser His Ser Ser Pro Leu Thr
1 5

<210> SEQ ID NO 27
<211> LENGTH: 16
<212> TYPE: PRT
<213> ORGANISM: Streptococcus pneumoniae

<400> SEQUENCE: 27

Ala Arg Asp Arg Ala Gly Ile Asp Gly Tyr Asn Tyr Tyr Phe Asp Tyr
1 5 10 15

<210> SEQ ID NO 28
<211> LENGTH: 8
<212> TYPE: PRT
<213> ORGANISM: Streptococcus pneumoniae

<400> SEQUENCE: 28

Gln Gln Tyr Tyr Ser Phe Tyr Thr
1 5

<210> SEQ ID NO 29
<211> LENGTH: 13
<212> TYPE: PRT
<213> ORGANISM: Streptococcus pneumoniae

<400> SEQUENCE: 29

Ala Arg Glu Val Ala Ala Glu Gly Lys Ala Phe Asp Tyr
1 5 10

<210> SEQ ID NO 30
<211> LENGTH: 9
<212> TYPE: PRT
<213> ORGANISM: Streptococcus pneumoniae

<400> SEQUENCE: 30

Gln Gln Tyr Tyr Thr Pro Pro Leu Thr
1 5

<210> SEQ ID NO 31
<211> LENGTH: 9
<212> TYPE: PRT
<213> ORGANISM: Streptococcus pneumoniae

<400> SEQUENCE: 31

Ala Arg Gly Gln Ser Tyr Pro Gly Ile
1 5

<210> SEQ ID NO 32
<211> LENGTH: 9
<212> TYPE: PRT
<213> ORGANISM: Streptococcus pneumoniae

<400> SEQUENCE: 32

Gln Gln Tyr Asn Asn Trp Pro Arg Thr
1 5

<210> SEQ ID NO 33
<211> LENGTH: 15
<212> TYPE: PRT
<213> ORGANISM: Streptococcus pneumoniae

<400> SEQUENCE: 33

Ala Gly Arg Ala Tyr Ser Ser Gly Tyr Tyr Tyr Leu Ile Asp Tyr
1 5 10 15

<210> SEQ ID NO 34
<211> LENGTH: 9
<212> TYPE: PRT
<213> ORGANISM: Streptococcus pneumoniae

<400> SEQUENCE: 34

Gln His Tyr His Asn Trp Pro Pro Thr
1 5

<210> SEQ ID NO 35
<211> LENGTH: 15
<212> TYPE: PRT
<213> ORGANISM: Streptococcus pneumoniae

<400> SEQUENCE: 35

Ala Lys Gly Cys Ser Asn Gly Gly Asn Cys Phe Leu Ile Asp Tyr
1 5 10 15

<210> SEQ ID NO 36
<211> LENGTH: 9
<212> TYPE: PRT
<213> ORGANISM: Streptococcus pneumoniae

<400> SEQUENCE: 36

Gln Gln Tyr Tyr Asn Ala Pro Leu Thr
1 5

<210> SEQ ID NO 37
<211> LENGTH: 16
<212> TYPE: PRT
<213> ORGANISM: Streptococcus pneumoniae

<400> SEQUENCE: 37

Ala Lys Gly Gly Tyr Tyr Glu Ser Gly Thr Met Arg Ala Phe Asp Ile
1 5 10 15

<210> SEQ ID NO 38
<211> LENGTH: 9
<212> TYPE: PRT
<213> ORGANISM: Streptococcus pneumoniae

<400> SEQUENCE: 38

Gln Gln Arg Ser Asn Trp Pro Ala Thr
1 5

<210> SEQ ID NO 39
<211> LENGTH: 9
<212> TYPE: PRT
<213> ORGANISM: Streptococcus pneumoniae

<400> SEQUENCE: 39

Ala Arg Gly Glu Ser Asn Phe Arg Tyr
1 5

<210> SEQ ID NO 40
<211> LENGTH: 9
<212> TYPE: PRT
<213> ORGANISM: Streptococcus pneumoniae

<400> SEQUENCE: 40

Gln Gln Phe Val Ser Phe Pro Arg Thr
1 5

<210> SEQ ID NO 41
<211> LENGTH: 12
<212> TYPE: PRT
<213> ORGANISM: Streptococcus pneumoniae

<400> SEQUENCE: 41

Ala Arg Asp Ser Thr Ser Pro Ala Arg Phe Gly Tyr
1 5 10

<210> SEQ ID NO 42
<211> LENGTH: 11
<212> TYPE: PRT
<213> ORGANISM: Streptococcus pneumoniae

<400> SEQUENCE: 42

Gln His Tyr Gly Thr Ser Pro Pro Arg Tyr Thr
1 5 10

<210> SEQ ID NO 43
<211> LENGTH: 12
<212> TYPE: PRT
<213> ORGANISM: Streptococcus pneumoniae

<400> SEQUENCE: 43

Ala Thr Gly Gly Met Thr Ser Ser Trp Tyr Gly Tyr
1 5 10

<210> SEQ ID NO 44
<211> LENGTH: 9
<212> TYPE: PRT
<213> ORGANISM: Streptococcus pneumoniae

<400> SEQUENCE: 44

Gln Gln Tyr Tyr Ser Thr Pro Tyr Thr
1 5

<210> SEQ ID NO 45
<211> LENGTH: 18
<212> TYPE: PRT
<213> ORGANISM: Streptococcus pneumoniae

<400> SEQUENCE: 45

Ser Met Gly Pro Pro Tyr Cys Thr Gly Gly Ser Cys Tyr Ser Ala Cys
1 5 10 15

Asp Phe

<210> SEQ ID NO 46
<211> LENGTH: 10
<212> TYPE: PRT
<213> ORGANISM: Streptococcus pneumoniae

<400> SEQUENCE: 46

Gln Arg Tyr Gly Asn Ser Pro Pro Tyr Thr
1 5 10

<210> SEQ ID NO 47
<211> LENGTH: 15
<212> TYPE: PRT
<213> ORGANISM: Streptococcus pneumoniae

<400> SEQUENCE: 47

```
Thr Thr Asp Ile Gly Lys Gly Trp Tyr Thr His Tyr Pro Asp Leu
1               5                   10                  15
```

<210> SEQ ID NO 48
<211> LENGTH: 9
<212> TYPE: PRT
<213> ORGANISM: Streptococcus pneumoniae

<400> SEQUENCE: 48

```
Leu Gln Tyr Arg Ser Ala Pro Phe Thr
1               5
```

<210> SEQ ID NO 49
<211> LENGTH: 14
<212> TYPE: PRT
<213> ORGANISM: Streptococcus pneumoniae

<400> SEQUENCE: 49

```
Val Lys Glu Tyr Ser Trp Gly Tyr Tyr Arg Thr Ala Asp Tyr
1               5                   10
```

<210> SEQ ID NO 50
<211> LENGTH: 9
<212> TYPE: PRT
<213> ORGANISM: Streptococcus pneumoniae

<400> SEQUENCE: 50

```
Gln Gln Tyr Ser Thr Tyr Pro Trp Thr
1               5
```

<210> SEQ ID NO 51
<211> LENGTH: 10
<212> TYPE: PRT
<213> ORGANISM: Streptococcus pneumoniae

<400> SEQUENCE: 51

```
Ala Arg Ser Pro Gly Gly Tyr Phe Asp Tyr
1               5                   10
```

<210> SEQ ID NO 52
<211> LENGTH: 9
<212> TYPE: PRT
<213> ORGANISM: Streptococcus pneumoniae

<400> SEQUENCE: 52

```
Gln Gln Tyr Ser Thr Trp Leu Trp Thr
1               5
```

<210> SEQ ID NO 53
<211> LENGTH: 7
<212> TYPE: PRT
<213> ORGANISM: Streptococcus pneumoniae

<400> SEQUENCE: 53

```
Thr Thr Asp Asp Leu Lys Asn
1               5
```

<210> SEQ ID NO 54
<211> LENGTH: 9
<212> TYPE: PRT
<213> ORGANISM: Streptococcus pneumoniae

<400> SEQUENCE: 54

Gln Gln Arg Tyr Arg Ile Pro Tyr Ser
1 5

<210> SEQ ID NO 55
<211> LENGTH: 22
<212> TYPE: PRT
<213> ORGANISM: Streptococcus pneumoniae

<400> SEQUENCE: 55

Ala Arg Gly Arg Asp Cys Tyr Gly Gly Asn Cys Val Ile Tyr Phe His
1 5 10 15

Tyr Tyr Gly Leu Asp Val
20

<210> SEQ ID NO 56
<211> LENGTH: 9
<212> TYPE: PRT
<213> ORGANISM: Streptococcus pneumoniae

<400> SEQUENCE: 56

Met Arg Ala Leu Gln Thr Pro Tyr Thr
1 5

<210> SEQ ID NO 57
<211> LENGTH: 14
<212> TYPE: PRT
<213> ORGANISM: Streptococcus pneumoniae

<400> SEQUENCE: 57

Val Lys Glu Ser Ala Thr Gly Trp Tyr Arg Thr Ala Asp Tyr
1 5 10

<210> SEQ ID NO 58
<211> LENGTH: 9
<212> TYPE: PRT
<213> ORGANISM: Streptococcus pneumoniae

<400> SEQUENCE: 58

His Gln Tyr Asn Lys Tyr Pro Trp Thr
1 5

<210> SEQ ID NO 59
<211> LENGTH: 16
<212> TYPE: PRT
<213> ORGANISM: Streptococcus pneumoniae

<400> SEQUENCE: 59

Ala Arg Asp Ile Pro Thr Thr Phe Gly Ile Gly Glu Ala Phe Asp Ile
1 5 10 15

<210> SEQ ID NO 60
<211> LENGTH: 8
<212> TYPE: PRT
<213> ORGANISM: Streptococcus pneumoniae

<400> SEQUENCE: 60

Gln Gln Tyr Tyr Ser Trp Gly Thr
1 5

<210> SEQ ID NO 61
<211> LENGTH: 9
<212> TYPE: PRT

<213> ORGANISM: Streptococcus pneumoniae

<400> SEQUENCE: 61

Ala Arg Asp Asp Ser Ala Phe Asp Tyr
1 5

<210> SEQ ID NO 62
<211> LENGTH: 9
<212> TYPE: PRT
<213> ORGANISM: Streptococcus pneumoniae

<400> SEQUENCE: 62

Met Gln Ala Ser Gln Ser Thr Trp Thr
1 5

<210> SEQ ID NO 63
<211> LENGTH: 14
<212> TYPE: PRT
<213> ORGANISM: Streptococcus pneumoniae

<400> SEQUENCE: 63

Ala Lys Gly Cys Ser Gly Glu Asn Cys Phe Tyr Met Asp Asp
1 5 10

<210> SEQ ID NO 64
<211> LENGTH: 9
<212> TYPE: PRT
<213> ORGANISM: Streptococcus pneumoniae

<400> SEQUENCE: 64

Gln Gln Cys Tyr Asn Ala Pro Leu Thr
1 5

<210> SEQ ID NO 65
<211> LENGTH: 22
<212> TYPE: PRT
<213> ORGANISM: Streptococcus pneumoniae

<400> SEQUENCE: 65

Thr Arg Glu Ile Gly Ala Val Val Val Asp Ala Thr Ser Leu Gly Trp
1 5 10 15

Leu Gly Tyr Phe Asp Tyr
20

<210> SEQ ID NO 66
<211> LENGTH: 10
<212> TYPE: PRT
<213> ORGANISM: Streptococcus pneumoniae

<400> SEQUENCE: 66

Gln Gln Tyr Asn Asn Trp Pro Pro Val Thr
1 5 10

<210> SEQ ID NO 67
<211> LENGTH: 8
<212> TYPE: PRT
<213> ORGANISM: Streptococcus pneumoniae

<400> SEQUENCE: 67

Ala Gly Trp Gly Arg Thr Gln Asp
1 5

<210> SEQ ID NO 68
<211> LENGTH: 9

<212> TYPE: PRT
<213> ORGANISM: Streptococcus pneumoniae

<400> SEQUENCE: 68

Met Gln Tyr Thr Phe Trp Pro His Thr
1 5

<210> SEQ ID NO 69
<211> LENGTH: 14
<212> TYPE: PRT
<213> ORGANISM: Streptococcus pneumoniae

<400> SEQUENCE: 69

Thr Lys Glu Gly Ala Pro Pro Gly Lys Tyr Ala Phe Asp Ile
1 5 10

<210> SEQ ID NO 70
<211> LENGTH: 11
<212> TYPE: PRT
<213> ORGANISM: Streptococcus pneumoniae

<400> SEQUENCE: 70

Gln His Arg Gly Glu Trp Pro Pro Gly Ala Thr
1 5 10

<210> SEQ ID NO 71
<211> LENGTH: 11
<212> TYPE: PRT
<213> ORGANISM: Streptococcus pneumoniae

<400> SEQUENCE: 71

Leu Lys Asp Ser Ser Gln Tyr Ser Phe Asp Ala
1 5 10

<210> SEQ ID NO 72
<211> LENGTH: 9
<212> TYPE: PRT
<213> ORGANISM: Streptococcus pneumoniae

<400> SEQUENCE: 72

Gln Gln Phe Lys Gly Tyr Pro Leu Thr
1 5

<210> SEQ ID NO 73
<211> LENGTH: 9
<212> TYPE: PRT
<213> ORGANISM: Streptococcus pneumoniae

<400> SEQUENCE: 73

Ala Arg Gly Asp Gly Tyr Asn Phe Phe
1 5

<210> SEQ ID NO 74
<211> LENGTH: 9
<212> TYPE: PRT
<213> ORGANISM: Streptococcus pneumoniae

<400> SEQUENCE: 74

Gln Gln Ile Asn Ser Tyr Pro Arg Thr
1 5

<210> SEQ ID NO 75
<211> LENGTH: 18
<212> TYPE: PRT
<213> ORGANISM: Streptococcus pneumoniae

<400> SEQUENCE: 75

Ala Lys Cys Gly Ala Glu Asp Ser Thr Thr Val Trp Leu Asn Trp Phe
1 5 10 15

Asp Pro

<210> SEQ ID NO 76
<211> LENGTH: 9
<212> TYPE: PRT
<213> ORGANISM: Streptococcus pneumoniae

<400> SEQUENCE: 76

Gln Gln Arg Ala Asp Trp Pro Leu Thr
1 5

<210> SEQ ID NO 77
<211> LENGTH: 13
<212> TYPE: PRT
<213> ORGANISM: Streptococcus pneumoniae

<400> SEQUENCE: 77

Ala Lys Pro Asn Tyr Phe Gly Ser Gly Ser Pro Asp Tyr
1 5 10

<210> SEQ ID NO 78
<211> LENGTH: 10
<212> TYPE: PRT
<213> ORGANISM: Streptococcus pneumoniae

<400> SEQUENCE: 78

Leu Gln Cys Ser Asn Trp Pro Met Tyr Thr
1 5 10

<210> SEQ ID NO 79
<211> LENGTH: 14
<212> TYPE: PRT
<213> ORGANISM: Streptococcus pneumoniae

<400> SEQUENCE: 79

Val Lys Glu Gln Asp Tyr Gly Tyr Tyr Arg Thr Ala Asp His
1 5 10

<210> SEQ ID NO 80
<211> LENGTH: 9
<212> TYPE: PRT
<213> ORGANISM: Streptococcus pneumoniae

<400> SEQUENCE: 80

Gln Gln Tyr Asp Lys Tyr Pro Trp Thr
1 5

<210> SEQ ID NO 81
<211> LENGTH: 19
<212> TYPE: PRT
<213> ORGANISM: Streptococcus pneumoniae

<400> SEQUENCE: 81

Val Arg Val Ala Val Pro Ala Ala Thr Tyr Thr Arg Gly Asn Asp Ala
1 5 10 15

Phe Asp Ile

<210> SEQ ID NO 82
<211> LENGTH: 9

<212> TYPE: PRT
<213> ORGANISM: Streptococcus pneumoniae

<400> SEQUENCE: 82

Leu Gln His Ser Ser Phe Pro Trp Thr
1 5

<210> SEQ ID NO 83
<211> LENGTH: 10
<212> TYPE: PRT
<213> ORGANISM: Streptococcus pneumoniae

<400> SEQUENCE: 83

Thr Thr Ala His Gly Pro Val Gly Asp His
1 5 10

<210> SEQ ID NO 84
<211> LENGTH: 10
<212> TYPE: PRT
<213> ORGANISM: Streptococcus pneumoniae

<400> SEQUENCE: 84

Gln Gln Tyr Tyr Thr Thr Pro Ser Ile Thr
1 5 10

<210> SEQ ID NO 85
<211> LENGTH: 19
<212> TYPE: PRT
<213> ORGANISM: Streptococcus pneumoniae

<400> SEQUENCE: 85

Ala Arg Ala Gly Gly Cys Ser Ser Thr Arg Cys His Thr Thr Pro Gly
1 5 10 15

Phe Asp Tyr

<210> SEQ ID NO 86
<211> LENGTH: 10
<212> TYPE: PRT
<213> ORGANISM: Streptococcus pneumoniae

<400> SEQUENCE: 86

Gln Gln Tyr Tyr Thr Thr Pro Pro Ile Thr
1 5 10

<210> SEQ ID NO 87
<211> LENGTH: 11
<212> TYPE: PRT
<213> ORGANISM: Streptococcus pneumoniae

<400> SEQUENCE: 87

Ala Ser Leu Ser Gly Thr Asn Ala Phe Asp Ile
1 5 10

<210> SEQ ID NO 88
<211> LENGTH: 8
<212> TYPE: PRT
<213> ORGANISM: Streptococcus pneumoniae

<400> SEQUENCE: 88

Gln Gln Arg Ser Ser Gly Arg Thr
1 5

<210> SEQ ID NO 89
<211> LENGTH: 13

<212> TYPE: PRT
<213> ORGANISM: Streptococcus pneumoniae

<400> SEQUENCE: 89

Ala Lys Pro Arg Gly Tyr Ser Tyr Gly Tyr Phe Asp Tyr
1 5 10

<210> SEQ ID NO 90
<211> LENGTH: 9
<212> TYPE: PRT
<213> ORGANISM: Streptococcus pneumoniae

<400> SEQUENCE: 90

Gln Gln Tyr Gly Ile Ser Pro Arg Thr
1 5

<210> SEQ ID NO 91
<211> LENGTH: 9
<212> TYPE: PRT
<213> ORGANISM: Streptococcus pneumoniae

<400> SEQUENCE: 91

Ala Pro Pro Ala Arg Arg Leu Asp Tyr
1 5

<210> SEQ ID NO 92
<211> LENGTH: 9
<212> TYPE: PRT
<213> ORGANISM: Streptococcus pneumoniae

<400> SEQUENCE: 92

Met Gln Gly Thr His His Pro Trp Thr
1 5

<210> SEQ ID NO 93
<211> LENGTH: 9
<212> TYPE: PRT
<213> ORGANISM: Streptococcus pneumoniae

<400> SEQUENCE: 93

Ala Arg Ser Asn Ala Gly His Glu Ala
1 5

<210> SEQ ID NO 94
<211> LENGTH: 9
<212> TYPE: PRT
<213> ORGANISM: Streptococcus pneumoniae

<400> SEQUENCE: 94

Gln Gln Tyr Tyr Ser Thr Pro Leu Thr
1 5

<210> SEQ ID NO 95
<211> LENGTH: 11
<212> TYPE: PRT
<213> ORGANISM: Streptococcus pneumoniae

<400> SEQUENCE: 95

Ala Arg Asp Ile Pro His Ala Asn Leu Asp Tyr
1 5 10

<210> SEQ ID NO 96
<211> LENGTH: 9
<212> TYPE: PRT
<213> ORGANISM: Streptococcus pneumoniae

<400> SEQUENCE: 96

Leu Gln His Thr Thr Phe Pro Trp Thr
1 5

<210> SEQ ID NO 97
<211> LENGTH: 14
<212> TYPE: PRT
<213> ORGANISM: Streptococcus pneumoniae

<400> SEQUENCE: 97

Val Lys Asp Arg Val Pro Pro Gly Asp Val Pro Gly Asp Phe
1 5 10

<210> SEQ ID NO 98
<211> LENGTH: 10
<212> TYPE: PRT
<213> ORGANISM: Streptococcus pneumoniae

<400> SEQUENCE: 98

Gln Gln Arg Arg Thr Trp Pro Pro Leu Thr
1 5 10

<210> SEQ ID NO 99
<211> LENGTH: 12
<212> TYPE: PRT
<213> ORGANISM: Streptococcus pneumoniae

<400> SEQUENCE: 99

Ala Thr Leu Leu Leu Arg Asp Asn Gln Leu Asp Val
1 5 10

<210> SEQ ID NO 100
<211> LENGTH: 8
<212> TYPE: PRT
<213> ORGANISM: Streptococcus pneumoniae

<400> SEQUENCE: 100

Met Gln Gly Thr His Trp Arg Thr
1 5

<210> SEQ ID NO 101
<211> LENGTH: 14
<212> TYPE: PRT
<213> ORGANISM: Streptococcus pneumoniae

<400> SEQUENCE: 101

Val Lys Glu Gln Gly Phe Gly Tyr Tyr Arg Thr Ala Asp Tyr
1 5 10

<210> SEQ ID NO 102
<211> LENGTH: 9
<212> TYPE: PRT
<213> ORGANISM: Streptococcus pneumoniae

<400> SEQUENCE: 102

His Gln Tyr Asp Lys Tyr Pro Trp Thr
1 5

<210> SEQ ID NO 103
<211> LENGTH: 8
<212> TYPE: PRT
<213> ORGANISM: Streptococcus pneumoniae

<400> SEQUENCE: 103

Ala Arg Arg Asn Asp Phe Asn Ile
1 5

<210> SEQ ID NO 104
<211> LENGTH: 9
<212> TYPE: PRT
<213> ORGANISM: Streptococcus pneumoniae

<400> SEQUENCE: 104

Gln Gln Tyr Gly Ser Ser Pro Phe Thr
1 5

<210> SEQ ID NO 105
<211> LENGTH: 16
<212> TYPE: PRT
<213> ORGANISM: Streptococcus pneumoniae

<400> SEQUENCE: 105

Ser Ile Trp Trp Gly Thr Ser Val Gln Tyr Pro Leu Val Leu Asp Tyr
1 5 10 15

<210> SEQ ID NO 106
<211> LENGTH: 10
<212> TYPE: PRT
<213> ORGANISM: Streptococcus pneumoniae

<400> SEQUENCE: 106

Gln Gln Tyr Ser Lys Trp Pro Pro Ile Thr
1 5 10

<210> SEQ ID NO 107
<211> LENGTH: 14
<212> TYPE: PRT
<213> ORGANISM: Streptococcus pneumoniae

<400> SEQUENCE: 107

Val Lys Glu Gln Asp Tyr Gly Tyr Tyr Arg Thr Ala Asp His
1 5 10

<210> SEQ ID NO 108
<211> LENGTH: 9
<212> TYPE: PRT
<213> ORGANISM: Streptococcus pneumoniae

<400> SEQUENCE: 108

Gln Gln Tyr Asp Lys Tyr Pro Trp Thr
1 5

<210> SEQ ID NO 109
<211> LENGTH: 9
<212> TYPE: PRT
<213> ORGANISM: Streptococcus pneumoniae

<400> SEQUENCE: 109

Ala Arg Gly His Gly Phe Asn Ala Tyr
1 5

<210> SEQ ID NO 110
<211> LENGTH: 9
<212> TYPE: PRT
<213> ORGANISM: Streptococcus pneumoniae

<400> SEQUENCE: 110

Gln Gln Tyr Gly Asn Ser Pro Arg Thr
1 5

<210> SEQ ID NO 111
<211> LENGTH: 13
<212> TYPE: PRT
<213> ORGANISM: Streptococcus pneumoniae

<400> SEQUENCE: 111

Thr Thr Val Arg Asn Met Ala Asp Leu Ser Leu Asn His
1 5 10

<210> SEQ ID NO 112
<211> LENGTH: 9
<212> TYPE: PRT
<213> ORGANISM: Streptococcus pneumoniae

<400> SEQUENCE: 112

Gln Gln Tyr Asp Asp Ser Arg Trp Thr
1 5

<210> SEQ ID NO 113
<211> LENGTH: 11
<212> TYPE: PRT
<213> ORGANISM: Streptococcus pneumoniae

<400> SEQUENCE: 113

Ala Thr Gly Asn Arg Gly Ser Leu Pro Arg Arg
1 5 10

<210> SEQ ID NO 114
<211> LENGTH: 9
<212> TYPE: PRT
<213> ORGANISM: Streptococcus pneumoniae

<400> SEQUENCE: 114

Met Gln Ala Leu Arg Ser Pro Tyr Thr
1 5

<210> SEQ ID NO 115
<211> LENGTH: 11
<212> TYPE: PRT
<213> ORGANISM: Streptococcus pneumoniae

<400> SEQUENCE: 115

Val Arg Asp Gly Trp Asp Thr Phe Phe Asp Ser
1 5 10

<210> SEQ ID NO 116
<211> LENGTH: 9
<212> TYPE: PRT
<213> ORGANISM: Streptococcus pneumoniae

<400> SEQUENCE: 116

Met Gln Gly Arg Tyr Trp Pro Tyr Thr
1 5

<210> SEQ ID NO 117
<211> LENGTH: 6
<212> TYPE: PRT
<213> ORGANISM: Streptococcus pneumoniae

<400> SEQUENCE: 117

Val Asn Phe Gln Leu Gly
1               5

<210> SEQ ID NO 118
<211> LENGTH: 9
<212> TYPE: PRT
<213> ORGANISM: Streptococcus pneumoniae

<400> SEQUENCE: 118

Gln Gln Tyr Gly Asn Ser Pro Arg Thr
1               5

<210> SEQ ID NO 119
<211> LENGTH: 16
<212> TYPE: PRT
<213> ORGANISM: Streptococcus pneumoniae

<400> SEQUENCE: 119

Ala Arg Ala Glu Tyr Cys Ser Pro Gly Asp Cys Phe Leu Ile Asp Thr
1               5                   10                  15

<210> SEQ ID NO 120
<211> LENGTH: 8
<212> TYPE: PRT
<213> ORGANISM: Streptococcus pneumoniae

<400> SEQUENCE: 120

Met Gln Gly Thr His Trp Arg Thr
1               5

<210> SEQ ID NO 121
<211> LENGTH: 12
<212> TYPE: PRT
<213> ORGANISM: Streptococcus pneumoniae

<400> SEQUENCE: 121

Leu Arg Gly Asn Pro Pro Ser Ser Pro Thr Asp Tyr
1               5                   10

<210> SEQ ID NO 122
<211> LENGTH: 9
<212> TYPE: PRT
<213> ORGANISM: Streptococcus pneumoniae

<400> SEQUENCE: 122

Gln Gln Tyr Asn Ser Tyr Pro Leu Thr
1               5

<210> SEQ ID NO 123
<211> LENGTH: 12
<212> TYPE: PRT
<213> ORGANISM: Streptococcus pneumoniae

<400> SEQUENCE: 123

Ala Lys Val Val Tyr Ser Arg Pro Pro Met Asp Val
1               5                   10

<210> SEQ ID NO 124
<211> LENGTH: 9
<212> TYPE: PRT
<213> ORGANISM: Streptococcus pneumoniae

<400> SEQUENCE: 124

Gln Gln Ser Tyr Ser Thr Pro Trp Thr
1 5

<210> SEQ ID NO 125
<211> LENGTH: 11
<212> TYPE: PRT
<213> ORGANISM: Streptococcus pneumoniae

<400> SEQUENCE: 125

Ala Arg Ala Ser Arg Glu Thr Gly Glu Pro Tyr
1 5 10

<210> SEQ ID NO 126
<211> LENGTH: 9
<212> TYPE: PRT
<213> ORGANISM: Streptococcus pneumoniae

<400> SEQUENCE: 126

Met Gln Ala Thr His Trp Pro Trp Thr
1 5

<210> SEQ ID NO 127
<211> LENGTH: 348
<212> TYPE: DNA
<213> ORGANISM: Streptococcus pneumoniae

<400> SEQUENCE: 127
gaggtgcagc tgttggagtc gggggaggc ttggtacagc ctgggggtc cctgagagtc 60 tcctgtgcag cctctggatt cacctttagc aactctggca tgagttgggt ccgccaggct 120
ccagggaagg ggctggagtg ggtctcaggt attggtggtg gtggtggtag tgcatactac 180
gcagactccg tgaagggccg gttcaccatc tccagagaca attccaagaa cacgctgtat 240
ctacaaatga acaatttgag agccgaggac acggccgtat actactgtgc gaaaggagtt 300
accagttttg actactgggg ccagggaatc ctggtcaccg tctcctca 348

<210> SEQ ID NO 128
<211> LENGTH: 354
<212> TYPE: DNA
<213> ORGANISM: Streptococcus pneumoniae

<400> SEQUENCE: 128
gaggtgcagc tggtggagtc tgggggaggc ttggtccagc ctgggggtc cctgagactc 60 tcctgtgcag cctctggatt caccgtcagt agcgactata tgagttgggt ccgccaggct 120
ccagggaagg ggctggagtg ggtctcagtt atgtatagcg ggggtagcac atactacgca 180
gacgccgtga aggacagatt caccatctcc agagacaatt ccaagaatat actgtatctt 240
caaatgaaca gcctgagagc cgaggacacg gcggtttatt actgtgcgag agatcccggg 300
ataaggaacg gtatgggcgt ctggggccaa gggaccacgg tcaccgtctc ctca 354

<210> SEQ ID NO 129
<211> LENGTH: 363
<212> TYPE: DNA
<213> ORGANISM: Streptococcus pneumoniae

<400> SEQUENCE: 129
gaggtgcagc tgttggagtc tgggggagcc ttggtacagc cggggggtc cctgagactt 60 tcctgtgcag cctctggatt cacctttacc agctttgcca tgggctgggt ccgccaggct 120

```
ccagggaagg ggctggagtg ggtctcagct gtgactggca gtggttatta caaaaactat    180

gcagactccg tgaagggccg gttcaccatc tccagagaca attccgacaa tactctctat    240

ctgcaaatga acagcctgag aggcgacgac acggccctat attactgtgc gaaagcacat    300

agaggtgact ggaataactt ctttgactat tggggccagg gaaccctggt caccgtctcc    360

tca                                                                  363
```

<210> SEQ ID NO 130
<211> LENGTH: 345
<212> TYPE: DNA
<213> ORGANISM: Streptococcus pneumoniae

<400> SEQUENCE: 130

```
caggtgcagc tgcaggagtc gggcccagga ctagtgaagc cttcggagac cctgtccctc     60

acctgctctg tgtctgctga ctccttcagt ccttacaagt ggagctggat ccggcagccc    120

ccagggaagg gactggaatg gattggatat atctattcca gtgggaacac caactacaac    180

ccccccctca agagtcgagt caccatatca ctggacacgt ccaagaatca ggtctccctg    240

aggctgagct ctgtggccgc tgcggacacg gccatgtatt actgtgcgag agagtggagt    300

ggttttgatt tctggggcca aggaacaatg gtcaccgtct cttca                    345
```

<210> SEQ ID NO 131
<211> LENGTH: 345
<212> TYPE: DNA
<213> ORGANISM: Streptococcus pneumoniae

<400> SEQUENCE: 131

```
gaggtgcagc tggtggagtc tgggggaggc ttggtccagc ctgggggggtc cctgagactc     60

tcctgtgcag cctctggatt cacctttact aactattgga tgagctgggt ccgccaggct    120

ccagggaagg ggctggagtg ggtggccaac ataaagcaag atggacgtga gacatactat    180

gtggactctg tgaagggccg attcaccatc tccagagaca acgccaagaa ctcagtgtct    240

ctacagatga gtagcctgag agccgaggac acggccgtgt attactgtgc gcgagggcag    300

tggctggcct tccggggcca gggaaccctg gtcaccgtct cctca                    345
```

<210> SEQ ID NO 132
<211> LENGTH: 348
<212> TYPE: DNA
<213> ORGANISM: Streptococcus pneumoniae

<400> SEQUENCE: 132

```
gaggtgcagc tggtggagtc tgggggaggc ttggtccaga ttggggggtc cctgagactc     60

tcctgtgcag cctctggatt cacctttagt acctattgga tgagctgggt ccgccaggct    120

ccagggaagg ggctggagtg cgtggccagc ataaaggagg atggaagtga gagatactat    180

gtggactctg tgaagggccg attcaccatc tccagagaca acgccaagaa ctcactgcat    240

ctgcagatgg acagcctgag agccgcggac acggctgtgt atttctgtgc gagaggccgg    300

aacaacttcc gacactgggg ccagggaacc ctggtcaccg tctcctca                 348
```

<210> SEQ ID NO 133
<211> LENGTH: 378
<212> TYPE: DNA
<213> ORGANISM: Streptococcus pneumoniae

<400> SEQUENCE: 133
gaggtgcagc tggtggagtc tgggggaggc ttggtccagc ctgggggtc cctgagactc 60 tcctgtgcag cctctggatt cgccatcagt ggtaactaca tgagttgggt ccgccaggct 120
ccagggaagg gcctggagtg ggtctcactt atttattgga ctgatgacac agtctacgca 180
gactccgtga agggcagatt caccatctcc agggacgtct ccaagaacat ggtgcatctt 240
caaatgagca gcctgagagt cgaggacacg gctgtttatt actgtgcgag agaattaggt 300
gtttttcatt cagggggga ccagtggctg ggccctttag actgctgggg ccagggaacc 360
ctggtcaccg tctcctca 378

<210> SEQ ID NO 134
<211> LENGTH: 360
<212> TYPE: DNA
<213> ORGANISM: Streptococcus pneumoniae

<400> SEQUENCE: 134
gaggtgcagc tggtggagtc tgggggaggc ttggtgcagc cagggcagtc cctgagactt 60
tcctgtacag tttctggatt cagcgtagaa gaccatggtc tgaactgggt ccgccaggct 120
ccagggaagg ggctggagtg ggtagggttc attagaagga aaagttctgg tgggacagaa 180
tacgccgcgt ctgtgaaagg ccgattcacc atctcaagag atgattccaa gagcgccgtc 240
tatctgcaaa tgaacagcct gaagatggag gacacaggcg tatattattg tcttcgctgg 300
acgggtggag tgagttttgg tgcctactgg ggccagggaa ccctggtcac cgtctcctca 360

<210> SEQ ID NO 135
<211> LENGTH: 348
<212> TYPE: DNA
<213> ORGANISM: Streptococcus pneumoniae

<400> SEQUENCE: 135
gaggtgcagc tggtggagtc cgggggaggc ttagttcagc ctgggggtc cctgagactc 60 tcctgtgcag cctctggatt caccttcact agctggatgc actgggtccg ccaagctcca 120
gggaaggggc tggtgtgggt ctcacatatt aatactgatg ggagtagcac aagctacgcg 180
gactccgtga agggccgatt caccatctcc agagacaacg ccaagaacac gctgtatctg 240
caaatgaaca gtctgagagc cgaggacacg gctgtgtatt actgtgcaag agattattac 300
cactccgttg actactgggg ccagggaacc ctggtcaccg tctcctca 348

<210> SEQ ID NO 136
<211> LENGTH: 351
<212> TYPE: DNA
<213> ORGANISM: Streptococcus pneumoniae

<400> SEQUENCE: 136
caggtgcagc tgcaggagtc gggcccagga atggtgaagc cttcggagac cctgtccctc 60
atctgcagtg tctctggtgc ctccgtcagt cgtgaccact ggagctggat ccgccagtcc 120
ccagggaagg gactggagtg gattgtctat atatataaca gtgagagcat cgaatacaat 180
ccctccctca agagtcgagt caccatatcc gtagacacgt ccaagaacca ggtctccctg 240
acagtgactt ctgtgaccgc tgcagacacg gccttctatt actgtgcgcg agggccagat 300
gcccacaaaa ctggctactg gggcccggga accctggtca ccgtctcctc a 351

<210> SEQ ID NO 137

<211> LENGTH: 351
<212> TYPE: DNA
<213> ORGANISM: Streptococcus pneumoniae

<400> SEQUENCE: 137

```
gaggtgcagc tggtggagtc cgggggaggc ttagttcagc ctggggggtc gctgagactc     60

tcctgcgcag cctctggatt caccttcagt aacttctgga tgtactgggt ccgccaagtt    120

ccagggaagg ggctggtgtg cgtctcacgt attaatagag atgggagtat cacattgtac    180

gcggactccg tgaggggccg attcaccatc tccagagaca acgccaagaa cacgctgtat    240

ctgcaaatga acagtctgag agtcgaggac acggctgtgt attactgtgc aagagattcc    300

tataccagcc ctgactactg gggccagggg accctggtca ccgtctcctc a             351
```

<210> SEQ ID NO 138
<211> LENGTH: 360
<212> TYPE: DNA
<213> ORGANISM: Streptococcus pneumoniae

<400> SEQUENCE: 138

```
gaggtgcagc tggtggagtc tgggggaggc ttggtaaagc cggggggagtc ccttagactc     60

tcctgtgcga cctcaggatt aactttcagt aacgtatgga tgagctgggt ccgccaggct    120

ccagggaagg ggctggagtg ggttgggcgt cttaaaaaca agcctgatgg tggaacaaca    180

gactacgcag cacccgtgaa gggcagattc accatctcaa gagatgattc aaaaaccacg    240

ctgtatctgg aaatgaacag cctgaaagtc gaggacacag ccgtgtatta ctgtaccaca    300

gataacggag tcaaggcttt tgatatctgg ggccaaggga caatggtcac cgtctcttca    360
```

<210> SEQ ID NO 139
<211> LENGTH: 354
<212> TYPE: DNA
<213> ORGANISM: Streptococcus pneumoniae

<400> SEQUENCE: 139

```
gaggtgcagc tggtggagtc cgggggaggc ttagttcagc ctggggggtc cctgagactc     60

tcctgtgcag cctctggatt caccttcagt acctactgga tgcactgggt ccgccaaact    120

ccggagaagg ggctggtatg ggtctcacgt attcatcctg atgggagtaa cacagcctac    180

gcggactccg tgaagggccg attcaccatc tccagagaca acgccaagaa cacgctgtat    240

ctgcaaatga atagtctgag agtcgaggac acggcttttt attattgtac aagagggggt    300

tccggggcta cgatcaatta ctggggccag ggaatcctgg tcaccgtctc ctca          354
```

<210> SEQ ID NO 140
<211> LENGTH: 372
<212> TYPE: DNA
<213> ORGANISM: Streptococcus pneumoniae

<400> SEQUENCE: 140

```
caggtgcagc tgcaggagtc gggcccaggg ctggtgaagc cttcacagac cctgtccctc     60

acctgcactg tctctggtgg ctccatcagc ggtggtactt actcctggac ctggatccgg    120

cagcccgccg ggaagggact ggagtggatt gggcgtattt ttgctagtgg gagcaccaac    180

tacaattcct ccctcaagag tcgagtcacc attttagtag acacgtccaa gaacctgttc    240

tccctgagcc tgagctctgt gaccgccgca gacacggcca tgtattactg tgcgagagat    300

cgagccggta tagatggcta caattactac tttgactact ggggccaggg aaccctggtc    360

accgtctcct ca                                                        372
```

<210> SEQ ID NO 141
<211> LENGTH: 359
<212> TYPE: DNA
<213> ORGANISM: Streptococcus pneumoniae

<400> SEQUENCE: 141
aggtgcagct ggtgcagtct ggggctgagg tgaagaagcc tggggcctca gtgaaggttt 60
cctgcaagac atctggatac accctcacca gttactatat gcactgggtg cgacaggccc 120
ctggacaagg gcttgagtgg ctgggagtga tcaggcctac ggacgctagc acaaggtccg 180
cacagaagtt ccagggcaga atcaccatga ccagggacac gtccacgagc acactctaca 240
tggagctgag tagcctgaga tctgaagaca cggccgtgta ctattgtgcg agagaagtgg 300
cagcagaagg taaagctttc gactactggg gccagggaac cctggtcacc gtctcctca 359

<210> SEQ ID NO 142
<211> LENGTH: 348
<212> TYPE: DNA
<213> ORGANISM: Streptococcus pneumoniae

<400> SEQUENCE: 142
gaggtgcagc tggtggagtc tgggggaggc ttggtccagc ctggggggtc cctgagactc 60
tcctgtgcag cctctggatt cacctttagt agctattgga tgagctgggt ccgccaggct 120
ccagggaagg gactggagtg ggtgggcaaa ataaaggaag acggaagtga gaaatactat 180
gtggactctg tgaagggccg attcgccatc tccagagaca acgccaagaa ctccctgtct 240
ctgcaaatga acagcctgag agccgaggac acggccgtgt attactgtgc gagaggtcaa 300
tcatatccgg gaatttgggg ccaagggaca atggtcaccg tctcttca 348

<210> SEQ ID NO 143
<211> LENGTH: 363
<212> TYPE: DNA
<213> ORGANISM: Streptococcus pneumoniae

<400> SEQUENCE: 143
caggtgcagc tgcaggagtc gggcccagga ctggtgaagc cttcggagac cctgtccctc 60
acctgcactg tctctggtgg ctccatcact aattactact ggggctggat ccggcagccc 120
ccaggggagg gactggagtg gattggctat atctattaca gtggaagcac caactacaac 180
ccctccctca agagtcgagt caccatatca gtagacacgt ccaagaacca gttctcccta 240
aagctgacct ctgtaaccgc cgcagacacg gccgtgtatt actgtgcggg tcgggcttac 300
agtagtggtt actactacct aattgactac tggggccagg gaaccctggt caccgtctcc 360
tca 363

<210> SEQ ID NO 144
<211> LENGTH: 321
<212> TYPE: DNA
<213> ORGANISM: Streptococcus pneumoniae

<400> SEQUENCE: 144
gaaattgtgt tgacgcagtc tccaggcacc ctgtctttgt ctccagggga aagagccacc 60
ctctcctgca gggccagtca gagtgttacc tacttagcct ggtaccagca gaaacctggc 120
caggctccca ggctcctctt ctatggtaca tccagcaggg ccactggcat cccagacagg 180
ttcagtggca gtgggtctgg gacagacttc actctcacca tcagcagagt ggagcctgaa 240
gattttgcag tgtattactg tcagcagttt ggcagctcac ctccggacac tttcggcgga 300
gggaccaagg tggaaatcaa a 321

<210> SEQ ID NO 145
<211> LENGTH: 332
<212> TYPE: DNA
<213> ORGANISM: Streptococcus pneumoniae

<400> SEQUENCE: 145
ttgtgatgac tcagtctcca ctctccctgc ccgtcaccct tggacagccg gcctccatct 60
cctgcagggc tagtcaaggc ctcgaacaca gtgatggaaa cacctacttg agttggtttc 120
agcagaggcc aggccgatct ccccggcgcc taatttataa ggtttctaac cgggactctg 180
gggtcccaga cagattcagt ggcagtgggt caggcactga tttcacactg gaaatcacca 240
gggtggaggc tgaggatgtt ggagtttatt actgcatgca agttacacac tggccgagga 300
cgttcggcca agggaccaag gtggaaatca aa 332

<210> SEQ ID NO 146
<211> LENGTH: 321
<212> TYPE: DNA
<213> ORGANISM: Streptococcus pneumoniae

<400> SEQUENCE: 146
gaaattgtgt tgacacagtc tccaggcacc ctgtcgttgt ctccagggga aagagccacc 60
ctctcctgca gggccagtca gagtattagt ccccacttgg cctggtacca acagaaacct 120
ggccagtctc ccaggctcct catatatgat gcatccaaca gggccactgg catcccagcc 180
aggttcagtg gcagtgagtc tgggacagac ttcactctca gcatcagcag cctagagcct 240
gaagattttg cagtttatta ctgtcagcag agtggcgact ggcctctcac tttcggcgga 300
gggaccaagg tggagatcaa a 321

<210> SEQ ID NO 147
<211> LENGTH: 324
<212> TYPE: DNA
<213> ORGANISM: Streptococcus pneumoniae

<400> SEQUENCE: 147
gaaattgtgt tgacgcagtc tccaggcacc ctgtctttgt ctccagggga aagagccacc 60
ctctcctgca gggccagtca gagtgtttac agcatctact tcgcctggta ccagcagaaa 120
cccggccagg ctcccaggcc cctcatttat ggtgtctcca acagggccac tggcatccca 180
gacaggttca gtggcagtgg gtctgggaca gacttcactc tcaccatcag cagactggag 240
ccagaagatt ttgcagtgta ttactgtcag cagtatggta gtttacctcg gacgttcggc 300
caagggacca aggtggaaat caaa 324

<210> SEQ ID NO 148
<211> LENGTH: 332
<212> TYPE: DNA
<213> ORGANISM: Streptococcus pneumoniae

<400> SEQUENCE: 148
ttgtgatgac tcagtctcca ctctccctgc ccgtcaccct tggacagccg gcctccatct 60
cctgcaggtc tagtcgaagc ctcgtataca gtgatggagg cacctacttg aattggtttc 120
agcagaggcc aggccaatct ccaaggcgcc taatttggca cgtttctaac cgggactctg 180
gggtcccaga cagattcagc ggcagtgggt caggcactga tttcacactg aaaatcagca 240
gggtggaggc tgaggatgtt ggggtttatt actgcatgca aggtacacac tggccttaca 300
cttttggcca ggggaccaag gtggaaatca aa 332

<210> SEQ ID NO 149
<211> LENGTH: 321
<212> TYPE: DNA
<213> ORGANISM: Streptococcus pneumoniae

<400> SEQUENCE: 149
gacatccaga tgacccagtc tccatcttcc ctgtctgcat ctgtaggaga cagagtcacc 60
atcacttgcc aggcgagtca ggacattagg aagcttttaa attggtatca gcagagacca 120
gggaaagccc ctaacctcct gatctacgat gcatccaatt tggaaacagg ggtcccatca 180
aggttcagtg gaagtggatc tgggacacat tttagtttca ccatcaccag cctgcagcct 240
gaagatattg caacatatta ctgtcaacag tttgaaagtt tccctcgcac cttcggccct 300
gggaccaaag tggatatcaa a 321

<210> SEQ ID NO 150
<211> LENGTH: 327
<212> TYPE: DNA
<213> ORGANISM: Streptococcus pneumoniae

<400> SEQUENCE: 150
gaaatagtga tgacgcagtc tccagccacc ctgtctgtgt ctccagggga aacagccacc 60
ctctcctgca gggccagtca gagtgttaac agcttcttag cctggtacca gcagaaacct 120
ggccaggctc ccaggctcct catctatgct gcatccacca gggccactgg tgtcccagcc 180
aggttcagtg gcagtgggtc tgggacagag ttcactctca ccatcagcag cctgcagtct 240
gaagattttg cagtttacta ctgtcaccag tataaaaact ggcctccgat gggcactttc 300
ggccctggga ccaaagtgga tatcaaa 327

<210> SEQ ID NO 151
<211> LENGTH: 318
<212> TYPE: DNA
<213> ORGANISM: Streptococcus pneumoniae

<400> SEQUENCE: 151
gacatccaga tgacccagtc tccttccacc ctgtcttctt ctgtcggaga cagagtcact 60
atcacttgcc gggccagtca gaatattggt gtctccttgg cctggtatca gcagaaacca 120
gggaaagccc ctaacctcct gatctataag gcgtcttatt tagaaacggg ggtcccatca 180
aggttcagcg gcagtggatc tgggacagaa ttcactctca ccatcagcag cctacagcct 240
gatgattttg caacttatta ttgccaacag tatgatattt atttgacatt cggccaaggg 300
accaaggtgg aaatcaaa 318

<210> SEQ ID NO 152
<211> LENGTH: 332
<212> TYPE: DNA
<213> ORGANISM: Streptococcus pneumoniae

<400> SEQUENCE: 152
ttgtgatgac tcagtctcca ctctccctgc ccgtcaccct tggacagccg gcctccatct 60
cctgcaggtc tagtcaaagt ctcgcacaca gtgatggaaa tacctacttg aattggtttc 120
agcagaggcc aggccaatct ccaaggcgcc taatttataa ggtttctaac cgggactctg 180

```
gggtcccaga cagattcagc ggcagtgggt caggcactga tttcacactg aaaatcagca    240

gggtggaggc tgaggatgtt ggggtttatt actgcatgca aggtacacac tggccgtaca    300

cttttggcca ggggaccaag gtggaaatca aa                                  332


<210> SEQ ID NO 153
<211> LENGTH: 339
<212> TYPE: DNA
<213> ORGANISM: Streptococcus pneumoniae

<400> SEQUENCE: 153

gacatcgtga tgacccagtc tccagactcc ctggctgtgt ctctgggcga gagggccacc     60

atcaactgca agtccagcca gagtgtttta tacagcccca acaataagaa ttacttagct    120

tggttccagc agaagccagg acagcctcct aaattactca tttactgggc atctatccgg    180

gactccgggg tccctgaccg attcagtggc agcgggtctg ggacagattt cactctcacc    240

gtcagcagtc tgcaggctga cgatgtggca gtttattact gtcagcaata tgctgctact    300

ccgtggacgt tcggccaagg gaccaaggtg gaaatcaaa                           339


<210> SEQ ID NO 154
<211> LENGTH: 332
<212> TYPE: DNA
<213> ORGANISM: Streptococcus pneumoniae

<400> SEQUENCE: 154

ttgtgatgac tcagtctcca ctctccctgc ccgtcaccct tggacagccg gcctccatct     60

cctgcagttc tagtcaaagc ctcgtataca gtgatggaaa cacctacttg agttggtttc    120

agcagaggcc aggccaatct ccccggcgcc taatttataa ggtttctaac cgggactctg    180

gggtcccaga cagattcagc ggcagtgggt caggcactga tttcacactg agaatcagca    240

gggtggaggc tgaggatgtt ggggtttatt actgcatgca aggttcacac tggccgctca    300

ctttcggcgg agggaccaag gtggagatca aa                                  332


<210> SEQ ID NO 155
<211> LENGTH: 339
<212> TYPE: DNA
<213> ORGANISM: Streptococcus pneumoniae

<400> SEQUENCE: 155

gacatcgtga tgacccagtc tccagactcc ctggctgtgt ctctgggcga gagggccacc     60

atcaactgca agtccagcct gagtgtttta tccagctcca ataatgagaa ctacttagct    120

tggtaccagc agaaaccagg acagcctcct aagctgctca tttactgggc atctacccgg    180

ggatccgggg tccctggccg attcagtggc agcgggtctg ggacagattt cactctcacc    240

atcagcagcc tgcaggctga agatgtggca gtttattact gtcaccaata ttatactact    300

cccttcgctt tcggccctgg gaccaaagtg gatatcaaa                           339


<210> SEQ ID NO 156
<211> LENGTH: 321
<212> TYPE: DNA
<213> ORGANISM: Streptococcus pneumoniae

<400> SEQUENCE: 156

gacatccaga tgacccagtc tccgtcctcc ctgtctgcat ctgtgggaga cagtgtcacc     60

atcacttgcc gggcaagtca gagcattagc agctatttaa attggtatca ccaaaaacca    120

gggaaagccc ctaaactcct gatctatggt gcatccactt tgcaaagtgg ggtcccatca    180
```

aggttcggtg gcagtggatc tgggacagat ttcactctca ccatcagcag tctgcaacct 240
gacgattttg caacttacta ctgtcaacag agtcacagtt cccctctcac tttcggcgga 300
gggaccaagg tggagatcaa a 321

<210> SEQ ID NO 157
<211> LENGTH: 318
<212> TYPE: DNA
<213> ORGANISM: Streptococcus pneumoniae

<400> SEQUENCE: 157
gacatccaga tgacccagtc tccttccacc ctgtctgcct ctgtaggaga cagagtcacc 60
atcacttgtc gggccagtcg gagtcttggt agctggttgg cctggtatca gcagagccca 120
gggaaagccc ctaagctcct gatctataag gcgtctactt tagaaagtgg ggtcccatca 180
cggttcagcg gcagtggatc tgggacagaa ttcactctca ccatcagcag cctgcagcct 240
gatgattttg caacttatta ctgccaacag tattatagct tctacacttt tggccagggg 300
accaaggtgg aaatcaaa 318

<210> SEQ ID NO 158
<211> LENGTH: 339
<212> TYPE: DNA
<213> ORGANISM: Streptococcus pneumoniae

<400> SEQUENCE: 158
gacatcgtga tgacccagtc tgcagactcc ctggctgtgt ctctgggcga gagggccacc 60
atcaactgca agtccagcca gagtcttttc tacagttcca acaagaagaa ctacttagct 120
tggtaccagc agaagccagg acagcctcct aaactgatca tttactgggc atctacccgg 180
gaatccgggg tccctgaccg attcagtggc agcgggtctg ggacagattt cactctcacc 240
atcaccagcc tgcgggctga agatgtggca gtttattact gtcagcaata ttatactcct 300
cctctcacat tcggcggagg gaccaaggtg gaaatcaaa 339

<210> SEQ ID NO 159
<211> LENGTH: 321
<212> TYPE: DNA
<213> ORGANISM: Streptococcus pneumoniae

<400> SEQUENCE: 159
gaaatagtga tgacgcagtc tccagccacc ctgtctgtgt ctccagggga aagagccacc 60
ctctcctgca gggccagtca gagtgttagc ggcgacttag tctggtacca gcagaaacct 120
ggccaggctc ccaggctcct catctatggt gccaccacca gggcctctgg tgtcccagcc 180
aggttcagtg gcagtgggtc tgggacagag ttcactctca ccatcagcag cctgcagtct 240
gaagattttg caatttatta ctgtcagcag tataataact ggccccggac gttcggccaa 300
gggaccaagg tggaaatcaa a 321

<210> SEQ ID NO 160
<211> LENGTH: 321
<212> TYPE: DNA
<213> ORGANISM: Streptococcus pneumoniae

<400> SEQUENCE: 160
gaaatagtga tgacgcagtc tccagccacc ctgtctgtgt ctccagggga aagagccacc 60
ctctcctgca gggccagtca gagtgttggc aacaacttag cctggtttca gcagaaacct 120

```
ggccaggctc ccaggctcct catctatggt gcatccacca gggccactgg tatcccagcc    180

aggttcagtg gcagtgggtc tgggacagag ttcactctca ccatcagcag cctgcagtct    240

gaagattttg cagtttatca ctgtcaacac tatcataact ggcctcccac ttttggccag    300

gggaccaagg tggaaatcaa a                                              321
```

<210> SEQ ID NO 161
<211> LENGTH: 366
<212> TYPE: DNA
<213> ORGANISM: Streptococcus pneumoniae

<400> SEQUENCE: 161

```
caggtgcagc tggtggagtc tgggggaggc gtggtccagc ctgggaggtc cctgagactc     60

tcctgtgcag cctctggatt caccttcagc aaccatggca tgcactggct ccgccagact    120

ccaggcaagg ggctggagtg ggtggcagtc atttcatatg atggaagtac caaatactat    180

gcagactccg tgaagggccg atgcaccctc tccagagaca attccaagga aacggtgttt    240

ctgcaaatga acagcctgag acctgaggac acggctgtgt attattgtgc gaaagggtgt    300

tctaatggtg gtaactgctt tttgattgac tactggggcc cgggaaccct ggtcaccgtc    360

tcctca                                                               366
```

<210> SEQ ID NO 162
<211> LENGTH: 369
<212> TYPE: DNA
<213> ORGANISM: Streptococcus pneumoniae

<400> SEQUENCE: 162

```
gaggtgcagc tgttggagtc ggggggagac ttggtgcagc ctgggggtc cctgagactc     60

tcctgtgcag cctctggatt cgacttcagt atttatggca tgaactgggt ccgccaggct    120

ccagggaagg ggcttgaatg ggtctcagtt attagtggtg atggcactat catatactac    180

gcagactccg tgaagggccg gttcactatc tccagagaca attccaagaa cacactgttt    240

ttgcaagtga acagcgtgag agccgaggac acggccgtat attactgtgc gaaggggggc    300

tactatgaat cggggactat gcgggctttt gatatctggg gccaagggac aatggtcacc    360

gtctcttca                                                            369
```

<210> SEQ ID NO 163
<211> LENGTH: 351
<212> TYPE: DNA
<213> ORGANISM: Streptococcus pneumoniae

<400> SEQUENCE: 163

```
gaggtgcagc tggtggagga gtctggggga ggcttggtcc agcctggggg gtccctgaga     60

ctctcctgtg cagcctctgg atacaccttt agtagttatt caatgagttg ggtccgccag    120

gctccaggga aggggctgga gtgggtggcc agcattaagc cagaaggaag tgagaaattc    180

tatgtggact ctgtgaaggg ccgattcact atctccagag acaacgccaa gaactcactg    240

tatctgcaaa tgaacagcct gagaggcgag gacacggctg tctactactg tgcgagaggg    300

gaatctaatt tccgatactg gcaccaggga accctggtca ccgtctcctc a             351
```

<210> SEQ ID NO 164
<211> LENGTH: 357
<212> TYPE: DNA
<213> ORGANISM: Streptococcus pneumoniae

<400> SEQUENCE: 164

```
gaggtgcagc tggtggagtc tgggggagcc ttggtccagc ctggggggtc cctgagactc     60
tcctgtgcag cctctggatt catcttcagt aactcttgga tgggctggtt ccgccaggct    120
ccagggaagc ggccggagtt cgtggccaac ataaaaccag atggaagtga gaaattccat    180
gtggactctg tgaagggccg attcaccatc tccagagaca acgccgagaa ctcactgtat    240
ctgctgatga acagcctgag agccgaggac acggctgtct attactgcgc gagagatagc    300
acttccccgg cccgttttgg gtactggggc cagggaaccc tggtcaccgt ctcctca       357
```

<210> SEQ ID NO 165
<211> LENGTH: 354
<212> TYPE: DNA
<213> ORGANISM: Streptococcus pneumoniae

<400> SEQUENCE: 165

```
gaggtgcagc tggtggagac tggaggaggc ttgatccagc ctggggggtc cctgaggctc     60
tcctgtgcag cctctgggtt aaacgtcaat agttactaca tgaactgggt ccgccaggct    120
ccagggaagg ggctggagtg ggtctcagtt atttatagcg gtggtggcac aaactacgca    180
gactccgtga ggggccgatt catcatctcc agagacaatt ccaggaacgc gctttatctt    240
caaatgaaca gcctgagagc cgaggacacg gccgtgtatt actgtgcgac gggcgggatg    300
accagtagtt ggtacggcta ctggggccag ggaaccctgg tcaccgtctc ctca          354
```

<210> SEQ ID NO 166
<211> LENGTH: 374
<212> TYPE: DNA
<213> ORGANISM: Streptococcus pneumoniae

<400> SEQUENCE: 166

```
aggtgcagct ggtgcagtct ggggccgagg tgaagaagcc tggggcctca gtgaaggttt     60
cctgcaaggc atctgaatac actttcatca actaccttgt gttctgggtg cgacaggccc    120
ctggacaagg gcttgagtgg atgggagaaa tgaaccccac tcgtgggagc acaagctacg    180
cacagaagtt ccagggcaga gtcaccatga ccagggacac gtccacgagc acagtctaca    240
tggagttgag cagcctgaga tctgacgaca cggccgttta ttactgctcc atgggtccgc    300
cctattgtac tggtggaagc tgttactccg cctgtgattt ctggggcccg ggaaccctgg    360
tcaccgtctc ctca                                                      374
```

<210> SEQ ID NO 167
<211> LENGTH: 372
<212> TYPE: DNA
<213> ORGANISM: Streptococcus pneumoniae

<400> SEQUENCE: 167

```
gaggtgcagc tggtggagtc tgggggaggc ttgatgaaac ctggggggtc ccttagactc     60
tcctgtgcag tctctgggtt cactttcact aacgcctggc tgagctgggt ccgccagcct    120
ccagggaagg ggctggagtg ggttggccgt gcttacagca gttctggcgg ttggacaatg    180
gactactctt cacccgtgag gggcagattc accatcacaa gagacgattc aaaaaacaca    240
ctgtatctgc aaatgaacaa cctgaaaacc gaggacacag ccgtgtatta ctgtaccaca    300
gatattggca aaggctggta cacgcactat cctgacctct ggggccaggg aaccctggtc    360
accgtctcct ca                                                        372
```

<210> SEQ ID NO 168
<211> LENGTH: 363
<212> TYPE: DNA
<213> ORGANISM: Streptococcus pneumoniae

<400> SEQUENCE: 168

```
caggtgcagc tggtggagtc tgggggaggc gtggtccagc ctgggaagtc cctcagactc     60
tcctgtgtag cctctggatt caccttaagt acctgtggca tgcactgggt ccgccaggct    120
ccaggcaagg ggctggagtg ggtggcagtt acaacatatg atggagatcg taaatataat    180
gtagactccg tgaagggccg attcaccatc tccagagaca attccaagaa cacggtgtat    240
ctgcaaatgg acggcctcaa agccgaggac acggctgtgt atcactgtgt gaaagaatat    300
agttggggtt actacagaac tgcggactac tggggccagg gaaccctggt caccgtctcc    360
tca                                                                  363
```

<210> SEQ ID NO 169
<211> LENGTH: 351
<212> TYPE: DNA
<213> ORGANISM: Streptococcus pneumoniae

<400> SEQUENCE: 169

```
gaggtgcagc tggtggagtc cgggggaggc ttagttcagc cggggggtc cctgagactc     60
tcctgtgtag cctctggatt caccttcagt acttactgga tgcactgggt ccgccaacct    120
ccggggaagg ggctggtgtg ggtctcacgt attaatcctg atggcagtag cacaaactac    180
gcggactccg tgaacggccg attcaccatc tccagagaca acgccaagaa cacgctgtat    240
cttgaaatga acagtttgag agtcgaggac acagctctct attactgtgc aagaagtcct    300
gggggttact ttgactactg gggccacagc accctggtca ccgtctcctc a             351
```

<210> SEQ ID NO 170
<211> LENGTH: 348
<212> TYPE: DNA
<213> ORGANISM: Streptococcus pneumoniae

<400> SEQUENCE: 170

```
gaggtgcagc tggtggagtc tgggggaggc ttggtgaagc ctggggggtc ccttacactc     60
tcctgtgcag tctctggatt cactttcagt accggctgga tgagctgggt ccgccaggct    120
ccagggaagg ggctggactg ggttggccgt attaaaagca aaactgctgg tgggacaaca    180
gactatgctg cacccgtgaa agacagattc accatctcaa gagatgattc aaaaaacacg    240
ctgtatctgc aactgagcag ccttaaaacc gaggacacag ccgtgtatta ctgtaccaca    300
gatgacctga aaaactgggg ccagggaacc ctggtcaccg tctcctca                 348
```

<210> SEQ ID NO 171
<211> LENGTH: 387
<212> TYPE: DNA
<213> ORGANISM: Streptococcus pneumoniae

<400> SEQUENCE: 171

```
gaggtgcagc tggtggagtc tgggggaggc ttggtgcagc cggggggtc cctgagactc     60
tcctgtgcag cctctggatt caccttcagt agttatagca tgaactgggt ccgccaggtc    120
ccgggaaagg ggctggagtg ggtctcatac acaagtacta aaagtgatat caaatactac    180
gcggactctg tggaaggccg attcaccatt tccagagaca atgccaagaa ctcattgtat    240
ctgcaaatga acagcctgag agacgaagac acggctgtct attattgtgc gagaggacga    300
```

gattgttatg ggggtaactg cgtcatctac ttccactact acggtttgga cgtctggggc 360
caagggacca cggtcaccgt ctcctca 387

<210> SEQ ID NO 172
<211> LENGTH: 369
<212> TYPE: DNA
<213> ORGANISM: Streptococcus pneumoniae

<400> SEQUENCE: 172
caggtgcagc tggtggagtc tgggggaggc gtggtccagc ctgggggtc cctgagactc 60 tcctgtgtag tctctggatt caccctcagt tcctgtggca tgcattgggt ccgccagtct 120
ccaggcaagg ggctggagtg gctgtcagtt agcacctatg atggagatgg caatcagaaa 180
tactatgcgg cctccgtgaa gggccgattc ctcatctcca gagacacttc gaagaacacg 240
gtgtatctcc atatgaacag cctgacagct gaggacacgg ctctatatta ttgtgtgaaa 300
gagagtgcca ctggctggta tcgcaccgct gattactggg gccagggaac cctggtcacc 360
gtctcctca 369

<210> SEQ ID NO 173
<211> LENGTH: 366
<212> TYPE: DNA
<213> ORGANISM: Streptococcus pneumoniae

<400> SEQUENCE: 173
gaggtgcagc tggtggagtc tgggggaggc ttggtccagc ctgggggtc cttgagactc 60 tcctgtgcag cctctggatt caccgtcagt agcatattca tgagctgggt ccgccaggct 120
ccagggcagg ggctggagtg ggtctcagtc atctataccg atggaaaaac atattatgca 180
cactccgtgg agggccgatt caccatctcc agagacgatt ccaagaatat ggtgtatctt 240
caattgagca gcctgagaac tgaggacacg gctgtttatt actgtgcgag agatattcca 300
acgacatttg gaataggtga agcttttgat atctggggcc aggggacaat ggtcaccgtc 360
tcttca 366

<210> SEQ ID NO 174
<211> LENGTH: 347
<212> TYPE: DNA
<213> ORGANISM: Streptococcus pneumoniae

<400> SEQUENCE: 174
aggtgcagct ggtgcagtct ggggctgagg tgaagaagcc tggggcctca gtgaagcttt 60
cctgcaagac atctggatac tccttcacca gcaactattt gcactgggtg cgacaggccc 120
ctggacaagg acttgagtgg atgggaatgg tctacccaaa tgatggtact acaacctacg 180
ctcagaagtt tcagggcaga gtcaccatga ccagtgagac gtccacaacc acaatctaca 240
tggacctgag cggcctgaca tctgaggaca cggccatata ttactgtgct agagacgatt 300
cggcctttga ctactggggc cagggaaccc tggtcaccgt ctcctca 347

<210> SEQ ID NO 175
<211> LENGTH: 363
<212> TYPE: DNA
<213> ORGANISM: Streptococcus pneumoniae

<400> SEQUENCE: 175
caggtgcagc tggtggagtc tgggggaggc gtggtccagc ctgggaggtc cctgagactc 60
tcctgtgaag cctctggatt catcttcagt agcaatggca tgcactgggt ccgccaggct 120
ccaggcaagg ggctggagtg ggtggcagtt atatcatctg atggaagtag gagatactat 180
gcagactcaa tgaagggccg attcaccatc tccagagaca actccaagaa cacgctgtat 240
ctgcaattga acagcctgag agctgacgac acggctgtct attactgtgc gaaaggctgt 300
agtggtgaaa attgcttcta tatggacgac tggggcaaag ggaccacggt caccgtctcc 360
tca 363

<210> SEQ ID NO 176
<211> LENGTH: 386
<212> TYPE: DNA
<213> ORGANISM: Streptococcus pneumoniae

<400> SEQUENCE: 176
aggtgcagct ggtgcagtct ggggctgagg tgaagaagcc tggggcctca ctgaaggtct 60
cctgcaaggc atctggatac accttcagac agaactattt ccactgggtg cgacaggccc 120
ctggacaagg gcttgagtgg atgggagtaa tcaacccgag tgatggtagt acaaagttcg 180
cacagaagtt ccagggcaga gtcagcatga ccagggacac gtccacgagc acagtttaca 240
tggacctgag cagtctgaca tctgaggaca cggccgtcta ttattgtacg agagagatcg 300
gcgcagtggt agtagatgct acgtcgttgg ggtggttggg ctactttgac tactggggcc 360
agggaaccct ggtcaccgtc tcctca 386

<210> SEQ ID NO 177
<211> LENGTH: 345
<212> TYPE: DNA
<213> ORGANISM: Streptococcus pneumoniae

<400> SEQUENCE: 177
gaggtgcagc tggtggagtc tgggggaggc ttggtccagc cggggggtc cctgagtctc 60 tcctgtgaag cctctggatt aaccttcagt ggctactgga tgaactgggt ccgccaggct 120
ccagggaagg ggctggagtg ggtggccaac ataaatccag aaggaagtga gaggagatac 180
gtggagtctg tgcagggccg attcaccgtc tccagagaca acccgaagaa caccctgtat 240
ttgcaaatga acagcctgag agtcgaggac acggctctgt attactgtgc gggctggggg 300
agaacccagg actggggcca gggagccctg gtcaccgtct cctca 345

<210> SEQ ID NO 178
<211> LENGTH: 363
<212> TYPE: DNA
<213> ORGANISM: Streptococcus pneumoniae

<400> SEQUENCE: 178
caggtgcagc tggtggagtc tgggggaggc gtggtccagc ctgggaggtc cctgagactc 60
tcctgtgcag cctctggact caccttcagc aattatggca tgcactgggt ccgccaggct 120
ccagggaagg ggctggagtg ggttgcagtt gtgtcggcaa ggggaggaac tacatattat 180
gcagactccg tgaagggccg attcaccatc tccagagaca attccaagaa cacgatgtct 240

```
ctgcaaatga acggcctgag acctgacgac acggctgtgt atttttgtac gaaagaagga    300

gcaccacctg gaaaatatgc ttttgatatc tggggccaag ggacaatggt caccgtctct    360

tca                                                                  363
```

<210> SEQ ID NO 179
<211> LENGTH: 360
<212> TYPE: DNA
<213> ORGANISM: Streptococcus pneumoniae

<400> SEQUENCE: 179

```
gaggtgcagc tggtggagtc tgggggaggc ttggtccagc ctggaggatc cctgagactc     60

tcctgcgcag cctccggatt caccttcagt gactaccgca tggactgggt ccgccaggct    120

ccagggaggg ggctggagtg gattgcccgt attagacaca gagatgcagg ctatagcaca    180

gaatacgccg cgtctgtgag gggcagattc accgtctcaa gagatgactc acagagtaca    240

ctgtacctgc agatgaacag cttgaaagcc gacgacacgg ccgtgtatat ttgtcttaaa    300

gattcttcgc aatactcttt tgatgcgtgg ggccaaggga caatggtcac cgtctcttca    360
```

<210> SEQ ID NO 180
<211> LENGTH: 339
<212> TYPE: DNA
<213> ORGANISM: Streptococcus pneumoniae

<400> SEQUENCE: 180

```
gacatcgtga tgacccagtc tccagactcc ctggctgtgt ctctgggcga gagggccacc     60

atcaactgca agtccagtca gagtatttta tccagatcca acaataagaa ctacttagcc    120

tggtaccagc agaaaccagg acagcctcct aaattgctcc tttattgggc atctacccgg    180

gaatccgggg tccctgaccg attcagtgtc agcgggtctg ggtcagattt cactctcacc    240

atcagtagcc tgcaggctga ggatgtggca gtttattact gtcagcagta ttataatgct    300

cccctcactt tcggcggagg gaccaaggtg gagatcaaa                           339
```

<210> SEQ ID NO 181
<211> LENGTH: 321
<212> TYPE: DNA
<213> ORGANISM: Streptococcus pneumoniae

<400> SEQUENCE: 181

```
gaaattgtgt tgacacagtc tccagccacc ctgtctttgt ctccagggga aagggccacc     60

ctctcctgca gggccagtca gactgttagc aggtacttag cctggtacca acaaaagcct    120

ggccaggctc ccaggctcct catctatgct gcatccaaca gggccactgg catcccaacc    180

aggttcagtg gcagtgggtc tgggacagac ttcactctca ccatcagcag cctagagcct    240

gaagattttg cattttatta ctgtcagcag cgtagcaact ggcctgccac tttcggcgga    300

gggaccaagg tggagatcaa a                                              321
```

<210> SEQ ID NO 182
<211> LENGTH: 321
<212> TYPE: DNA
<213> ORGANISM: Streptococcus pneumoniae

<400> SEQUENCE: 182

```
gacatccaga tgacccagtc tccttcctcc ctgtctgcat ctgtaggaga cagtgtcacc     60

atcacttgcc aggcgagtca ggacattaga gaccgtttaa attggtatca gcagaagcca    120
```

gggaaagccc ctaacctcct gatctacgat gcatcaagtt tggaaacagg ggtcccatca 180
aggttcagag gaagtggatc tgggacagat tttactttca ccatcagcag cctgcagcct 240
gaagatattg caacatatta ctgtcaacag tttgttagtt tccctcgaac tttcggcccg 300
gggaccaaag tggatatcaa a 321

<210> SEQ ID NO 183
<211> LENGTH: 330
<212> TYPE: DNA
<213> ORGANISM: Streptococcus pneumoniae

<400> SEQUENCE: 183
gaaattgtgt tgacgcagtc tccaggcatc ctgtctttgt ctccagggga aagagccacc 60
ctctcctgca gggccagtca gagtgttagc agcaggtcct tgtcctggta ccagcagaga 120
cctggcctgg ctcccaggct cctcatctat gctgcatcca gcagggccgc tgtcacccca 180
gacaggttca ctgccagcgg gtctgggaca gacttcactc tcaccatcag cagtctggag 240
cctgaagatt ttgcagtgta ttactgtcag cactatggta cctcacctcc gaggtacact 300
tttgggcagg ggaccaaggt ggagatcaaa 330

<210> SEQ ID NO 184
<211> LENGTH: 339
<212> TYPE: DNA
<213> ORGANISM: Streptococcus pneumoniae

<400> SEQUENCE: 184
gacatcgtga tgacccagtc cccagactcc ctggctgtgt ctctgggcga gagggccacc 60
atcaactgca agtccagcca gagtgtttta cacagctcca acaataagaa ctactttgct 120
tggtaccagc agaaaccagg acagcctcct aagctgctca ttcactgggc atctacccgg 180
gcatccgggg tccctgaccg attcagtggc agcgggtctg ggacagattt cactctcacc 240
atcagcagcc tgcaggctga agatgtgaca atttattact gtcagcaata ttatagtact 300
ccgtacactt ttggccaggg gaccaaggtg gaaatcaaa 339

<210> SEQ ID NO 185
<211> LENGTH: 327
<212> TYPE: DNA
<213> ORGANISM: Streptococcus pneumoniae

<400> SEQUENCE: 185
gaaattgtgt tgacgcagtc tccaggcacc ctgtctttgt ctccagggga aagagccacc 60
ctctcctgca gggccagtcc gagtcttgac agcgcctact tagcctggta ccagcagaag 120
cctggccagg ctcccaggct cctcatctat ggtgcatcct ccagggtcac tggcatccca 180
gataggttca gtggcagtgc gtcagggaca gacttcactc tcaccatcag cagactggag 240
cctgaagatt ttgcagtgta ctactgtcag cggtatggta actcacctcc gtacactttt 300
ggccagggga ccaaggtgga gatcaaa 327

<210> SEQ ID NO 186
<211> LENGTH: 339
<212> TYPE: DNA
<213> ORGANISM: Streptococcus pneumoniae

<400> SEQUENCE: 186
gacatcgtga tgacccagtc tccagactcc ctggctgtgt ctctgggcga gagggccacc 60
atcagctgca agtccagcca gagtctttta tacagttcca gcaataagaa ctacctagct 120
tggttccagc agaaaccagg acaggctcct aagttgctca tttactgggc atctacccgg 180
gaatccgggg tccctgaccg attcagtggc agcgggtctg ggacagattt cactctcacc 240
atcagcagcc tgcagactga agatgtggca gtttattatt gtctgcaata tcgtagtgct 300
ccgttcactt tcggcggagg gaccaaggtg gagatcaaa 339

<210> SEQ ID NO 187
<211> LENGTH: 321
<212> TYPE: DNA
<213> ORGANISM: Streptococcus pneumoniae

<400> SEQUENCE: 187
gacatccaga tgacccagtc tccttccacc cagtctgcat ctgtaggaga cagagtcacc 60
atcacttgcc gggccagtca gagtattagt agttggttgg cctggtatca gcagaaacca 120
gggaaagccc ctaaggtcct gatctatgcg gtgtctagtt tagaaagtgg ggtcccatca 180
aggttcagcg gcagtggatc tgggacagaa ttcactctca ccatcagcag cctgcagcct 240
gaggattttg caacttatta ctgccaacaa tatagtactt atccctggac gttcggccca 300
gggaccaagg tggaaatcaa a 321

<210> SEQ ID NO 188
<211> LENGTH: 321
<212> TYPE: DNA
<213> ORGANISM: Streptococcus pneumoniae

<400> SEQUENCE: 188
gaaatagtga tgacgcagtc tccagcctcc ctgtctgtgt ctccagggga aacagccacc 60
ctctcctgca gggccagtca gagtgttggc agcaccttag cctggtacca gcagaagccc 120
ggccaggctc ccaggctcct catctataat gtattcacca gggccgctgg tgtcccagcc 180
aggttcagtg gcagtgggtc taggacggag ttcactctca ccatcagcag cctgcagtct 240
gaagattttg cagtttatta ctgtcagcag tatagtacct ggctgtggac gttcggccaa 300
gggaccaagg tggaaatcaa a 321

<210> SEQ ID NO 189
<211> LENGTH: 321
<212> TYPE: DNA
<213> ORGANISM: Streptococcus pneumoniae

<400> SEQUENCE: 189
gacatccaga tgacccagtc tccatcctcc ctgtctgcat ctgtaggaga cagagtcacc 60
atcacttgcc gggcaagtca gcgcattagc agctacttga attggtatca gcagaaacca 120
gggaaagccc ctaacctcct gatctacgct gcagccagtt tgcatgatgg ggtcccatca 180
aggttcagtg gcagtggatc tgggacagat ttcactctca ccatcagcag tctgcaacct 240
gaagattttg caacttatta ttgtcaacag cgttacagaa tcccgtacag ttttggcccg 300
gggaccaagg tggagatcaa a 321

<210> SEQ ID NO 190
<211> LENGTH: 336
<212> TYPE: DNA
<213> ORGANISM: Streptococcus pneumoniae

<400> SEQUENCE: 190

```
gatattgtga tgactcagtc tccactctcc ctgtccgtca cccctggaga gccggcctcc     60
atctcctgca ggtctagtca gagcctcctt cagggtaatg gacacaacta tttggattgg    120
tacctgcaga agccaggaca gtctccacaa ctcctgatct atttgggttc tattcgggcc    180
tccggggtcc ctgacaggtt cagtggcagt ggatcaggca cagattttat actgaaaatc    240
agcagagtgg aggctgagga tgttggggtt tattactgca tgcgagctct acaaactccg    300
tacacttttg gccaggggac caaggtggaa atcaaa                              336
```

<210> SEQ ID NO 191
<211> LENGTH: 321
<212> TYPE: DNA
<213> ORGANISM: Streptococcus pneumoniae

<400> SEQUENCE: 191

```
gacatccaga tgacccagtc gccttccacc ctgtctgcat ctgttggaga cagagtcacc     60
ctcacttgtc gggccagtga gactcttaat aactggttgg cctggtttca gcaaaagcca    120
gggaaagccc ctaccctcct gatctatgag gcgtctagtt tagaaagtgg agtcccatca    180
aggttcagcg gcagtggatc tgggacagac ttcgctctca ccatcagcag cctgcagccc    240
gatgattttg caacttatta ttgccaccag tataataaat acccgtggac gttcggccaa    300
gggaccaagg tggagatcaa a                                              321
```

<210> SEQ ID NO 192
<211> LENGTH: 318
<212> TYPE: DNA
<213> ORGANISM: Streptococcus pneumoniae

<400> SEQUENCE: 192

```
gacatccaga tgacccagtc tccttccacc ttgtctgcat ctgtaggaga cagagtcacc     60
atcacttgtc gggccagtca gagtattagt ggctggttgg cctggtatca gcagaaagca    120
gggaaagccc ctaagctcct gatctataag gcgtctagtt tagaaagtgg ggtcccatca    180
aggttcagcg gcagtggatc tgggacagag ttcactctca ccatcagcag cctgcagcct    240
gatgattttg caacttatta ctgccagcag tattatagtt ggggaacgtt cggccaaggg    300
accaaggtgg agatcaaa                                                  318
```

<210> SEQ ID NO 193
<211> LENGTH: 336
<212> TYPE: DNA
<213> ORGANISM: Streptococcus pneumoniae

<400> SEQUENCE: 193

```
gatattgtga tgacccagac tccactctcc ttacctgtca cccttggaca gccggcctcc     60
atctcctgca tatctagtca aagcctcgta cacagtgatg gaaacaccta cttgagttgg    120
cttcagcaga ggccaggcca gcctccaaga ctcctgattt ataagatttc taaccggttc    180
tctggggtcc cagacagatt cagtggcagt ggggcaggga cagatttcac actgaaaatc    240
agcagggtgg aagctgagga tgtcggggtt tattactgca tgcaagcttc acaatctacg    300
tggacgctcg gccaagggac caaggtggag atcaaa                              336
```

<210> SEQ ID NO 194
<211> LENGTH: 339
<212> TYPE: DNA

<213> ORGANISM: Streptococcus pneumoniae

<400> SEQUENCE: 194
gacatcgtga tgacccagtc tccagactcc ctggctgtgc ctctgggcga gagggccacc 60
atcaactgca cgtccagcca gactgtttta tccagttcca acaataagaa ctacttagtt 120
tggtaccagc agaaaccagg acagcctcct aagttgctcc tttactgggc gtctacccgg 180
gcatccgggg tccctgaccg attcagtggg agcgggtctg ggacagattt cactctcacc 240
attagcagtc tgcaggctga agatgtggca gtttattact gtcagcaatg ttataatgct 300
ccgctcactt tcggccgagg gaccaaggtg gagatcaaa 339

<210> SEQ ID NO 195
<211> LENGTH: 324
<212> TYPE: DNA
<213> ORGANISM: Streptococcus pneumoniae

<400> SEQUENCE: 195
gaaatagtga tgacgcagtc tccagccacc ctgtctgtgt ttccagggga aggagtcacc 60
ctctcctgca gggccagtca gagtattagc aacaacttgg cctggtacca gcagaaacct 120
ggccaggctc ccaggctcct catgtatgat gcatccacca gggccactgg tatcccagcc 180
aggttcagtg gcagtgggtc tgggacagag ttcactctca ccatcagcag cctgcagtct 240
gaagatttcg cagtttatta ctgtcagcag tataataact ggcctccggt cacgttcggc 300
caagggacca aggtggaaat caaa 324

<210> SEQ ID NO 196
<211> LENGTH: 332
<212> TYPE: DNA
<213> ORGANISM: Streptococcus pneumoniae

<400> SEQUENCE: 196
ttgtgatgac tcagtctcca ctctccctgc ccgtcaccct tggacagtcg gcctccgtct 60
cctgcaggtc aagtcaaagc ctcggcccca gtgacggaag cacccgcttg gattggtttc 120
aacagaggcc aggccaatct ccaaggcgcc taatttatgc ggtttctaac cgggactctg 180
gggtcccaga cagattcagc ggcagcgggt caggcagtga tttcacactg agaatcagca 240
gagtggaggc tgaggatgtt ggggtttatt actgcatgca atatacatac tggcctcaca 300
cttttggcca ggggaccaag gtggaaatca aa 332

<210> SEQ ID NO 197
<211> LENGTH: 327
<212> TYPE: DNA
<213> ORGANISM: Streptococcus pneumoniae

<400> SEQUENCE: 197
gaaattgtgt tgacacagtc tccagccacc ctgtctttgt ctccagggga aagagccacc 60
ctctcctgca gggccagtca gagtgttagc agttccttag cctggtacca acaaaaacct 120
ggccaggctc ccaggctcct catctatgat gcatccaaga gggccactga catcccagcc 180
aggttcagtg gcagtgggtc tgggacagac ttcactctca ccatcagcag cctagagcct 240
gaagattttg cggtttatta ctgtcagcac cggggggagt ggcctccggg ggccactttc 300
ggccctggga ccaaagtgga tatcaaa 327

<210> SEQ ID NO 198
<211> LENGTH: 321

```
<212> TYPE: DNA
<213> ORGANISM: Streptococcus pneumoniae

<400> SEQUENCE: 198

gacatccagt tgacccagtc tccatccttc ctgtctgcat ctgtaggaga cagagtcacc     60

atcacttgcc gggccagtca gggcattgat actcgtttga tctggtatca acagaagcca    120

ggggaagccc ctaagctcct gatctatgaa gcatccactt tgcaaagtgg ggccccatca    180

aggttcagcg gcagtggatt cgggacagaa ttcactctca caatcagcag tctgcagcct    240

gaagactttg caacttatta ctgtcaacag tttaaaggtt acccgctcac tttcggcggg    300

gggaccaagg tggagatcaa a                                              321


<210> SEQ ID NO 199
<211> LENGTH: 345
<212> TYPE: DNA
<213> ORGANISM: Streptococcus pneumoniae

<400> SEQUENCE: 199

caggtgcagc tgcaggagtc gggcccagga ctggtgaagc cttcggagac cctgtccctc     60

acctgcactg tctctggtgg ctccatcagt agtcactact ggagctggat ccggcagccc    120

ccagcgaagg gactggagtg gattgggtat atctatcaca gtgggatgac caactacaac    180

ccctccctca agagtcgagt caccatatca atagacacgt ccaagaacca gttctccctg    240

aagttgagct ctgtgaccgc tgcggacacg gccgtgtatt actgtgcgag aggtgatggc    300

tacaatttct tctggggcca gggaacgctg gtcaccgtct cctca                    345


<210> SEQ ID NO 200
<211> LENGTH: 375
<212> TYPE: DNA
<213> ORGANISM: Streptococcus pneumoniae

<400> SEQUENCE: 200

caggtgcagc tggtggagtc tgggggaggc gtggtccagc ctgggggggtc cctgagactc     60

tcctgtgcag cgtctggact cacgttcagt aaccaagatt tccactgggt ccgccaggct    120

ccaggcaagg ggctggaatg ggtggcattt atacgttatg atggaggttt taaaaactat    180

gcagactccg tgaagggccg attcaccatc tccagagaca attcccagaa aatgctgtat    240

ctgcaaatgg acagcctgag agttgaagac acggctgtgt attactgtgc gaagtgcggc    300

gcagaggact ctactactgt ctggctgaat tggttcgacc cctggggcca gggaaccctg    360

gtcaccgtct cctca                                                     375


<210> SEQ ID NO 201
<211> LENGTH: 360
<212> TYPE: DNA
<213> ORGANISM: Streptococcus pneumoniae

<400> SEQUENCE: 201

gaggtgcagc tgttggagtc tgggggaggc ttggtagagc ctgggggggtc cctgagactc     60

tcctgtgcag cctctggatt cacctttagc agctatgcca tgagctgggt ccgccaggct    120

ccagggaagg ggctggagtg ggtctcagct attagtgaca gtggtggtag cacatactac    180

gcagactccg tgaagggccg gttcaccatc tccagagaca agtccaagaa cacgctgtat    240

ctgcaaatga acagcctgag agccgaggac acggccgtat attactgtgc gaaaccgaat    300

tactttggtt cggggagtcc cgactactgg ggccagggaa cgctggtcac cgtctcctca    360
```

<210> SEQ ID NO 202
<211> LENGTH: 345
<212> TYPE: DNA
<213> ORGANISM: Streptococcus pneumoniae

<400> SEQUENCE: 202
caggtgcagc tgcaggagtc gggcccagga ctggtgaagc cttcggagac cctgtccctc 60
acctgcactg tctctggtgc ctccatcagt agtcactact ggagctggat ccggcagccc 120
ccagggaagg gactggagtg gattgggtat atctatcaca gtgggattac caactacaac 180
ccctccctca agagtcgagt caccatatca atagacacgt ccaagaacca gtactccctg 240
aagctgagct ctgtgaccgc tgcggacacg gccgtgtatt actgtgcgag aggtgatggc 300
tacaatttct actggggcca gggaacgctg gtcaccgtct cctca 345

<210> SEQ ID NO 203
<211> LENGTH: 378
<212> TYPE: DNA
<213> ORGANISM: Streptococcus pneumoniae

<400> SEQUENCE: 203
gaggtgcagc tggtggagtc tgggggaggt gtggtacggc ctggggggtc cctgagactc 60
tcctgtgcag cctctggatt cacctttgat gattatggca tgacctgggt ccgccaagct 120
ccagggaagg ggctggagtg gatctctggt atttgttgca acggtggttg ctcaggttat 180
gcagactctg tgaagggccg attcaccatc tccagagaca acgccaagaa gtccctgttt 240
ctggtcatga acagtctgag agccgaggac acggccttgt attactgtgt gagagtggca 300
gtaccagctg ctacatacac ccgagggaat gatgcttttg atatttgggg ccaagggaca 360
atggtcaccg tctcttca 378

<210> SEQ ID NO 204
<211> LENGTH: 357
<212> TYPE: DNA
<213> ORGANISM: Streptococcus pneumoniae

<400> SEQUENCE: 204
gaggtgcagc tggtggagtc tgggggaggc ttggtagagc ctggggggtc cctcagactc 60
tcctgtgcag tctctggttt cactttcact gacgcctgga tgacctgggt ccgccaggct 120
ccagggaagg ggctagattg ggttggccat gtaaaaagta aatatgatgg tgcgacaaca 180
gagtacgctg cacccgtgca aggcagattc accatctcaa gagatgattc aaagaagaca 240
atatatctgc aaatgaacag cctgaacacc gaggacacag gcgtctattt ttgtaccaca 300
gctcatggcc cggtgggtga ccattggggc cagggaacac tggtcaccgt ctcctca 357

<210> SEQ ID NO 205
<211> LENGTH: 378
<212> TYPE: DNA
<213> ORGANISM: Streptococcus pneumoniae

<400> SEQUENCE: 205
gaggtgcagc tggtggagtc tgggggaggc ttggtccagc cggggggggtc cctgagactc 60 tcctgtgcag cctctggatt cagctttgat acctcttgga tgacctgggt ccgccaggct 120
ccagggaagg ggctggagtg ggtggccacc ataaaccagg gtggaagtga caaatactat 180
gtggactctg tgaagggccg attcaccatc tccagagaca acgccaagaa ctcactgtat 240
ctgcaaatga acagcctgcg agccgaggac acggctgtat attactgtgc gagagcgggc 300

```
gggtgtagct ctaccagatg ccatacaacc ccgggatttg actactgggg ccagggagcg    360

ctggtcaccg tctcctca                                                  378


<210> SEQ ID NO 206
<211> LENGTH: 353
<212> TYPE: DNA
<213> ORGANISM: Streptococcus pneumoniae

<400> SEQUENCE: 206

tgcagctgca ggagtcgggc ccaggactgg tgaagccttc ggagaccctg tccctcacct     60

gcactgtctc tggtagctcc atcagcagta gtagttacta ctggggctgg gtccgccagt    120

ccccagggaa gggactggag tggattggga gtatctatca cagtgggacc atctactaca    180

acccgtccct caggagtcga gtcaccatat ccgtagacac gtccaagaac cagttctccc    240

tgaagctgaa ctctgtgacc gccgcagaca cggctgttta ttactgtgcg agtcttagtg    300

gcacaaatgc ttttgatatc tggggccaag ggacaatggt caccgtctct tca           353


<210> SEQ ID NO 207
<211> LENGTH: 360
<212> TYPE: DNA
<213> ORGANISM: Streptococcus pneumoniae

<400> SEQUENCE: 207

gaggtgcagc tgttggagtc tgggggggc ttggtacagc ctgggggggtc cctgagactc     60

tcctgtgcag cctctggatt cacctttagc agccatgaca tgagttgggt ccgcctggct    120

ccagggaagg ggccggagtg ggtctcagct cttggtgctg gagatgcttg gacacactac    180

gcaaactccg tgaggggccg gttcaccatc tccagagacg attccaagaa cacgctgtat    240

ctgcaaatga acagcctgag agccgaagac acggccgtgt atttctgtgc gaaaccccgt    300

ggatactcct atggctactt tgactactgg ggccaaggaa cgctggtcac cgtctcctca    360


<210> SEQ ID NO 208
<211> LENGTH: 351
<212> TYPE: DNA
<213> ORGANISM: Streptococcus pneumoniae

<400> SEQUENCE: 208

gaggtgcagc tggtggagtc tgggggaggc ttggtccagc ctggggggtc cctgagactc     60

tcctgtggag cctctggatt cacctttagt acctattgga tgacctgggt ccgccaggct    120

ccagggaagg gcctggagtg ggtggccaat ataaaccaag atggaagtga gaaacaatat    180

gtggactctg tgaagggccg attcaccatc tccagagaca acgccaagaa ctcactgtat    240

ctgcagatga acagcctgag agtcgaggat acggctattt attactgtgc gagaccccca    300

gctcgccgac ttgactactg gggccaggga tcgctggtca ccgtctcctc a             351


<210> SEQ ID NO 209
<211> LENGTH: 348
<212> TYPE: DNA
<213> ORGANISM: Streptococcus pneumoniae

<400> SEQUENCE: 209

gaggtgcagc tggtggagtc cgggggaggc ttagttcagc ctggggggtc cctgagactc     60

tcctgtgcag cctctgaatt caccttcagt gactactgga tgcactgggt ccgccaagct    120

ccagggaagg ggctggtctg ggtctcacgt attaatactg acgggagtac cacaacctac    180
```

```
gcggactccg tgaagggccg attcaccatc tccagagaca acgccaagaa cacgctgtat    240

ctacaaatga acagtctgag ggccgaggac acggctgtgt attactgtgc aagatctaat    300

gcggggcacg aagcgtgggg ccagggaacg ctggtcaccg tctcctca                 348


<210> SEQ ID NO 210
<211> LENGTH: 353
<212> TYPE: DNA
<213> ORGANISM: Streptococcus pneumoniae

<400> SEQUENCE: 210

aggtgcagct ggtgcagtct ggggctgagg tgaagaagcc tggggcctca gtgagggttt     60

cctgcaaggc atctggatac accttcacca actactggat acactgggtg cgacaggccc    120

ctggacaagg gcttgagtgg atgggaatga tcgcccctaa ggaaggttac acattctacg    180

cacagcaatt acagggcaga gtcaccgtga ccagggacac gtcgacgagc gcggtttaca    240

tggagctgaa cagcctgaga tctgaggaca cggccgtata tttctgtgcg agagacattc    300

cccacgctaa tttggactat tggggccagg ggacgctggt caccgtctcc tca           353


<210> SEQ ID NO 211
<211> LENGTH: 363
<212> TYPE: DNA
<213> ORGANISM: Streptococcus pneumoniae

<400> SEQUENCE: 211

gaggtgcagc tgttggagtc tgggggagga ttggtacagc ctgggggtc cctgagactc      60

tcctgtgcag cctctggatt cacctttagc gattatacca tgaattgggc ccgccaggct    120

ccagggaagg ggctggagtg ggtctcagct attagagaga gtggtgacag cacatactac    180

gcagactccg tgacgggccg gttcaccatc tccagggaca attccagaaa cacactttat    240

ctgcacatga acagcctgag agccgaggac acggccatgt atttttgtgt gaaagacagg    300

gtgccgccgg gtgacgtgcc gggtgacttc tggggcccgg gaacgctggt caccgtctcc    360

tca                                                                  363


<210> SEQ ID NO 212
<211> LENGTH: 321
<212> TYPE: DNA
<213> ORGANISM: Streptococcus pneumoniae

<400> SEQUENCE: 212

gacatccagt tgacccagtc tccatccttc ctgtctgcat ctgtaggaga cagagtcacc     60

atcacttgcc gggccagtca ggacatgacc cattctttag cctggtatca gcaaaaacca    120

gggaaagccc ctaacctcct gatctataat gcatacactt tgcaaagtgg ggtcccatca    180

aggttcagcg gcagtggatc tgggacagaa ttcactctca caatcagcag cctgcagcct    240

gaagattttg caacttatta ctgtcaacag attaatagtt accctcgaac ttttggccag    300

gggaccaagg tggagatcaa a                                              321


<210> SEQ ID NO 213
<211> LENGTH: 321
<212> TYPE: DNA
<213> ORGANISM: Streptococcus pneumoniae

<400> SEQUENCE: 213

gaaattgtgt tgacacagtc tccaggcacc ctgtctttgt ctccagggga aagagccact     60

ctctcctgca gggccagtca gaatattggc accgccttag cctggtacca acagaaacct    120
```

ggccaggctc ccagactcat catctatgaa acatccaaca gggccactga cgtcccagcc 180
aggttcagtg gcagtgggtc tgggacagac ttcactctca ccatcagcag cctggagcgt 240
gaagattttg ccctttatta ctgtcaacag cgtgccgact ggccgctcac tttcggcgga 300
gggaccaagg tggagatcaa a 321

<210> SEQ ID NO 214
<211> LENGTH: 324
<212> TYPE: DNA
<213> ORGANISM: Streptococcus pneumoniae

<400> SEQUENCE: 214
gaaattgtgt tgacacagtc tccagccacc ctgtctttgt ctccagggga aagagccacc 60
ctctcctgca gggccagtca gagtgttagc agctacttag cctggtacca acagagacct 120
ggccaggctc ccaggctcgt catctatgct gcatccaaca gggccactgg catcccagcc 180
aggttcagtg gcagtgggtc tgggacagac ttcactctca ccatcagcag cctagagcct 240
gaagattttg cagtttatta ctgtctgcag tgtagcaact ggcccatgta cacttttggc 300
caggggacca aggtggagat caaa 324

<210> SEQ ID NO 215
<211> LENGTH: 321
<212> TYPE: DNA
<213> ORGANISM: Streptococcus pneumoniae

<400> SEQUENCE: 215
gacatccagt tgacccagtc tccatccttc ctgtctgcat ctgtagggga cagagtcacc 60
atcacttgcc gggccagtca ggacattacc gattctttag cctggtatca gcaaaaacca 120
gggaaagccc ctaacctcct gatctatact gcatccactt tgcaaagtgg ggtcccatca 180
aggttcagcg gcagtggatc tgggacagaa ttcactctca caatcagcag cctgcagcct 240
gaagatttta caacttatta ctgtcaacag attaatagtt accctcgaac ttttggccag 300
gggaccaagg tggagatcaa a 321

<210> SEQ ID NO 216
<211> LENGTH: 321
<212> TYPE: DNA
<213> ORGANISM: Streptococcus pneumoniae

<400> SEQUENCE: 216
gacatccaga tgacccagtc tccatcctcc ctgtctgcat ctgtaggaga cagagtcacc 60
atcacttgcc gggcaagtca gggcattaga aatgatttag gctggtatca gcagaaacca 120
gggaaagccc ctaagcgcct gatctatgct gcatccagtt tgcaaagtgg ggtcccatca 180
aggttcagcg gcagtggatc tgggacagaa ttcactctca caatcagcag cctgcagcct 240
gaagattttg caagttatta ctgtctacag catagtagtt tcccgtggac gttcggccag 300
gggaccaagg tggaaatcaa a 321

<210> SEQ ID NO 217
<211> LENGTH: 342
<212> TYPE: DNA
<213> ORGANISM: Streptococcus pneumoniae

<400> SEQUENCE: 217
gacatcgtga tgacccagtc tccagactcc ctggctgtgt ctctgggcga gagggccgcc 60
atcaactgca agtccagcca gagtgtctta gacagctcca acatgaagag gtacttagcc 120
tggtatcagc tgaaagcagg acagcctcct aggttgctca tttacttggc ttccacccgg 180
gaatccgggg tcccggaccg attcagtggc agcgggtccg ggacagattt caatctcact 240
atcagcagcc tgcaggctga agatgtggca gtttattact gtcagcaata ttatacaacc 300
ccttcgatca ccttcggcca agggacacga ctggagatta aa 342

<210> SEQ ID NO 218
<211> LENGTH: 342
<212> TYPE: DNA
<213> ORGANISM: Streptococcus pneumoniae

<400> SEQUENCE: 218
gacatcgtga tgacccagtc tccagactcc ctggctgtgt ctctgggcga gagggccacc 60
atcaactgca agtccagcca gagtgtttta tacagctcca acaataagaa ctacttagct 120
tggtaccagc agaaaccagg tcagcctcct aagatgctca tttactgggc atctacccgg 180
gagtccgggg tccctgaccg attcagtggc agcgggtctg ggacagattt cactctcacc 240
atcagcagcc tgcaggctga agatgtggca gtttattact gtcagcaata ttatactact 300
cctcccatca ccttcggcca agggacacga ctggagatta aa 342

<210> SEQ ID NO 219
<211> LENGTH: 318
<212> TYPE: DNA
<213> ORGANISM: Streptococcus pneumoniae

<400> SEQUENCE: 219
gaaattgtgt tgacacagtc tccagccacc ctgtctttgt ctccagggga aagagccacc 60
ctctcctgca gggccagtca gagtgttagt atctacttag cctggtacca acagaaacct 120
ggccaggctc ccaggctcct catctatgat tcatccaaca gggccactgg catcccagcc 180
aggttcagtg gcagtgggtc tgggacagac ttcactctca ccatcagcag cctagagccc 240
gaagattttg cggtttatta ctgtcagcag cgtagcagcg ggcgaacgtt cggccaaggg 300
accaaggtgg agatcaaa 318

<210> SEQ ID NO 220
<211> LENGTH: 324
<212> TYPE: DNA
<213> ORGANISM: Streptococcus pneumoniae

<400> SEQUENCE: 220
gaaattgtgt tgacgcagtc tccaggcacc ctgtctttgt ctccagggga aagagccacc 60
ctctcctgca gggccagtca gactgttacc aacaactact tagcctggta ccaacacaaa 120
cctggcctgg cgcccaggct cctcatcttt gatgcatcca tcagggccac tggcatccca 180
gacaggttca gtggcagtgg gtctggggca gacttcactc tcaccatcag cagactggag 240
cctgaagatt ttacattcta ttactgtcag caatatggta tttcacctcg aacttttggc 300
caggggacca aggtggagat caaa 324

<210> SEQ ID NO 221
<211> LENGTH: 336
<212> TYPE: DNA

<213> ORGANISM: Streptococcus pneumoniae

<400> SEQUENCE: 221
gatattgtga tgacccagac tccactctct ctgtccgtca cccctggaca gccggcctcc 60
atctcctgca agtctagtca gagtctcctg gatagtgatg gaaggaccta tttcttttgg 120
tatttgcaga agccaggcca gtctccacaa ctcctgatct atgaagtttc caaccggttc 180
tctggagtgc cagataggtt cagtggcagc gggtcaggga cagatttcac actgaaaatc 240
agccgggtgg agtctgaaga tgttggggtt tattactgca tgcaaggtac acaccatccg 300
tggacgttcg gccaagggac caaggtggaa atcaaa 336

<210> SEQ ID NO 222
<211> LENGTH: 340
<212> TYPE: DNA
<213> ORGANISM: Streptococcus pneumoniae

<400> SEQUENCE: 222
gacatcgtga tgacccagtc tccagactcc ctggctgtgt ctctgggcga gagggccacc 60
gtcaactgca agtccagcca gagtgtttta tacagctcca acagtaagaa ctacttagct 120
tggtaccagc agaaaccagg acagcctcct aagctgctca tttactgggc atctacccgg 180
gaatccgggg tccctgaccg attcagtggc agcgggtctg ggacagattt cactctcacc 240
atcagcagcc tgcaggctga agatgtggca gtgtattact gtcagcaata ttatagtact 300
cctctcactt tcggcggagg gaccaaggtg gagatcaaac 340

<210> SEQ ID NO 223
<211> LENGTH: 322
<212> TYPE: DNA
<213> ORGANISM: Streptococcus pneumoniae

<400> SEQUENCE: 223
gacatccaga tgacccagtc tccatcctcc ctgtctgcat ctgtgggaga cagagtcacc 60
atcacttgcc gggcaagtca gggcattggg aatgatttag gctggtatca gcatgaacca 120
gggaaagccc ctaagcgcct gatctatgca gcatccagtt tgcaaagtgg ggtcccatcg 180
aggttcagcg gcagtgcatc tgggacagaa ttcactctca caatcaccag cctgcagcct 240
gaagattttg caacttatta ctgtctacaa catactactt tcccgtggac gttcggccaa 300
gggaccaagg tggaaatcaa ac 322

<210> SEQ ID NO 224
<211> LENGTH: 325
<212> TYPE: DNA
<213> ORGANISM: Streptococcus pneumoniae

<400> SEQUENCE: 224
gaaattgtgt tgacacagtc tccagccacc ctgtctttgt ctccagggga aagagccacc 60
ctctcctgca gggccagtca gagtgttggc agtcacttcg cctggtacca acagaaacct 120
ggccaggctc ccaggctcct catctatggt gcatccaaca gggcccctgg catcccacct 180
aggttcagtg ccagtggatc tgggacagac ttcactctca ccatcagcag cctagagcct 240
gaagattttg caatttatta ctgtcaacag cgtaggacct ggcctccgct aaccttcggc 300
caagggacac gactggagat taaac 325

<210> SEQ ID NO 225
<211> LENGTH: 357

<212> TYPE: DNA
<213> ORGANISM: Streptococcus pneumoniae

<400> SEQUENCE: 225
gaggtgcagc tggtggagtc tgggggaggc ttggtacagc ctggagggtc cctgagactc 60
tcctgtgtag cctctggatt cagtttcagt ggtcatgaaa tgaactgggt ccgccagcct 120
ccagggaagg ggctggagtg ggtttcacac attggcagtg gtggtgatta tataggttac 180
gcagactctg tgaagggccg attcaccgtc tctagagaca acgccaagaa tttactctat 240
ctgcaaatga acagcctgag agccgacgac acggctgttt attactgtgc gaccttgctt 300
ttgcgagaca accaactgga cgtctggggc caagggacca cggtcaccgt ctcctca 357

<210> SEQ ID NO 226
<211> LENGTH: 363
<212> TYPE: DNA
<213> ORGANISM: Streptococcus pneumoniae

<400> SEQUENCE: 226
caggtgcagc tggtggagtc tgggggaggc gtggtccagc cagggaggtc cctaagactc 60
tcctgtgcag cctctggatt caccctcagt agttgtggca tgcactggat ccgccaggct 120
ccaggcaagg ggctggagtg ggtggcagtt ataacatatg atggacgaag tcacttcaac 180
gcagacgccg tgaagggccg attcaccatc tccagagaca gatccatgaa cacggtgtct 240
ctgcaaatgg acagcctgag acccgaggac acggctgttt attactgtgt caaagaacaa 300
ggctttggtt actaccggac cgccgactac tggggccagg gaaccctggt caccgtctcc 360
tca 363

<210> SEQ ID NO 227
<211> LENGTH: 342
<212> TYPE: DNA
<213> ORGANISM: Streptococcus pneumoniae

<400> SEQUENCE: 227
caggtgcagc tgcaggagtc gggcccagga ctggtgaggc cttcggagac cctgtccctc 60
acctgcactg tctctggtgg ctccatcagt agtgaccact ggagttggat ccggcagccc 120
ccaggcaagg gactggagtg gattgggaat gtctattaca gtgggcgcac ctactacaac 180
ccctccttca agagtcgagt caccatatca gtagccacgt ccaagaacca gttctccctg 240
aaggtgacct ctgtgaccgc cgcagacacg gccatttatt actgtgcgag gcgaaatgat 300
tttaatatct ggggccaggg gacaatggtc accgtctctt ca 342

<210> SEQ ID NO 228
<211> LENGTH: 369
<212> TYPE: DNA
<213> ORGANISM: Streptococcus pneumoniae

<400> SEQUENCE: 228
gaggtgcagc tgttggagtc tgggggaggc ttggtacagc ctgggggtc cctgagactc 60 tcctgtgcag cctctggatt cacctttagt aaatatgccg tgagctgggt ccgccaggct 120
ccagggaagg ggctggagtg ggtctcagct gtcagtggta atggtgactc cacatactac 180
gcagaccccg tgaggggccg gttcaccatc tccagagaca attccaagaa caccctgtat 240
ctgcaaatga acagcctgag agccgaggac acggccctat attactgttc gatctggtgg 300

```
gggacttcag tacagtaccc attggtgctc gactactggg gcctgggaac cctggtcacc    360

gtctcctca                                                            369


<210> SEQ ID NO 229
<211> LENGTH: 363
<212> TYPE: DNA
<213> ORGANISM: Streptococcus pneumoniae

<400> SEQUENCE: 229

caggtgcagc tggtggagtc gggggaggc gtggtccagc ctgggaggtc cctaagactc     60

ctgtgtgcag cctctggatt caccctcagt acttgtggca tgcactggat ccgccagact    120

cctggcaagg ggctggagtg ggtggcagtt aaaacatatg acggaagaga ggagttctac    180

gcagactccg tgaagggccg attcaccatt tccagagacg agtccatgaa cacgctgtct    240

ttgcagatga acagcctgag acctgaagac acggctgtat attactgtgt caaagaacaa    300

gactacggtt actaccggac cgccgaccac tggggccagg gaaccctggt caccgtctcc    360

tca                                                                  363


<210> SEQ ID NO 230
<211> LENGTH: 351
<212> TYPE: DNA
<213> ORGANISM: Streptococcus pneumoniae

<400> SEQUENCE: 230

caggtgcagc tgcaggaggc gggcccagga ctggtgaagc cttcacagac cctgtccctc     60

acctgcactg tctctggtgg ctccatcagc agtggtggtt actactggag ctggatccgc    120

cagcacccag ggaagggcct ggagtggatt gggtacatct attacagtgg gagcacctac    180

tacaacccgt ccctcaagag tcgagtcacc atatcagtag acacgtccaa gaaccagtat    240

tccctgaagc tgagttctgt gaccgccgca gacacggccg tatattactg tgcgagaggg    300

catggcttca acgcctactg gggccaggga accctggtca ccgtctcctc a             351


<210> SEQ ID NO 231
<211> LENGTH: 366
<212> TYPE: DNA
<213> ORGANISM: Streptococcus pneumoniae

<400> SEQUENCE: 231

gaggtgcagc tggtggagtc cgggggaggc ttggtaaagc cgggggagtc ccttagactc     60

tcgtgtgcaa cctctggagt caacttcaac atcgcctgga tgacctgggt ccgccaggct    120

ccagggaagg gactggagtg ggttggccgt attaaaagca aaattggtgg tgggacaaca    180

gactatgctg cacccgtgaa aggcagattc accatgtcaa tagatgattc aaaaaatacc    240

ctatatctgc aaatgaacag cctgaaaacc gaggacacag ccgtgtatta ttgtaccaca    300

gtccgcaata tggccgactt gtcccttaat cactggggcc agggaaccct ggtcaccgtc    360

tcctca                                                               366


<210> SEQ ID NO 232
<211> LENGTH: 354
<212> TYPE: DNA
<213> ORGANISM: Streptococcus pneumoniae
```

<400> SEQUENCE: 232

```
gaggtgcagc tggtggagtc tgggggaggc ttggtacagc ctggagcgtc cctgacactg     60
tcatgtgtag tctctggatt caccttcatt ggcactgaaa tgacctggat tcgccaggct    120
ccagggaagg ggctggaggg actttcgtac atcagtggga gtggcgggac aacatactac    180
gcagagtctg tgaggggccg attcaccatc tccagagaca acgccaagaa gtcactgttt    240
ctgcaaatga ccagcctgac agccgaggac acggctgttt actactgtgc gacaggcaac    300
cggggatcac ttcctcgccg ctggggccag ggaaccctgg tcaccgtctc ctca          354
```

<210> SEQ ID NO 233
<211> LENGTH: 354
<212> TYPE: DNA
<213> ORGANISM: Streptococcus pneumoniae

<400> SEQUENCE: 233

```
gaggtgcagc tggtggagtt tgggggaggc ttggtccagc ctggggggtc cctgagactc     60
tcctgtgtag cctctggatt cacctttagt tcctcttgga tgagttgggt ccgccaggct    120
ccagggaagg ggctggagtg cgtgggcaac ataaagccgg atgcaagttt ggtgtcctat    180
gtggactctg tgaagggccg agtcaccatc tccagagaca acgccaagaa ttcactgttt    240
ctggatatga gcagcctgag agtcgaggac acggccgtct actactgtgt gagagacggg    300
tgggacacct tctttgactc ctggggccag ggaaccctgg tcaccgtctc ctca          354
```

<210> SEQ ID NO 234
<211> LENGTH: 339
<212> TYPE: DNA
<213> ORGANISM: Streptococcus pneumoniae

<400> SEQUENCE: 234

```
gaggtgcagc tggtggagtc cgggggaggc ttagttcagc cggggggggtc cctgagactc     60
tcctgtgcag cctctggatt cacctttagt aactactgga tgaggtgggt ccgccaatct    120
ccagggaagg ggctggtgtg ggtctcacat attaaccctg atgggagttt tacaaactac    180
gcggactccg tgaagggccg attcaccatc tccagagaca acaccaagaa cacactgtat    240
ctgcaaatga acagtctgag agccgaggac acggctgtgt attactgtgt gaattttcaa    300
ctggggtggg gccagggaac cctggtcacc gtctcctca                           339
```

<210> SEQ ID NO 235
<211> LENGTH: 369
<212> TYPE: DNA
<213> ORGANISM: Streptococcus pneumoniae

<400> SEQUENCE: 235

```
caggtgcagc tggtggagtc tgggggaggc gtagtccagc ctgggaggtc cctgaaactc     60
tcctgtgcag tcgctggatt caccttcagg acctatgcta tgcactgggt ccgccaggct    120
ccaggcaggg ggctggagtg ggtggcactt atatcaaatg atggaaccaa aaaatactcc    180
gcagactccg tgaggggcca cttcaccatc tccagagaca attccaagga cacgctgtat    240
ctgcaaatga acagcctgcg acctgacgac acggctgtct attactgtgc gagagcggag    300
tattgtagtc ctggtgactg cttccttatt gacacctggg gccagggaac cctggtcacc    360
gtctcctca                                                            369
```

<210> SEQ ID NO 236

<211> LENGTH: 357
<212> TYPE: DNA
<213> ORGANISM: Streptococcus pneumoniae

<400> SEQUENCE: 236

```
caggtgcagc tggtggagtc tgggggaggc gtggtccagc ctgggaggtc cctgagactc     60

tcctgtgcag tgtctggatt caccttcagt agatacggca tgcactgggt ccgccaggct    120

ccaggcaagg ggctggagtg ggtggtagtt atatggcatg atggaagtaa tacatactat    180

gcagactccg tgaagggccg attcaccatc tccagagacg actccaagaa cacggtgtat    240

ctgcaaatga acagcctcag agtcgaggac acggctatgt attactgtct gagaggcaac    300

ccacctagca gccccaccga ctactggggc cagggaaccc tggtcaccgt ctcctca       357
```

<210> SEQ ID NO 237
<211> LENGTH: 357
<212> TYPE: DNA
<213> ORGANISM: Streptococcus pneumoniae

<400> SEQUENCE: 237

```
gaggtgcagc tgttggagtc tgggggaggc ttggtacagc ctggggggtc cctgagactc     60

tcctgtgaag tctctggatt catctttagc aactatgcca tgacctgggt ccgccaggct    120

ccagggaagg ggctgcagtg ggtctcagct attggcacta gtggtggtga cacacactac    180

gcagactccg tgaagggccg gttcaccatc tccagacaca attcccagaa caccctgtat    240

ctgcagatga acagcctgag agccgaggac acggccatat attactgtgc gaaagtcgtt    300

tatagcaggc ctcctatgga cgtctggggc caagggacca cggtcaccgt ctcctca       357
```

<210> SEQ ID NO 238
<211> LENGTH: 354
<212> TYPE: DNA
<213> ORGANISM: Streptococcus pneumoniae

<400> SEQUENCE: 238

```
gaggtgcagc tggtggagtc tgggggaggc ttggtccagc ctggggggtc cctgagactc     60

tcctgtgcag cctctggatt cacctttagt aatcgttgga tgagttgggt ccgccaggct    120

ccagggaagg ggctggaatg ggtggccaac ataaacgaag atggaagtca gaaacactat    180

gtggactctg tgaggggccg attcaccatc tccagagaca acgccaagaa ctcactgtct    240

ctgcaaatgg acagcctgag agtcgaggat acggccgtgt attattgcgc gagagcatcg    300

agggagaccg gtgaacctta ctggggccag ggaaccctgg tcaccgtctc ctca          354
```

<210> SEQ ID NO 239
<211> LENGTH: 329
<212> TYPE: DNA
<213> ORGANISM: Streptococcus pneumoniae

<400> SEQUENCE: 239

```
ttgtgatgac tcagtctcca ctctccctgc ccgtcaccct tggacagtcg gcctccatct     60

cctgcaggtc tagtcgaagc ctcgtattca gtgatggaaa cacctacttg aattggtttc    120

agcagaggcc aggccgatct ccaaggcgcc taatttataa ggtttctaag cgggactctg    180

gggtcccaga cagattcagc ggcagtgggt cagacactga tttcacactg aaaatcagca    240

gggtggaggc tgaggatgtt ggggtttatt actgcatgca aggtacacac tggcggacgt    300

tcggccaagg gaccaaggtg gagatcaaa                                      329
```

<210> SEQ ID NO 240
<211> LENGTH: 321
<212> TYPE: DNA
<213> ORGANISM: Streptococcus pneumoniae

<400> SEQUENCE: 240
gacatccaga tgacccagtc tccttccaca ctgtctgcat ctgtgggaga cagagtcacc 60
atcacttgcc gggccagtca gagtattaat tcctggttgg cctggtatca gcggaaacca 120
gggaaaaccc ctaaactcct catctatgag gcgtccagtt tagaaagtgg ggtcccatca 180
aggttcagcg gcagtagatc tgggacagag ttcaccctca ccatcagcag cctgcaggct 240
gatgattttg caacttatta ctgccaccag tatgataaat atccgtggac gttcggccaa 300
gggaccaagg tggagatcaa a 321

<210> SEQ ID NO 241
<211> LENGTH: 324
<212> TYPE: DNA
<213> ORGANISM: Streptococcus pneumoniae

<400> SEQUENCE: 241
gaaattgtgt tgacgcagtc tccaggcacc ctgtctttgt ctccagggga aagagccacc 60
ctctcctgca gggccagtca gagtgtgacc aacaactatt tggtctggca ccagcagaaa 120
cctggccagg ctcccaggct cctcatttct gatgcatcca acagggccac tggcatccca 180
gacaggttca gtggcagtgg gtctgggaca gacttcactc tcaccatcaa cagactggag 240
cctgaagatt tcgcagtgta ttactgtcag caatacggta gctcaccttt cactttcggc 300
cctgggacca aagtggatat caaa 324

<210> SEQ ID NO 242
<211> LENGTH: 324
<212> TYPE: DNA
<213> ORGANISM: Streptococcus pneumoniae

<400> SEQUENCE: 242
gaaatagtga tgacgcagtc tccagccacc ctgtctgtgt ctccagggga aagagtcacc 60
ctctcctgca gggccagtca gagtattggc agcagcttag cctggtacct gcagaaacct 120
ggccaggctc ccagagtcct catctatggt gcatccacca ggacccctgg caccccagcc 180
aggttcagtg gcagtgggtc tgggacagag ttcactctca ccatcagcag cctgcagtct 240
gaagatcttg cgatttatta ttgtcaacag tatagtaagt ggcctccgat caccttcggc 300
caagggacac gactggagat taaa 324

<210> SEQ ID NO 243
<211> LENGTH: 321
<212> TYPE: DNA
<213> ORGANISM: Streptococcus pneumoniae

<400> SEQUENCE: 243
gacatccaga tgacccagtc tccctccatc ctgtctgcat ctgtaggaga cagagtcacc 60
atcaattgcc gggccagtca gagtattaat gcctggttgg cctggtatca gcagaaacca 120
gggaaagccc ctaaattcct aatttataag gcgtctagtt tagaaagtgg ggtctcgtca 180
aggttcagcg gcagtggatc tgggacagaa ttcaccctca tcatcagcag cctgcagcct 240
gatgattttg caacttatta ctgccaacag tatgataaat atccgtggac gttcggccgg 300
gggaccaagg tggagatcaa a 321

<210> SEQ ID NO 244
<211> LENGTH: 324
<212> TYPE: DNA
<213> ORGANISM: Streptococcus pneumoniae

<400> SEQUENCE: 244
gaaattgtgt tgacgcagtc tccaggcacc ctgtctttct ctccagggga tagagccacc 60
ctctcctgca gggccagtca gagtgttagc agcagctcct tagcctggta ccagcagaga 120
cctggccagg ctcccagcct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta actcacctcg gacgttcggc 300
caagggacca aggtggagat caaa 324

<210> SEQ ID NO 245
<211> LENGTH: 324
<212> TYPE: DNA
<213> ORGANISM: Streptococcus pneumoniae

<400> SEQUENCE: 245
gaaattgtgt tgacgcagtc tccaggcacc ctgtctttgt ctccagggga aagagccacc 60
ctctcctgca gggccagtca gagtgtcagc agcacctact taaactggta ccagcagaag 120
cctggccagg ctcccaggct cctcatctat ggtgcgtcca ccagggccac tggcatccca 180
gacaggttca gtggcagtgg gtctggggca gacttcactc taaccatcag cagactggag 240
cctgaagact ttgcagtgta ctactgtcag caatatgatg actcacggtg gacgttcggc 300
caagggacca aggtggaaat caaa 324

<210> SEQ ID NO 246
<211> LENGTH: 336
<212> TYPE: DNA
<213> ORGANISM: Streptococcus pneumoniae

<400> SEQUENCE: 246
gatattgtga tgactcagtc tccactctcc ctgcccgtca cccctggaga gccggcctcc 60
atctcctgca ggtctggtca gagcctcctg tatagtgatg gaaacaacta tttggattgg 120
tatctgcaga agccagggca gtctccacag ctcctgatct atttgggttc taatcgggcc 180
tccggggtcc ctgacaggtt cagtggcagt gaatcaggca cagattttac actgaaaatc 240
agcagagtgg aggctgggga tgttgggatt tattactgca tgcaagctct acgaagtccg 300
tacacttttg gccaggggac caaggtggag atcaaa 336

<210> SEQ ID NO 247
<211> LENGTH: 332
<212> TYPE: DNA
<213> ORGANISM: Streptococcus pneumoniae

<400> SEQUENCE: 247
ttgtgatgac tcagtctcca ctctccctgc ccgtcaccct tggacagccg gcctccatct 60
cctgcaggtc tagtcaaagc cccgtataca gtgatggaaa cacctacctg aattggtttc 120
agcagaggcc aggccaatct ccaaggcgcc taatttataa ggtttctaac cgggactccg 180
gggtcccaga cagattcagc ggcagtgggt caggcactga tttcacactg aatatcagcg 240
gggtggaggc tgaggacgtt ggggtttatt actgcatgca aggtagatac tggccgtaca 300
cttttggcca ggggaccaag gtggagatca aa 332

<210> SEQ ID NO 248
<211> LENGTH: 324
<212> TYPE: DNA
<213> ORGANISM: Streptococcus pneumoniae

<400> SEQUENCE: 248
gaaattgtgt tgacgcagtc tccaggcacc ctgtctttct ctccagggga tagagccacc 60
ctctcctgca gggccagtca gagtgtaagc agcagcgcct tagcctggta ccagcagaaa 120
cctggccagg ctcccagcct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta actcacctcg gacgttcggc 300
caagggacca aggtggaaat caaa 324

<210> SEQ ID NO 249
<211> LENGTH: 330
<212> TYPE: DNA
<213> ORGANISM: Streptococcus pneumoniae

<400> SEQUENCE: 249
ttgtgatgac tcagtctcca ctctccctgc ccgtcaccct tggacagtcg gcctccatct 60
cctgcaggtc tagtcgaagc ctcgtattca gtgatggaaa cacctacttg aattggtttc 120
agcagaggcc aggccgatct ccaaggcgcc taatttataa ggtttctaag cgggactctg 180
gggtcccaga cagattcagc ggcagtgggt cagacactga tttcacactg aaaatcagca 240
gggtggaggc tgaggatgtt ggggtttatt actgcatgca aggtacacac tggcggacgt 300
tcggccaagg gaccaaggtg gaaatcaaac 330

<210> SEQ ID NO 250
<211> LENGTH: 321
<212> TYPE: DNA
<213> ORGANISM: Streptococcus pneumoniae

<400> SEQUENCE: 250
gacatccaga tgacccagtc tccttcctca ctgtctgcat ctgtagggga cagaatcacc 60
atcacttgtc gggcgagtca gggcattaac aattatttag cctggtttca gcagaagcca 120
gggaaagccc ctaagaccct gatctactct acatccactt tgcaaagtgg ggtcccatca 180
aagttcagcg gcagtggatc tgggacagtt ttcactctca ccatcagcaa cctgcagcct 240
gaagattttg caacttatta ctgtcaacaa tataatagtt acccgctcac tttcggcgga 300
gggaccaagg tggagatcaa a 321

<210> SEQ ID NO 251
<211> LENGTH: 321
<212> TYPE: DNA
<213> ORGANISM: Streptococcus pneumoniae

<400> SEQUENCE: 251
gacatccaga tgacccagtc tccatcctcc ctgtctgcat ctgtaggaga cagagtcacc 60
atcacttgcc gggcaagtca gaccattagc aactatttaa attggtttca gcagaaacca 120
gggaaagccc ctaggctcct gatctatgct gcatcgagtt tgcaaagtgg ggtcccatca 180
aggttcagtg gcagtggatc tgtgacagat ttcactctca ccatcagcag tctgcaacct 240

```
gaagattttg caacttactt ctgtcaacag agttacagca ccccgtggac gttcggccaa    300

gggaccaagg tggaaatcaa a                                              321


<210> SEQ ID NO 252
<211> LENGTH: 332
<212> TYPE: DNA
<213> ORGANISM: Streptococcus pneumoniae

<400> SEQUENCE: 252

ttgtgatgac tcagtctcca ttctccctgc ccgtcaccct tggacagccg gcctccatct     60

cctgcaggtc tagtcaaagc ctcgtataca gtgatggaaa cacctacttg aattggtttc    120

agcagaggcc aggccaatct ccaaggcgcc tgatttataa gctttctaac cgggactctg    180

gggtcccaga cagattcagc ggcagtgggt caggcactga tttcacactg aaaatcagca    240

gggtggaggc tgaggatgtt ggggtttatt actgcatgca agctacacac tggccttgga    300

cgttcggcca agggaccaag gtggaaatca aa                                  332


<210> SEQ ID NO 253
<211> LENGTH: 116
<212> TYPE: PRT
<213> ORGANISM: Streptococcus pneumoniae

<400> SEQUENCE: 253

Glu Val Gln Leu Leu Glu Ser Gly Gly Gly Leu Val Gln Pro Gly Gly
1               5                   10                  15

Ser Leu Arg Val Ser Cys Ala Ala Ser Gly Phe Thr Phe Ser Asn Ser
            20                  25                  30

Gly Met Ser Trp Val Arg Gln Ala Pro Gly Lys Gly Leu Glu Trp Val
        35                  40                  45

Ser Gly Ile Gly Gly Gly Gly Gly Ser Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Lys Gly Val Thr Ser Phe Asp Tyr Trp Gly Gln Gly Ile Leu Val
            100                 105                 110

Thr Val Ser Ser
        115


<210> SEQ ID NO 254
<211> LENGTH: 118
<212> TYPE: PRT
<213> ORGANISM: Streptococcus pneumoniae

<400> SEQUENCE: 254

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asp
            20                  25                  30

Tyr Met Ser Trp Val Arg Gln Ala Pro Gly Lys Gly Leu Glu Trp Val
        35                  40                  45

Ser Val Met Tyr Ser Gly Gly Ser Thr Tyr Tyr Ala Asp Ala Val Lys
    50                  55                  60

Asp Arg Phe Thr Ile Ser Arg Asp Asn Ser Lys Asn Ile Leu Tyr Leu
65                  70                  75                  80
```

```
Gln Met Asn Ser Leu Arg Ala Glu Asp Thr Ala Val Tyr Tyr Cys Ala
                85                  90                  95

Arg Asp Pro Gly Ile Arg Asn Gly Met Gly Val Trp Gly Gln Gly Thr
            100                 105                 110

Thr Val Thr Val Ser Ser
        115


<210> SEQ ID NO 255
<211> LENGTH: 121
<212> TYPE: PRT
<213> ORGANISM: Streptococcus pneumoniae

<400> SEQUENCE: 255

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Thr Ser Phe
            20                  25                  30

Ala Met Gly Trp Val Arg Gln Ala Pro Gly Lys Gly Leu Glu Trp Val
        35                  40                  45

Ser Ala Val Thr Gly Ser Gly Tyr Tyr Lys Asn Tyr Ala Asp Ser Val
    50                  55                  60

Lys Gly Arg Phe Thr Ile Ser Arg Asp Asn Ser Asp Asn Thr Leu Tyr
65                  70                  75                  80

Leu Gln Met Asn Ser Leu Arg Gly Asp Asp Thr Ala Leu Tyr Tyr Cys
                85                  90                  95

Ala Lys Ala His Arg Gly Asp Trp Asn Asn Phe Phe Asp Tyr Trp Gly
            100                 105                 110

Gln Gly Thr Leu Val Thr Val Ser Ser
        115                 120


<210> SEQ ID NO 256
<211> LENGTH: 115
<212> TYPE: PRT
<213> ORGANISM: Streptococcus pneumoniae

<400> SEQUENCE: 256

Gln Val Gln Leu Gln Glu Ser Gly Pro Gly Leu Val Lys Pro Ser Glu
1               5                   10                  15

Thr Leu Ser Leu Thr Cys Ser Val Ser Ala Asp Ser Phe Ser Pro Tyr
            20                  25                  30

Lys Trp Ser Trp Ile Arg Gln Pro Pro Gly Lys Gly Leu Glu Trp Ile
        35                  40                  45

Gly Tyr Ile Tyr Ser Ser Gly Asn Thr Asn Tyr Asn Pro Pro Leu Lys
    50                  55                  60

Ser Arg Val Thr Ile Ser Leu Asp Thr Ser Lys Asn Gln Val Ser Leu
65                  70                  75                  80

Arg Leu Ser Ser Val Ala Ala Ala Asp Thr Ala Met Tyr Tyr Cys Ala
                85                  90                  95

Arg Glu Trp Ser Gly Phe Asp Phe Trp Gly Gln Gly Thr Met Val Thr
            100                 105                 110

Val Ser Ser
        115


<210> SEQ ID NO 257
<211> LENGTH: 115
<212> TYPE: PRT
<213> ORGANISM: Streptococcus pneumoniae
```

<400> SEQUENCE: 257

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Arg Glu Thr Tyr Tyr Val Asp Ser Val
    50                  55                  60

Lys Gly Arg Phe Thr Ile Ser Arg Asp Asn Ala Lys Asn Ser Val Ser
65                  70                  75                  80

Leu Gln Met Ser Ser Leu Arg Ala Glu Asp Thr Ala Val Tyr Tyr Cys
                85                  90                  95

Ala Arg Gly Gln Trp Leu Ala Phe Arg Gly Gln Gly Thr Leu Val Thr
            100                 105                 110

Val Ser Ser
        115
```

<210> SEQ ID NO 258
<211> LENGTH: 116
<212> TYPE: PRT
<213> ORGANISM: Streptococcus pneumoniae

<400> SEQUENCE: 258

```
Glu Val Gln Leu Val Glu Ser Gly Gly Gly Leu Val Gln Ile Gly Gly
1               5                   10                  15

Ser Leu Arg Leu Ser Cys Ala Ala Ser Gly Phe Thr Phe Ser Thr Tyr
            20                  25                  30

Trp Met Ser Trp Val Arg Gln Ala Pro Gly Lys Gly Leu Glu Cys Val
        35                  40                  45

Ala Ser Ile Lys Glu Asp Gly Ser Glu Arg Tyr Tyr Val Asp Ser Val
    50                  55                  60

Lys Gly Arg Phe Thr Ile Ser Arg Asp Asn Ala Lys Asn Ser Leu His
65                  70                  75                  80

Leu Gln Met Asp Ser Leu Arg Ala Ala Asp Thr Ala Val Tyr Phe Cys
                85                  90                  95

Ala Arg Gly Arg Asn Asn Phe Arg His Trp Gly Gln Gly Thr Leu Val
            100                 105                 110

Thr Val Ser Ser
        115
```

<210> SEQ ID NO 259
<211> LENGTH: 126
<212> TYPE: PRT
<213> ORGANISM: Streptococcus pneumoniae

<400> SEQUENCE: 259

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Trp Thr Asp Asp Thr Val Tyr Ala Asp Ser Val Lys
    50                  55                  60
```

```
Gly Arg Phe Thr Ile Ser Arg Asp Val Ser Lys Asn Met Val His Leu
65                  70                  75                  80

Gln Met Ser Ser Leu Arg Val Glu Asp Thr Ala Val Tyr Tyr Cys Ala
                85                  90                  95

Arg Glu Leu Gly Val Phe His Ser Gly Gly Asp Gln Trp Leu Gly Pro
            100                 105                 110

Leu Asp Cys Trp Gly Gln Gly Thr Leu Val Thr Val Ser Ser
        115                 120                 125


<210> SEQ ID NO 260
<211> LENGTH: 120
<212> TYPE: PRT
<213> ORGANISM: Streptococcus pneumoniae

<400> SEQUENCE: 260

Glu Val Gln Leu Val Glu Ser Gly Gly Gly Leu Val Gln Pro Gly Gln
1               5                   10                  15

Ser Leu Arg Leu Ser Cys Thr Val Ser Gly Phe Ser Val Glu Asp His
            20                  25                  30

Gly Leu Asn Trp Val Arg Gln Ala Pro Gly Lys Gly Leu Glu Trp Val
        35                  40                  45

Gly Phe Ile Arg Arg Lys Ser Ser Gly Gly Thr Glu Tyr Ala Ala Ser
    50                  55                  60

Val Lys Gly Arg Phe Thr Ile Ser Arg Asp Asp Ser Lys Ser Ala Val
65                  70                  75                  80

Tyr Leu Gln Met Asn Ser Leu Lys Met Glu Asp Thr Gly Val Tyr Tyr
                85                  90                  95

Cys Leu Arg Trp Thr Gly Gly Val Ser Phe Gly Ala Tyr Trp Gly Gln
            100                 105                 110

Gly Thr Leu Val Thr Val Ser Ser
        115                 120


<210> SEQ ID NO 261
<211> LENGTH: 116
<212> TYPE: PRT
<213> ORGANISM: Streptococcus pneumoniae

<400> SEQUENCE: 261

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Trp
            20                  25                  30

Met His Trp Val Arg Gln Ala Pro Gly Lys Gly Leu Val Trp Val Ser
        35                  40                  45

His Ile Asn Thr Asp Gly Ser Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Tyr Tyr His Ser Val Asp Tyr Trp Gly Gln Gly Thr Leu Val
            100                 105                 110

Thr Val Ser Ser
        115


<210> SEQ ID NO 262
<211> LENGTH: 117
```

```
<212> TYPE: PRT
<213> ORGANISM: Streptococcus pneumoniae

<400> SEQUENCE: 262

Gln Val Gln Leu Gln Glu Ser Gly Pro Gly Met Val Lys Pro Ser Glu
1               5                   10                  15

Thr Leu Ser Leu Ile Cys Ser Val Ser Gly Ala Ser Val Ser Arg Asp
            20                  25                  30

His Trp Ser Trp Ile Arg Gln Ser Pro Gly Lys Gly Leu Glu Trp Ile
        35                  40                  45

Val Tyr Ile Tyr Asn Ser Glu Ser Ile Glu Tyr Asn Pro Ser Leu Lys
    50                  55                  60

Ser Arg Val Thr Ile Ser Val Asp Thr Ser Lys Asn Gln Val Ser Leu
65                  70                  75                  80

Thr Val Thr Ser Val Thr Ala Ala Asp Thr Ala Phe Tyr Tyr Cys Ala
                85                  90                  95

Arg Gly Pro Asp Ala His Lys Thr Gly Tyr Trp Gly Pro Gly Thr Leu
            100                 105                 110

Val Thr Val Ser Ser
        115


<210> SEQ ID NO 263
<211> LENGTH: 117
<212> TYPE: PRT
<213> ORGANISM: Streptococcus pneumoniae

<400> SEQUENCE: 263

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Trp Met Tyr Trp Val Arg Gln Val Pro Gly Lys Gly Leu Val Cys Val
        35                  40                  45

Ser Arg Ile Asn Arg Asp Gly Ser Ile Thr Leu Tyr Ala Asp Ser Val
    50                  55                  60

Arg Gly Arg Phe Thr Ile Ser Arg Asp Asn Ala Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Asp Ser Tyr Thr Ser Pro Asp Tyr Trp Gly Gln Gly Thr Leu
            100                 105                 110

Val Thr Val Ser Ser
        115


<210> SEQ ID NO 264
<211> LENGTH: 120
<212> TYPE: PRT
<213> ORGANISM: Streptococcus pneumoniae

<400> SEQUENCE: 264

Glu Val Gln Leu Val Glu Ser Gly Gly Gly Leu Val Lys Pro Gly Glu
1               5                   10                  15

Ser Leu Arg Leu Ser Cys Ala Thr Ser Gly Leu Thr Phe Ser Asn Val
            20                  25                  30

Trp Met Ser Trp Val Arg Gln Ala Pro Gly Lys Gly Leu Glu Trp Val
        35                  40                  45
```

```
Gly Arg Leu Lys Asn Lys Pro Asp Gly Gly Thr Thr Asp Tyr Ala Ala
    50                  55                  60

Pro Val Lys Gly Arg Phe Thr Ile Ser Arg Asp Asp Ser Lys Thr Thr
65                  70                  75                  80

Leu Tyr Leu Glu Met Asn Ser Leu Lys Val Glu Asp Thr Ala Val Tyr
                85                  90                  95

Tyr Cys Thr Thr Asp Asn Gly Val Lys Ala Phe Asp Ile Trp Gly Gln
            100                 105                 110

Gly Thr Met Val Thr Val Ser Ser
        115                 120


<210> SEQ ID NO 265
<211> LENGTH: 118
<212> TYPE: PRT
<213> ORGANISM: Streptococcus pneumoniae

<400> SEQUENCE: 265

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Trp Met His Trp Val Arg Gln Thr Pro Glu Lys Gly Leu Val Trp Val
        35                  40                  45

Ser Arg Ile His Pro Asp Gly Ser Asn Thr Ala Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Val Glu Asp Thr Ala Phe Tyr Tyr Cys
                85                  90                  95

Thr Arg Gly Gly Ser Gly Ala Thr Ile Asn Tyr Trp Gly Gln Gly Ile
            100                 105                 110

Leu Val Thr Val Ser Ser
        115


<210> SEQ ID NO 266
<211> LENGTH: 124
<212> TYPE: PRT
<213> ORGANISM: Streptococcus pneumoniae

<400> SEQUENCE: 266

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Gly Gly
            20                  25                  30

Thr Tyr Ser Trp Thr Trp Ile Arg Gln Pro Ala Gly Lys Gly Leu Glu
        35                  40                  45

Trp Ile Gly Arg Ile Phe Ala Ser Gly Ser Thr Asn Tyr Asn Ser Ser
    50                  55                  60

Leu Lys Ser Arg Val Thr Ile Leu Val Asp Thr Ser Lys Asn Leu Phe
65                  70                  75                  80

Ser Leu Ser Leu Ser Ser Val Thr Ala Ala Asp Thr Ala Met Tyr Tyr
                85                  90                  95

Cys Ala Arg Asp Arg Ala Gly Ile Asp Gly Tyr Asn Tyr Tyr Phe Asp
            100                 105                 110

Tyr Trp Gly Gln Gly Thr Leu Val Thr Val Ser Ser
        115                 120
```

```
<210> SEQ ID NO 267
<211> LENGTH: 119
<212> TYPE: PRT
<213> ORGANISM: Streptococcus pneumoniae

<400> SEQUENCE: 267

Val Gln Leu Val Gln Ser Gly Ala Glu Val Lys Lys Pro Gly Ala Ser
1               5                   10                  15

Val Lys Val Ser Cys Lys Thr Ser Gly Tyr Thr Leu Thr Ser Tyr Tyr
            20                  25                  30

Met His Trp Val Arg Gln Ala Pro Gly Gln Gly Leu Glu Trp Leu Gly
        35                  40                  45

Val Ile Arg Pro Thr Asp Ala Ser Thr Arg Ser Ala Gln Lys Phe Gln
    50                  55                  60

Gly Arg Ile Thr Met Thr Arg Asp Thr Ser Thr Ser Thr Leu Tyr Met
65                  70                  75                  80

Glu Leu Ser Ser Leu Arg Ser Glu Asp Thr Ala Val Tyr Tyr Cys Ala
                85                  90                  95

Arg Glu Val Ala Ala Glu Gly Lys Ala Phe Asp Tyr Trp Gly Gln Gly
            100                 105                 110

Thr Leu Val Thr Val Ser Ser
        115


<210> SEQ ID NO 268
<211> LENGTH: 116
<212> TYPE: PRT
<213> ORGANISM: Streptococcus pneumoniae

<400> SEQUENCE: 268

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Gly Lys Ile Lys Glu Asp Gly Ser Glu Lys Tyr Tyr Val Asp Ser Val
    50                  55                  60

Lys Gly Arg Phe Ala Ile Ser Arg Asp Asn Ala Lys Asn Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gln Ser Tyr Pro Gly Ile Trp Gly Gln Gly Thr Met Val
            100                 105                 110

Thr Val Ser Ser
        115


<210> SEQ ID NO 269
<211> LENGTH: 121
<212> TYPE: PRT
<213> ORGANISM: Streptococcus pneumoniae

<400> SEQUENCE: 269

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Asn Tyr
            20                  25                  30
```

```
Tyr Trp Gly Trp Ile Arg Gln Pro Pro Gly Glu Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Gly Arg Ala Tyr Ser Ser Gly Tyr Tyr Tyr Leu Ile Asp Tyr Trp Gly
            100                 105                 110

Gln Gly Thr Leu Val Thr Val Ser Ser
        115                 120
```

<210> SEQ ID NO 270
<211> LENGTH: 107
<212> TYPE: PRT
<213> ORGANISM: Streptococcus pneumoniae

<400> SEQUENCE: 270

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Tyr Leu
            20                  25                  30

Ala Trp Tyr Gln Gln Lys Pro Gly Gln Ala Pro Arg Leu Leu Phe Tyr
        35                  40                  45

Gly Thr Ser Ser Arg Ala Thr Gly Ile Pro Asp Arg Phe Ser Gly Ser
    50                  55                  60

Gly Ser Gly Thr Asp Phe Thr Leu Thr Ile Ser Arg Val Glu Pro Glu
65                  70                  75                  80

Asp Phe Ala Val Tyr Tyr Cys Gln Gln Phe Gly Ser Ser Pro Pro Asp
                85                  90                  95

Thr Phe Gly Gly Gly Thr Lys Val Glu Ile Lys
            100                 105
```

<210> SEQ ID NO 271
<211> LENGTH: 110
<212> TYPE: PRT
<213> ORGANISM: Streptococcus pneumoniae

<400> SEQUENCE: 271

```
Val Met Thr Gln Ser Pro Leu Ser Leu Pro Val Thr Leu Gly Gln Pro
1               5                   10                  15

Ala Ser Ile Ser Cys Arg Ala Ser Gln Gly Leu Glu His Ser Asp Gly
            20                  25                  30

Asn Thr Tyr Leu Ser Trp Phe Gln Gln Arg Pro Gly Arg Ser Pro Arg
        35                  40                  45

Arg Leu Ile Tyr Lys Val Ser Asn Arg Asp Ser Gly Val Pro Asp Arg
    50                  55                  60

Phe Ser Gly Ser Gly Ser Gly Thr Asp Phe Thr Leu Glu Ile Thr Arg
65                  70                  75                  80

Val Glu Ala Glu Asp Val Gly Val Tyr Tyr Cys Met Gln Val Thr His
                85                  90                  95

Trp Pro Arg Thr Phe Gly Gln Gly Thr Lys Val Glu Ile Lys
            100                 105                 110
```

<210> SEQ ID NO 272
<211> LENGTH: 107

```
<212> TYPE: PRT
<213> ORGANISM: Streptococcus pneumoniae

<400> SEQUENCE: 272

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Pro His
            20                  25                  30

Leu Ala Trp Tyr Gln Gln Lys Pro Gly Gln Ser Pro Arg Leu Leu Ile
        35                  40                  45

Tyr Asp Ala Ser Asn Arg Ala Thr Gly Ile Pro Ala Arg Phe Ser Gly
    50                  55                  60

Ser Glu Ser Gly Thr Asp Phe Thr Leu Ser Ile Ser Ser Leu Glu Pro
65                  70                  75                  80

Glu Asp Phe Ala Val Tyr Tyr Cys Gln Gln Ser Gly Asp Trp Pro Leu
                85                  90                  95

Thr Phe Gly Gly Gly Thr Lys Val Glu Ile Lys
            100                 105


<210> SEQ ID NO 273
<211> LENGTH: 108
<212> TYPE: PRT
<213> ORGANISM: Streptococcus pneumoniae

<400> SEQUENCE: 273

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Tyr Ser Ile
            20                  25                  30

Tyr Phe Ala Trp Tyr Gln Gln Lys Pro Gly Gln Ala Pro Arg Pro Leu
        35                  40                  45

Ile Tyr Gly Val Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Arg Thr Phe Gly Gln Gly Thr Lys Val Glu Ile Lys
            100                 105


<210> SEQ ID NO 274
<211> LENGTH: 110
<212> TYPE: PRT
<213> ORGANISM: Streptococcus pneumoniae

<400> SEQUENCE: 274

Val Met Thr Gln Ser Pro Leu Ser Leu Pro Val Thr Leu Gly Gln Pro
1               5                   10                  15

Ala Ser Ile Ser Cys Arg Ser Ser Arg Ser Leu Val Tyr Ser Asp Gly
            20                  25                  30

Gly Thr Tyr Leu Asn Trp Phe Gln Gln Arg Pro Gly Gln Ser Pro Arg
        35                  40                  45

Arg Leu Ile Trp His Val Ser Asn Arg Asp Ser Gly Val Pro Asp Arg
    50                  55                  60

Phe Ser Gly Ser Gly Ser Gly Thr Asp Phe Thr Leu Lys Ile Ser Arg
65                  70                  75                  80
```

```
Val Glu Ala Glu Asp Val Gly Val Tyr Tyr Cys Met Gln Gly Thr His
                85                  90                  95

Trp Pro Tyr Thr Phe Gly Gln Gly Thr Lys Val Glu Ile Lys
            100                 105                 110


<210> SEQ ID NO 275
<211> LENGTH: 107
<212> TYPE: PRT
<213> ORGANISM: Streptococcus pneumoniae

<400> SEQUENCE: 275

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Arg Lys Leu
            20                  25                  30

Leu Asn Trp Tyr Gln Gln Arg Pro Gly Lys Ala Pro Asn Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr His Phe Ser Phe Thr Ile Thr Ser Leu Gln Pro
65                  70                  75                  80

Glu Asp Ile Ala Thr Tyr Tyr Cys Gln Gln Phe Glu Ser Phe Pro Arg
                85                  90                  95

Thr Phe Gly Pro Gly Thr Lys Val Asp Ile Lys
            100                 105


<210> SEQ ID NO 276
<211> LENGTH: 109
<212> TYPE: PRT
<213> ORGANISM: Streptococcus pneumoniae

<400> SEQUENCE: 276

Glu Ile Val Met Thr Gln Ser Pro Ala Thr Leu Ser Val Ser Pro Gly
1               5                   10                  15

Glu Thr Ala Thr Leu Ser Cys Arg Ala Ser Gln Ser Val Asn Ser Phe
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys His Gln Tyr Lys Asn Trp Pro Pro
                85                  90                  95

Met Gly Thr Phe Gly Pro Gly Thr Lys Val Asp Ile Lys
            100                 105


<210> SEQ ID NO 277
<211> LENGTH: 106
<212> TYPE: PRT
<213> ORGANISM: Streptococcus pneumoniae

<400> SEQUENCE: 277

Asp Ile Gln Met Thr Gln Ser Pro Ser Thr Leu Ser Ser Ser Val Gly
1               5                   10                  15

Asp Arg Val Thr Ile Thr Cys Arg Ala Ser Gln Asn Ile Gly Val Ser
            20                  25                  30
```

```
Leu Ala Trp Tyr Gln Gln Lys Pro Gly Lys Ala Pro Asn Leu Leu Ile
        35                  40                  45

Tyr Lys Ala Ser Tyr Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ile Tyr Leu Thr
                85                  90                  95

Phe Gly Gln Gly Thr Lys Val Glu Ile Lys
            100                 105


<210> SEQ ID NO 278
<211> LENGTH: 110
<212> TYPE: PRT
<213> ORGANISM: Streptococcus pneumoniae

<400> SEQUENCE: 278

Val Met Thr Gln Ser Pro Leu Ser Leu Pro Val Thr Leu Gly Gln Pro
1               5                   10                  15

Ala Ser Ile Ser Cys Arg Ser Ser Gln Ser Leu Ala His Ser Asp Gly
            20                  25                  30

Asn Thr Tyr Leu Asn Trp Phe Gln Gln Arg Pro Gly Gln Ser Pro Arg
        35                  40                  45

Arg Leu Ile Tyr Lys Val Ser Asn Arg Asp Ser Gly Val Pro Asp Arg
    50                  55                  60

Phe Ser Gly Ser Gly Ser Gly Thr Asp Phe Thr Leu Lys Ile Ser Arg
65                  70                  75                  80

Val Glu Ala Glu Asp Val Gly Val Tyr Tyr Cys Met Gln Gly Thr His
                85                  90                  95

Trp Pro Tyr Thr Phe Gly Gln Gly Thr Lys Val Glu Ile Lys
            100                 105                 110


<210> SEQ ID NO 279
<211> LENGTH: 113
<212> TYPE: PRT
<213> ORGANISM: Streptococcus pneumoniae

<400> SEQUENCE: 279

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Pro Asn Asn Lys Asn Tyr Leu Ala Trp Phe Gln Gln Lys Pro Gly Gln
        35                  40                  45

Pro Pro Lys Leu Leu Ile Tyr Trp Ala Ser Ile Arg Asp Ser Gly Val
    50                  55                  60

Pro Asp Arg Phe Ser Gly Ser Gly Ser Gly Thr Asp Phe Thr Leu Thr
65                  70                  75                  80

Val Ser Ser Leu Gln Ala Asp Asp Val Ala Val Tyr Tyr Cys Gln Gln
                85                  90                  95

Tyr Ala Ala Thr Pro Trp Thr Phe Gly Gln Gly Thr Lys Val Glu Ile
            100                 105                 110

Lys


<210> SEQ ID NO 280
<211> LENGTH: 110
<212> TYPE: PRT
```

<213> ORGANISM: Streptococcus pneumoniae

<400> SEQUENCE: 280

```
Val Met Thr Gln Ser Pro Leu Ser Leu Pro Val Thr Leu Gly Gln Pro
1               5                   10                  15

Ala Ser Ile Ser Cys Ser Ser Ser Gln Ser Leu Val Tyr Ser Asp Gly
            20                  25                  30

Asn Thr Tyr Leu Ser Trp Phe Gln Gln Arg Pro Gly Gln Ser Pro Arg
        35                  40                  45

Arg Leu Ile Tyr Lys Val Ser Asn Arg Asp Ser Gly Val Pro Asp Arg
    50                  55                  60

Phe Ser Gly Ser Gly Ser Gly Thr Asp Phe Thr Leu Arg Ile Ser Arg
65                  70                  75                  80

Val Glu Ala Glu Asp Val Gly Val Tyr Tyr Cys Met Gln Gly Ser His
                85                  90                  95

Trp Pro Leu Thr Phe Gly Gly Gly Thr Lys Val Glu Ile Lys
            100                 105                 110
```

<210> SEQ ID NO 281
<211> LENGTH: 113
<212> TYPE: PRT
<213> ORGANISM: Streptococcus pneumoniae

<400> SEQUENCE: 281

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Leu Ser Val Leu Ser Ser
            20                  25                  30

Ser Asn Asn Glu Asn Tyr Leu Ala Trp Tyr Gln Gln Lys Pro Gly Gln
        35                  40                  45

Pro Pro Lys Leu Leu Ile Tyr Trp Ala Ser Thr Arg Gly Ser Gly Val
    50                  55                  60

Pro Gly Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Thr Thr Pro Phe Ala Phe Gly Pro Gly Thr Lys Val Asp Ile
            100                 105                 110

Lys
```

<210> SEQ ID NO 282
<211> LENGTH: 107
<212> TYPE: PRT
<213> ORGANISM: Streptococcus pneumoniae

<400> SEQUENCE: 282

```
Asp Ile Gln Met Thr Gln Ser Pro Ser Ser Leu Ser Ala Ser Val Gly
1               5                   10                  15

Asp Ser Val Thr Ile Thr Cys Arg Ala Ser Gln Ser Ile Ser Ser Tyr
            20                  25                  30

Leu Asn Trp Tyr His Gln Lys Pro Gly Lys Ala Pro Lys Leu Leu Ile
        35                  40                  45

Tyr Gly Ala Ser Thr Leu Gln Ser Gly Val Pro Ser Arg Phe Gly Gly
    50                  55                  60

Ser Gly Ser Gly Thr Asp Phe Thr Leu Thr Ile Ser Ser Leu Gln Pro
65                  70                  75                  80
```

```
Asp Asp Phe Ala Thr Tyr Tyr Cys Gln Gln Ser His Ser Ser Pro Leu
                85                  90                  95

Thr Phe Gly Gly Gly Thr Lys Val Glu Ile Lys
            100                 105


<210> SEQ ID NO 283
<211> LENGTH: 106
<212> TYPE: PRT
<213> ORGANISM: Streptococcus pneumoniae

<400> SEQUENCE: 283

Asp Ile Gln Met Thr Gln Ser Pro Ser Thr Leu Ser Ala Ser Val Gly
1               5                   10                  15

Asp Arg Val Thr Ile Thr Cys Arg Ala Ser Arg Ser Leu Gly Ser Trp
            20                  25                  30

Leu Ala Trp Tyr Gln Gln Ser Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Ser Phe Tyr Thr
                85                  90                  95

Phe Gly Gln Gly Thr Lys Val Glu Ile Lys
            100                 105


<210> SEQ ID NO 284
<211> LENGTH: 113
<212> TYPE: PRT
<213> ORGANISM: Streptococcus pneumoniae

<400> SEQUENCE: 284

Asp Ile Val Met Thr Gln Ser Ala Asp Ser Leu Ala Val Ser Leu Gly
1               5                   10                  15

Glu Arg Ala Thr Ile Asn Cys Lys Ser Ser Gln Ser Leu Phe Tyr Ser
            20                  25                  30

Ser Asn Lys Lys Asn Tyr Leu Ala Trp Tyr Gln Gln Lys Pro Gly Gln
        35                  40                  45

Pro Pro Lys Leu Ile Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Thr Ser Leu Arg Ala Glu Asp Val Ala Val Tyr Tyr Cys Gln Gln
                85                  90                  95

Tyr Tyr Thr Pro Pro Leu Thr Phe Gly Gly Gly Thr Lys Val Glu Ile
            100                 105                 110

Lys


<210> SEQ ID NO 285
<211> LENGTH: 107
<212> TYPE: PRT
<213> ORGANISM: Streptococcus pneumoniae

<400> SEQUENCE: 285

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Gly Asp
            20                  25                  30
```

```
Leu Val Trp Tyr Gln Gln Lys Pro Gly Gln Ala Pro Arg Leu Leu Ile
        35                  40                  45

Tyr Gly Ala Thr Thr Arg Ala Ser Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys Gln Gln Tyr Asn Asn Trp Pro Arg
                85                  90                  95

Thr Phe Gly Gln Gly Thr Lys Val Glu Ile Lys
            100                 105


<210> SEQ ID NO 286
<211> LENGTH: 107
<212> TYPE: PRT
<213> ORGANISM: Streptococcus pneumoniae

<400> SEQUENCE: 286

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Asn Asn
            20                  25                  30

Leu Ala Trp Phe Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr His Cys Gln His Tyr His Asn Trp Pro Pro
                85                  90                  95

Thr Phe Gly Gln Gly Thr Lys Val Glu Ile Lys
            100                 105


<210> SEQ ID NO 287
<211> LENGTH: 122
<212> TYPE: PRT
<213> ORGANISM: Streptococcus pneumoniae

<400> SEQUENCE: 287

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn His
            20                  25                  30

Gly Met His Trp Leu Arg Gln Thr Pro Gly Lys Gly Leu Glu Trp Val
        35                  40                  45

Ala Val Ile Ser Tyr Asp Gly Ser Thr Lys Tyr Tyr Ala Asp Ser Val
    50                  55                  60

Lys Gly Arg Cys Thr Leu Ser Arg Asp Asn Ser Lys Glu Thr Val Phe
65                  70                  75                  80

Leu Gln Met Asn Ser Leu Arg Pro Glu Asp Thr Ala Val Tyr Tyr Cys
                85                  90                  95

Ala Lys Gly Cys Ser Asn Gly Gly Asn Cys Phe Leu Ile Asp Tyr Trp
            100                 105                 110

Gly Pro Gly Thr Leu Val Thr Val Ser Ser
        115                 120


<210> SEQ ID NO 288
```

```
<211> LENGTH: 123
<212> TYPE: PRT
<213> ORGANISM: Streptococcus pneumoniae

<400> SEQUENCE: 288

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Asp Phe Ser Ile Tyr
            20                  25                  30

Gly Met Asn Trp Val Arg Gln Ala Pro Gly Lys Gly Leu Glu Trp Val
        35                  40                  45

Ser Val Ile Ser Gly Asp Gly Thr Ile Ile Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Val Asn Ser Val Arg Ala Glu Asp Thr Ala Val Tyr Tyr Cys
                85                  90                  95

Ala Lys Gly Gly Tyr Tyr Glu Ser Gly Thr Met Arg Ala Phe Asp Ile
            100                 105                 110

Trp Gly Gln Gly Thr Met Val Thr Val Ser Ser
        115                 120


<210> SEQ ID NO 289
<211> LENGTH: 116
<212> TYPE: PRT
<213> ORGANISM: Streptococcus pneumoniae

<400> SEQUENCE: 289

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Ser Met Ser Trp Val Arg Gln Ala Pro Gly Lys Gly Leu Glu Trp Val
        35                  40                  45

Ala Ser Ile Lys Pro Glu Gly Ser Glu Lys Phe Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Gly Glu Asp Thr Ala Val Tyr Tyr Cys
                85                  90                  95

Ala Arg Gly Glu Ser Asn Phe Arg Tyr Trp His Gln Gly Thr Leu Val
            100                 105                 110

Thr Val Ser Ser
        115


<210> SEQ ID NO 290
<211> LENGTH: 119
<212> TYPE: PRT
<213> ORGANISM: Streptococcus pneumoniae

<400> SEQUENCE: 290

Glu Val Gln Leu Val Glu Ser Gly Gly Ala Leu Val Gln Pro Gly Gly
1               5                   10                  15

Ser Leu Arg Leu Ser Cys Ala Ala Ser Gly Phe Ile Phe Ser Asn Ser
            20                  25                  30

Trp Met Gly Trp Phe Arg Gln Ala Pro Gly Lys Arg Pro Glu Phe Val
        35                  40                  45
```

```
Ala Asn Ile Lys Pro Asp Gly Ser Glu Lys Phe His Val Asp Ser Val
    50                  55                  60

Lys Gly Arg Phe Thr Ile Ser Arg Asp Asn Ala Glu Asn Ser Leu Tyr
65                  70                  75                  80

Leu Leu Met Asn Ser Leu Arg Ala Glu Asp Thr Ala Val Tyr Tyr Cys
                85                  90                  95

Ala Arg Asp Ser Thr Ser Pro Ala Arg Phe Gly Tyr Trp Gly Gln Gly
            100                 105                 110

Thr Leu Val Thr Val Ser Ser
        115


<210> SEQ ID NO 291
<211> LENGTH: 118
<212> TYPE: PRT
<213> ORGANISM: Streptococcus pneumoniae

<400> SEQUENCE: 291

Glu Val Gln Leu Val Glu Thr Gly Gly Gly Leu Ile Gln Pro Gly Gly
1               5                   10                  15

Ser Leu Arg Leu Ser Cys Ala Ala Ser Gly Leu Asn Val Asn Ser Tyr
            20                  25                  30

Tyr Met Asn Trp Val Arg Gln Ala Pro Gly Lys Gly Leu Glu Trp Val
        35                  40                  45

Ser Val Ile Tyr Ser Gly Gly Gly Thr Asn Tyr Ala Asp Ser Val Arg
    50                  55                  60

Gly Arg Phe Ile Ile Ser Arg Asp Asn Ser Arg Asn Ala Leu Tyr Leu
65                  70                  75                  80

Gln Met Asn Ser Leu Arg Ala Glu Asp Thr Ala Val Tyr Tyr Cys Ala
                85                  90                  95

Thr Gly Gly Met Thr Ser Ser Trp Tyr Gly Tyr Trp Gly Gln Gly Thr
            100                 105                 110

Leu Val Thr Val Ser Ser
        115


<210> SEQ ID NO 292
<211> LENGTH: 124
<212> TYPE: PRT
<213> ORGANISM: Streptococcus pneumoniae

<400> SEQUENCE: 292

Val Gln Leu Val Gln Ser Gly Ala Glu Val Lys Lys Pro Gly Ala Ser
1               5                   10                  15

Val Lys Val Ser Cys Lys Ala Ser Glu Tyr Thr Phe Ile Asn Tyr Leu
            20                  25                  30

Val Phe Trp Val Arg Gln Ala Pro Gly Gln Gly Leu Glu Trp Met Gly
        35                  40                  45

Glu Met Asn Pro Thr Arg Gly Ser Thr Ser Tyr Ala Gln Lys Phe Gln
    50                  55                  60

Gly Arg Val Thr Met Thr Arg Asp Thr Ser Thr Ser Thr Val Tyr Met
65                  70                  75                  80

Glu Leu Ser Ser Leu Arg Ser Asp Asp Thr Ala Val Tyr Tyr Cys Ser
                85                  90                  95

Met Gly Pro Pro Tyr Cys Thr Gly Gly Ser Cys Tyr Ser Ala Cys Asp
            100                 105                 110

Phe Trp Gly Pro Gly Thr Leu Val Thr Val Ser Ser
        115                 120
```

<210> SEQ ID NO 293
<211> LENGTH: 124
<212> TYPE: PRT
<213> ORGANISM: Streptococcus pneumoniae

<400> SEQUENCE: 293

```
Glu Val Gln Leu Val Glu Ser Gly Gly Gly Leu Met Lys Pro Gly Gly
1               5                   10                  15

Ser Leu Arg Leu Ser Cys Ala Val Ser Gly Phe Thr Phe Thr Asn Ala
            20                  25                  30

Trp Leu Ser Trp Val Arg Gln Pro Pro Gly Lys Gly Leu Glu Trp Val
        35                  40                  45

Gly Arg Ala Tyr Ser Ser Ser Gly Gly Trp Thr Met Asp Tyr Ser Ser
    50                  55                  60

Pro Val Arg Gly Arg Phe Thr Ile Thr Arg Asp Asp Ser Lys Asn Thr
65                  70                  75                  80

Leu Tyr Leu Gln Met Asn Asn Leu Lys Thr Glu Asp Thr Ala Val Tyr
                85                  90                  95

Tyr Cys Thr Thr Asp Ile Gly Lys Gly Trp Tyr Thr His Tyr Pro Asp
            100                 105                 110

Leu Trp Gly Gln Gly Thr Leu Val Thr Val Ser Ser
        115                 120
```

<210> SEQ ID NO 294
<211> LENGTH: 121
<212> TYPE: PRT
<213> ORGANISM: Streptococcus pneumoniae

<400> SEQUENCE: 294

```
Gln Val Gln Leu Val Glu Ser Gly Gly Gly Val Val Gln Pro Gly Lys
1               5                   10                  15

Ser Leu Arg Leu Ser Cys Val Ala Ser Gly Phe Thr Leu Ser Thr Cys
            20                  25                  30

Gly Met His Trp Val Arg Gln Ala Pro Gly Lys Gly Leu Glu Trp Val
        35                  40                  45

Ala Val Thr Thr Tyr Asp Gly Asp Arg Lys Tyr Asn Val Asp Ser Val
    50                  55                  60

Lys Gly Arg Phe Thr Ile Ser Arg Asp Asn Ser Lys Asn Thr Val Tyr
65                  70                  75                  80

Leu Gln Met Asp Gly Leu Lys Ala Glu Asp Thr Ala Val Tyr His Cys
                85                  90                  95

Val Lys Glu Tyr Ser Trp Gly Tyr Tyr Arg Thr Ala Asp Tyr Trp Gly
            100                 105                 110

Gln Gly Thr Leu Val Thr Val Ser Ser
        115                 120
```

<210> SEQ ID NO 295
<211> LENGTH: 117
<212> TYPE: PRT
<213> ORGANISM: Streptococcus pneumoniae

<400> SEQUENCE: 295

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Thr Tyr
            20                  25                  30
```

```
Trp Met His Trp Val Arg Gln Pro Pro Gly Lys Gly Leu Val Trp Val
        35                  40                  45

Ser Arg Ile Asn Pro Asp Gly Ser Ser Thr Asn Tyr Ala Asp Ser Val
    50                  55                  60

Asn Gly Arg Phe Thr Ile Ser Arg Asp Asn Ala Lys Asn Thr Leu Tyr
65                  70                  75                  80

Leu Glu Met Asn Ser Leu Arg Val Glu Asp Thr Ala Leu Tyr Tyr Cys
                85                  90                  95

Ala Arg Ser Pro Gly Gly Tyr Phe Asp Tyr Trp Gly His Ser Thr Leu
            100                 105                 110

Val Thr Val Ser Ser
        115


<210> SEQ ID NO 296
<211> LENGTH: 116
<212> TYPE: PRT
<213> ORGANISM: Streptococcus pneumoniae

<400> SEQUENCE: 296

Glu Val Gln Leu Val Glu Ser Gly Gly Gly Leu Val Lys Pro Gly Gly
1               5                   10                  15

Ser Leu Thr Leu Ser Cys Ala Val Ser Gly Phe Thr Phe Ser Thr Gly
            20                  25                  30

Trp Met Ser Trp Val Arg Gln Ala Pro Gly Lys Gly Leu Asp Trp Val
        35                  40                  45

Gly Arg Ile Lys Ser Lys Thr Ala Gly Gly Thr Thr Asp Tyr Ala Ala
    50                  55                  60

Pro Val Lys Asp Arg Phe Thr Ile Ser Arg Asp Asp Ser Lys Asn Thr
65                  70                  75                  80

Leu Tyr Leu Gln Leu Ser Ser Leu Lys Thr Glu Asp Thr Ala Val Tyr
                85                  90                  95

Tyr Cys Thr Thr Asp Asp Leu Lys Asn Trp Gly Gln Gly Thr Leu Val
            100                 105                 110

Thr Val Ser Ser
        115


<210> SEQ ID NO 297
<211> LENGTH: 129
<212> TYPE: PRT
<213> ORGANISM: Streptococcus pneumoniae

<400> SEQUENCE: 297

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Val Pro Gly Lys Gly Leu Glu Trp Val
        35                  40                  45

Ser Tyr Thr Ser Thr Lys Ser Asp Ile Lys Tyr Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Gly Arg Asp Cys Tyr Gly Gly Asn Cys Val Ile Tyr Phe His
            100                 105                 110
```

Tyr Tyr Gly Leu Asp Val Trp Gly Gln Gly Thr Thr Val Thr Val Ser
        115                 120                 125

Ser

<210> SEQ ID NO 298
<211> LENGTH: 121
<212> TYPE: PRT
<213> ORGANISM: Streptococcus pneumoniae

<400> SEQUENCE: 298

Gln Val Gln Leu Val Glu Ser Gly Gly Gly Val Val Gln Pro Gly Gly
1               5                   10                  15

Ser Leu Arg Leu Ser Cys Val Val Ser Gly Phe Thr Leu Ser Ser Cys
            20                  25                  30

Gly Met His Trp Val Arg Gln Ser Pro Gly Lys Gly Leu Glu Trp Leu
        35                  40                  45

Ser Val Ser Thr Tyr Asp Gly Asn Gln Lys Tyr Tyr Ala Ala Ser Val
    50                  55                  60

Lys Gly Arg Phe Leu Ile Ser Arg Asp Thr Ser Lys Asn Thr Val Tyr
65                  70                  75                  80

Leu His Met Asn Ser Leu Thr Ala Glu Asp Thr Ala Leu Tyr Tyr Cys
                85                  90                  95

Val Lys Glu Ser Ala Thr Gly Trp Tyr Arg Thr Ala Asp Tyr Trp Gly
            100                 105                 110

Gln Gly Thr Leu Val Thr Val Ser Ser
        115                 120

<210> SEQ ID NO 299
<211> LENGTH: 122
<212> TYPE: PRT
<213> ORGANISM: Streptococcus pneumoniae

<400> SEQUENCE: 299

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ile
            20                  25                  30

Phe Met Ser Trp Val Arg Gln Ala Pro Gly Gln Gly Leu Glu Trp Val
        35                  40                  45

Ser Val Ile Tyr Thr Asp Gly Lys Thr Tyr Tyr Ala His Ser Val Glu
    50                  55                  60

Gly Arg Phe Thr Ile Ser Arg Asp Asp Ser Lys Asn Met Val Tyr Leu
65                  70                  75                  80

Gln Leu Ser Ser Leu Arg Thr Glu Asp Thr Ala Val Tyr Tyr Cys Ala
                85                  90                  95

Arg Asp Ile Pro Thr Thr Phe Gly Ile Gly Glu Ala Phe Asp Ile Trp
            100                 105                 110

Gly Gln Gly Thr Met Val Thr Val Ser Ser
        115                 120

<210> SEQ ID NO 300
<211> LENGTH: 115
<212> TYPE: PRT
<213> ORGANISM: Streptococcus pneumoniae

<400> SEQUENCE: 300

```
Val Gln Leu Val Gln Ser Gly Ala Glu Val Lys Lys Pro Gly Ala Ser
1               5                   10                  15

Val Lys Leu Ser Cys Lys Thr Ser Gly Tyr Ser Phe Thr Ser Asn Tyr
            20                  25                  30

Leu His Trp Val Arg Gln Ala Pro Gly Gln Gly Leu Glu Trp Met Gly
        35                  40                  45

Met Val Tyr Pro Asn Asp Gly Thr Thr Thr Tyr Ala Gln Lys Phe Gln
    50                  55                  60

Gly Arg Val Thr Met Thr Ser Glu Thr Ser Thr Thr Thr Ile Tyr Met
65                  70                  75                  80

Asp Leu Ser Gly Leu Thr Ser Glu Asp Thr Ala Ile Tyr Tyr Cys Ala
                85                  90                  95

Arg Asp Asp Ser Ala Phe Asp Tyr Trp Gly Gln Gly Thr Leu Val Thr
            100                 105                 110

Val Ser Ser
        115
```

<210> SEQ ID NO 301
<211> LENGTH: 121
<212> TYPE: PRT
<213> ORGANISM: Streptococcus pneumoniae

<400> SEQUENCE: 301

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Ile Phe Ser Ser Asn
            20                  25                  30

Gly Met His Trp Val Arg Gln Ala Pro Gly Lys Gly Leu Glu Trp Val
        35                  40                  45

Ala Val Ile Ser Ser Asp Gly Ser Arg Arg Tyr Tyr Ala Asp Ser Met
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Asp Asp Thr Ala Val Tyr Tyr Cys
                85                  90                  95

Ala Lys Gly Cys Ser Gly Glu Asn Cys Phe Tyr Met Asp Asp Trp Gly
            100                 105                 110

Lys Gly Thr Thr Val Thr Val Ser Ser
        115                 120
```

<210> SEQ ID NO 302
<211> LENGTH: 128
<212> TYPE: PRT
<213> ORGANISM: Streptococcus pneumoniae

<400> SEQUENCE: 302

```
Val Gln Leu Val Gln Ser Gly Ala Glu Val Lys Lys Pro Gly Ala Ser
1               5                   10                  15

Leu Lys Val Ser Cys Lys Ala Ser Gly Tyr Thr Phe Arg Gln Asn Tyr
            20                  25                  30

Phe His Trp Val Arg Gln Ala Pro Gly Gln Gly Leu Glu Trp Met Gly
        35                  40                  45

Val Ile Asn Pro Ser Asp Gly Ser Thr Lys Phe Ala Gln Lys Phe Gln
    50                  55                  60
```

```
Gly Arg Val Ser Met Thr Arg Asp Thr Ser Thr Ser Thr Val Tyr Met
65                  70                  75                  80

Asp Leu Ser Ser Leu Thr Ser Glu Asp Thr Ala Val Tyr Tyr Cys Thr
                85                  90                  95

Arg Glu Ile Gly Ala Val Val Val Asp Ala Thr Ser Leu Gly Trp Leu
            100                 105                 110

Gly Tyr Phe Asp Tyr Trp Gly Gln Gly Thr Leu Val Thr Val Ser Ser
        115                 120                 125


<210> SEQ ID NO 303
<211> LENGTH: 115
<212> TYPE: PRT
<213> ORGANISM: Streptococcus pneumoniae

<400> SEQUENCE: 303

Glu Val Gln Leu Val Glu Ser Gly Gly Gly Leu Val Gln Pro Gly Gly
1               5                   10                  15

Ser Leu Ser Leu Ser Cys Glu Ala Ser Gly Leu Thr Phe Ser Gly Tyr
            20                  25                  30

Trp Met Asn Trp Val Arg Gln Ala Pro Gly Lys Gly Leu Glu Trp Val
        35                  40                  45

Ala Asn Ile Asn Pro Glu Gly Ser Glu Arg Arg Tyr Val Glu Ser Val
    50                  55                  60

Gln Gly Arg Phe Thr Val Ser Arg Asp Asn Pro Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Gly Trp Gly Arg Thr Gln Asp Trp Gly Gln Gly Ala Leu Val Thr
            100                 105                 110

Val Ser Ser
        115


<210> SEQ ID NO 304
<211> LENGTH: 121
<212> TYPE: PRT
<213> ORGANISM: Streptococcus pneumoniae

<400> SEQUENCE: 304

Gln Val Gln Leu Val Glu Ser Gly Gly Gly Val Val Gln Pro Gly Arg
1               5                   10                  15

Ser Leu Arg Leu Ser Cys Ala Ala Ser Gly Leu Thr Phe Ser Asn Tyr
            20                  25                  30

Gly Met His Trp Val Arg Gln Ala Pro Gly Lys Gly Leu Glu Trp Val
        35                  40                  45

Ala Val Val Ser Ala Arg Gly Gly Thr Thr Tyr Tyr Ala Asp Ser Val
    50                  55                  60

Lys Gly Arg Phe Thr Ile Ser Arg Asp Asn Ser Lys Asn Thr Met Ser
65                  70                  75                  80

Leu Gln Met Asn Gly Leu Arg Pro Asp Asp Thr Ala Val Tyr Phe Cys
                85                  90                  95

Thr Lys Glu Gly Ala Pro Pro Gly Lys Tyr Ala Phe Asp Ile Trp Gly
            100                 105                 110

Gln Gly Thr Met Val Thr Val Ser Ser
        115                 120


<210> SEQ ID NO 305
<211> LENGTH: 120
```

<212> TYPE: PRT
<213> ORGANISM: Streptococcus pneumoniae

<400> SEQUENCE: 305

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Arg Met Asp Trp Val Arg Gln Ala Pro Gly Arg Gly Leu Glu Trp Ile
        35                  40                  45

Ala Arg Ile Arg His Arg Asp Ala Gly Tyr Ser Thr Glu Tyr Ala Ala
    50                  55                  60

Ser Val Arg Gly Arg Phe Thr Val Ser Arg Asp Asp Ser Gln Ser Thr
65                  70                  75                  80

Leu Tyr Leu Gln Met Asn Ser Leu Lys Ala Asp Asp Thr Ala Val Tyr
                85                  90                  95

Ile Cys Leu Lys Asp Ser Ser Gln Tyr Ser Phe Asp Ala Trp Gly Gln
            100                 105                 110

Gly Thr Met Val Thr Val Ser Ser
        115                 120
```

<210> SEQ ID NO 306
<211> LENGTH: 113
<212> TYPE: PRT
<213> ORGANISM: Streptococcus pneumoniae

<400> SEQUENCE: 306

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Ser Arg
            20                  25                  30

Ser Asn Asn Lys Asn Tyr Leu Ala Trp Tyr Gln Gln Lys Pro Gly Gln
        35                  40                  45

Pro Pro Lys Leu Leu Leu Tyr Trp Ala Ser Thr Arg Glu Ser Gly Val
    50                  55                  60

Pro Asp Arg Phe Ser Val Ser Gly Ser Gly Ser Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Ala Pro Leu Thr Phe Gly Gly Gly Thr Lys Val Glu Ile
            100                 105                 110

Lys
```

<210> SEQ ID NO 307
<211> LENGTH: 107
<212> TYPE: PRT
<213> ORGANISM: Streptococcus pneumoniae

<400> SEQUENCE: 307

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Val Ser Arg Tyr
            20                  25                  30

Leu Ala Trp Tyr Gln Gln Lys Pro Gly Gln Ala Pro Arg Leu Leu Ile
        35                  40                  45

Tyr Ala Ala Ser Asn Arg Ala Thr Gly Ile Pro Thr Arg Phe Ser Gly
    50                  55                  60
```

```
Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Ser Asn Trp Pro Ala
                85                  90                  95

Thr Phe Gly Gly Gly Thr Lys Val Glu Ile Lys
            100                 105


<210> SEQ ID NO 308
<211> LENGTH: 107
<212> TYPE: PRT
<213> ORGANISM: Streptococcus pneumoniae

<400> SEQUENCE: 308

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Arg Asp Arg
            20                  25                  30

Leu Asn Trp Tyr Gln Gln Lys Pro Gly Lys Ala Pro Asn Leu Leu Ile
        35                  40                  45

Tyr Asp Ala Ser Ser Leu Glu Thr Gly Val Pro Ser Arg Phe Arg Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Val Ser Phe Pro Arg
                85                  90                  95

Thr Phe Gly Pro Gly Thr Lys Val Asp Ile Lys
            100                 105


<210> SEQ ID NO 309
<211> LENGTH: 110
<212> TYPE: PRT
<213> ORGANISM: Streptococcus pneumoniae

<400> SEQUENCE: 309

Glu Ile Val Leu Thr Gln Ser Pro Gly Ile Leu Ser Leu Ser Pro Gly
1               5                   10                  15

Glu Arg Ala Thr Leu Ser Cys Arg Ala Ser Gln Ser Val Ser Ser Arg
            20                  25                  30

Ser Leu Ser Trp Tyr Gln Gln Arg Pro Gly Leu Ala Pro Arg Leu Leu
        35                  40                  45

Ile Tyr Ala Ala Ser Ser Arg Ala Ala Val Thr Pro Asp Arg Phe Thr
    50                  55                  60

Ala Ser Gly Ser Gly Thr Asp Phe Thr Leu Thr Ile Ser Ser Leu Glu
65                  70                  75                  80

Pro Glu Asp Phe Ala Val Tyr Tyr Cys Gln His Tyr Gly Thr Ser Pro
                85                  90                  95

Pro Arg Tyr Thr Phe Gly Gln Gly Thr Lys Val Glu Ile Lys
            100                 105                 110


<210> SEQ ID NO 310
<211> LENGTH: 113
<212> TYPE: PRT
<213> ORGANISM: Streptococcus pneumoniae

<400> SEQUENCE: 310

Asp Ile Val Met Thr Gln Ser Pro Asp Ser Leu Ala Val Ser Leu Gly
1               5                   10                  15
```

```
Glu Arg Ala Thr Ile Asn Cys Lys Ser Ser Gln Ser Val Leu His Ser
            20                  25                  30

Ser Asn Asn Lys Asn Tyr Phe Ala Trp Tyr Gln Gln Lys Pro Gly Gln
        35                  40                  45

Pro Pro Lys Leu Leu Ile His Trp Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Thr Ile Tyr Tyr Cys Gln Gln
                85                  90                  95

Tyr Tyr Ser Thr Pro Tyr Thr Phe Gly Gln Gly Thr Lys Val Glu Ile
            100                 105                 110

Lys


<210> SEQ ID NO 311
<211> LENGTH: 109
<212> TYPE: PRT
<213> ORGANISM: Streptococcus pneumoniae

<400> SEQUENCE: 311

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Pro Ser Leu Asp Ser Ala
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Val Thr Gly Ile Pro Asp Arg Phe Ser
    50                  55                  60

Gly Ser Ala Ser Gly Thr Asp Phe Thr Leu Thr Ile Ser Arg Leu Glu
65                  70                  75                  80

Pro Glu Asp Phe Ala Val Tyr Tyr Cys Gln Arg Tyr Gly Asn Ser Pro
                85                  90                  95

Pro Tyr Thr Phe Gly Gln Gly Thr Lys Val Glu Ile Lys
            100                 105


<210> SEQ ID NO 312
<211> LENGTH: 113
<212> TYPE: PRT
<213> ORGANISM: Streptococcus pneumoniae

<400> SEQUENCE: 312

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Tyr Ser
            20                  25                  30

Ser Ser Asn Lys Asn Tyr Leu Ala Trp Phe Gln Gln Lys Pro Gly Gln
        35                  40                  45

Ala Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Thr Glu Asp Val Ala Val Tyr Tyr Cys Leu Gln
                85                  90                  95

Tyr Arg Ser Ala Pro Phe Thr Phe Gly Gly Gly Thr Lys Val Glu Ile
            100                 105                 110

Lys
```

<210> SEQ ID NO 313
<211> LENGTH: 107
<212> TYPE: PRT
<213> ORGANISM: Streptococcus pneumoniae

<400> SEQUENCE: 313

```
Asp Ile Gln Met Thr Gln Ser Pro Ser Thr Gln Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Ala Val Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Thr Tyr Pro Trp
                85                  90                  95

Thr Phe Gly Pro Gly Thr Lys Val Glu Ile Lys
            100                 105
```

<210> SEQ ID NO 314
<211> LENGTH: 107
<212> TYPE: PRT
<213> ORGANISM: Streptococcus pneumoniae

<400> SEQUENCE: 314

```
Glu Ile Val Met Thr Gln Ser Pro Ala Ser Leu Ser Val Ser Pro Gly
1               5                   10                  15

Glu Thr Ala Thr Leu Ser Cys Arg Ala Ser Gln Ser Val Gly Ser Thr
            20                  25                  30

Leu Ala Trp Tyr Gln Gln Lys Pro Gly Gln Ala Pro Arg Leu Leu Ile
        35                  40                  45

Tyr Asn Val Phe Thr Arg Ala Ala Gly Val Pro Ala Arg Phe Ser Gly
    50                  55                  60

Ser Gly Ser Arg Thr Glu Phe Thr Leu Thr Ile Ser Ser Leu Gln Ser
65                  70                  75                  80

Glu Asp Phe Ala Val Tyr Tyr Cys Gln Gln Tyr Ser Thr Trp Leu Trp
                85                  90                  95

Thr Phe Gly Gln Gly Thr Lys Val Glu Ile Lys
            100                 105
```

<210> SEQ ID NO 315
<211> LENGTH: 107
<212> TYPE: PRT
<213> ORGANISM: Streptococcus pneumoniae

<400> SEQUENCE: 315

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ala Ser Leu His Asp Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Arg Ile Pro Tyr
                85                  90                  95

Ser Phe Gly Pro Gly Thr Lys Val Glu Ile Lys
            100                 105


<210> SEQ ID NO 316
<211> LENGTH: 112
<212> TYPE: PRT
<213> ORGANISM: Streptococcus pneumoniae

<400> SEQUENCE: 316

Asp Ile Val Met Thr Gln Ser Pro Leu Ser Leu Ser Val Thr Pro Gly
1               5                   10                  15

Glu Pro Ala Ser Ile Ser Cys Arg Ser Ser Gln Ser Leu Leu Gln Gly
            20                  25                  30

Asn Gly His Asn Tyr Leu Asp Trp Tyr Leu Gln Lys Pro Gly Gln Ser
        35                  40                  45

Pro Gln Leu Leu Ile Tyr Leu Gly Ser Ile Arg Ala Ser Gly Val Pro
    50                  55                  60

Asp Arg Phe Ser Gly Ser Gly Ser Gly Thr Asp Phe Ile Leu Lys Ile
65                  70                  75                  80

Ser Arg Val Glu Ala Glu Asp Val Gly Val Tyr Tyr Cys Met Arg Ala
                85                  90                  95

Leu Gln Thr Pro Tyr Thr Phe Gly Gln Gly Thr Lys Val Glu Ile Lys
            100                 105                 110


<210> SEQ ID NO 317
<211> LENGTH: 107
<212> TYPE: PRT
<213> ORGANISM: Streptococcus pneumoniae

<400> SEQUENCE: 317

Asp Ile Gln Met Thr Gln Ser Pro Ser Thr Leu Ser Ala Ser Val Gly
1               5                   10                  15

Asp Arg Val Thr Leu Thr Cys Arg Ala Ser Glu Thr Leu Asn Asn Trp
            20                  25                  30

Leu Ala Trp Phe Gln Gln Lys Pro Gly Lys Ala Pro Thr Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Asp Phe Ala Leu Thr Ile Ser Ser Leu Gln Pro
65                  70                  75                  80

Asp Asp Phe Ala Thr Tyr Tyr Cys His Gln Tyr Asn Lys Tyr Pro Trp
                85                  90                  95

Thr Phe Gly Gln Gly Thr Lys Val Glu Ile Lys
            100                 105


<210> SEQ ID NO 318
<211> LENGTH: 106
<212> TYPE: PRT
<213> ORGANISM: Streptococcus pneumoniae

<400> SEQUENCE: 318

Asp Ile Gln Met Thr Gln Ser Pro Ser Thr Leu Ser Ala Ser Val Gly
1               5                   10                  15
```

```
Asp Arg Val Thr Ile Thr Cys Arg Ala Ser Gln Ser Ile Ser Gly Trp
            20                  25                  30

Leu Ala Trp Tyr Gln Gln Lys Ala Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Ser Trp Gly Thr
                85                  90                  95

Phe Gly Gln Gly Thr Lys Val Glu Ile Lys
            100                 105


<210> SEQ ID NO 319
<211> LENGTH: 112
<212> TYPE: PRT
<213> ORGANISM: Streptococcus pneumoniae

<400> SEQUENCE: 319

Asp Ile Val Met Thr Gln Thr Pro Leu Ser Leu Pro Val Thr Leu Gly
1               5                   10                  15

Gln Pro Ala Ser Ile Ser Cys Ile Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Gln Ser Thr Trp Thr Leu Gly Gln Gly Thr Lys Val Glu Ile Lys
            100                 105                 110


<210> SEQ ID NO 320
<211> LENGTH: 113
<212> TYPE: PRT
<213> ORGANISM: Streptococcus pneumoniae

<400> SEQUENCE: 320

Asp Ile Val Met Thr Gln Ser Pro Asp Ser Leu Ala Val Pro Leu Gly
1               5                   10                  15

Glu Arg Ala Thr Ile Asn Cys Thr Ser Ser Gln Thr Val Leu Ser Ser
            20                  25                  30

Ser Asn Asn Lys Asn Tyr Leu Val Trp Tyr Gln Gln Lys Pro Gly Gln
        35                  40                  45

Pro Pro Lys Leu Leu Leu Tyr Trp Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Cys Tyr Asn Ala Pro Leu Thr Phe Gly Arg Gly Thr Lys Val Glu Ile
            100                 105                 110

Lys
```

<210> SEQ ID NO 321
<211> LENGTH: 108
<212> TYPE: PRT
<213> ORGANISM: Streptococcus pneumoniae

<400> SEQUENCE: 321

```
Glu Ile Val Met Thr Gln Ser Pro Ala Thr Leu Ser Val Phe Pro Gly
1               5                   10                  15

Glu Gly Val Thr Leu Ser Cys Arg Ala Ser Gln Ser Ile Ser Asn Asn
            20                  25                  30

Leu Ala Trp Tyr Gln Gln Lys Pro Gly Gln Ala Pro Arg Leu Leu Met
        35                  40                  45

Tyr Asp Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Val Thr Phe Gly Gln Gly Thr Lys Val Glu Ile Lys
            100                 105
```

<210> SEQ ID NO 322
<211> LENGTH: 110
<212> TYPE: PRT
<213> ORGANISM: Streptococcus pneumoniae

<400> SEQUENCE: 322

```
Val Met Thr Gln Ser Pro Leu Ser Leu Pro Val Thr Leu Gly Gln Ser
1               5                   10                  15

Ala Ser Val Ser Cys Arg Ser Ser Gln Ser Leu Gly Pro Ser Asp Gly
            20                  25                  30

Ser Thr Arg Leu Asp Trp Phe Gln Gln Arg Pro Gly Gln Ser Pro Arg
        35                  40                  45

Arg Leu Ile Tyr Ala Val Ser Asn Arg Asp Ser Gly Val Pro Asp Arg
    50                  55                  60

Phe Ser Gly Ser Gly Ser Gly Ser Asp Phe Thr Leu Arg Ile Ser Arg
65                  70                  75                  80

Val Glu Ala Glu Asp Val Gly Val Tyr Tyr Cys Met Gln Tyr Thr Tyr
                85                  90                  95

Trp Pro His Thr Phe Gly Gln Gly Thr Lys Val Glu Ile Lys
            100                 105                 110
```

<210> SEQ ID NO 323
<211> LENGTH: 109
<212> TYPE: PRT
<213> ORGANISM: Streptococcus pneumoniae

<400> SEQUENCE: 323

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Asp Ile Pro Ala Arg Phe Ser Gly
    50                  55                  60
```

```
Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Gly Glu Trp Pro Pro
                85                  90                  95

Gly Ala Thr Phe Gly Pro Gly Thr Lys Val Asp Ile Lys
            100                 105


<210> SEQ ID NO 324
<211> LENGTH: 107
<212> TYPE: PRT
<213> ORGANISM: Streptococcus pneumoniae

<400> SEQUENCE: 324

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Asp Thr Arg
            20                  25                  30

Leu Ile Trp Tyr Gln Gln Lys Pro Gly Glu Ala Pro Lys Leu Leu Ile
        35                  40                  45

Tyr Glu Ala Ser Thr Leu Gln Ser Gly Ala Pro Ser Arg Phe Ser Gly
    50                  55                  60

Ser Gly Phe Gly Thr Glu Phe Thr Leu Thr Ile Ser Ser Leu Gln Pro
65                  70                  75                  80

Glu Asp Phe Ala Thr Tyr Tyr Cys Gln Gln Phe Lys Gly Tyr Pro Leu
                85                  90                  95

Thr Phe Gly Gly Gly Thr Lys Val Glu Ile Lys
            100                 105


<210> SEQ ID NO 325
<211> LENGTH: 115
<212> TYPE: PRT
<213> ORGANISM: Streptococcus pneumoniae

<400> SEQUENCE: 325

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser His
            20                  25                  30

Tyr Trp Ser Trp Ile Arg Gln Pro Pro Ala Lys Gly Leu Glu Trp Ile
        35                  40                  45

Gly Tyr Ile Tyr His Ser Gly Met Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Asp Gly Tyr Asn Phe Phe Trp Gly Gln Gly Thr Leu Val Thr
            100                 105                 110

Val Ser Ser
        115


<210> SEQ ID NO 326
<211> LENGTH: 125
<212> TYPE: PRT
<213> ORGANISM: Streptococcus pneumoniae
```

```
<400> SEQUENCE: 326

Gln Val Gln Leu Val Glu Ser Gly Gly Gly Val Val Gln Pro Gly Gly
1               5                   10                  15

Ser Leu Arg Leu Ser Cys Ala Ala Ser Gly Leu Thr Phe Ser Asn Gln
            20                  25                  30

Asp Phe His Trp Val Arg Gln Ala Pro Gly Lys Gly Leu Glu Trp Val
        35                  40                  45

Ala Phe Ile Arg Tyr Asp Gly Gly Phe Lys Asn Tyr Ala Asp Ser Val
    50                  55                  60

Lys Gly Arg Phe Thr Ile Ser Arg Asp Asn Ser Gln Lys Met Leu Tyr
65                  70                  75                  80

Leu Gln Met Asp Ser Leu Arg Val Glu Asp Thr Ala Val Tyr Tyr Cys
                85                  90                  95

Ala Lys Cys Gly Ala Glu Asp Ser Thr Thr Val Trp Leu Asn Trp Phe
            100                 105                 110

Asp Pro Trp Gly Gln Gly Thr Leu Val Thr Val Ser Ser
        115                 120                 125


<210> SEQ ID NO 327
<211> LENGTH: 120
<212> TYPE: PRT
<213> ORGANISM: Streptococcus pneumoniae

<400> SEQUENCE: 327

Glu Val Gln Leu Leu Glu Ser Gly Gly Gly Leu Val Glu Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Asp Ser Gly Gly Ser Thr Tyr Tyr Ala Asp Ser Val
    50                  55                  60

Lys Gly Arg Phe Thr Ile Ser Arg Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asn Tyr Phe Gly Ser Gly Ser Pro Asp Tyr Trp Gly Gln
            100                 105                 110

Gly Thr Leu Val Thr Val Ser Ser
        115                 120


<210> SEQ ID NO 328
<211> LENGTH: 115
<212> TYPE: PRT
<213> ORGANISM: Streptococcus pneumoniae

<400> SEQUENCE: 328

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser His
            20                  25                  30

Tyr Trp Ser Trp Ile Arg Gln Pro Pro Gly Lys Gly Leu Glu Trp Ile
        35                  40                  45

Gly Tyr Ile Tyr His Ser Gly Ile Thr Asn Tyr Asn Pro Ser Leu Lys
    50                  55                  60
```

```
Ser Arg Val Thr Ile Ser Ile Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Arg Gly Asp Gly Tyr Asn Phe Tyr Trp Gly Gln Gly Thr Leu Val Thr
            100                 105                 110

Val Ser Ser
        115


<210> SEQ ID NO 329
<211> LENGTH: 126
<212> TYPE: PRT
<213> ORGANISM: Streptococcus pneumoniae

<400> SEQUENCE: 329

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Thr Trp Val Arg Gln Ala Pro Gly Lys Gly Leu Glu Trp Ile
        35                  40                  45

Ser Gly Ile Cys Cys Asn Gly Gly Cys Ser Gly Tyr Ala Asp Ser Val
    50                  55                  60

Lys Gly Arg Phe Thr Ile Ser Arg Asp Asn Ala Lys Lys Ser Leu Phe
65                  70                  75                  80

Leu Val Met Asn Ser Leu Arg Ala Glu Asp Thr Ala Leu Tyr Tyr Cys
                85                  90                  95

Val Arg Val Ala Val Pro Ala Ala Thr Tyr Thr Arg Gly Asn Asp Ala
            100                 105                 110

Phe Asp Ile Trp Gly Gln Gly Thr Met Val Thr Val Ser Ser
        115                 120                 125


<210> SEQ ID NO 330
<211> LENGTH: 119
<212> TYPE: PRT
<213> ORGANISM: Streptococcus pneumoniae

<400> SEQUENCE: 330

Glu Val Gln Leu Val Glu Ser Gly Gly Gly Leu Val Glu Pro Gly Gly
1               5                   10                  15

Ser Leu Arg Leu Ser Cys Ala Val Ser Gly Phe Thr Phe Thr Asp Ala
            20                  25                  30

Trp Met Thr Trp Val Arg Gln Ala Pro Gly Lys Gly Leu Asp Trp Val
        35                  40                  45

Gly His Val Lys Ser Lys Tyr Asp Gly Ala Thr Thr Glu Tyr Ala Ala
    50                  55                  60

Pro Val Gln Gly Arg Phe Thr Ile Ser Arg Asp Asp Ser Lys Lys Thr
65                  70                  75                  80

Ile Tyr Leu Gln Met Asn Ser Leu Asn Thr Glu Asp Thr Gly Val Tyr
                85                  90                  95

Phe Cys Thr Thr Ala His Gly Pro Val Gly Asp His Trp Gly Gln Gly
            100                 105                 110

Thr Leu Val Thr Val Ser Ser
        115


<210> SEQ ID NO 331
<211> LENGTH: 126
```

```
<212> TYPE: PRT
<213> ORGANISM: Streptococcus pneumoniae

<400> SEQUENCE: 331

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Asp Thr Ser
            20                  25                  30

Trp Met Thr Trp Val Arg Gln Ala Pro Gly Lys Gly Leu Glu Trp Val
        35                  40                  45

Ala Thr Ile Asn Gln Gly Gly Ser Asp Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Gly Cys Ser Ser Thr Arg Cys His Thr Thr Pro Gly
            100                 105                 110

Phe Asp Tyr Trp Gly Gln Gly Ala Leu Val Thr Val Ser Ser
        115                 120                 125


<210> SEQ ID NO 332
<211> LENGTH: 117
<212> TYPE: PRT
<213> ORGANISM: Streptococcus pneumoniae

<400> SEQUENCE: 332

Gln Leu Gln Glu Ser Gly Pro Gly Leu Val Lys Pro Ser Glu Thr Leu
1               5                   10                  15

Ser Leu Thr Cys Thr Val Ser Gly Ser Ser Ile Ser Ser Ser Ser Tyr
            20                  25                  30

Tyr Trp Gly Trp Val Arg Gln Ser Pro Gly Lys Gly Leu Glu Trp Ile
        35                  40                  45

Gly Ser Ile Tyr His Ser Gly Thr Ile Tyr Tyr Asn Pro Ser Leu Arg
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Ser Leu Ser Gly Thr Asn Ala Phe Asp Ile Trp Gly Gln Gly Thr Met
            100                 105                 110

Val Thr Val Ser Ser
        115


<210> SEQ ID NO 333
<211> LENGTH: 120
<212> TYPE: PRT
<213> ORGANISM: Streptococcus pneumoniae

<400> SEQUENCE: 333

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met Ser Trp Val Arg Leu Ala Pro Gly Lys Gly Pro Glu Trp Val
        35                  40                  45
```

```
Ser Ala Leu Gly Ala Gly Asp Ala Trp Thr His Tyr Ala Asn Ser Val
    50                  55                  60

Arg Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Pro Arg Gly Tyr Ser Tyr Gly Tyr Phe Asp Tyr Trp Gly Gln
            100                 105                 110

Gly Thr Leu Val Thr Val Ser Ser
        115                 120


<210> SEQ ID NO 334
<211> LENGTH: 117
<212> TYPE: PRT
<213> ORGANISM: Streptococcus pneumoniae

<400> SEQUENCE: 334

Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Ser Thr Tyr
            20                  25                  30

Trp Met Thr Trp Val Arg Gln Ala Pro Gly Lys Gly Leu Glu Trp Val
        35                  40                  45

Ala Asn Ile Asn Gln Asp Gly Ser Glu Lys Gln Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Ile Tyr Tyr Cys
                85                  90                  95

Ala Arg Pro Pro Ala Arg Arg Leu Asp Tyr Trp Gly Gln Gly Ser Leu
            100                 105                 110

Val Thr Val Ser Ser
        115


<210> SEQ ID NO 335
<211> LENGTH: 116
<212> TYPE: PRT
<213> ORGANISM: Streptococcus pneumoniae

<400> SEQUENCE: 335

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Phe Ser Asp Tyr
            20                  25                  30

Trp Met His Trp Val Arg Gln Ala Pro Gly Lys Gly Leu Val Trp Val
        35                  40                  45

Ser Arg Ile Asn Thr Asp Gly Ser Thr Thr Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Gly His Glu Ala Trp Gly Gln Gly Thr Leu Val
            100                 105                 110

Thr Val Ser Ser
        115
```

<210> SEQ ID NO 336
<211> LENGTH: 117
<212> TYPE: PRT
<213> ORGANISM: Streptococcus pneumoniae

<400> SEQUENCE: 336

```
Val Gln Leu Val Gln Ser Gly Ala Glu Val Lys Lys Pro Gly Ala Ser
1               5                   10                  15

Val Arg Val Ser Cys Lys Ala Ser Gly Tyr Thr Phe Thr Asn Tyr Trp
            20                  25                  30

Ile His Trp Val Arg Gln Ala Pro Gly Gln Gly Leu Glu Trp Met Gly
        35                  40                  45

Met Ile Ala Pro Lys Glu Gly Tyr Thr Phe Tyr Ala Gln Gln Leu Gln
    50                  55                  60

Gly Arg Val Thr Val Thr Arg Asp Thr Ser Thr Ser Ala Val Tyr Met
65                  70                  75                  80

Glu Leu Asn Ser Leu Arg Ser Glu Asp Thr Ala Val Tyr Phe Cys Ala
                85                  90                  95

Arg Asp Ile Pro His Ala Asn Leu Asp Tyr Trp Gly Gln Gly Thr Leu
            100                 105                 110

Val Thr Val Ser Ser
        115
```

<210> SEQ ID NO 337
<211> LENGTH: 121
<212> TYPE: PRT
<213> ORGANISM: Streptococcus pneumoniae

<400> SEQUENCE: 337

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Thr Met Asn Trp Ala Arg Gln Ala Pro Gly Lys Gly Leu Glu Trp Val
        35                  40                  45

Ser Ala Ile Arg Glu Ser Gly Asp Ser Thr Tyr Tyr Ala Asp Ser Val
    50                  55                  60

Thr Gly Arg Phe Thr Ile Ser Arg Asp Asn Ser Arg Asn Thr Leu Tyr
65                  70                  75                  80

Leu His Met Asn Ser Leu Arg Ala Glu Asp Thr Ala Met Tyr Phe Cys
                85                  90                  95

Val Lys Asp Arg Val Pro Pro Gly Asp Val Pro Gly Asp Phe Trp Gly
            100                 105                 110

Pro Gly Thr Leu Val Thr Val Ser Ser
        115                 120
```

<210> SEQ ID NO 338
<211> LENGTH: 107
<212> TYPE: PRT
<213> ORGANISM: Streptococcus pneumoniae

<400> SEQUENCE: 338

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asp Met Thr His Ser
            20                  25                  30
```

```
Leu Ala Trp Tyr Gln Gln Lys Pro Gly Lys Ala Pro Asn Leu Leu Ile
        35                  40                  45

Tyr Asn Ala Tyr Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ile Asn Ser Tyr Pro Arg
                85                  90                  95

Thr Phe Gly Gln Gly Thr Lys Val Glu Ile Lys
            100                 105


<210> SEQ ID NO 339
<211> LENGTH: 107
<212> TYPE: PRT
<213> ORGANISM: Streptococcus pneumoniae

<400> SEQUENCE: 339

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Asn Ile Gly Thr Ala
            20                  25                  30

Leu Ala Trp Tyr Gln Gln Lys Pro Gly Gln Ala Pro Arg Leu Ile Ile
        35                  40                  45

Tyr Glu Thr Ser Asn Arg Ala Thr Asp Val Pro Ala Arg Phe Ser Gly
    50                  55                  60

Ser Gly Ser Gly Thr Asp Phe Thr Leu Thr Ile Ser Ser Leu Glu Arg
65                  70                  75                  80

Glu Asp Phe Ala Leu Tyr Tyr Cys Gln Gln Arg Ala Asp Trp Pro Leu
                85                  90                  95

Thr Phe Gly Gly Gly Thr Lys Val Glu Ile Lys
            100                 105


<210> SEQ ID NO 340
<211> LENGTH: 108
<212> TYPE: PRT
<213> ORGANISM: Streptococcus pneumoniae

<400> SEQUENCE: 340

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Arg Pro Gly Gln Ala Pro Arg Leu Val Ile
        35                  40                  45

Tyr Ala Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Leu Gln Cys Ser Asn Trp Pro Met
                85                  90                  95

Tyr Thr Phe Gly Gln Gly Thr Lys Val Glu Ile Lys
            100                 105


<210> SEQ ID NO 341
<211> LENGTH: 107
<212> TYPE: PRT
<213> ORGANISM: Streptococcus pneumoniae
```

<400> SEQUENCE: 341

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asp Ile Thr Asp Ser
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Thr Thr Tyr Tyr Cys Gln Gln Ile Asn Ser Tyr Pro Arg
                85                  90                  95

Thr Phe Gly Gln Gly Thr Lys Val Glu Ile Lys
            100                 105
```

<210> SEQ ID NO 342
<211> LENGTH: 107
<212> TYPE: PRT
<213> ORGANISM: Streptococcus pneumoniae

<400> SEQUENCE: 342

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ser Tyr Tyr Cys Leu Gln His Ser Ser Phe Pro Trp
                85                  90                  95

Thr Phe Gly Gln Gly Thr Lys Val Glu Ile Lys
            100                 105
```

<210> SEQ ID NO 343
<211> LENGTH: 114
<212> TYPE: PRT
<213> ORGANISM: Streptococcus pneumoniae

<400> SEQUENCE: 343

```
Asp Ile Val Met Thr Gln Ser Pro Asp Ser Leu Ala Val Ser Leu Gly
1               5                   10                  15

Glu Arg Ala Ala Ile Asn Cys Lys Ser Ser Gln Ser Val Leu Asp Ser
            20                  25                  30

Ser Asn Met Lys Arg Tyr Leu Ala Trp Tyr Gln Leu Lys Ala Gly Gln
        35                  40                  45

Pro Pro Arg Leu Leu Ile Tyr Leu Ala Ser Thr Arg Glu Ser Gly Val
    50                  55                  60

Pro Asp Arg Phe Ser Gly Ser Gly Ser Gly Thr Asp Phe Asn Leu Thr
65                  70                  75                  80

Ile Ser Ser Leu Gln Ala Glu Asp Val Ala Val Tyr Tyr Cys Gln Gln
                85                  90                  95
```

```
Tyr Tyr Thr Thr Pro Ser Ile Thr Phe Gly Gln Gly Thr Arg Leu Glu
            100                 105                 110

Ile Lys


<210> SEQ ID NO 344
<211> LENGTH: 114
<212> TYPE: PRT
<213> ORGANISM: Streptococcus pneumoniae

<400> SEQUENCE: 344

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Met Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Pro Ile Thr Phe Gly Gln Gly Thr Arg Leu Glu
            100                 105                 110

Ile Lys


<210> SEQ ID NO 345
<211> LENGTH: 106
<212> TYPE: PRT
<213> ORGANISM: Streptococcus pneumoniae

<400> SEQUENCE: 345

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ile Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ser Gly Arg Thr
                85                  90                  95

Phe Gly Gln Gly Thr Lys Val Glu Ile Lys
            100                 105


<210> SEQ ID NO 346
<211> LENGTH: 108
<212> TYPE: PRT
<213> ORGANISM: Streptococcus pneumoniae

<400> SEQUENCE: 346

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Thr Asn Asn
            20                  25                  30
```

```
Tyr Leu Ala Trp Tyr Gln His Lys Pro Gly Leu Ala Pro Arg Leu Leu
        35                  40                  45

Ile Phe Asp Ala Ser Ile Arg Ala Thr Gly Ile Pro Asp Arg Phe Ser
    50                  55                  60

Gly Ser Gly Ser Gly Ala Asp Phe Thr Leu Thr Ile Ser Arg Leu Glu
65                  70                  75                  80

Pro Glu Asp Phe Thr Phe Tyr Tyr Cys Gln Gln Tyr Gly Ile Ser Pro
                85                  90                  95

Arg Thr Phe Gly Gln Gly Thr Lys Val Glu Ile Lys
            100                 105


<210> SEQ ID NO 347
<211> LENGTH: 112
<212> TYPE: PRT
<213> ORGANISM: Streptococcus pneumoniae

<400> SEQUENCE: 347

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Arg Thr Tyr Phe Phe Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ser Glu Asp Val Gly Val Tyr Tyr Cys Met Gln Gly
                85                  90                  95

Thr His His Pro Trp Thr Phe Gly Gln Gly Thr Lys Val Glu Ile Lys
            100                 105                 110


<210> SEQ ID NO 348
<211> LENGTH: 113
<212> TYPE: PRT
<213> ORGANISM: Streptococcus pneumoniae

<400> SEQUENCE: 348

Asp Ile Val Met Thr Gln Ser Pro Asp Ser Leu Ala Val Ser Leu Gly
1               5                   10                  15

Glu Arg Ala Thr Val Asn Cys Lys Ser Ser Gln Ser Val Leu Tyr Ser
            20                  25                  30

Ser Asn Ser Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys


<210> SEQ ID NO 349
<211> LENGTH: 107
```

<212> TYPE: PRT
<213> ORGANISM: Streptococcus pneumoniae

<400> SEQUENCE: 349

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asn Asp
            20                  25                  30

Leu Gly Trp Tyr Gln His Glu Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Ala Ser Gly Thr Glu Phe Thr Leu Thr Ile Thr Ser Leu Gln Pro
65                  70                  75                  80

Glu Asp Phe Ala Thr Tyr Tyr Cys Leu Gln His Thr Thr Phe Pro Trp
                85                  90                  95

Thr Phe Gly Gln Gly Thr Lys Val Glu Ile Lys
            100                 105
```

<210> SEQ ID NO 350
<211> LENGTH: 108
<212> TYPE: PRT
<213> ORGANISM: Streptococcus pneumoniae

<400> SEQUENCE: 350

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser His
            20                  25                  30

Phe Ala Trp Tyr Gln Gln Lys Pro Gly Gln Ala Pro Arg Leu Leu Ile
        35                  40                  45

Tyr Gly Ala Ser Asn Arg Ala Pro Gly Ile Pro Pro Arg Phe Ser Ala
    50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Arg Arg Thr Trp Pro Pro
                85                  90                  95

Leu Thr Phe Gly Gln Gly Thr Arg Leu Glu Ile Lys
            100                 105
```

<210> SEQ ID NO 351
<211> LENGTH: 119
<212> TYPE: PRT
<213> ORGANISM: Streptococcus pneumoniae

<400> SEQUENCE: 351

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Ser Phe Ser Gly His
            20                  25                  30

Glu Met Asn Trp Val Arg Gln Pro Pro Gly Lys Gly Leu Glu Trp Val
        35                  40                  45

Ser His Ile Gly Ser Gly Gly Asp Tyr Ile Gly Tyr Ala Asp Ser Val
    50                  55                  60

Lys Gly Arg Phe Thr Val Ser Arg Asp Asn Ala Lys Asn Leu Leu Tyr
65                  70                  75                  80
```

```
Leu Gln Met Asn Ser Leu Arg Ala Asp Asp Thr Ala Val Tyr Tyr Cys
                85                  90                  95

Ala Thr Leu Leu Leu Arg Asp Asn Gln Leu Asp Val Trp Gly Gln Gly
            100                 105                 110

Thr Thr Val Thr Val Ser Ser
        115


<210> SEQ ID NO 352
<211> LENGTH: 121
<212> TYPE: PRT
<213> ORGANISM: Streptococcus pneumoniae

<400> SEQUENCE: 352

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Ser Cys
            20                  25                  30

Gly Met His Trp Ile Arg Gln Ala Pro Gly Lys Gly Leu Glu Trp Val
        35                  40                  45

Ala Val Ile Thr Tyr Asp Gly Arg Ser His Phe Asn Ala Asp Ala Val
    50                  55                  60

Lys Gly Arg Phe Thr Ile Ser Arg Asp Arg Ser Met Asn Thr Val Ser
65                  70                  75                  80

Leu Gln Met Asp Ser Leu Arg Pro Glu Asp Thr Ala Val Tyr Tyr Cys
                85                  90                  95

Val Lys Glu Gln Gly Phe Gly Tyr Tyr Arg Thr Ala Asp Tyr Trp Gly
            100                 105                 110

Gln Gly Thr Leu Val Thr Val Ser Ser
        115                 120


<210> SEQ ID NO 353
<211> LENGTH: 114
<212> TYPE: PRT
<213> ORGANISM: Streptococcus pneumoniae

<400> SEQUENCE: 353

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Ser Ser Asp
            20                  25                  30

His Trp Ser Trp Ile Arg Gln Pro Pro Gly Lys Gly Leu Glu Trp Ile
        35                  40                  45

Gly Asn Val Tyr Tyr Ser Gly Arg Thr Tyr Tyr Asn Pro Ser Phe Lys
    50                  55                  60

Ser Arg Val Thr Ile Ser Val Ala Thr Ser Lys Asn Gln Phe Ser Leu
65                  70                  75                  80

Lys Val Thr Ser Val Thr Ala Ala Asp Thr Ala Ile Tyr Tyr Cys Ala
                85                  90                  95

Arg Arg Asn Asp Phe Asn Ile Trp Gly Gln Gly Thr Met Val Thr Val
            100                 105                 110

Ser Ser


<210> SEQ ID NO 354
<211> LENGTH: 123
<212> TYPE: PRT
<213> ORGANISM: Streptococcus pneumoniae
```

<400> SEQUENCE: 354

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ala Val Ser Trp Val Arg Gln Ala Pro Gly Lys Gly Leu Glu Trp Val
        35                  40                  45

Ser Ala Val Ser Gly Asn Gly Asp Ser Thr Tyr Tyr Ala Asp Pro Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ser Ile Trp Trp Gly Thr Ser Val Gln Tyr Pro Leu Val Leu Asp Tyr
            100                 105                 110

Trp Gly Leu Gly Thr Leu Val Thr Val Ser Ser
        115                 120

<210> SEQ ID NO 355
<211> LENGTH: 121
<212> TYPE: PRT
<213> ORGANISM: Streptococcus pneumoniae

<400> SEQUENCE: 355

Gln Val Gln Leu Val Glu Ser Gly Gly Gly Val Val Gln Pro Gly Arg
1               5                   10                  15

Ser Leu Arg Leu Leu Cys Ala Ala Ser Gly Phe Thr Leu Ser Thr Cys
            20                  25                  30

Gly Met His Trp Ile Arg Gln Thr Pro Gly Lys Gly Leu Glu Trp Val
        35                  40                  45

Ala Val Lys Thr Tyr Asp Gly Arg Glu Glu Phe Tyr Ala Asp Ser Val
    50                  55                  60

Lys Gly Arg Phe Thr Ile Ser Arg Asp Glu Ser Met Asn Thr Leu Ser
65                  70                  75                  80

Leu Gln Met Asn Ser Leu Arg Pro Glu Asp Thr Ala Val Tyr Tyr Cys
                85                  90                  95

Val Lys Glu Gln Asp Tyr Gly Tyr Tyr Arg Thr Ala Asp His Trp Gly
            100                 105                 110

Gln Gly Thr Leu Val Thr Val Ser Ser
        115                 120

<210> SEQ ID NO 356
<211> LENGTH: 117
<212> TYPE: PRT
<213> ORGANISM: Streptococcus pneumoniae

<400> SEQUENCE: 356

Gln Val Gln Leu Gln Glu Ala Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

```
Leu Lys Ser Arg Val Thr Ile Ser Val Asp Thr Ser Lys Asn Gln Tyr
65                  70                  75                  80

Ser Leu Lys Leu Ser Ser Val Thr Ala Ala Asp Thr Ala Val Tyr Tyr
                85                  90                  95

Cys Ala Arg Gly His Gly Phe Asn Ala Tyr Trp Gly Gln Gly Thr Leu
            100                 105                 110

Val Thr Val Ser Ser
        115


<210> SEQ ID NO 357
<211> LENGTH: 122
<212> TYPE: PRT
<213> ORGANISM: Streptococcus pneumoniae

<400> SEQUENCE: 357

Glu Val Gln Leu Val Glu Ser Gly Gly Gly Leu Val Lys Pro Gly Glu
1               5                   10                  15

Ser Leu Arg Leu Ser Cys Ala Thr Ser Gly Val Asn Phe Asn Ile Ala
            20                  25                  30

Trp Met Thr Trp Val Arg Gln Ala Pro Gly Lys Gly Leu Glu Trp Val
        35                  40                  45

Gly Arg Ile Lys Ser Lys Ile Gly Gly Gly Thr Thr Asp Tyr Ala Ala
    50                  55                  60

Pro Val Lys Gly Arg Phe Thr Met Ser Ile Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Val Arg Asn Met Ala Asp Leu Ser Leu Asn His Trp
            100                 105                 110

Gly Gln Gly Thr Leu Val Thr Val Ser Ser
        115                 120


<210> SEQ ID NO 358
<211> LENGTH: 118
<212> TYPE: PRT
<213> ORGANISM: Streptococcus pneumoniae

<400> SEQUENCE: 358

Glu Val Gln Leu Val Glu Ser Gly Gly Gly Leu Val Gln Pro Gly Ala
1               5                   10                  15

Ser Leu Thr Leu Ser Cys Val Val Ser Gly Phe Thr Phe Ile Gly Thr
            20                  25                  30

Glu Met Thr Trp Ile Arg Gln Ala Pro Gly Lys Gly Leu Glu Gly Leu
        35                  40                  45

Ser Tyr Ile Ser Gly Ser Gly Gly Thr Thr Tyr Tyr Ala Glu Ser Val
    50                  55                  60

Arg Gly Arg Phe Thr Ile Ser Arg Asp Asn Ala Lys Lys Ser Leu Phe
65                  70                  75                  80

Leu Gln Met Thr Ser Leu Thr Ala Glu Asp Thr Ala Val Tyr Tyr Cys
                85                  90                  95

Ala Thr Gly Asn Arg Gly Ser Leu Pro Arg Arg Trp Gly Gln Gly Thr
            100                 105                 110

Leu Val Thr Val Ser Ser
        115


<210> SEQ ID NO 359
```

<211> LENGTH: 118
<212> TYPE: PRT
<213> ORGANISM: Streptococcus pneumoniae

<400> SEQUENCE: 359

```
Glu Val Gln Leu Val Glu Phe Gly Gly Gly Leu Val Gln Pro Gly Gly
1               5                   10                  15

Ser Leu Arg Leu Ser Cys Val Ala Ser Gly Phe Thr Phe Ser Ser Ser
            20                  25                  30

Trp Met Ser Trp Val Arg Gln Ala Pro Gly Lys Gly Leu Glu Cys Val
        35                  40                  45

Gly Asn Ile Lys Pro Asp Ala Ser Leu Val Ser Tyr Val Asp Ser Val
    50                  55                  60

Lys Gly Arg Val Thr Ile Ser Arg Asp Asn Ala Lys Asn Ser Leu Phe
65                  70                  75                  80

Leu Asp Met Ser Ser Leu Arg Val Glu Asp Thr Ala Val Tyr Tyr Cys
                85                  90                  95

Val Arg Asp Gly Trp Asp Thr Phe Phe Asp Ser Trp Gly Gln Gly Thr
            100                 105                 110

Leu Val Thr Val Ser Ser
        115
```

<210> SEQ ID NO 360
<211> LENGTH: 113
<212> TYPE: PRT
<213> ORGANISM: Streptococcus pneumoniae

<400> SEQUENCE: 360

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Arg Trp Val Arg Gln Ser Pro Gly Lys Gly Leu Val Trp Val
        35                  40                  45

Ser His Ile Asn Pro Asp Gly Ser Phe Thr Asn Tyr Ala Asp Ser Val
    50                  55                  60

Lys Gly Arg Phe Thr Ile Ser Arg Asp Asn Thr Lys Asn Thr Leu Tyr
65                  70                  75                  80

Leu Gln Met Asn Ser Leu Arg Ala Glu Asp Thr Ala Val Tyr Tyr Cys
                85                  90                  95

Val Asn Phe Gln Leu Gly Trp Gly Gln Gly Thr Leu Val Thr Val Ser
            100                 105                 110

Ser
```

<210> SEQ ID NO 361
<211> LENGTH: 123
<212> TYPE: PRT
<213> ORGANISM: Streptococcus pneumoniae

<400> SEQUENCE: 361

```
Gln Val Gln Leu Val Glu Ser Gly Gly Gly Val Val Gln Pro Gly Arg
1               5                   10                  15

Ser Leu Lys Leu Ser Cys Ala Val Ala Gly Phe Thr Phe Arg Thr Tyr
            20                  25                  30

Ala Met His Trp Val Arg Gln Ala Pro Gly Arg Gly Leu Glu Trp Val
        35                  40                  45
```

```
Ala Leu Ile Ser Asn Asp Gly Thr Lys Lys Tyr Ser Ala Asp Ser Val
    50                  55                  60

Arg Gly His Phe Thr Ile Ser Arg Asp Asn Ser Lys Asp Thr Leu Tyr
65                  70                  75                  80

Leu Gln Met Asn Ser Leu Arg Pro Asp Asp Thr Ala Val Tyr Tyr Cys
                85                  90                  95

Ala Arg Ala Glu Tyr Cys Ser Pro Gly Asp Cys Phe Leu Ile Asp Thr
            100                 105                 110

Trp Gly Gln Gly Thr Leu Val Thr Val Ser Ser
        115                 120


<210> SEQ ID NO 362
<211> LENGTH: 119
<212> TYPE: PRT
<213> ORGANISM: Streptococcus pneumoniae

<400> SEQUENCE: 362

Gln Val Gln Leu Val Glu Ser Gly Gly Gly Val Val Gln Pro Gly Arg
1               5                   10                  15

Ser Leu Arg Leu Ser Cys Ala Val Ser Gly Phe Thr Phe Ser Arg Tyr
            20                  25                  30

Gly Met His Trp Val Arg Gln Ala Pro Gly Lys Gly Leu Glu Trp Val
        35                  40                  45

Val Val Ile Trp His Asp Gly Ser Asn Thr Tyr Tyr Ala Asp Ser Val
    50                  55                  60

Lys Gly Arg Phe Thr Ile Ser Arg Asp Asp Ser Lys Asn Thr Val Tyr
65                  70                  75                  80

Leu Gln Met Asn Ser Leu Arg Val Glu Asp Thr Ala Met Tyr Tyr Cys
                85                  90                  95

Leu Arg Gly Asn Pro Pro Ser Ser Pro Thr Asp Tyr Trp Gly Gln Gly
            100                 105                 110

Thr Leu Val Thr Val Ser Ser
        115


<210> SEQ ID NO 363
<211> LENGTH: 119
<212> TYPE: PRT
<213> ORGANISM: Streptococcus pneumoniae

<400> SEQUENCE: 363

Glu Val Gln Leu Leu Glu Ser Gly Gly Gly Leu Val Gln Pro Gly Gly
1               5                   10                  15

Ser Leu Arg Leu Ser Cys Glu Val Ser Gly Phe Ile Phe Ser Asn Tyr
            20                  25                  30

Ala Met Thr Trp Val Arg Gln Ala Pro Gly Lys Gly Leu Gln Trp Val
        35                  40                  45

Ser Ala Ile Gly Thr Ser Gly Gly Asp Thr His Tyr Ala Asp Ser Val
    50                  55                  60

Lys Gly Arg Phe Thr Ile Ser Arg His Asn Ser Gln Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Val Val Tyr Ser Arg Pro Pro Met Asp Val Trp Gly Gln Gly
            100                 105                 110

Thr Thr Val Thr Val Ser Ser
        115
```

<210> SEQ ID NO 364
<211> LENGTH: 118
<212> TYPE: PRT
<213> ORGANISM: Streptococcus pneumoniae

<400> SEQUENCE: 364

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Arg
            20                  25                  30

Trp Met Ser Trp Val Arg Gln Ala Pro Gly Lys Gly Leu Glu Trp Val
        35                  40                  45

Ala Asn Ile Asn Glu Asp Gly Ser Gln Lys His Tyr Val Asp Ser Val
    50                  55                  60

Arg Gly Arg Phe Thr Ile Ser Arg Asp Asn Ala Lys Asn Ser Leu Ser
65                  70                  75                  80

Leu Gln Met Asp Ser Leu Arg Val Glu Asp Thr Ala Val Tyr Tyr Cys
                85                  90                  95

Ala Arg Ala Ser Arg Glu Thr Gly Glu Pro Tyr Trp Gly Gln Gly Thr
            100                 105                 110

Leu Val Thr Val Ser Ser
        115
```

<210> SEQ ID NO 365
<211> LENGTH: 109
<212> TYPE: PRT
<213> ORGANISM: Streptococcus pneumoniae

<400> SEQUENCE: 365

```
Val Met Thr Gln Ser Pro Leu Ser Leu Pro Val Thr Leu Gly Gln Ser
1               5                   10                  15

Ala Ser Ile Ser Cys Arg Ser Ser Arg Ser Leu Val Phe Ser Asp Gly
            20                  25                  30

Asn Thr Tyr Leu Asn Trp Phe Gln Gln Arg Pro Gly Arg Ser Pro Arg
        35                  40                  45

Arg Leu Ile Tyr Lys Val Ser Lys Arg Asp Ser Gly Val Pro Asp Arg
    50                  55                  60

Phe Ser Gly Ser Gly Ser Asp Thr Asp Phe Thr Leu Lys Ile Ser Arg
65                  70                  75                  80

Val Glu Ala Glu Asp Val Gly Val Tyr Tyr Cys Met Gln Gly Thr His
                85                  90                  95

Trp Arg Thr Phe Gly Gln Gly Thr Lys Val Glu Ile Lys
            100                 105
```

<210> SEQ ID NO 366
<211> LENGTH: 107
<212> TYPE: PRT
<213> ORGANISM: Streptococcus pneumoniae

<400> SEQUENCE: 366

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Ser Trp
            20                  25                  30

Leu Ala Trp Tyr Gln Arg Lys Pro Gly Lys Thr Pro Lys Leu Leu Ile
        35                  40                  45
```

```
Tyr Glu Ala Ser Ser Leu Glu Ser Gly Val Pro Ser Arg Phe Ser Gly
    50                  55                  60

Ser Arg Ser Gly Thr Glu Phe Thr Leu Thr Ile Ser Ser Leu Gln Ala
65                  70                  75                  80

Asp Asp Phe Ala Thr Tyr Tyr Cys His Gln Tyr Asp Lys Tyr Pro Trp
                85                  90                  95

Thr Phe Gly Gln Gly Thr Lys Val Glu Ile Lys
            100                 105


<210> SEQ ID NO 367
<211> LENGTH: 108
<212> TYPE: PRT
<213> ORGANISM: Streptococcus pneumoniae

<400> SEQUENCE: 367

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Asn Asn
            20                  25                  30

Tyr Leu Val Trp His Gln Gln Lys Pro Gly Gln Ala Pro Arg Leu Leu
        35                  40                  45

Ile Ser Asp Ala Ser Asn Arg Ala Thr Gly Ile Pro Asp Arg Phe Ser
    50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105


<210> SEQ ID NO 368
<211> LENGTH: 108
<212> TYPE: PRT
<213> ORGANISM: Streptococcus pneumoniae

<400> SEQUENCE: 368

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Ile Gly Ser Ser
            20                  25                  30

Leu Ala Trp Tyr Leu Gln Lys Pro Gly Gln Ala Pro Arg Val Leu Ile
        35                  40                  45

Tyr Gly Ala Ser Thr Arg Thr Pro Gly Thr Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Leu Ala Ile Tyr Tyr Cys Gln Gln Tyr Ser Lys Trp Pro Pro
                85                  90                  95

Ile Thr Phe Gly Gln Gly Thr Arg Leu Glu Ile Lys
            100                 105


<210> SEQ ID NO 369
<211> LENGTH: 107
<212> TYPE: PRT
<213> ORGANISM: Streptococcus pneumoniae
```

```
<400> SEQUENCE: 369

Asp Ile Gln Met Thr Gln Ser Pro Ser Ile Leu Ser Ala Ser Val Gly
1               5                   10                  15

Asp Arg Val Thr Ile Asn Cys Arg Ala Ser Gln Ser Ile Asn Ala Trp
            20                  25                  30

Leu Ala Trp Tyr Gln Gln Lys Pro Gly Lys Ala Pro Lys Phe Leu Ile
        35                  40                  45

Tyr Lys Ala Ser Ser Leu Glu Ser Gly Val Ser Ser Arg Phe Ser Gly
    50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Asp Lys Tyr Pro Trp
                85                  90                  95

Thr Phe Gly Arg Gly Thr Lys Val Glu Ile Lys
            100                 105


<210> SEQ ID NO 370
<211> LENGTH: 108
<212> TYPE: PRT
<213> ORGANISM: Streptococcus pneumoniae

<400> SEQUENCE: 370

Glu Ile Val Leu Thr Gln Ser Pro Gly Thr Leu Ser Phe Ser Pro Gly
1               5                   10                  15

Asp Arg Ala Thr Leu Ser Cys Arg Ala Ser Gln Ser Val Ser Ser Ser
            20                  25                  30

Ser Leu Ala Trp Tyr Gln Gln Arg Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Arg Thr Phe Gly Gln Gly Thr Lys Val Glu Ile Lys
            100                 105


<210> SEQ ID NO 371
<211> LENGTH: 108
<212> TYPE: PRT
<213> ORGANISM: Streptococcus pneumoniae

<400> SEQUENCE: 371

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Asn Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
    50                  55                  60

Gly Ser Gly Ser Gly Ala Asp Phe Thr Leu Thr Ile Ser Arg Leu Glu
65                  70                  75                  80

Pro Glu Asp Phe Ala Val Tyr Tyr Cys Gln Gln Tyr Asp Asp Ser Arg
                85                  90                  95
```

```
Trp Thr Phe Gly Gln Gly Thr Lys Val Glu Ile Lys
            100                 105


<210> SEQ ID NO 372
<211> LENGTH: 112
<212> TYPE: PRT
<213> ORGANISM: Streptococcus pneumoniae

<400> SEQUENCE: 372

Asp Ile Val Met Thr Gln Ser Pro Leu Ser Leu Pro Val Thr Pro Gly
1               5                   10                  15

Glu Pro Ala Ser Ile Ser Cys Arg Ser Gly Gln Ser Leu Leu Tyr Ser
            20                  25                  30

Asp Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Glu Ser Gly Thr Asp Phe Thr Leu Lys Ile
65                  70                  75                  80

Ser Arg Val Glu Ala Gly Asp Val Gly Ile Tyr Tyr Cys Met Gln Ala
                85                  90                  95

Leu Arg Ser Pro Tyr Thr Phe Gly Gln Gly Thr Lys Val Glu Ile Lys
            100                 105                 110


<210> SEQ ID NO 373
<211> LENGTH: 110
<212> TYPE: PRT
<213> ORGANISM: Streptococcus pneumoniae

<400> SEQUENCE: 373

Val Met Thr Gln Ser Pro Leu Ser Leu Pro Val Thr Leu Gly Gln Pro
1               5                   10                  15

Ala Ser Ile Ser Cys Arg Ser Ser Gln Ser Pro Val Tyr Ser Asp Gly
            20                  25                  30

Asn Thr Tyr Leu Asn Trp Phe Gln Gln Arg Pro Gly Gln Ser Pro Arg
        35                  40                  45

Arg Leu Ile Tyr Lys Val Ser Asn Arg Asp Ser Gly Val Pro Asp Arg
    50                  55                  60

Phe Ser Gly Ser Gly Ser Gly Thr Asp Phe Thr Leu Asn Ile Ser Gly
65                  70                  75                  80

Val Glu Ala Glu Asp Val Gly Val Tyr Tyr Cys Met Gln Gly Arg Tyr
                85                  90                  95

Trp Pro Tyr Thr Phe Gly Gln Gly Thr Lys Val Glu Ile Lys
            100                 105                 110


<210> SEQ ID NO 374
<211> LENGTH: 108
<212> TYPE: PRT
<213> ORGANISM: Streptococcus pneumoniae

<400> SEQUENCE: 374

Glu Ile Val Leu Thr Gln Ser Pro Gly Thr Leu Ser Phe Ser Pro Gly
1               5                   10                  15

Asp Arg Ala Thr Leu Ser Cys Arg Ala Ser Gln Ser Val Ser Ser Ser
            20                  25                  30

Ala Leu Ala Trp Tyr Gln Gln Lys Pro Gly Gln Ala Pro Ser Leu Leu
        35                  40                  45
```

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Arg Thr Phe Gly Gln Gly Thr Lys Val Glu Ile Lys
            100                 105


<210> SEQ ID NO 375
<211> LENGTH: 109
<212> TYPE: PRT
<213> ORGANISM: Streptococcus pneumoniae

<400> SEQUENCE: 375

Val Met Thr Gln Ser Pro Leu Ser Leu Pro Val Thr Leu Gly Gln Ser
1               5                   10                  15

Ala Ser Ile Ser Cys Arg Ser Ser Arg Ser Leu Val Phe Ser Asp Gly
            20                  25                  30

Asn Thr Tyr Leu Asn Trp Phe Gln Gln Arg Pro Gly Arg Ser Pro Arg
        35                  40                  45

Arg Leu Ile Tyr Lys Val Ser Lys Arg Asp Ser Gly Val Pro Asp Arg
    50                  55                  60

Phe Ser Gly Ser Gly Ser Asp Thr Asp Phe Thr Leu Lys Ile Ser Arg
65                  70                  75                  80

Val Glu Ala Glu Asp Val Gly Val Tyr Tyr Cys Met Gln Gly Thr His
                85                  90                  95

Trp Arg Thr Phe Gly Gln Gly Thr Lys Val Glu Ile Lys
            100                 105


<210> SEQ ID NO 376
<211> LENGTH: 107
<212> TYPE: PRT
<213> ORGANISM: Streptococcus pneumoniae

<400> SEQUENCE: 376

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Gly Ile Asn Asn Tyr
            20                  25                  30

Leu Ala Trp Phe Gln Gln Lys Pro Gly Lys Ala Pro Lys Thr Leu Ile
        35                  40                  45

Tyr Ser Thr Ser Thr Leu Gln Ser Gly Val Pro Ser Lys Phe Ser Gly
    50                  55                  60

Ser Gly Ser Gly Thr Val Phe Thr Leu Thr Ile Ser Asn Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105


<210> SEQ ID NO 377
<211> LENGTH: 107
<212> TYPE: PRT
<213> ORGANISM: Streptococcus pneumoniae
```

```
<400> SEQUENCE: 377

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Tyr
            20                  25                  30

Leu Asn Trp Phe Gln Gln Lys Pro Gly Lys Ala Pro Arg Leu Leu Ile
        35                  40                  45

Tyr Ala Ala Ser Ser Leu Gln Ser Gly Val Pro Ser Arg Phe Ser Gly
    50                  55                  60

Ser Gly Ser Val Thr Asp Phe Thr Leu Thr Ile Ser Ser Leu Gln Pro
65                  70                  75                  80

Glu Asp Phe Ala Thr Tyr Phe Cys Gln Gln Ser Tyr Ser Thr Pro Trp
                85                  90                  95

Thr Phe Gly Gln Gly Thr Lys Val Glu Ile Lys
            100                 105


<210> SEQ ID NO 378
<211> LENGTH: 110
<212> TYPE: PRT
<213> ORGANISM: Streptococcus pneumoniae

<400> SEQUENCE: 378

Val Met Thr Gln Ser Pro Phe Ser Leu Pro Val Thr Leu Gly Gln Pro
1               5                   10                  15

Ala Ser Ile Ser Cys Arg Ser Ser Gln Ser Leu Val Tyr Ser Asp Gly
            20                  25                  30

Asn Thr Tyr Leu Asn Trp Phe Gln Gln Arg Pro Gly Gln Ser Pro Arg
        35                  40                  45

Arg Leu Ile Tyr Lys Leu Ser Asn Arg Asp Ser Gly Val Pro Asp Arg
    50                  55                  60

Phe Ser Gly Ser Gly Ser Gly Thr Asp Phe Thr Leu Lys Ile Ser Arg
65                  70                  75                  80

Val Glu Ala Glu Asp Val Gly Val Tyr Tyr Cys Met Gln Ala Thr His
                85                  90                  95

Trp Pro Trp Thr Phe Gly Gln Gly Thr Lys Val Glu Ile Lys
            100                 105                 110
```

What is claimed:

1. A panel comprising two or more serotype specific antibodies or binding fragments thereof that bind to *Streptococcus pneumoniae* or bind to antigens of *S. pneumoniae* immobilized on a solid support, wherein the one or more serotype specific antibodies or binding fragments thereof comprise:

a heavy chain variable domain polypeptide selected from the group consisting of the amino acid sequence set forth in SEQ ID NOS: 258 to 268, 287 to 293, 305, 325 to 330, and 355 to 359; and a light chain variable domain polypeptide selected from the group consisting of the amino acid sequence set forth SEQ ID NOS: 270 to 285, 306 to 312, 324, 338 to 343, and 369 to 373.

2. The panel of claim 1, wherein the solid support comprises one or more beads, a dipstick, a filter, a membrane, a plate, a chip, or a column matrix.

3. The panel of claim 1, wherein the solid support comprises one or more beads.

4. The panel of claim 3, wherein the one or more serotype specific antibodies immobilized on the one or more beads are specific for a serotype of *S. pneumoniae* or an antigen of *S. pneumoniae.*

5. The panel of claim 1, wherein the solid support comprises a dipstick.

6. The panel of claim 1, wherein the one or more serotype specific antibodies are monoclonal antibodies.

7. The panel of claim 1, wherein the one or more serotype specific antibodies bind to at least 18 *S. pneumoniae* serotypes.

8. The panel of claim 1, wherein the one or more serotype specific antibodies that bind to serotypes selected from 1, 2, 3, 4, 5, 6B, 8, 9N, 9V, 11B, 14, 15B, 17F, 18C, 19A, 19F, 20, 22F, 23F, 33F, and CWPS cross react with more than one serotype.

9. The panel of claim 3, wherein the one or more serotype specific antibodies that bind to serotypes 1, 2, 3, 4, 5, 6B, 8, 9N, 9V, 11B, 14, 15B, 17F, 18C, 19A, 19F, 20, 22F, 23F, 33F, and CWPS cross react with more than one serotype.

10. The panel of claim 5, wherein the one or more serotype specific antibodies bind to serotypes 1, 2, 3, 4, 5, 6B, 8, 9N, 9V, 11B, 14, 15B, 17F, 18C, 19A, 19F, 20, 22F, 23F, 33F, and CWPS.

11. The panel of claim 1, wherein the serotype specific antibodies are linked to a detectable label.

12. The panel of claim 11, wherein the detectable label comprises a radioactive tag, a fluorescent tag, or a biological or enzymatic tag.

13. A kit for the detection of *Streptococcus pneumoniae* comprising a panel comprising one or more serotype specific antibodies or binding fragments thereof that bind to *Streptococcus pneumoniae* or bind to antigens of *S. pneumoniae* immobilized on a solid support, a suitable container, and an immunodetection reagent, wherein the antibodies or binding fragments thereof comprise:

a heavy chain variable domain polypeptide selected from the group consisting of the amino acid sequence set forth in SEQ ID NOS: 258 to 268, 287 to 293, 305, 325 to 330, and 355 to 359; and a light chain variable domain polypeptide selected from the group consisting of the amino acid sequence set forth SEQ ID NOS: 270 to 285, 306 to 312, 324, 338 to 343, and 369 to 373, wherein the panel includes antibodies or binding fragments thereof selected to bind to *S. pneumoniae* serotypes 1, 2, 3, 4, 5, 6B, 8, 9N, 9V, 11B, 14, 15B, 17F, 18C, 19A, 19F, 20, 22F, 23F, 33F, and CWPS.

14. The kit of claim 13, wherein the support comprises one or more beads, a dipstick, a filter, a membrane, a plate, a chip, or a column matrix.

15. The kit of claim 13, wherein the support comprises one or more beads.

16. The kit of claim 15, wherein the one or more serotype specific antibodies immobilized on the one or more beads are specific for a serotype of *S. pneumoniae* or an antigen of *S. pneumoniae*.

17. The kit of claim 13, wherein the support comprises a dipstick.

18. The kit of claim 13, wherein immunodetection reagent comprises at least a second antibody that binds an immunocomplex formed when an antibody in the antibody panel binds *S. pneumoniae* or *S. pneumoniae* antigen.

19. The kit of claim 18, wherein the one or more serotype specific antibodies are linked to a detectable label.

20. The kit of claim 19, wherein the detectable label comprising a radioactive tag, a fluorescent tag, or a biological or enzymatic tag.

21. The kit of claim 13, wherein the kit further comprises an aliquoted composition of *S. pneumoniae* or *S. pneumoniae* antigens that may be used to prepare a standard curve.

* * * * *

UNITED STATES PATENT AND TRADEMARK OFFICE

CERTIFICATE OF CORRECTION

PATENT NO. : 11,567,077 B2
APPLICATION NO. : 15/058814
DATED : January 31, 2023
INVENTOR(S) : Kenneth Smith It is certified that error appears in the above-identified patent and that said Letters Patent is hereby corrected as shown below:

In the Specification

In the Sequence Listing starting at Column 109 through Column 273, before the claim listing, SEQ. ID NOs. 127 through 378 contain the line "<213> ORGANISM: Streptococcus pneumoniae" which should be changed to "<213> ORGANISM: Homo sapiens".

Attached is the replacement Sequence Listing.

Signed and Sealed this
Sixth Day of June, 2023

Katherine Kelly Vidal

Katherine Kelly Vidal
*Director of the United States Patent and Trademark Office*

SEQUENCE LISTING

```
<110>  SMITH, KENNETH

<120>  HUMAN STREPTOCOCCUS PNEUMONIAE ANTIBODIES AND USES THEREFOR

<130>  OMRF:1023DIV

<140>  US 15/058,814
<141>  2016-03-02

<150>  US 13/740,934
<151>  2013-01-14

<150>  US 61/593,654
<151>  2012-02-01

<160>  378

<170>  PatentIn version 3.5

<210>  1
<211>  9
<212>  PRT
<213>  Streptococcus pneumoniae

<400>  1

Ala Lys Gly Val Thr Ser Phe Asp Tyr
1               5


<210>  2
<211>  10
<212>  PRT
<213>  Streptococcus pneumoniae

<400>  2

Gln Gln Phe Gly Ser Ser Pro Pro Asp Thr
1               5                   10


<210>  3
<211>  12
<212>  PRT
<213>  Streptococcus pneumoniae

<400>  3
```

Ala Arg Asp Pro Gly Ile Arg Asn Gly Met Gly Val
1 5 10

<210> 4
<211> 9
<212> PRT
<213> Streptococcus pneumoniae

<400> 4

Met Gln Val Thr His Trp Pro Arg Thr
1 5

<210> 5
<211> 14
<212> PRT
<213> Streptococcus pneumoniae

<400> 5

Ala Lys Ala His Arg Gly Asp Trp Asn Asn Phe Phe Asp Tyr
1 5 10

<210> 6
<211> 9
<212> PRT
<213> Streptococcus pneumoniae

<400> 6

Gln Gln Ser Gly Asp Trp Pro Leu Thr
1 5

<210> 7
<211> 9
<212> PRT
<213> Streptococcus pneumoniae

<400> 7

Ala Arg Glu Trp Ser Gly Phe Asp Phe
1 5

<210> 8
<211> 9

<212> PRT
<213> Streptococcus pneumoniae

<400> 8

Gln Gln Tyr Gly Ser Leu Pro Arg Thr
1               5

<210> 9
<211> 8
<212> PRT
<213> Streptococcus pneumoniae

<400> 9

Ala Arg Gly Gln Trp Leu Ala Phe
1               5

<210> 10
<211> 9
<212> PRT
<213> Streptococcus pneumoniae

<400> 10

Met Gln Gly Thr His Trp Pro Tyr Thr
1               5

<210> 11
<211> 9
<212> PRT
<213> Streptococcus pneumoniae

<400> 11

Ala Arg Gly Arg Asn Asn Phe Arg His
1               5

<210> 12
<211> 9
<212> PRT
<213> Streptococcus pneumoniae

<400> 12

Gln Gln Phe Glu Ser Phe Pro Arg Thr

```
1               5


<210>  13
<211>  20
<212>  PRT
<213>  Streptococcus pneumoniae

<400>  13

Ala Arg Glu Leu Gly Val Phe His Ser Gly Gly Asp Gln Trp Leu Gly
1               5                   10                  15


Pro Leu Asp Cys
            20


<210>  14
<211>  11
<212>  PRT
<213>  Streptococcus pneumoniae

<400>  14

His Gln Tyr Lys Asn Trp Pro Pro Met Gly Thr
1               5                   10


<210>  15
<211>  11
<212>  PRT
<213>  Streptococcus pneumoniae

<400>  15

Arg Trp Thr Gly Gly Val Ser Phe Gly Ala Tyr
1               5                   10


<210>  16
<211>  8
<212>  PRT
<213>  Streptococcus pneumoniae

<400>  16

Gln Gln Tyr Asp Ile Tyr Leu Thr
1               5
```

<210> 17
<211> 10
<212> PRT
<213> Streptococcus pneumoniae

<400> 17

Ala Arg Asp Tyr Tyr His Ser Val Asp Tyr
1 5 10

<210> 18
<211> 9
<212> PRT
<213> Streptococcus pneumoniae

<400> 18

Met Gln Gly Thr His Trp Pro Tyr Thr
1 5

<210> 19
<211> 11
<212> PRT
<213> Streptococcus pneumoniae

<400> 19

Ala Arg Gly Pro Asp Ala His Lys Thr Gly Tyr
1 5 10

<210> 20
<211> 9
<212> PRT
<213> Streptococcus pneumoniae

<400> 20

Gln Gln Tyr Ala Ala Thr Pro Trp Thr
1 5

<210> 21
<211> 10
<212> PRT
<213> Streptococcus pneumoniae

<400> 21

Ala Arg Asp Ser Tyr Thr Ser Pro Asp Tyr
1 5 10

<210> 22
<211> 9
<212> PRT
<213> Streptococcus pneumoniae

<400> 22

Met Gln Gly Ser His Trp Pro Leu Thr
1 5

<210> 23
<211> 11
<212> PRT
<213> Streptococcus pneumoniae

<400> 23

Thr Thr Asp Asn Gly Val Lys Ala Phe Asp Ile
1 5 10

<210> 24
<211> 9
<212> PRT
<213> Streptococcus pneumoniae

<400> 24

His Gln Tyr Tyr Thr Thr Pro Phe Ala
1 5

<210> 25
<211> 11
<212> PRT
<213> Streptococcus pneumoniae

<400> 25

Thr Arg Gly Gly Ser Gly Ala Thr Ile Asn Tyr
1 5 10

<210> 26
<211> 9
<212> PRT
<213> Streptococcus pneumoniae

<400> 26

Gln Gln Ser His Ser Ser Pro Leu Thr
1 5

<210> 27
<211> 16
<212> PRT
<213> Streptococcus pneumoniae

<400> 27

Ala Arg Asp Arg Ala Gly Ile Asp Gly Tyr Asn Tyr Tyr Phe Asp Tyr
1 5 10 15

<210> 28
<211> 8
<212> PRT
<213> Streptococcus pneumoniae

<400> 28

Gln Gln Tyr Tyr Ser Phe Tyr Thr
1 5

<210> 29
<211> 13
<212> PRT
<213> Streptococcus pneumoniae

<400> 29

Ala Arg Glu Val Ala Ala Glu Gly Lys Ala Phe Asp Tyr
1 5 10

<210> 30
<211> 9
<212> PRT
<213> Streptococcus pneumoniae

<400> 30

```
Gln Gln Tyr Tyr Thr Pro Pro Leu Thr
1               5


<210>  31
<211>  9
<212>  PRT
<213>  Streptococcus pneumoniae

<400>  31

Ala Arg Gly Gln Ser Tyr Pro Gly Ile
1               5


<210>  32
<211>  9
<212>  PRT
<213>  Streptococcus pneumoniae

<400>  32

Gln Gln Tyr Asn Asn Trp Pro Arg Thr
1               5


<210>  33
<211>  15
<212>  PRT
<213>  Streptococcus pneumoniae

<400>  33

Ala Gly Arg Ala Tyr Ser Ser Gly Tyr Tyr Tyr Leu Ile Asp Tyr
1               5                   10                  15


<210>  34
<211>  9
<212>  PRT
<213>  Streptococcus pneumoniae

<400>  34

Gln His Tyr His Asn Trp Pro Pro Thr
1               5


<210>  35
```

<211> 15
<212> PRT
<213> Streptococcus pneumoniae

<400> 35

Ala Lys Gly Cys Ser Asn Gly Gly Asn Cys Phe Leu Ile Asp Tyr
1 5 10 15

<210> 36
<211> 9
<212> PRT
<213> Streptococcus pneumoniae

<400> 36

Gln Gln Tyr Tyr Asn Ala Pro Leu Thr
1 5

<210> 37
<211> 16
<212> PRT
<213> Streptococcus pneumoniae

<400> 37

Ala Lys Gly Gly Tyr Tyr Glu Ser Gly Thr Met Arg Ala Phe Asp Ile
1 5 10 15

<210> 38
<211> 9
<212> PRT
<213> Streptococcus pneumoniae

<400> 38

Gln Gln Arg Ser Asn Trp Pro Ala Thr
1 5

<210> 39
<211> 9
<212> PRT
<213> Streptococcus pneumoniae

<400> 39

Ala Arg Gly Glu Ser Asn Phe Arg Tyr
1               5

<210>  40
<211>  9
<212>  PRT
<213>  Streptococcus pneumoniae

<400>  40

Gln Gln Phe Val Ser Phe Pro Arg Thr
1               5

<210>  41
<211>  12
<212>  PRT
<213>  Streptococcus pneumoniae

<400>  41

Ala Arg Asp Ser Thr Ser Pro Ala Arg Phe Gly Tyr
1               5                   10

<210>  42
<211>  11
<212>  PRT
<213>  Streptococcus pneumoniae

<400>  42

Gln His Tyr Gly Thr Ser Pro Pro Arg Tyr Thr
1               5                   10

<210>  43
<211>  12
<212>  PRT
<213>  Streptococcus pneumoniae

<400>  43

Ala Thr Gly Gly Met Thr Ser Ser Trp Tyr Gly Tyr
1               5                   10

<210>  44
<211>  9

<212> PRT
<213> Streptococcus pneumoniae

<400> 44

Gln Gln Tyr Tyr Ser Thr Pro Tyr Thr
1 5

<210> 45
<211> 18
<212> PRT
<213> Streptococcus pneumoniae

<400> 45

Ser Met Gly Pro Pro Tyr Cys Thr Gly Gly Ser Cys Tyr Ser Ala Cys
1 5 10 15

Asp Phe

<210> 46
<211> 10
<212> PRT
<213> Streptococcus pneumoniae

<400> 46

Gln Arg Tyr Gly Asn Ser Pro Pro Tyr Thr
1 5 10

<210> 47
<211> 15
<212> PRT
<213> Streptococcus pneumoniae

<400> 47

Thr Thr Asp Ile Gly Lys Gly Trp Tyr Thr His Tyr Pro Asp Leu
1 5 10 15

<210> 48
<211> 9
<212> PRT
<213> Streptococcus pneumoniae

<400> 48

Leu Gln Tyr Arg Ser Ala Pro Phe Thr
1 5

<210> 49
<211> 14
<212> PRT
<213> Streptococcus pneumoniae

<400> 49

Val Lys Glu Tyr Ser Trp Gly Tyr Tyr Arg Thr Ala Asp Tyr
1 5 10

<210> 50
<211> 9
<212> PRT
<213> Streptococcus pneumoniae

<400> 50

Gln Gln Tyr Ser Thr Tyr Pro Trp Thr
1 5

<210> 51
<211> 10
<212> PRT
<213> Streptococcus pneumoniae

<400> 51

Ala Arg Ser Pro Gly Gly Tyr Phe Asp Tyr
1 5 10

<210> 52
<211> 9
<212> PRT
<213> Streptococcus pneumoniae

<400> 52

Gln Gln Tyr Ser Thr Trp Leu Trp Thr
1 5

<210> 53
<211> 7
<212> PRT
<213> Streptococcus pneumoniae

<400> 53

Thr Thr Asp Asp Leu Lys Asn
1 5

<210> 54
<211> 9
<212> PRT
<213> Streptococcus pneumoniae

<400> 54

Gln Gln Arg Tyr Arg Ile Pro Tyr Ser
1 5

<210> 55
<211> 22
<212> PRT
<213> Streptococcus pneumoniae

<400> 55

Ala Arg Gly Arg Asp Cys Tyr Gly Gly Asn Cys Val Ile Tyr Phe His
1 5 10 15

Tyr Tyr Gly Leu Asp Val
20

<210> 56
<211> 9
<212> PRT
<213> Streptococcus pneumoniae

<400> 56

Met Arg Ala Leu Gln Thr Pro Tyr Thr
1 5

<210> 57

<211> 14
<212> PRT
<213> Streptococcus pneumoniae

<400> 57

```
Val Lys Glu Ser Ala Thr Gly Trp Tyr Arg Thr Ala Asp Tyr
1               5                   10
```

<210> 58
<211> 9
<212> PRT
<213> Streptococcus pneumoniae

<400> 58

```
His Gln Tyr Asn Lys Tyr Pro Trp Thr
1               5
```

<210> 59
<211> 16
<212> PRT
<213> Streptococcus pneumoniae

<400> 59

```
Ala Arg Asp Ile Pro Thr Thr Phe Gly Ile Gly Glu Ala Phe Asp Ile
1               5                   10                  15
```

<210> 60
<211> 8
<212> PRT
<213> Streptococcus pneumoniae

<400> 60

```
Gln Gln Tyr Tyr Ser Trp Gly Thr
1               5
```

<210> 61
<211> 9
<212> PRT
<213> Streptococcus pneumoniae

<400> 61

Ala Arg Asp Asp Ser Ala Phe Asp Tyr
1               5

<210>  62
<211>  9
<212>  PRT
<213>  Streptococcus pneumoniae

<400>  62

Met Gln Ala Ser Gln Ser Thr Trp Thr
1               5

<210>  63
<211>  14
<212>  PRT
<213>  Streptococcus pneumoniae

<400>  63

Ala Lys Gly Cys Ser Gly Glu Asn Cys Phe Tyr Met Asp Asp
1               5                   10

<210>  64
<211>  9
<212>  PRT
<213>  Streptococcus pneumoniae

<400>  64

Gln Gln Cys Tyr Asn Ala Pro Leu Thr
1               5

<210>  65
<211>  22
<212>  PRT
<213>  Streptococcus pneumoniae

<400>  65

Thr Arg Glu Ile Gly Ala Val Val Val Asp Ala Thr Ser Leu Gly Trp
1               5                   10                  15

Leu Gly Tyr Phe Asp Tyr
            20

```
<210>  66
<211>  10
<212>  PRT
<213>  Streptococcus pneumoniae

<400>  66

Gln Gln Tyr Asn Asn Trp Pro Pro Val Thr
1               5                   10


<210>  67
<211>  8
<212>  PRT
<213>  Streptococcus pneumoniae

<400>  67

Ala Gly Trp Gly Arg Thr Gln Asp
1               5


<210>  68
<211>  9
<212>  PRT
<213>  Streptococcus pneumoniae

<400>  68

Met Gln Tyr Thr Phe Trp Pro His Thr
1               5


<210>  69
<211>  14
<212>  PRT
<213>  Streptococcus pneumoniae

<400>  69

Thr Lys Glu Gly Ala Pro Pro Gly Lys Tyr Ala Phe Asp Ile
1               5                   10


<210>  70
<211>  11
<212>  PRT
<213>  Streptococcus pneumoniae
```

<400> 70

Gln His Arg Gly Glu Trp Pro Pro Gly Ala Thr
1               5                   10

<210> 71
<211> 11
<212> PRT
<213> Streptococcus pneumoniae

<400> 71

Leu Lys Asp Ser Ser Gln Tyr Ser Phe Asp Ala
1               5                   10

<210> 72
<211> 9
<212> PRT
<213> Streptococcus pneumoniae

<400> 72

Gln Gln Phe Lys Gly Tyr Pro Leu Thr
1               5

<210> 73
<211> 9
<212> PRT
<213> Streptococcus pneumoniae

<400> 73

Ala Arg Gly Asp Gly Tyr Asn Phe Phe
1               5

<210> 74
<211> 9
<212> PRT
<213> Streptococcus pneumoniae

<400> 74

Gln Gln Ile Asn Ser Tyr Pro Arg Thr
1               5

<210> 75
<211> 18
<212> PRT
<213> Streptococcus pneumoniae

<400> 75

Ala Lys Cys Gly Ala Glu Asp Ser Thr Thr Val Trp Leu Asn Trp Phe
1               5                   10                  15

Asp Pro

<210> 76
<211> 9
<212> PRT
<213> Streptococcus pneumoniae

<400> 76

Gln Gln Arg Ala Asp Trp Pro Leu Thr
1               5

<210> 77
<211> 13
<212> PRT
<213> Streptococcus pneumoniae

<400> 77

Ala Lys Pro Asn Tyr Phe Gly Ser Gly Ser Pro Asp Tyr
1               5                   10

<210> 78
<211> 10
<212> PRT
<213> Streptococcus pneumoniae

<400> 78

Leu Gln Cys Ser Asn Trp Pro Met Tyr Thr
1               5                   10

<210> 79

<211> 14
<212> PRT
<213> Streptococcus pneumoniae

<400> 79

Val Lys Glu Gln Asp Tyr Gly Tyr Tyr Arg Thr Ala Asp His
1 5 10

<210> 80
<211> 9
<212> PRT
<213> Streptococcus pneumoniae

<400> 80

Gln Gln Tyr Asp Lys Tyr Pro Trp Thr
1 5

<210> 81
<211> 19
<212> PRT
<213> Streptococcus pneumoniae

<400> 81

Val Arg Val Ala Val Pro Ala Ala Thr Tyr Thr Arg Gly Asn Asp Ala
1 5 10 15

Phe Asp Ile

<210> 82
<211> 9
<212> PRT
<213> Streptococcus pneumoniae

<400> 82

Leu Gln His Ser Ser Phe Pro Trp Thr
1 5

<210> 83
<211> 10
<212> PRT

<213> Streptococcus pneumoniae

<400> 83

Thr Thr Ala His Gly Pro Val Gly Asp His
1 5 10

<210> 84
<211> 10
<212> PRT
<213> Streptococcus pneumoniae

<400> 84

Gln Gln Tyr Tyr Thr Thr Pro Ser Ile Thr
1 5 10

<210> 85
<211> 19
<212> PRT
<213> Streptococcus pneumoniae

<400> 85

Ala Arg Ala Gly Gly Cys Ser Ser Thr Arg Cys His Thr Thr Pro Gly
1 5 10 15

Phe Asp Tyr

<210> 86
<211> 10
<212> PRT
<213> Streptococcus pneumoniae

<400> 86

Gln Gln Tyr Tyr Thr Thr Pro Pro Ile Thr
1 5 10

<210> 87
<211> 11
<212> PRT
<213> Streptococcus pneumoniae

<400> 87

Ala Ser Leu Ser Gly Thr Asn Ala Phe Asp Ile
1 5 10

<210> 88
<211> 8
<212> PRT
<213> Streptococcus pneumoniae

<400> 88

Gln Gln Arg Ser Ser Gly Arg Thr
1 5

<210> 89
<211> 13
<212> PRT
<213> Streptococcus pneumoniae

<400> 89

Ala Lys Pro Arg Gly Tyr Ser Tyr Gly Tyr Phe Asp Tyr
1 5 10

<210> 90
<211> 9
<212> PRT
<213> Streptococcus pneumoniae

<400> 90

Gln Gln Tyr Gly Ile Ser Pro Arg Thr
1 5

<210> 91
<211> 9
<212> PRT
<213> Streptococcus pneumoniae

<400> 91

Ala Pro Pro Ala Arg Arg Leu Asp Tyr
1 5

<210> 92
<211> 9
<212> PRT
<213> Streptococcus pneumoniae

<400> 92

Met Gln Gly Thr His His Pro Trp Thr
1 5

<210> 93
<211> 9
<212> PRT
<213> Streptococcus pneumoniae

<400> 93

Ala Arg Ser Asn Ala Gly His Glu Ala
1 5

<210> 94
<211> 9
<212> PRT
<213> Streptococcus pneumoniae

<400> 94

Gln Gln Tyr Tyr Ser Thr Pro Leu Thr
1 5

<210> 95
<211> 11
<212> PRT
<213> Streptococcus pneumoniae

<400> 95

Ala Arg Asp Ile Pro His Ala Asn Leu Asp Tyr
1 5 10

<210> 96
<211> 9
<212> PRT
<213> Streptococcus pneumoniae

<400> 96

```
Leu Gln His Thr Thr Phe Pro Trp Thr
1               5


<210>  97
<211>  14
<212>  PRT
<213>  Streptococcus pneumoniae

<400>  97

Val Lys Asp Arg Val Pro Pro Gly Asp Val Pro Gly Asp Phe
1               5                   10


<210>  98
<211>  10
<212>  PRT
<213>  Streptococcus pneumoniae

<400>  98

Gln Gln Arg Arg Thr Trp Pro Pro Leu Thr
1               5                   10


<210>  99
<211>  12
<212>  PRT
<213>  Streptococcus pneumoniae

<400>  99

Ala Thr Leu Leu Leu Arg Asp Asn Gln Leu Asp Val
1               5                   10


<210>  100
<211>  8
<212>  PRT
<213>  Streptococcus pneumoniae

<400>  100

Met Gln Gly Thr His Trp Arg Thr
1               5


<210>  101
```

<211> 14
<212> PRT
<213> Streptococcus pneumoniae

<400> 101

```
Val Lys Glu Gln Gly Phe Gly Tyr Tyr Arg Thr Ala Asp Tyr
1               5                   10
```

<210> 102
<211> 9
<212> PRT
<213> Streptococcus pneumoniae

<400> 102

```
His Gln Tyr Asp Lys Tyr Pro Trp Thr
1               5
```

<210> 103
<211> 8
<212> PRT
<213> Streptococcus pneumoniae

<400> 103

```
Ala Arg Arg Asn Asp Phe Asn Ile
1               5
```

<210> 104
<211> 9
<212> PRT
<213> Streptococcus pneumoniae

<400> 104

```
Gln Gln Tyr Gly Ser Ser Pro Phe Thr
1               5
```

<210> 105
<211> 16
<212> PRT
<213> Streptococcus pneumoniae

<400> 105

Ser Ile Trp Trp Gly Thr Ser Val Gln Tyr Pro Leu Val Leu Asp Tyr
1               5                   10                  15

<210>  106
<211>  10
<212>  PRT
<213>  Streptococcus pneumoniae

<400>  106

Gln Gln Tyr Ser Lys Trp Pro Pro Ile Thr
1               5                   10

<210>  107
<211>  14
<212>  PRT
<213>  Streptococcus pneumoniae

<400>  107

Val Lys Glu Gln Asp Tyr Gly Tyr Tyr Arg Thr Ala Asp His
1               5                   10

<210>  108
<211>  9
<212>  PRT
<213>  Streptococcus pneumoniae

<400>  108

Gln Gln Tyr Asp Lys Tyr Pro Trp Thr
1               5

<210>  109
<211>  9
<212>  PRT
<213>  Streptococcus pneumoniae

<400>  109

Ala Arg Gly His Gly Phe Asn Ala Tyr
1               5

<210>  110
<211>  9

<212> PRT
<213> Streptococcus pneumoniae

<400> 110

Gln Gln Tyr Gly Asn Ser Pro Arg Thr
1 5

<210> 111
<211> 13
<212> PRT
<213> Streptococcus pneumoniae

<400> 111

Thr Thr Val Arg Asn Met Ala Asp Leu Ser Leu Asn His
1 5 10

<210> 112
<211> 9
<212> PRT
<213> Streptococcus pneumoniae

<400> 112

Gln Gln Tyr Asp Asp Ser Arg Trp Thr
1 5

<210> 113
<211> 11
<212> PRT
<213> Streptococcus pneumoniae

<400> 113

Ala Thr Gly Asn Arg Gly Ser Leu Pro Arg Arg
1 5 10

<210> 114
<211> 9
<212> PRT
<213> Streptococcus pneumoniae

<400> 114

Met Gln Ala Leu Arg Ser Pro Tyr Thr 1 5

<210> 115
<211> 11
<212> PRT
<213> Streptococcus pneumoniae

<400> 115

Val Arg Asp Gly Trp Asp Thr Phe Phe Asp Ser
1 5 10

<210> 116
<211> 9
<212> PRT
<213> Streptococcus pneumoniae

<400> 116

Met Gln Gly Arg Tyr Trp Pro Tyr Thr
1 5

<210> 117
<211> 6
<212> PRT
<213> Streptococcus pneumoniae

<400> 117

Val Asn Phe Gln Leu Gly
1 5

<210> 118
<211> 9
<212> PRT
<213> Streptococcus pneumoniae

<400> 118

Gln Gln Tyr Gly Asn Ser Pro Arg Thr
1 5

<210> 119
<211> 16
<212> PRT

<213> Streptococcus pneumoniae

<400> 119

```
Ala Arg Ala Glu Tyr Cys Ser Pro Gly Asp Cys Phe Leu Ile Asp Thr
1               5                   10                  15
```

<210> 120
<211> 8
<212> PRT
<213> Streptococcus pneumoniae

<400> 120

```
Met Gln Gly Thr His Trp Arg Thr
1               5
```

<210> 121
<211> 12
<212> PRT
<213> Streptococcus pneumoniae

<400> 121

```
Leu Arg Gly Asn Pro Pro Ser Ser Pro Thr Asp Tyr
1               5                   10
```

<210> 122
<211> 9
<212> PRT
<213> Streptococcus pneumoniae

<400> 122

```
Gln Gln Tyr Asn Ser Tyr Pro Leu Thr
1               5
```

<210> 123
<211> 12
<212> PRT
<213> Streptococcus pneumoniae

<400> 123

```
Ala Lys Val Val Tyr Ser Arg Pro Pro Met Asp Val
1               5                   10
```

<210> 124
<211> 9
<212> PRT
<213> Streptococcus pneumoniae

<400> 124

Gln Gln Ser Tyr Ser Thr Pro Trp Thr
1 5

<210> 125
<211> 11
<212> PRT
<213> Streptococcus pneumoniae

<400> 125

Ala Arg Ala Ser Arg Glu Thr Gly Glu Pro Tyr
1 5 10

<210> 126
<211> 9
<212> PRT
<213> Streptococcus pneumoniae

<400> 126

Met Gln Ala Thr His Trp Pro Trp Thr
1 5

<210> 127
<211> 348
<212> DNA
<213> Homo sapiens

<400> 127
gaggtgcagc tgttggagtc ggggggaggc ttggtacagc ctggggggtc cctgagagtc 60
tcctgtgcag cctctggatt cacctttagc aactctggca tgagttgggt ccgccaggct 120
ccagggaagg ggctggagtg ggtctcaggt attggtggtg gtggtggtag tgcatactac 180
gcagactccg tgaagggccg gttcaccatc tccagagaca attccaagaa cacgctgtat 240
ctacaaatga acaatttgag agccgaggac acggccgtat actactgtgc gaaaggagtt 300
accagttttg actactgggg ccagggaatc ctggtcaccg tctcctca 348

<210> 128
<211> 354
<212> DNA
<213> Homo sapiens

<400> 128
gaggtgcagc tggtggagtc tgggggaggc ttggtccagc ctggggggtc cctgagactc 60
tcctgtgcag cctctggatt caccgtcagt agcgactata tgagttgggt ccgccaggct 120
ccagggaagg ggctggagtg ggtctcagtt atgtatagcg gggtagcac atactacgca 180 gacgccgtga aggacagatt caccatctcc agagacaatt ccaagaatat actgtatctt 240
caaatgaaca gcctgagagc cgaggacacg gcggtttatt actgtgcgag agatcccggg 300
ataaggaacg gtatgggcgt ctggggccaa gggaccacgg tcaccgtctc ctca 354

<210> 129
<211> 363
<212> DNA
<213> Homo sapiens

<400> 129
gaggtgcagc tgttggagtc tgggggagcc ttggtacagc cggggggtc cctgagactt 60 tcctgtgcag cctctggatt cacctttacc agctttgcca tgggctgggt ccgccaggct 120
ccagggaagg ggctggagtg ggtctcagct gtgactggca gtggttatta caaaaactat 180
gcagactccg tgaagggccg gttcaccatc tccagagaca attccgacaa tactctctat 240
ctgcaaatga acagcctgag aggcgacgac acggccctat attactgtgc gaaagcacat 300
agaggtgact ggaataactt ctttgactat tggggccagg gaaccctggt caccgtctcc 360
tca 363

<210> 130
<211> 345
<212> DNA
<213> Homo sapiens

<400> 130
caggtgcagc tgcaggagtc gggcccagga ctagtgaagc cttcggagac cctgtccctc 60
acctgctctg tgtctgctga ctccttcagt ccttacaagt ggagctggat ccggcagccc 120
ccagggaagg gactggaatg gattggatat atctattcca gtgggaacac caactacaac 180
ccccccctca agagtcgagt caccatatca ctggacacgt ccaagaatca ggtctccctg 240
aggctgagct ctgtggccgc tgcggacacg gccatgtatt actgtgcgag agagtggagt 300
ggttttgatt tctggggcca aggaacaatg gtcaccgtct cttca 345

<210> 131
<211> 345
<212> DNA
<213> Homo sapiens

<400> 131
gaggtgcagc tggtggagtc tgggggaggc ttggtccagc ctggggggtc cctgagactc 60
tcctgtgcag cctctggatt cacctttact aactattgga tgagctgggt ccgccaggct 120
ccagggaagg ggctggagtg ggtggccaac ataaagcaag atggacgtga gacatactat 180
gtggactctg tgaagggccg attcaccatc tccagagaca acgccaagaa ctcagtgtct 240
ctacagatga gtagcctgag agccgaggac acggccgtgt attactgtgc gcgagggcag 300
tggctggcct tccggggcca gggaaccctg gtcaccgtct cctca 345

<210> 132
<211> 348
<212> DNA
<213> Homo sapiens

<400> 132
gaggtgcagc tggtggagtc tgggggaggc ttggtccaga ttgggggtc cctgagactc 60 tcctgtgcag cctctggatt cacctttagt acctattgga tgagctgggt ccgccaggct 120
ccagggaagg ggctggagtg cgtggccagc ataaaggagg atggaagtga gagatactat 180
gtggactctg tgaagggccg attcaccatc tccagagaca acgccaagaa ctcactgcat 240
ctgcagatgg acagcctgag agccgcggac acggctgtgt atttctgtgc gagaggccgg 300
aacaacttcc gacactgggg ccagggaacc ctggtcaccg tctcctca 348

<210> 133
<211> 378
<212> DNA
<213> Homo sapiens

<400> 133
gaggtgcagc tggtggagtc tgggggaggc ttggtccagc ctggggggtc cctgagactc 60
tcctgtgcag cctctggatt cgccatcagt ggtaactaca tgagttgggt ccgccaggct 120
ccagggaagg gcctggagtg ggtctcactt atttattgga ctgatgacac agtctacgca 180
gactccgtga agggcagatt caccatctcc agggacgtct ccaagaacat ggtgcatctt 240
caaatgagca gcctgagagt cgaggacacg gctgtttatt actgtgcgag agaattaggt 300
gtttttcatt caggggggga ccagtggctg ggccctttag actgctgggg ccagggaacc 360
ctggtcaccg tctcctca 378

<210> 134
<211> 360
<212> DNA
<213> Homo sapiens

<400> 134
gaggtgcagc tggtggagtc tgggggaggc ttggtgcagc cagggcagtc cctgagactt 60
tcctgtacag tttctggatt cagcgtagaa gaccatggtc tgaactgggt ccgccaggct 120
ccagggaagg ggctggagtg ggtagggttc attagaagga aaagttctgg tgggacagaa 180
tacgccgcgt ctgtgaaagg ccgattcacc atctcaagag atgattccaa gagcgccgtc 240
tatctgcaaa tgaacagcct gaagatggag gacacaggcg tatattattg tcttcgctgg 300
acgggtggag tgagttttgg tgcctactgg ggccagggaa ccctggtcac cgtctcctca 360

<210> 135
<211> 348
<212> DNA
<213> Homo sapiens

<400> 135
gaggtgcagc tggtggagtc cgggggaggc ttagttcagc ctggggggtc cctgagactc 60
tcctgtgcag cctctggatt caccttcact agctggatgc actgggtccg ccaagctcca 120
gggaaggggc tggtgtgggt ctcacatatt aatactgatg ggagtagcac aagctacgcg 180
gactccgtga agggccgatt caccatctcc agagacaacg ccaagaacac gctgtatctg 240
caaatgaaca gtctgagagc cgaggacacg gctgtgtatt actgtgcaag agattattac 300
cactccgttg actactgggg ccagggaacc ctggtcaccg tctcctca 348

<210> 136
<211> 351
<212> DNA
<213> Homo sapiens

<400> 136
caggtgcagc tgcaggagtc gggcccagga atggtgaagc cttcggagac cctgtccctc 60
atctgcagtg tctctggtgc ctccgtcagt cgtgaccact ggagctggat ccgccagtcc 120
ccagggaagg gactggagtg gattgtctat atatataaca gtgagagcat cgaatacaat 180
ccctccctca agagtcgagt caccatatcc gtagacacgt ccaagaacca ggtctccctg 240
acagtgactt ctgtgaccgc tgcagacacg gccttctatt actgtgcgcg agggccagat 300
gcccacaaaa ctggctactg gggcccggga accctggtca ccgtctcctc a 351

<210> 137
<211> 351
<212> DNA
<213> Homo sapiens

<400> 137
gaggtgcagc tggtggagtc cgggggaggc ttagttcagc ctgggggtc gctgagactc 60 tcctgcgcag cctctggatt caccttcagt aacttctgga tgtactgggt ccgccaagtt 120
ccagggaagg ggctggtgtg cgtctcacgt attaatagag atgggagtat cacattgtac 180
gcggactccg tgaggggccg attcaccatc tccagagaca acgccaagaa cacgctgtat 240
ctgcaaatga acagtctgag agtcgaggac acggctgtgt attactgtgc aagagattcc 300
tataccagcc ctgactactg gggccagggg accctggtca ccgtctcctc a 351

<210> 138
<211> 360

<212> DNA
<213> Homo sapiens

<400> 138
gaggtgcagc tggtggagtc tgggggaggc ttggtaaagc cgggggagtc ccttagactc 60
tcctgtgcga cctcaggatt aactttcagt aacgtatgga tgagctgggt ccgccaggct 120
ccagggaagg ggctggagtg ggttgggcgt cttaaaaaca agcctgatgg tggaacaaca 180
gactacgcag cacccgtgaa gggcagattc accatctcaa gagatgattc aaaaaccacg 240
ctgtatctgg aaatgaacag cctgaaagtc gaggacacag ccgtgtatta ctgtaccaca 300
gataacggag tcaaggcttt tgatatctgg ggccaaggga caatggtcac cgtctcttca 360

<210> 139
<211> 354
<212> DNA
<213> Homo sapiens

<400> 139
gaggtgcagc tggtggagtc cgggggaggc ttagttcagc ctggggggtc cctgagactc 60
tcctgtgcag cctctggatt caccttcagt acctactgga tgcactgggt ccgccaaact 120
ccggagaagg ggctggtatg ggtctcacgt attcatcctg atgggagtaa cacagcctac 180
gcggactccg tgaagggccg attcaccatc tccagagaca acgccaagaa cacgctgtat 240
ctgcaaatga atagtctgag agtcgaggac acggcttttt attattgtac aagagggggt 300
tccggggcta cgatcaatta ctggggccag ggaatcctgg tcaccgtctc ctca 354

<210> 140
<211> 372
<212> DNA
<213> Homo sapiens

<400> 140
caggtgcagc tgcaggagtc gggcccaggg ctggtgaagc cttcacagac cctgtccctc 60
acctgcactg tctctggtgg ctccatcagc ggtggtactt actcctggac ctggatccgg 120
cagcccgccg ggaagggact ggagtggatt gggcgtattt ttgctagtgg gagcaccaac 180
tacaattcct ccctcaagag tcgagtcacc attttagtag acacgtccaa gaacctgttc 240
tccctgagcc tgagctctgt gaccgccgca gacacggcca tgtattactg tgcgagagat 300
cgagccggta tagatggcta caattactac tttgactact ggggccaggg aaccctggtc 360
accgtctcct ca 372

<210> 141
<211> 359
<212> DNA
<213> Homo sapiens

<400> 141
aggtgcagct ggtgcagtct ggggctgagg tgaagaagcc tggggcctca gtgaaggttt 60
cctgcaagac atctggatac accctcacca gttactatat gcactgggtg cgacaggccc 120
ctggacaagg gcttgagtgg ctgggagtga tcaggcctac ggacgctagc acaaggtccg 180
cacagaagtt ccagggcaga atcaccatga ccagggacac gtccacgagc acactctaca 240
tggagctgag tagcctgaga tctgaagaca cggccgtgta ctattgtgcg agagaagtgg 300
cagcagaagg taaagctttc gactactggg gccagggaac cctggtcacc gtctcctca 359

<210> 142
<211> 348
<212> DNA
<213> Homo sapiens

<400> 142
gaggtgcagc tggtggagtc tgggggaggc ttggtccagc ctggggggtc cctgagactc 60
tcctgtgcag cctctggatt cacctttagt agctattgga tgagctgggt ccgccaggct 120
ccagggaagg gactggagtg ggtgggcaaa ataaaggaag acggaagtga gaaatactat 180
gtggactctg tgaagggccg attcgccatc tccagagaca acgccaagaa ctccctgtct 240
ctgcaaatga acagcctgag agccgaggac acggccgtgt attactgtgc gagaggtcaa 300
tcatatccgg gaatttgggg ccaagggaca atggtcaccg tctcttca 348

<210> 143
<211> 363
<212> DNA
<213> Homo sapiens

<400> 143
caggtgcagc tgcaggagtc gggcccagga ctggtgaagc cttcggagac cctgtccctc 60
acctgcactg tctctggtgg ctccatcact aattactact ggggctggat ccggcagccc 120
ccaggggagg gactggagtg gattggctat atctattaca gtggaagcac caactacaac 180
ccctccctca agagtcgagt caccatatca gtagacacgt ccaagaacca gttctcccta 240
aagctgacct ctgtaaccgc cgcagacacg gccgtgtatt actgtgcggg tcgggcttac 300
agtagtggtt actactacct aattgactac tggggccagg gaaccctggt caccgtctcc 360
tca 363

<210> 144
<211> 321
<212> DNA
<213> Homo sapiens

<400> 144
gaaattgtgt tgacgcagtc tccaggcacc ctgtctttgt ctccagggga aagagccacc 60
ctctcctgca gggccagtca gagtgttacc tacttagcct ggtaccagca gaaacctggc 120
caggctccca ggctcctctt ctatggtaca tccagcaggg ccactggcat cccagacagg 180
ttcagtggca gtgggtctgg gacagacttc actctcacca tcagcagagt ggagcctgaa 240
gattttgcag tgtattactg tcagcagttt ggcagctcac ctccggacac tttcggcgga 300
gggaccaagg tggaaatcaa a 321

<210> 145
<211> 332
<212> DNA
<213> Homo sapiens

<400> 145
ttgtgatgac tcagtctcca ctctccctgc ccgtcaccct tggacagccg gcctccatct 60
cctgcagggc tagtcaaggc ctcgaacaca gtgatggaaa cacctacttg agttggtttc 120
agcagaggcc aggccgatct ccccggcgcc taatttataa ggtttctaac cgggactctg 180
gggtcccaga cagattcagt ggcagtgggt caggcactga tttcacactg gaaatcacca 240
gggtggaggc tgaggatgtt ggagtttatt actgcatgca agttacacac tggccgagga 300

```
cgttcggcca agggaccaag gtggaaatca aa                                    332


<210>  146
<211>  321
<212>  DNA
<213>  Homo sapiens

<400>  146
gaaattgtgt tgacacagtc tccaggcacc ctgtcgttgt ctccagggga aagagccacc       60

ctctcctgca gggccagtca gagtattagt ccccacttgg cctggtacca acagaaacct      120

ggccagtctc ccaggctcct catatatgat gcatccaaca gggccactgg catcccagcc      180

aggttcagtg gcagtgagtc tgggacagac ttcactctca gcatcagcag cctagagcct      240

gaagattttg cagtttatta ctgtcagcag agtggcgact ggcctctcac tttcggcgga      300

gggaccaagg tggagatcaa a                                                321


<210>  147
<211>  324
<212>  DNA
<213>  Homo sapiens

<400>  147
gaaattgtgt tgacgcagtc tccaggcacc ctgtctttgt ctccagggga aagagccacc       60

ctctcctgca gggccagtca gagtgtttac agcatctact tcgcctggta ccagcagaaa      120

cccggccagg ctcccaggcc cctcatttat ggtgtctcca acagggccac tggcatccca      180

gacaggttca gtggcagtgg gtctgggaca gacttcactc tcaccatcag cagactggag      240

ccagaagatt ttgcagtgta ttactgtcag cagtatggta gtttacctcg gacgttcggc      300

caagggacca aggtggaaat caaa                                             324


<210>  148
<211>  332
<212>  DNA
<213>  Homo sapiens

<400>  148
ttgtgatgac tcagtctcca ctctccctgc ccgtcaccct tggacagccg gcctccatct       60
```

cctgcaggtc tagtcgaagc ctcgtataca gtgatggagg cacctacttg aattggtttc 120
agcagaggcc aggccaatct ccaaggcgcc taatttggca cgtttctaac cgggactctg 180
gggtcccaga cagattcagc ggcagtgggt caggcactga tttcacactg aaaatcagca 240
gggtggaggc tgaggatgtt ggggtttatt actgcatgca aggtacacac tggccttaca 300
cttttggcca ggggaccaag gtggaaatca aa 332

<210> 149
<211> 321
<212> DNA
<213> Homo sapiens

<400> 149
gacatccaga tgacccagtc tccatcttcc ctgtctgcat ctgtaggaga cagagtcacc 60
atcacttgcc aggcgagtca ggacattagg aagcttttaa attggtatca gcagagacca 120
gggaaagccc ctaacctcct gatctacgat gcatccaatt tggaaacagg ggtcccatca 180
aggttcagtg gaagtggatc tgggacacat tttagtttca ccatcaccag cctgcagcct 240
gaagatattg caacatatta ctgtcaacag tttgaaagtt tccctcgcac cttcggccct 300
gggaccaaag tggatatcaa a 321

<210> 150
<211> 327
<212> DNA
<213> Homo sapiens

<400> 150
gaaatagtga tgacgcagtc tccagccacc ctgtctgtgt ctccagggga aacagccacc 60
ctctcctgca gggccagtca gagtgttaac agcttcttag cctggtacca gcagaaacct 120
ggccaggctc ccaggctcct catctatgct gcatccacca gggccactgg tgtcccagcc 180
aggttcagtg gcagtgggtc tgggacagag ttcactctca ccatcagcag cctgcagtct 240
gaagattttg cagtttacta ctgtcaccag tataaaaact ggcctccgat gggcactttc 300
ggccctggga ccaaagtgga tatcaaa 327

<210> 151

<211> 318
<212> DNA
<213> Homo sapiens

<400> 151
gacatccaga tgacccagtc tccttccacc ctgtcttctt ctgtcggaga cagagtcact 60
atcacttgcc gggccagtca gaatattggt gtctccttgg cctggtatca gcagaaacca 120
gggaaagccc ctaacctcct gatctataag gcgtcttatt tagaaacggg ggtcccatca 180
aggttcagcg gcagtggatc tgggacagaa ttcactctca ccatcagcag cctacagcct 240
gatgattttg caacttatta ttgccaacag tatgatattt atttgacatt cggccaaggg 300
accaaggtgg aaatcaaa 318

<210> 152
<211> 332
<212> DNA
<213> Homo sapiens

<400> 152
ttgtgatgac tcagtctcca ctctccctgc ccgtcaccct tggacagccg gcctccatct 60
cctgcaggtc tagtcaaagt ctcgcacaca gtgatggaaa tacctacttg aattggtttc 120
agcagaggcc aggccaatct ccaaggcgcc taatttataa ggtttctaac cgggactctg 180
gggtcccaga cagattcagc ggcagtgggt caggcactga tttcacactg aaaatcagca 240
gggtggaggc tgaggatgtt ggggtttatt actgcatgca aggtacacac tggccgtaca 300
cttttggcca ggggaccaag gtggaaatca aa 332

<210> 153
<211> 339
<212> DNA
<213> Homo sapiens

<400> 153
gacatcgtga tgacccagtc tccagactcc ctggctgtgt ctctgggcga gagggccacc 60
atcaactgca agtccagcca gagtgtttta tacagcccca acaataagaa ttacttagct 120
tggttccagc agaagccagg acagcctcct aaattactca tttactgggc atctatccgg 180
gactccgggg tccctgaccg attcagtggc agcgggtctg ggacagattt cactctcacc 240
gtcagcagtc tgcaggctga cgatgtggca gtttattact gtcagcaata tgctgctact 300
ccgtggacgt tcggccaagg gaccaaggtg gaaatcaaa 339

<210> 154
<211> 332
<212> DNA
<213> Homo sapiens

<400> 154
ttgtgatgac tcagtctcca ctctccctgc ccgtcaccct tggacagccg gcctccatct 60
cctgcagttc tagtcaaagc ctcgtataca gtgatggaaa cacctacttg agttggtttc 120
agcagaggcc aggccaatct ccccggcgcc taatttataa ggtttctaac cgggactctg 180
gggtcccaga cagattcagc ggcagtgggt caggcactga tttcacactg agaatcagca 240
gggtggaggc tgaggatgtt ggggtttatt actgcatgca aggttcacac tggccgctca 300
ctttcggcgg agggaccaag gtggagatca aa 332

<210> 155
<211> 339
<212> DNA
<213> Homo sapiens

<400> 155
gacatcgtga tgacccagtc tccagactcc ctggctgtgt ctctgggcga gagggccacc 60
atcaactgca agtccagcct gagtgtttta tccagctcca ataatgagaa ctacttagct 120
tggtaccagc agaaaccagg acagcctcct aagctgctca tttactgggc atctacccgg 180
ggatccgggg tccctggccg attcagtggc agcgggtctg ggacagattt cactctcacc 240
atcagcagcc tgcaggctga agatgtggca gtttattact gtcaccaata ttatactact 300
cccttcgctt tcggccctgg gaccaaagtg gatatcaaa 339

<210> 156
<211> 321
<212> DNA
<213> Homo sapiens

<400> 156
gacatccaga tgacccagtc tccgtcctcc ctgtctgcat ctgtgggaga cagtgtcacc 60
atcacttgcc gggcaagtca gagcattagc agctatttaa attggtatca ccaaaaacca 120
gggaaagccc ctaaactcct gatctatggt gcatccactt tgcaaagtgg ggtcccatca 180
aggttcggtg gcagtggatc tgggacagat ttcactctca ccatcagcag tctgcaacct 240
gacgattttg caacttacta ctgtcaacag agtcacagtt cccctctcac tttcggcgga 300
gggaccaagg tggagatcaa a 321

<210> 157
<211> 318
<212> DNA
<213> Homo sapiens

<400> 157
gacatccaga tgacccagtc tccttccacc ctgtctgcct ctgtaggaga cagagtcacc 60
atcacttgtc gggccagtcg gagtcttggt agctggttgg cctggtatca gcagagccca 120
gggaaagccc ctaagctcct gatctataag gcgtctactt tagaaagtgg ggtcccatca 180
cggttcagcg gcagtggatc tgggacagaa ttcactctca ccatcagcag cctgcagcct 240
gatgattttg caacttatta ctgccaacag tattatagct tctacacttt tggccagggg 300
accaaggtgg aaatcaaa 318

<210> 158
<211> 339
<212> DNA
<213> Homo sapiens

<400> 158
gacatcgtga tgacccagtc tgcagactcc ctggctgtgt ctctgggcga gagggccacc 60
atcaactgca agtccagcca gagtcttttc tacagttcca acaagaagaa ctacttagct 120
tggtaccagc agaagccagg acagcctcct aaactgatca tttactgggc atctacccgg 180
gaatccgggg tccctgaccg attcagtggc agcgggtctg ggacagattt cactctcacc 240
atcaccagcc tgcgggctga agatgtggca gtttattact gtcagcaata ttatactcct 300
cctctcacat tcggcggagg gaccaaggtg gaaatcaaa 339

<210> 159
<211> 321
<212> DNA
<213> Homo sapiens

<400> 159
gaaatagtga tgacgcagtc tccagccacc ctgtctgtgt ctccagggga aagagccacc 60
ctctcctgca gggccagtca gagtgttagc ggcgacttag tctggtacca gcagaaacct 120
ggccaggctc ccaggctcct catctatggt gccaccacca gggcctctgg tgtcccagcc 180
aggttcagtg gcagtgggtc tgggacagag ttcactctca ccatcagcag cctgcagtct 240
gaagattttg caatttatta ctgtcagcag tataataact ggccccggac gttcggccaa 300
gggaccaagg tggaaatcaa a 321

<210> 160
<211> 321
<212> DNA
<213> Homo sapiens

<400> 160
gaaatagtga tgacgcagtc tccagccacc ctgtctgtgt ctccagggga aagagccacc 60
ctctcctgca gggccagtca gagtgttggc aacaacttag cctggtttca gcagaaacct 120
ggccaggctc ccaggctcct catctatggt gcatccacca gggccactgg tatcccagcc 180
aggttcagtg gcagtgggtc tgggacagag ttcactctca ccatcagcag cctgcagtct 240
gaagattttg cagtttatca ctgtcaacac tatcataact ggcctcccac ttttggccag 300
gggaccaagg tggaaatcaa a 321

<210> 161
<211> 366
<212> DNA
<213> Homo sapiens

<400> 161
caggtgcagc tggtggagtc tgggggaggc gtggtccagc ctgggaggtc cctgagactc 60
tcctgtgcag cctctggatt caccttcagc aaccatggca tgcactggct ccgccagact 120
ccaggcaagg ggctggagtg ggtggcagtc atttcatatg atggaagtac caaatactat 180

```
gcagactccg tgaagggccg atgcaccctc tccagagaca attccaagga aacggtgttt      240

ctgcaaatga acagcctgag acctgaggac acggctgtgt attattgtgc gaaagggtgt      300

tctaatggtg gtaactgctt tttgattgac tactggggcc cgggaaccct ggtcaccgtc      360

tcctca                                                                 366


<210>  162
<211>  369
<212>  DNA
<213>  Homo sapiens

<400>  162
gaggtgcagc tgttggagtc gggggagac ttggtgcagc ctggggggtc cctgagactc        60

tcctgtgcag cctctggatt cgacttcagt atttatggca tgaactgggt ccgccaggct      120

ccagggaagg ggcttgaatg ggtctcagtt attagtggtg atggcactat catatactac      180

gcagactccg tgaagggccg gttcactatc tccagagaca attccaagaa cacactgttt      240

ttgcaagtga acagcgtgag agccgaggac acggccgtat attactgtgc gaaggggggc      300

tactatgaat cggggactat gcgggctttt gatatctggg gccaagggac aatggtcacc      360

gtctcttca                                                              369


<210>  163
<211>  351
<212>  DNA
<213>  Homo sapiens

<400>  163
gaggtgcagc tggtggagga gtctggggga ggcttggtcc agcctggggg gtccctgaga       60

ctctcctgtg cagcctctgg atacaccttt agtagttatt caatgagttg ggtccgccag      120

gctccaggga aggggctgga gtgggtggcc agcattaagc cagaaggaag tgagaaattc      180

tatgtggact ctgtgaaggg ccgattcact atctccagag acaacgccaa gaactcactg      240

tatctgcaaa tgaacagcct gagaggcgag gacacggctg tctactactg tgcgagaggg      300

gaatctaatt tccgatactg gcaccaggga accctggtca ccgtctcctc a               351
```

<210> 164
<211> 357
<212> DNA
<213> Homo sapiens

<400> 164
gaggtgcagc tggtggagtc tgggggagcc ttggtccagc ctggggggtc cctgagactc 60
tcctgtgcag cctctggatt catcttcagt aactcttgga tgggctggtt ccgccaggct 120
ccagggaagc ggccggagtt cgtggccaac ataaaaccag atggaagtga gaaattccat 180
gtggactctg tgaagggccg attcaccatc tccagagaca acgccgagaa ctcactgtat 240
ctgctgatga acagcctgag agccgaggac acggctgtct attactgcgc gagagatagc 300
acttccccgg cccgttttgg gtactggggc cagggaaccc tggtcaccgt ctcctca 357

<210> 165
<211> 354
<212> DNA
<213> Homo sapiens

<400> 165
gaggtgcagc tggtggagac tggaggaggc ttgatccagc ctggggggtc cctgaggctc 60
tcctgtgcag cctctgggtt aaacgtcaat agttactaca tgaactgggt ccgccaggct 120
ccagggaagg ggctggagtg ggtctcagtt atttatagcg gtggtggcac aaactacgca 180
gactccgtga ggggccgatt catcatctcc agagacaatt ccaggaacgc gctttatctt 240
caaatgaaca gcctgagagc cgaggacacg gccgtgtatt actgtgcgac gggcgggatg 300
accagtagtt ggtacggcta ctggggccag ggaaccctgg tcaccgtctc ctca 354

<210> 166
<211> 374
<212> DNA
<213> Homo sapiens

<400> 166
aggtgcagct ggtgcagtct ggggccgagg tgaagaagcc tggggcctca gtgaaggttt 60
cctgcaaggc atctgaatac actttcatca actaccttgt gttctgggtg cgacaggccc 120
ctggacaagg gcttgagtgg atgggagaaa tgaaccccac tcgtgggagc acaagctacg 180
cacagaagtt ccagggcaga gtcaccatga ccagggacac gtccacgagc acagtctaca 240
tggagttgag cagcctgaga tctgacgaca cggccgttta ttactgctcc atgggtccgc 300
cctattgtac tggtggaagc tgttactccg cctgtgattt ctggggcccg ggaaccctgg 360
tcaccgtctc ctca 374

<210> 167
<211> 372
<212> DNA
<213> Homo sapiens

<400> 167
gaggtgcagc tggtggagtc tgggggaggc ttgatgaaac ctggggggtc ccttagactc 60
tcctgtgcag tctctgggtt cactttcact aacgcctggc tgagctgggt ccgccagcct 120
ccagggaagg ggctggagtg ggttggccgt gcttacagca gttctggcgg ttggacaatg 180
gactactctt cacccgtgag gggcagattc accatcacaa gagacgattc aaaaaacaca 240
ctgtatctgc aaatgaacaa cctgaaaacc gaggacacag ccgtgtatta ctgtaccaca 300
gatattggca aaggctggta cacgcactat cctgacctct ggggccaggg aaccctggtc 360
accgtctcct ca 372

<210> 168
<211> 363
<212> DNA
<213> Homo sapiens

<400> 168
caggtgcagc tggtggagtc tgggggaggc gtggtccagc ctgggaagtc cctcagactc 60
tcctgtgtag cctctggatt caccttaagt acctgtggca tgcactgggt ccgccaggct 120
ccaggcaagg ggctggagtg ggtggcagtt acaacatatg atggagatcg taaatataat 180
gtagactccg tgaagggccg attcaccatc tccagagaca attccaagaa cacggtgtat 240
ctgcaaatgg acggcctcaa agccgaggac acggctgtgt atcactgtgt gaaagaatat 300
agttggggtt actacagaac tgcggactac tggggccagg gaaccctggt caccgtctcc 360
tca 363

<210> 169
<211> 351
<212> DNA
<213> Homo sapiens

<400> 169
gaggtgcagc tggtggagtc cgggggaggc ttagttcagc cggggggtc cctgagactc 60 tcctgtgtag cctctggatt caccttcagt acttactgga tgcactgggt ccgccaacct 120
ccggggaagg ggctggtgtg ggtctcacgt attaatcctg atggcagtag cacaaactac 180
gcggactccg tgaacggccg attcaccatc tccagagaca acgccaagaa cacgctgtat 240
cttgaaatga acagtttgag agtcgaggac acagctctct attactgtgc aagaagtcct 300
gggggttact ttgactactg gggccacagc accctggtca ccgtctcctc a 351

<210> 170
<211> 348
<212> DNA
<213> Homo sapiens

<400> 170
gaggtgcagc tggtggagtc tgggggaggc ttggtgaagc ctggggggtc ccttacactc 60
tcctgtgcag tctctggatt cactttcagt accggctgga tgagctgggt ccgccaggct 120
ccagggaagg ggctggactg ggttggccgt attaaaagca aaactgctgg tgggacaaca 180
gactatgctg cacccgtgaa agacagattc accatctcaa gagatgattc aaaaaacacg 240
ctgtatctgc aactgagcag ccttaaaacc gaggacacag ccgtgtatta ctgtaccaca 300
gatgacctga aaaactgggg ccagggaacc ctggtcaccg tctcctca 348

<210> 171
<211> 387
<212> DNA
<213> Homo sapiens

<400> 171
gaggtgcagc tggtggagtc tgggggaggc ttggtgcagc cggggggtc cctgagactc 60 tcctgtgcag cctctggatt caccttcagt agttatagca tgaactgggt ccgccaggtc 120
ccgggaaagg ggctggagtg ggtctcatac acaagtacta aaagtgatat caaatactac 180
gcggactctg tggaaggccg attcaccatt tccagagaca atgccaagaa ctcattgtat 240
ctgcaaatga acagcctgag agacgaagac acggctgtct attattgtgc gagaggacga 300
gattgttatg ggggtaactg cgtcatctac ttccactact acggtttgga cgtctggggc 360
caagggacca cggtcaccgt ctcctca 387

<210> 172
<211> 369
<212> DNA
<213> Homo sapiens

<400> 172
caggtgcagc tggtggagtc tgggggaggc gtggtccagc ctgggggtc cctgagactc 60 tcctgtgtag tctctggatt caccctcagt tcctgtggca tgcattgggt ccgccagtct 120
ccaggcaagg ggctggagtg gctgtcagtt agcacctatg atggagatgg caatcagaaa 180
tactatgcgg cctccgtgaa gggccgattc ctcatctcca gagacacttc gaagaacacg 240
gtgtatctcc atatgaacag cctgacagct gaggacacgg ctctatatta ttgtgtgaaa 300
gagagtgcca ctggctggta tcgcaccgct gattactggg gccagggaac cctggtcacc 360
gtctcctca 369

<210> 173
<211> 366
<212> DNA
<213> Homo sapiens

<400> 173
gaggtgcagc tggtggagtc tgggggaggc ttggtccagc ctgggggtc cttgagactc 60 tcctgtgcag cctctggatt caccgtcagt agcatattca tgagctgggt ccgccaggct 120
ccagggcagg ggctggagtg ggtctcagtc atctataccg atggaaaaac atattatgca 180
cactccgtgg agggccgatt caccatctcc agagacgatt ccaagaatat ggtgtatctt 240
caattgagca gcctgagaac tgaggacacg gctgtttatt actgtgcgag agatattcca 300
acgacatttg gaataggtga agcttttgat atctggggcc aggggacaat ggtcaccgtc 360
tcttca 366

<210> 174
<211> 347
<212> DNA
<213> Homo sapiens

<400> 174
aggtgcagct ggtgcagtct ggggctgagg tgaagaagcc tggggcctca gtgaagcttt 60
cctgcaagac atctggatac tccttcacca gcaactattt gcactgggtg cgacaggccc 120
ctggacaagg acttgagtgg atgggaatgg tctacccaaa tgatggtact acaacctacg 180
ctcagaagtt tcagggcaga gtcaccatga ccagtgagac gtccacaacc acaatctaca 240
tggacctgag cggcctgaca tctgaggaca cggccatata ttactgtgct agagacgatt 300
cggcctttga ctactggggc cagggaaccc tggtcaccgt ctcctca 347

<210> 175
<211> 363
<212> DNA
<213> Homo sapiens

<400> 175
caggtgcagc tggtggagtc tgggggaggc gtggtccagc ctgggaggtc cctgagactc 60
tcctgtgaag cctctggatt catcttcagt agcaatggca tgcactgggt ccgccaggct 120
ccaggcaagg ggctggagtg ggtggcagtt atatcatctg atggaagtag gagatactat 180
gcagactcaa tgaagggccg attcaccatc tccagagaca actccaagaa cacgctgtat 240
ctgcaattga acagcctgag agctgacgac acggctgtct attactgtgc gaaaggctgt 300
agtggtgaaa attgcttcta tatggacgac tggggcaaag ggaccacggt caccgtctcc 360
tca 363

<210> 176
<211> 386
<212> DNA
<213> Homo sapiens

<400> 176
aggtgcagct ggtgcagtct ggggctgagg tgaagaagcc tggggcctca ctgaaggtct 60

```
cctgcaaggc atctggatac accttcagac agaactattt ccactgggtg cgacaggccc      120

ctggacaagg gcttgagtgg atgggagtaa tcaacccgag tgatggtagt acaaagttcg      180

cacagaagtt ccagggcaga gtcagcatga ccagggacac gtccacgagc acagtttaca      240

tggacctgag cagtctgaca tctgaggaca cggccgtcta ttattgtacg agagagatcg      300

gcgcagtggt agtagatgct acgtcgttgg ggtggttggg ctactttgac tactggggcc      360

agggaaccct ggtcaccgtc tcctca                                           386


<210>  177
<211>  345
<212>  DNA
<213>  Homo sapiens

<400>  177
gaggtgcagc tggtggagtc tgggggaggc ttggtccagc cggggggtc cctgagtctc        60

tcctgtgaag cctctggatt aaccttcagt ggctactgga tgaactgggt ccgccaggct      120

ccagggaagg ggctggagtg ggtggccaac ataaatccag aaggaagtga gaggagatac      180

gtggagtctg tgcagggccg attcaccgtc tccagagaca acccgaagaa caccctgtat      240

ttgcaaatga acagcctgag agtcgaggac acggctctgt attactgtgc gggctggggg      300

agaacccagg actggggcca gggagccctg gtcaccgtct cctca                      345


<210>  178
<211>  363
<212>  DNA
<213>  Homo sapiens

<400>  178
caggtgcagc tggtggagtc tgggggaggc gtggtccagc ctgggaggtc cctgagactc       60

tcctgtgcag cctctggact caccttcagc aattatggca tgcactgggt ccgccaggct      120

ccagggaagg ggctggagtg ggttgcagtt gtgtcggcaa ggggaggaac tacatattat      180

gcagactccg tgaagggccg attcaccatc tccagagaca attccaagaa cacgatgtct      240

ctgcaaatga acggcctgag acctgacgac acggctgtgt atttttgtac gaaagaagga      300

gcaccacctg gaaaatatgc ttttgatatc tggggccaag ggacaatggt caccgtctct      360
```

```
tca                                                                363


<210>  179
<211>  360
<212>  DNA
<213>  Homo sapiens

<400>  179
gaggtgcagc tggtggagtc tgggggaggc ttggtccagc ctggaggatc cctgagactc     60

tcctgcgcag cctccggatt caccttcagt gactaccgca tggactgggt ccgccaggct    120

ccagggaggg ggctggagtg gattgcccgt attagacaca gagatgcagg ctatagcaca    180

gaatacgccg cgtctgtgag gggcagattc accgtctcaa gagatgactc acagagtaca    240

ctgtacctgc agatgaacag cttgaaagcc gacgacacgg ccgtgtatat ttgtcttaaa    300

gattcttcgc aatactcttt tgatgcgtgg ggccaaggga caatggtcac cgtctcttca    360


<210>  180
<211>  339
<212>  DNA
<213>  Homo sapiens

<400>  180
gacatcgtga tgacccagtc tccagactcc ctggctgtgt ctctgggcga gagggccacc     60

atcaactgca agtccagtca gagtatttta tccagatcca acaataagaa ctacttagcc    120

tggtaccagc agaaaccagg acagcctcct aaattgctcc tttattgggc atctacccgg    180

gaatccgggg tccctgaccg attcagtgtc agcgggtctg ggtcagattt cactctcacc    240

atcagtagcc tgcaggctga ggatgtggca gtttattact gtcagcagta ttataatgct    300

cccctcactt tcggcggagg gaccaaggtg gagatcaaa                           339


<210>  181
<211>  321
<212>  DNA
<213>  Homo sapiens

<400>  181
gaaattgtgt tgacacagtc tccagccacc ctgtctttgt ctccagggga aagggccacc     60

ctctcctgca gggccagtca gactgttagc aggtacttag cctggtacca acaaaagcct    120
```

```
ggccaggctc ccaggctcct catctatgct gcatccaaca gggccactgg catcccaacc      180

aggttcagtg gcagtgggtc tgggacagac ttcactctca ccatcagcag cctagagcct      240

gaagattttg cattttatta ctgtcagcag cgtagcaact ggcctgccac tttcggcgga      300

gggaccaagg tggagatcaa a                                                321
```

<210> 182
<211> 321
<212> DNA
<213> Homo sapiens

<400> 182

```
gacatccaga tgacccagtc tccttcctcc ctgtctgcat ctgtaggaga cagtgtcacc       60

atcacttgcc aggcgagtca ggacattaga gaccgtttaa attggtatca gcagaagcca      120

gggaaagccc ctaacctcct gatctacgat gcatcaagtt tggaaacagg ggtcccatca      180

aggttcagag gaagtggatc tgggacagat tttactttca ccatcagcag cctgcagcct      240

gaagatattg caacatatta ctgtcaacag tttgttagtt tccctcgaac tttcggcccg      300

gggaccaaag tggatatcaa a                                                321
```

<210> 183
<211> 330
<212> DNA
<213> Homo sapiens

<400> 183

```
gaaattgtgt tgacgcagtc tccaggcatc ctgtctttgt ctccagggga aagagccacc       60

ctctcctgca gggccagtca gagtgttagc agcaggtcct tgtcctggta ccagcagaga      120

cctggcctgg ctcccaggct cctcatctat gctgcatcca gcagggccgc tgtcacccca      180

gacaggttca ctgccagcgg gtctgggaca gacttcactc tcaccatcag cagtctggag      240

cctgaagatt ttgcagtgta ttactgtcag cactatggta cctcacctcc gaggtacact      300

tttgggcagg ggaccaaggt ggagatcaaa                                       330
```

<210> 184
<211> 339

<212> DNA
<213> Homo sapiens

<400> 184
gacatcgtga tgacccagtc cccagactcc ctggctgtgt ctctgggcga gagggccacc 60
atcaactgca agtccagcca gagtgtttta cacagctcca acaataagaa ctactttgct 120
tggtaccagc agaaaccagg acagcctcct aagctgctca ttcactgggc atctacccgg 180
gcatccgggg tccctgaccg attcagtggc agcgggtctg ggacagattt cactctcacc 240
atcagcagcc tgcaggctga agatgtgaca atttattact gtcagcaata ttatagtact 300
ccgtacactt ttggccaggg gaccaaggtg gaaatcaaa 339

<210> 185
<211> 327
<212> DNA
<213> Homo sapiens

<400> 185
gaaattgtgt tgacgcagtc tccaggcacc ctgtctttgt ctccagggga aagagccacc 60
ctctcctgca gggccagtcc gagtcttgac agcgcctact tagcctggta ccagcagaag 120
cctggccagg ctcccaggct cctcatctat ggtgcatcct ccagggtcac tggcatccca 180
gataggttca gtggcagtgc gtcagggaca gacttcactc tcaccatcag cagactggag 240
cctgaagatt ttgcagtgta ctactgtcag cggtatggta actcacctcc gtacactttt 300
ggccagggga ccaaggtgga gatcaaa 327

<210> 186
<211> 339
<212> DNA
<213> Homo sapiens

<400> 186
gacatcgtga tgacccagtc tccagactcc ctggctgtgt ctctgggcga gagggccacc 60
atcagctgca agtccagcca gagtctttta tacagttcca gcaataagaa ctacctagct 120
tggttccagc agaaaccagg acaggctcct aagttgctca tttactgggc atctacccgg 180
gaatccgggg tccctgaccg attcagtggc agcgggtctg ggacagattt cactctcacc 240
atcagcagcc tgcagactga agatgtggca gtttattatt gtctgcaata tcgtagtgct 300
ccgttcactt tcggcggagg gaccaaggtg gagatcaaa 339

<210> 187
<211> 321
<212> DNA
<213> Homo sapiens

<400> 187
gacatccaga tgacccagtc tccttccacc cagtctgcat ctgtaggaga cagagtcacc 60
atcacttgcc gggccagtca gagtattagt agttggttgg cctggtatca gcagaaacca 120
gggaaagccc ctaaggtcct gatctatgcg gtgtctagtt tagaaagtgg ggtcccatca 180
aggttcagcg gcagtggatc tgggacagaa ttcactctca ccatcagcag cctgcagcct 240
gaggattttg caacttatta ctgccaacaa tatagtactt atccctggac gttcggccca 300
gggaccaagg tggaaatcaa a 321

<210> 188
<211> 321
<212> DNA
<213> Homo sapiens

<400> 188
gaaatagtga tgacgcagtc tccagcctcc ctgtctgtgt ctccagggga aacagccacc 60
ctctcctgca gggccagtca gagtgttggc agcaccttag cctggtacca gcagaagccc 120
ggccaggctc ccaggctcct catctataat gtattcacca gggccgctgg tgtcccagcc 180
aggttcagtg gcagtgggtc taggacggag ttcactctca ccatcagcag cctgcagtct 240
gaagattttg cagtttatta ctgtcagcag tatagtacct ggctgtggac gttcggccaa 300
gggaccaagg tggaaatcaa a 321

<210> 189
<211> 321
<212> DNA
<213> Homo sapiens

<400> 189
gacatccaga tgacccagtc tccatcctcc ctgtctgcat ctgtaggaga cagagtcacc 60

```
atcacttgcc gggcaagtca gcgcattagc agctacttga attggtatca gcagaaacca      120

gggaaagccc ctaacctcct gatctacgct gcagccagtt tgcatgatgg ggtcccatca      180

aggttcagtg gcagtggatc tgggacagat ttcactctca ccatcagcag tctgcaacct      240

gaagattttg caacttatta ttgtcaacag cgttacagaa tcccgtacag ttttggcccg      300

gggaccaagg tggagatcaa a                                                321


<210>  190
<211>  336
<212>  DNA
<213>  Homo sapiens

<400>  190
gatattgtga tgactcagtc tccactctcc ctgtccgtca cccctggaga gccggcctcc       60

atctcctgca ggtctagtca gagcctcctt cagggtaatg gacacaacta tttggattgg      120

tacctgcaga agccaggaca gtctccacaa ctcctgatct atttgggttc tattcgggcc      180

tccggggtcc ctgacaggtt cagtggcagt ggatcaggca cagattttat actgaaaatc      240

agcagagtgg aggctgagga tgttggggtt tattactgca tgcgagctct acaaactccg      300

tacacttttg gccaggggac caaggtggaa atcaaa                                336


<210>  191
<211>  321
<212>  DNA
<213>  Homo sapiens

<400>  191
gacatccaga tgacccagtc gccttccacc ctgtctgcat ctgttggaga cagagtcacc       60

ctcacttgtc gggccagtga gactcttaat aactggttgg cctggtttca gcaaaagcca      120

gggaaagccc ctaccctcct gatctatgag gcgtctagtt tagaaagtgg agtcccatca      180

aggttcagcg gcagtggatc tgggacagac ttcgctctca ccatcagcag cctgcagccc      240

gatgattttg caacttatta ttgccaccag tataataaat acccgtggac gttcggccaa      300

gggaccaagg tggagatcaa a                                                321
```

<210> 192
<211> 318
<212> DNA
<213> Homo sapiens

<400> 192
gacatccaga tgacccagtc tccttccacc ttgtctgcat ctgtaggaga cagagtcacc 60
atcacttgtc gggccagtca gagtattagt ggctggttgg cctggtatca gcagaaagca 120
gggaaagccc ctaagctcct gatctataag gcgtctagtt tagaaagtgg ggtcccatca 180
aggttcagcg gcagtggatc tgggacagag ttcactctca ccatcagcag cctgcagcct 240
gatgattttg caacttatta ctgccagcag tattatagtt ggggaacgtt cggccaaggg 300
accaaggtgg agatcaaa 318

<210> 193
<211> 336
<212> DNA
<213> Homo sapiens

<400> 193
gatattgtga tgacccagac tccactctcc ttacctgtca cccttggaca gccggcctcc 60
atctcctgca tatctagtca aagcctcgta cacagtgatg gaaacaccta cttgagttgg 120
cttcagcaga ggccaggcca gcctccaaga ctcctgattt ataagatttc taaccggttc 180
tctggggtcc cagacagatt cagtggcagt ggggcaggga cagatttcac actgaaaatc 240
agcagggtgg aagctgagga tgtcggggtt tattactgca tgcaagcttc acaatctacg 300
tggacgctcg gccaagggac caaggtggag atcaaa 336

<210> 194
<211> 339
<212> DNA
<213> Homo sapiens

<400> 194
gacatcgtga tgacccagtc tccagactcc ctggctgtgc ctctgggcga gagggccacc 60
atcaactgca cgtccagcca gactgtttta tccagttcca acaataagaa ctacttagtt 120
tggtaccagc agaaaccagg acagcctcct aagttgctcc tttactgggc gtctacccgg 180
gcatccgggg tccctgaccg attcagtggg agcgggtctg ggacagattt cactctcacc 240
attagcagtc tgcaggctga agatgtggca gtttattact gtcagcaatg ttataatgct 300
ccgctcactt tcggccgagg gaccaaggtg gagatcaaa 339

<210> 195
<211> 324
<212> DNA
<213> Homo sapiens

<400> 195
gaaatagtga tgacgcagtc tccagccacc ctgtctgtgt ttccagggga aggagtcacc 60
ctctcctgca gggccagtca gagtattagc aacaacttgg cctggtacca gcagaaacct 120
ggccaggctc ccaggctcct catgtatgat gcatccacca gggccactgg tatcccagcc 180
aggttcagtg gcagtgggtc tgggacagag ttcactctca ccatcagcag cctgcagtct 240
gaagatttcg cagtttatta ctgtcagcag tataataact ggcctccggt cacgttcggc 300
caagggacca aggtggaaat caaa 324

<210> 196
<211> 332
<212> DNA
<213> Homo sapiens

<400> 196
ttgtgatgac tcagtctcca ctctccctgc ccgtcaccct tggacagtcg gcctccgtct 60
cctgcaggtc aagtcaaagc ctcggcccca gtgacggaag cacccgcttg gattggtttc 120
aacagaggcc aggccaatct ccaaggcgcc taatttatgc ggtttctaac cgggactctg 180
gggtcccaga cagattcagc ggcagcgggt caggcagtga tttcacactg agaatcagca 240
gagtggaggc tgaggatgtt ggggtttatt actgcatgca atatacatac tggcctcaca 300
cttttggcca ggggaccaag gtggaaatca aa 332

<210> 197
<211> 327
<212> DNA
<213> Homo sapiens

<400> 197
gaaattgtgt tgacacagtc tccagccacc ctgtctttgt ctccagggga aagagccacc 60
ctctcctgca gggccagtca gagtgttagc agttccttag cctggtacca acaaaaacct 120
ggccaggctc ccaggctcct catctatgat gcatccaaga gggccactga catcccagcc 180
aggttcagtg gcagtgggtc tgggacagac ttcactctca ccatcagcag cctagagcct 240
gaagattttg cggtttatta ctgtcagcac cggggggagt ggcctccggg ggccactttc 300
ggccctggga ccaaagtgga tatcaaa 327

<210> 198
<211> 321
<212> DNA
<213> Homo sapiens

<400> 198
gacatccagt tgacccagtc tccatccttc ctgtctgcat ctgtaggaga cagagtcacc 60
atcacttgcc gggccagtca gggcattgat actcgtttga tctggtatca acagaagcca 120
ggggaagccc ctaagctcct gatctatgaa gcatccactt tgcaaagtgg ggccccatca 180
aggttcagcg gcagtggatt cgggacagaa ttcactctca caatcagcag tctgcagcct 240
gaagactttg caacttatta ctgtcaacag tttaaaggtt acccgctcac tttcggcggg 300
gggaccaagg tggagatcaa a 321

<210> 199
<211> 345
<212> DNA
<213> Homo sapiens

<400> 199
caggtgcagc tgcaggagtc gggcccagga ctggtgaagc cttcggagac cctgtccctc 60
acctgcactg tctctggtgg ctccatcagt agtcactact ggagctggat ccggcagccc 120
ccagcgaagg gactggagtg gattgggtat atctatcaca gtgggatgac caactacaac 180
ccctccctca agagtcgagt caccatatca atagacacgt ccaagaacca gttctccctg 240
aagttgagct ctgtgaccgc tgcggacacg gccgtgtatt actgtgcgag aggtgatggc 300
tacaatttct tctggggcca gggaacgctg gtcaccgtct cctca 345

<210> 200
<211> 375
<212> DNA
<213> Homo sapiens

<400> 200
caggtgcagc tggtggagtc tgggggaggc gtggtccagc ctgggggtc cctgagactc 60 tcctgtgcag cgtctggact cacgttcagt aaccaagatt tccactgggt ccgccaggct 120
ccaggcaagg ggctggaatg ggtggcattt atacgttatg atggaggttt taaaaactat 180
gcagactccg tgaagggccg attcaccatc tccagagaca attcccagaa aatgctgtat 240
ctgcaaatgg acagcctgag agttgaagac acggctgtgt attactgtgc gaagtgcggc 300
gcagaggact ctactactgt ctggctgaat tggttcgacc cctggggcca gggaaccctg 360
gtcaccgtct cctca 375

<210> 201
<211> 360
<212> DNA
<213> Homo sapiens

<400> 201
gaggtgcagc tgttggagtc tgggggaggc ttggtagagc ctgggggtc cctgagactc 60 tcctgtgcag cctctggatt cacctttagc agctatgcca tgagctgggt ccgccaggct 120
ccagggaagg ggctggagtg ggtctcagct attagtgaca gtggtggtag cacatactac 180
gcagactccg tgaagggccg gttcaccatc tccagagaca agtccaagaa cacgctgtat 240
ctgcaaatga acagcctgag agccgaggac acggccgtat attactgtgc gaaaccgaat 300
tactttggtt cggggagtcc cgactactgg ggccagggaa cgctggtcac cgtctcctca 360

<210> 202
<211> 345
<212> DNA
<213> Homo sapiens

<400> 202
caggtgcagc tgcaggagtc gggcccagga ctggtgaagc cttcggagac cctgtccctc 60
acctgcactg tctctggtgc ctccatcagt agtcactact ggagctggat ccggcagccc 120
ccagggaagg gactggagtg gattgggtat atctatcaca gtgggattac caactacaac 180
ccctccctca agagtcgagt caccatatca atagacacgt ccaagaacca gtactccctg 240
aagctgagct ctgtgaccgc tgcggacacg gccgtgtatt actgtgcgag aggtgatggc 300
tacaatttct actggggcca gggaacgctg gtcaccgtct cctca 345

<210> 203
<211> 378
<212> DNA
<213> Homo sapiens

<400> 203
gaggtgcagc tggtggagtc tgggggaggt gtggtacggc ctggggggtc cctgagactc 60
tcctgtgcag cctctggatt cacctttgat gattatggca tgacctgggt ccgccaagct 120
ccagggaagg ggctggagtg gatctctggt atttgttgca acggtggttg ctcaggttat 180
gcagactctg tgaagggccg attcaccatc tccagagaca acgccaagaa gtccctgttt 240
ctggtcatga acagtctgag agccgaggac acggccttgt attactgtgt gagagtggca 300
gtaccagctg ctacatacac ccgagggaat gatgcttttg atatttgggg ccaagggaca 360
atggtcaccg tctcttca 378

<210> 204
<211> 357
<212> DNA
<213> Homo sapiens

<400> 204
gaggtgcagc tggtggagtc tgggggaggc ttggtagagc ctggggggtc cctcagactc 60
tcctgtgcag tctctggttt cactttcact gacgcctgga tgacctgggt ccgccaggct 120
ccagggaagg ggctagattg ggttggccat gtaaaaagta aatatgatgg tgcgacaaca 180
gagtacgctg cacccgtgca aggcagattc accatctcaa gagatgattc aaagaagaca 240
atatatctgc aaatgaacag cctgaacacc gaggacacag gcgtctattt ttgtaccaca 300
gctcatggcc cggtgggtga ccattggggc cagggaacac tggtcaccgt ctcctca 357

<210> 205
<211> 378
<212> DNA
<213> Homo sapiens

<400> 205
gaggtgcagc tggtggagtc tgggggaggc ttggtccagc cggggggtc cctgagactc 60 tcctgtgcag cctctggatt cagctttgat acctcttgga tgacctgggt ccgccaggct 120
ccagggaagg ggctggagtg ggtggccacc ataaaccagg gtggaagtga caaatactat 180
gtggactctg tgaagggccg attcaccatc tccagagaca acgccaagaa ctcactgtat 240
ctgcaaatga acagcctgcg agccgaggac acggctgtat attactgtgc gagagcgggc 300
gggtgtagct ctaccagatg ccatacaacc ccgggatttg actactgggg ccagggagcg 360
ctggtcaccg tctcctca 378

<210> 206
<211> 353
<212> DNA
<213> Homo sapiens

<400> 206
tgcagctgca ggagtcgggc ccaggactgg tgaagccttc ggagaccctg tccctcacct 60
gcactgtctc tggtagctcc atcagcagta gtagttacta ctggggctgg gtccgccagt 120
ccccagggaa gggactggag tggattggga gtatctatca cagtgggacc atctactaca 180
acccgtccct caggagtcga gtcaccatat ccgtagacac gtccaagaac cagttctccc 240
tgaagctgaa ctctgtgacc gccgcagaca cggctgttta ttactgtgcg agtcttagtg 300
gcacaaatgc ttttgatatc tggggccaag ggacaatggt caccgtctct tca 353

<210> 207
<211> 360
<212> DNA
<213> Homo sapiens

<400> 207
gaggtgcagc tgttggagtc tgggggggc ttggtacagc ctggggggtc cctgagactc 60
tcctgtgcag cctctggatt cacctttagc agccatgaca tgagttgggt ccgcctggct 120
ccagggaagg ggccggagtg ggtctcagct cttggtgctg gagatgcttg gacacactac 180
gcaaactccg tgaggggccg gttcaccatc tccagagacg attccaagaa cacgctgtat 240
ctgcaaatga acagcctgag agccgaagac acggccgtgt atttctgtgc gaaaccccgt 300
ggatactcct atggctactt tgactactgg ggccaaggaa cgctggtcac cgtctcctca 360

<210> 208
<211> 351
<212> DNA
<213> Homo sapiens

<400> 208
gaggtgcagc tggtggagtc tgggggaggc ttggtccagc ctggggggtc cctgagactc 60
tcctgtggag cctctggatt cacctttagt acctattgga tgacctgggt ccgccaggct 120
ccagggaagg gcctggagtg ggtggccaat ataaaccaag atggaagtga gaaacaatat 180
gtggactctg tgaagggccg attcaccatc tccagagaca acgccaagaa ctcactgtat 240
ctgcagatga acagcctgag agtcgaggat acggctattt attactgtgc gagaccccca 300
gctcgccgac ttgactactg gggccaggga tcgctggtca ccgtctcctc a 351

<210> 209
<211> 348
<212> DNA
<213> Homo sapiens

<400> 209
gaggtgcagc tggtggagtc cgggggaggc ttagttcagc ctggggggtc cctgagactc 60
tcctgtgcag cctctgaatt caccttcagt gactactgga tgcactgggt ccgccaagct 120
ccagggaagg ggctggtctg ggtctcacgt attaatactg acgggagtac cacaacctac 180
gcggactccg tgaagggccg attcaccatc tccagagaca acgccaagaa cacgctgtat 240
ctacaaatga acagtctgag ggccgaggac acggctgtgt attactgtgc aagatctaat 300
gcggggcacg aagcgtgggg ccagggaacg ctggtcaccg tctcctca 348

<210> 210
<211> 353

<212> DNA
<213> Homo sapiens

<400> 210
aggtgcagct ggtgcagtct ggggctgagg tgaagaagcc tggggcctca gtgagggttt 60
cctgcaaggc atctggatac accttcacca actactggat acactgggtg cgacaggccc 120
ctggacaagg gcttgagtgg atgggaatga tcgcccctaa ggaaggttac acattctacg 180
cacagcaatt acagggcaga gtcaccgtga ccagggacac gtcgacgagc gcggtttaca 240
tggagctgaa cagcctgaga tctgaggaca cggccgtata tttctgtgcg agagacattc 300
cccacgctaa tttggactat tggggccagg ggacgctggt caccgtctcc tca 353

<210> 211
<211> 363
<212> DNA
<213> Homo sapiens

<400> 211
gaggtgcagc tgttggagtc tgggggagga ttggtacagc ctgggggtc cctgagactc 60 tcctgtgcag cctctggatt cacctttagc gattatacca tgaattgggc ccgccaggct 120
ccagggaagg ggctggagtg ggtctcagct attagagaga gtggtgacag cacatactac 180
gcagactccg tgacgggccg gttcaccatc tccagggaca attccagaaa cacactttat 240
ctgcacatga acagcctgag agccgaggac acggccatgt atttttgtgt gaaagacagg 300
gtgccgccgg gtgacgtgcc gggtgacttc tggggcccgg gaacgctggt caccgtctcc 360
tca 363

<210> 212
<211> 321
<212> DNA
<213> Homo sapiens

<400> 212
gacatccagt tgacccagtc tccatccttc ctgtctgcat ctgtaggaga cagagtcacc 60
atcacttgcc gggccagtca ggacatgacc cattctttag cctggtatca gcaaaaacca 120
gggaaagccc ctaacctcct gatctataat gcatacactt tgcaaagtgg ggtcccatca 180
aggttcagcg gcagtggatc tgggacagaa ttcactctca caatcagcag cctgcagcct 240
gaagattttg caacttatta ctgtcaacag attaatagtt accctcgaac ttttggccag 300
gggaccaagg tggagatcaa a 321

<210> 213
<211> 321
<212> DNA
<213> Homo sapiens

<400> 213
gaaattgtgt tgacacagtc tccaggcacc ctgtctttgt ctccagggga aagagccact 60
ctctcctgca gggccagtca gaatattggc accgccttag cctggtacca acagaaacct 120
ggccaggctc ccagactcat catctatgaa acatccaaca gggccactga cgtcccagcc 180
aggttcagtg gcagtgggtc tgggacagac ttcactctca ccatcagcag cctggagcgt 240
gaagattttg ccctttatta ctgtcaacag cgtgccgact ggccgctcac tttcggcgga 300
gggaccaagg tggagatcaa a 321

<210> 214
<211> 324
<212> DNA
<213> Homo sapiens

<400> 214
gaaattgtgt tgacacagtc tccagccacc ctgtctttgt ctccagggga aagagccacc 60
ctctcctgca gggccagtca gagtgttagc agctacttag cctggtacca acagagacct 120
ggccaggctc ccaggctcgt catctatgct gcatccaaca gggccactgg catcccagcc 180
aggttcagtg gcagtgggtc tgggacagac ttcactctca ccatcagcag cctagagcct 240
gaagattttg cagtttatta ctgtctgcag tgtagcaact ggcccatgta cacttttggc 300
caggggacca aggtggagat caaa 324

<210> 215
<211> 321
<212> DNA
<213> Homo sapiens

```
<400>  215
gacatccagt tgacccagtc tccatccttc ctgtctgcat ctgtagggga cagagtcacc       60

atcacttgcc gggccagtca ggacattacc gattctttag cctggtatca gcaaaaacca      120

gggaaagccc ctaacctcct gatctatact gcatccactt tgcaaagtgg ggtcccatca      180

aggttcagcg gcagtggatc tgggacagaa ttcactctca caatcagcag cctgcagcct      240

gaagatttta caacttatta ctgtcaacag attaatagtt accctcgaac ttttggccag      300

gggaccaagg tggagatcaa a                                                321


<210>  216
<211>  321
<212>  DNA
<213>  Homo sapiens

<400>  216
gacatccaga tgacccagtc tccatcctcc ctgtctgcat ctgtaggaga cagagtcacc       60

atcacttgcc gggcaagtca gggcattaga aatgatttag gctggtatca gcagaaacca      120

gggaaagccc ctaagcgcct gatctatgct gcatccagtt tgcaaagtgg ggtcccatca      180

aggttcagcg gcagtggatc tgggacagaa ttcactctca caatcagcag cctgcagcct      240

gaagattttg caagttatta ctgtctacag catagtagtt tcccgtggac gttcggccag      300

gggaccaagg tggaaatcaa a                                                321


<210>  217
<211>  342
<212>  DNA
<213>  Homo sapiens

<400>  217
gacatcgtga tgacccagtc tccagactcc ctggctgtgt ctctgggcga gagggccgcc       60

atcaactgca agtccagcca gagtgtctta gacagctcca acatgaagag gtacttagcc      120

tggtatcagc tgaaagcagg acagcctcct aggttgctca tttacttggc ttccacccgg      180

gaatccgggg tcccggaccg attcagtggc agcgggtccg ggacagattt caatctcact      240

atcagcagcc tgcaggctga agatgtggca gtttattact gtcagcaata ttatacaacc      300

ccttcgatca ccttcggcca agggacacga ctggagatta aa                         342
```

<210> 218
<211> 342
<212> DNA
<213> Homo sapiens

<400> 218
gacatcgtga tgacccagtc tccagactcc ctggctgtgt ctctgggcga gagggccacc 60
atcaactgca agtccagcca gagtgtttta tacagctcca acaataagaa ctacttagct 120
tggtaccagc agaaaccagg tcagcctcct aagatgctca tttactgggc atctacccgg 180
gagtccgggg tccctgaccg attcagtggc agcgggtctg ggacagattt cactctcacc 240
atcagcagcc tgcaggctga agatgtggca gtttattact gtcagcaata ttatactact 300
cctcccatca ccttcggcca agggacacga ctggagatta aa 342

<210> 219
<211> 318
<212> DNA
<213> Homo sapiens

<400> 219
gaaattgtgt tgacacagtc tccagccacc ctgtctttgt ctccagggga aagagccacc 60
ctctcctgca gggccagtca gagtgttagt atctacttag cctggtacca acagaaacct 120
ggccaggctc ccaggctcct catctatgat tcatccaaca gggccactgg catcccagcc 180
aggttcagtg gcagtgggtc tgggacagac ttcactctca ccatcagcag cctagagccc 240
gaagattttg cggtttatta ctgtcagcag cgtagcagcg ggcgaacgtt cggccaaggg 300
accaaggtgg agatcaaa 318

<210> 220
<211> 324
<212> DNA
<213> Homo sapiens

<400> 220
gaaattgtgt tgacgcagtc tccaggcacc ctgtctttgt ctccagggga aagagccacc 60
ctctcctgca gggccagtca gactgttacc aacaactact tagcctggta ccaacacaaa 120
cctggcctgg cgcccaggct cctcatcttt gatgcatcca tcagggccac tggcatccca 180
gacaggttca gtggcagtgg gtctggggca gacttcactc tcaccatcag cagactggag 240
cctgaagatt ttacattcta ttactgtcag caatatggta tttcacctcg aacttttggc 300
caggggacca aggtggagat caaa 324

<210> 221
<211> 336
<212> DNA
<213> Homo sapiens

<400> 221
gatattgtga tgacccagac tccactctct ctgtccgtca cccctggaca gccggcctcc 60
atctcctgca agtctagtca gagtctcctg gatagtgatg gaaggaccta tttcttttgg 120
tatttgcaga agccaggcca gtctccacaa ctcctgatct atgaagtttc caaccggttc 180
tctggagtgc cagataggtt cagtggcagc gggtcaggga cagatttcac actgaaaatc 240
agccgggtgg agtctgaaga tgttggggtt tattactgca tgcaaggtac acaccatccg 300
tggacgttcg gccaagggac caaggtggaa atcaaa 336

<210> 222
<211> 340
<212> DNA
<213> Homo sapiens

<400> 222
gacatcgtga tgacccagtc tccagactcc ctggctgtgt ctctgggcga gagggccacc 60
gtcaactgca agtccagcca gagtgtttta tacagctcca acagtaagaa ctacttagct 120
tggtaccagc agaaaccagg acagcctcct aagctgctca tttactgggc atctacccgg 180
gaatccgggg tccctgaccg attcagtggc agcgggtctg ggacagattt cactctcacc 240
atcagcagcc tgcaggctga agatgtggca gtgtattact gtcagcaata ttatagtact 300
cctctcactt tcggcggagg gaccaaggtg gagatcaaac 340

<210> 223
<211> 322
<212> DNA

<213> Homo sapiens

<400> 223
gacatccaga tgacccagtc tccatcctcc ctgtctgcat ctgtgggaga cagagtcacc 60
atcacttgcc gggcaagtca gggcattggg aatgatttag gctggtatca gcatgaacca 120
gggaaagccc ctaagcgcct gatctatgca gcatccagtt tgcaaagtgg ggtcccatcg 180
aggttcagcg gcagtgcatc tgggacagaa ttcactctca caatcaccag cctgcagcct 240
gaagattttg caacttatta ctgtctacaa catactactt tcccgtggac gttcggccaa 300
gggaccaagg tggaaatcaa ac 322

<210> 224
<211> 325
<212> DNA
<213> Homo sapiens

<400> 224
gaaattgtgt tgacacagtc tccagccacc ctgtctttgt ctccagggga aagagccacc 60
ctctcctgca gggccagtca gagtgttggc agtcacttcg cctggtacca acagaaacct 120
ggccaggctc ccaggctcct catctatggt gcatccaaca gggcccctgg catcccacct 180
aggttcagtg ccagtggatc tgggacagac ttcactctca ccatcagcag cctagagcct 240
gaagattttg caatttatta ctgtcaacag cgtaggacct ggcctccgct aaccttcggc 300
caagggacac gactggagat taaac 325

<210> 225
<211> 357
<212> DNA
<213> Homo sapiens

<400> 225
gaggtgcagc tggtggagtc tgggggaggc ttggtacagc ctggagggtc cctgagactc 60
tcctgtgtag cctctggatt cagtttcagt ggtcatgaaa tgaactgggt ccgccagcct 120
ccagggaagg ggctggagtg ggtttcacac attggcagtg gtggtgatta tataggttac 180
gcagactctg tgaagggccg attcaccgtc tctagagaca acgccaagaa tttactctat 240
ctgcaaatga acagcctgag agccgacgac acggctgttt attactgtgc gaccttgctt 300
ttgcgagaca accaactgga cgtctggggc caagggacca cggtcaccgt ctcctca 357

<210> 226
<211> 363
<212> DNA
<213> Homo sapiens

<400> 226
caggtgcagc tggtggagtc tgggggaggc gtggtccagc cagggaggtc cctaagactc 60
tcctgtgcag cctctggatt caccctcagt agttgtggca tgcactggat ccgccaggct 120
ccaggcaagg ggctggagtg ggtggcagtt ataacatatg atggacgaag tcacttcaac 180
gcagacgccg tgaagggccg attcaccatc tccagagaca gatccatgaa cacggtgtct 240
ctgcaaatgg acagcctgag acccgaggac acggctgttt attactgtgt caaagaacaa 300
ggctttggtt actaccggac cgccgactac tggggccagg gaaccctggt caccgtctcc 360
tca 363

<210> 227
<211> 342
<212> DNA
<213> Homo sapiens

<400> 227
caggtgcagc tgcaggagtc gggcccagga ctggtgaggc cttcggagac cctgtccctc 60
acctgcactg tctctggtgg ctccatcagt agtgaccact ggagttggat ccggcagccc 120
ccaggcaagg gactggagtg gattgggaat gtctattaca gtgggcgcac ctactacaac 180
ccctccttca agagtcgagt caccatatca gtagccacgt ccaagaacca gttctccctg 240
aaggtgacct ctgtgaccgc cgcagacacg gccatttatt actgtgcgag gcgaaatgat 300
tttaatatct ggggccaggg gacaatggtc accgtctctt ca 342

<210> 228
<211> 369
<212> DNA
<213> Homo sapiens

<400> 228
gaggtgcagc tgttggagtc tgggggaggc ttggtacagc ctggggggtc cctgagactc 60
tcctgtgcag cctctggatt cacctttagt aaatatgccg tgagctgggt ccgccaggct 120
ccagggaagg ggctggagtg ggtctcagct gtcagtggta atggtgactc cacatactac 180
gcagaccccg tgaggggccg gttcaccatc tccagagaca attccaagaa caccctgtat 240
ctgcaaatga acagcctgag agccgaggac acggccctat attactgttc gatctggtgg 300
gggacttcag tacagtaccc attggtgctc gactactggg gcctgggaac cctggtcacc 360
gtctcctca 369

<210> 229
<211> 363
<212> DNA
<213> Homo sapiens

<400> 229
caggtgcagc tggtggagtc gggggaggc gtggtccagc ctgggaggtc cctaagactc 60
ctgtgtgcag cctctggatt caccctcagt acttgtggca tgcactggat ccgccagact 120
cctggcaagg ggctggagtg ggtggcagtt aaaacatatg acggaagaga ggagttctac 180
gcagactccg tgaagggccg attcaccatt tccagagacg agtccatgaa cacgctgtct 240
ttgcagatga acagcctgag acctgaagac acggctgtat attactgtgt caaagaacaa 300
gactacggtt actaccggac cgccgaccac tggggccagg gaaccctggt caccgtctcc 360
tca 363

<210> 230
<211> 351
<212> DNA
<213> Homo sapiens

<400> 230
caggtgcagc tgcaggaggc gggcccagga ctggtgaagc cttcacagac cctgtccctc 60
acctgcactg tctctggtgg ctccatcagc agtggtggtt actactggag ctggatccgc 120
cagcacccag ggaagggcct ggagtggatt gggtacatct attacagtgg gagcacctac 180
tacaacccgt ccctcaagag tcgagtcacc atatcagtag acacgtccaa gaaccagtat 240
tccctgaagc tgagttctgt gaccgccgca gacacggccg tatattactg tgcgagaggg 300
catggcttca acgcctactg gggccaggga accctggtca ccgtctcctc a 351

<210> 231
<211> 366
<212> DNA
<213> Homo sapiens

<400> 231
gaggtgcagc tggtggagtc cgggggaggc ttggtaaagc cgggggagtc ccttagactc 60
tcgtgtgcaa cctctggagt caacttcaac atcgcctgga tgacctgggt ccgccaggct 120
ccagggaagg gactggagtg ggttggccgt attaaaagca aaattggtgg tgggacaaca 180
gactatgctg cacccgtgaa aggcagattc accatgtcaa tagatgattc aaaaaatacc 240
ctatatctgc aaatgaacag cctgaaaacc gaggacacag ccgtgtatta ttgtaccaca 300
gtccgcaata tggccgactt gtcccttaat cactggggcc agggaaccct ggtcaccgtc 360
tcctca 366

<210> 232
<211> 354
<212> DNA
<213> Homo sapiens

<400> 232
gaggtgcagc tggtggagtc tgggggaggc ttggtacagc ctggagcgtc cctgacactg 60
tcatgtgtag tctctggatt caccttcatt ggcactgaaa tgacctggat tcgccaggct 120
ccagggaagg ggctggaggg actttcgtac atcagtggga gtggcgggac aacatactac 180
gcagagtctg tgaggggccg attcaccatc tccagagaca acgccaagaa gtcactgttt 240
ctgcaaatga ccagcctgac agccgaggac acggctgttt actactgtgc gacaggcaac 300
cggggatcac ttcctcgccg ctggggccag ggaaccctgg tcaccgtctc ctca 354

<210> 233
<211> 354
<212> DNA
<213> Homo sapiens

<400> 233
gaggtgcagc tggtggagtt tgggggaggc ttggtccagc ctggggggtc cctgagactc 60
tcctgtgtag cctctggatt cacctttagt tcctcttgga tgagttgggt ccgccaggct 120
ccagggaagg ggctggagtg cgtgggcaac ataaagccgg atgcaagttt ggtgtcctat 180
gtggactctg tgaagggccg agtcaccatc tccagagaca acgccaagaa ttcactgttt 240
ctggatatga gcagcctgag agtcgaggac acggccgtct actactgtgt gagagacggg 300
tgggacacct tctttgactc ctggggccag ggaaccctgg tcaccgtctc ctca 354

<210> 234
<211> 339
<212> DNA
<213> Homo sapiens

<400> 234
gaggtgcagc tggtggagtc cgggggaggc ttagttcagc cggggggtc cctgagactc 60 tcctgtgcag cctctggatt cacctttagt aactactgga tgaggtgggt ccgccaatct 120
ccagggaagg ggctggtgtg ggtctcacat attaaccctg atgggagttt tacaaactac 180
gcggactccg tgaagggccg attcaccatc tccagagaca acaccaagaa cacactgtat 240
ctgcaaatga acagtctgag agccgaggac acggctgtgt attactgtgt gaattttcaa 300
ctggggtggg gccagggaac cctggtcacc gtctcctca 339

<210> 235
<211> 369
<212> DNA
<213> Homo sapiens

<400> 235
caggtgcagc tggtggagtc tgggggaggc gtagtccagc ctgggaggtc cctgaaactc 60
tcctgtgcag tcgctggatt caccttcagg acctatgcta tgcactgggt ccgccaggct 120
ccaggcaggg ggctggagtg ggtggcactt atatcaaatg atggaaccaa aaaatactcc 180
gcagactccg tgaggggcca cttcaccatc tccagagaca attccaagga cacgctgtat 240
ctgcaaatga acagcctgcg acctgacgac acggctgtct attactgtgc gagagcggag 300
tattgtagtc ctggtgactg cttccttatt gacacctggg gccagggaac cctggtcacc 360
gtctcctca 369

<210> 236
<211> 357
<212> DNA
<213> Homo sapiens

<400> 236
caggtgcagc tggtggagtc tgggggaggc gtggtccagc ctgggaggtc cctgagactc 60
tcctgtgcag tgtctggatt caccttcagt agatacggca tgcactgggt ccgccaggct 120
ccaggcaagg ggctggagtg ggtggtagtt atatggcatg atggaagtaa tacatactat 180
gcagactccg tgaagggccg attcaccatc tccagagacg actccaagaa cacggtgtat 240
ctgcaaatga acagcctcag agtcgaggac acggctatgt attactgtct gagaggcaac 300
ccacctagca gccccaccga ctactggggc cagggaaccc tggtcaccgt ctcctca 357

<210> 237
<211> 357
<212> DNA
<213> Homo sapiens

<400> 237
gaggtgcagc tgttggagtc tgggggaggc ttggtacagc ctggggggtc cctgagactc 60
tcctgtgaag tctctggatt catctttagc aactatgcca tgacctgggt ccgccaggct 120
ccagggaagg ggctgcagtg ggtctcagct attggcacta gtggtggtga cacacactac 180
gcagactccg tgaagggccg gttcaccatc tccagacaca attcccagaa caccctgtat 240
ctgcagatga acagcctgag agccgaggac acggccatat attactgtgc gaaagtcgtt 300
tatagcaggc ctcctatgga cgtctggggc caagggacca cggtcaccgt ctcctca 357

<210> 238
<211> 354
<212> DNA
<213> Homo sapiens

<400> 238
gaggtgcagc tggtggagtc tgggggaggc ttggtccagc ctggggggtc cctgagactc 60
tcctgtgcag cctctggatt cacctttagt aatcgttgga tgagttgggt ccgccaggct 120
ccagggaagg ggctggaatg ggtggccaac ataaacgaag atggaagtca gaaacactat 180
gtggactctg tgaggggccg attcaccatc tccagagaca acgccaagaa ctcactgtct 240
ctgcaaatgg acagcctgag agtcgaggat acggccgtgt attattgcgc gagagcatcg 300
agggagaccg gtgaacctta ctggggccag ggaaccctgg tcaccgtctc ctca 354

<210> 239
<211> 329
<212> DNA
<213> Homo sapiens

<400> 239
ttgtgatgac tcagtctcca ctctccctgc ccgtcaccct tggacagtcg gcctccatct 60
cctgcaggtc tagtcgaagc ctcgtattca gtgatggaaa cacctacttg aattggtttc 120
agcagaggcc aggccgatct ccaaggcgcc taatttataa ggtttctaag cgggactctg 180
gggtcccaga cagattcagc ggcagtgggt cagacactga tttcacactg aaaatcagca 240
gggtggaggc tgaggatgtt ggggtttatt actgcatgca aggtacacac tggcggacgt 300
tcggccaagg gaccaaggtg gagatcaaa 329

<210> 240
<211> 321
<212> DNA
<213> Homo sapiens

<400> 240
gacatccaga tgacccagtc tccttccaca ctgtctgcat ctgtgggaga cagagtcacc 60
atcacttgcc gggccagtca gagtattaat tcctggttgg cctggtatca gcggaaacca 120
gggaaaaccc ctaaactcct catctatgag gcgtccagtt tagaaagtgg ggtcccatca 180
aggttcagcg gcagtagatc tgggacagag ttcaccctca ccatcagcag cctgcaggct 240
gatgattttg caacttatta ctgccaccag tatgataaat atccgtggac gttcggccaa 300
gggaccaagg tggagatcaa a 321

<210> 241

<211> 324
<212> DNA
<213> Homo sapiens

<400> 241
gaaattgtgt tgacgcagtc tccaggcacc ctgtctttgt ctccagggga aagagccacc 60
ctctcctgca gggccagtca gagtgtgacc aacaactatt tggtctggca ccagcagaaa 120
cctggccagg ctcccaggct cctcatttct gatgcatcca acagggccac tggcatccca 180
gacaggttca gtggcagtgg gtctgggaca gacttcactc tcaccatcaa cagactggag 240
cctgaagatt tcgcagtgta ttactgtcag caatacggta gctcaccttt cactttcggc 300
cctgggacca aagtggatat caaa 324

<210> 242
<211> 324
<212> DNA
<213> Homo sapiens

<400> 242
gaaatagtga tgacgcagtc tccagccacc ctgtctgtgt ctccagggga aagagtcacc 60
ctctcctgca gggccagtca gagtattggc agcagcttag cctggtacct gcagaaacct 120
ggccaggctc ccagagtcct catctatggt gcatccacca ggacccctgg caccccagcc 180
aggttcagtg gcagtgggtc tgggacagag ttcactctca ccatcagcag cctgcagtct 240
gaagatcttg cgatttatta ttgtcaacag tatagtaagt ggcctccgat caccttcggc 300
caagggacac gactggagat taaa 324

<210> 243
<211> 321
<212> DNA
<213> Homo sapiens

<400> 243
gacatccaga tgacccagtc tccctccatc ctgtctgcat ctgtaggaga cagagtcacc 60
atcaattgcc gggccagtca gagtattaat gcctggttgg cctggtatca gcagaaacca 120
gggaaagccc ctaaattcct aatttataag gcgtctagtt tagaaagtgg ggtctcgtca 180
aggttcagcg gcagtggatc tgggacagaa ttcaccctca tcatcagcag cctgcagcct 240
gatgattttg caacttatta ctgccaacag tatgataaat atccgtggac gttcggccgg 300
gggaccaagg tggagatcaa a 321

<210> 244
<211> 324
<212> DNA
<213> Homo sapiens

<400> 244
gaaattgtgt tgacgcagtc tccaggcacc ctgtctttct ctccagggga tagagccacc 60
ctctcctgca gggccagtca gagtgttagc agcagctcct tagcctggta ccagcagaga 120
cctggccagg ctcccagcct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta actcacctcg gacgttcggc 300
caagggacca aggtggagat caaa 324

<210> 245
<211> 324
<212> DNA
<213> Homo sapiens

<400> 245
gaaattgtgt tgacgcagtc tccaggcacc ctgtctttgt ctccagggga aagagccacc 60
ctctcctgca gggccagtca gagtgtcagc agcacctact taaactggta ccagcagaag 120
cctggccagg ctcccaggct cctcatctat ggtgcgtcca ccagggccac tggcatccca 180
gacaggttca gtggcagtgg gtctggggca gacttcactc taaccatcag cagactggag 240
cctgaagact ttgcagtgta ctactgtcag caatatgatg actcacggtg gacgttcggc 300
caagggacca aggtggaaat caaa 324

<210> 246
<211> 336
<212> DNA
<213> Homo sapiens

<400> 246
gatattgtga tgactcagtc tccactctcc ctgcccgtca cccctggaga gccggcctcc 60
atctcctgca ggtctggtca gagcctcctg tatagtgatg gaaacaacta tttggattgg 120
tatctgcaga agccagggca gtctccacag ctcctgatct atttgggttc taatcgggcc 180
tccggggtcc ctgacaggtt cagtggcagt gaatcaggca cagattttac actgaaaatc 240
agcagagtgg aggctgggga tgttgggatt tattactgca tgcaagctct acgaagtccg 300
tacacttttg gccaggggac caaggtggag atcaaa 336

<210> 247
<211> 332
<212> DNA
<213> Homo sapiens

<400> 247
ttgtgatgac tcagtctcca ctctccctgc ccgtcaccct tggacagccg gcctccatct 60
cctgcaggtc tagtcaaagc cccgtataca gtgatggaaa cacctacctg aattggtttc 120
agcagaggcc aggccaatct ccaaggcgcc taatttataa ggtttctaac cgggactccg 180
gggtcccaga cagattcagc ggcagtgggt caggcactga tttcacactg aatatcagcg 240
gggtggaggc tgaggacgtt ggggtttatt actgcatgca aggtagatac tggccgtaca 300
cttttggcca ggggaccaag gtggagatca aa 332

<210> 248
<211> 324
<212> DNA
<213> Homo sapiens

<400> 248
gaaattgtgt tgacgcagtc tccaggcacc ctgtctttct ctccagggga tagagccacc 60
ctctcctgca gggccagtca gagtgtaagc agcagcgcct tagcctggta ccagcagaaa 120
cctggccagg ctcccagcct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta actcacctcg gacgttcggc 300
caagggacca aggtggaaat caaa 324

<210> 249
<211> 330
<212> DNA
<213> Homo sapiens

<400> 249
ttgtgatgac tcagtctcca ctctccctgc ccgtcaccct tggacagtcg gcctccatct 60
cctgcaggtc tagtcgaagc ctcgtattca gtgatggaaa cacctacttg aattggtttc 120
agcagaggcc aggccgatct ccaaggcgcc taatttataa ggtttctaag cgggactctg 180
gggtcccaga cagattcagc ggcagtgggt cagacactga tttcacactg aaaatcagca 240
gggtggaggc tgaggatgtt ggggtttatt actgcatgca aggtacacac tggcggacgt 300
tcggccaagg gaccaaggtg gaaatcaaac 330

<210> 250
<211> 321
<212> DNA
<213> Homo sapiens

<400> 250
gacatccaga tgacccagtc tccttcctca ctgtctgcat ctgtagggga cagaatcacc 60
atcacttgtc gggcgagtca gggcattaac aattatttag cctggtttca gcagaagcca 120
gggaaagccc ctaagaccct gatctactct acatccactt tgcaaagtgg ggtcccatca 180
aagttcagcg gcagtggatc tgggacagtt ttcactctca ccatcagcaa cctgcagcct 240
gaagattttg caacttatta ctgtcaacaa tataatagtt acccgctcac tttcggcgga 300
gggaccaagg tggagatcaa a 321

<210> 251
<211> 321
<212> DNA
<213> Homo sapiens

<400> 251
gacatccaga tgacccagtc tccatcctcc ctgtctgcat ctgtaggaga cagagtcacc 60
atcacttgcc gggcaagtca gaccattagc aactatttaa attggtttca gcagaaacca 120
gggaaagccc ctaggctcct gatctatgct gcatcgagtt tgcaaagtgg ggtcccatca 180
aggttcagtg gcagtggatc tgtgacagat ttcactctca ccatcagcag tctgcaacct 240
gaagattttg caacttactt ctgtcaacag agttacagca ccccgtggac gttcggccaa 300
gggaccaagg tggaaatcaa a 321

<210> 252
<211> 332
<212> DNA
<213> Homo sapiens

<400> 252
ttgtgatgac tcagtctcca ttctccctgc ccgtcaccct tggacagccg gcctccatct 60
cctgcaggtc tagtcaaagc ctcgtataca gtgatggaaa cacctacttg aattggtttc 120
agcagaggcc aggccaatct ccaaggcgcc tgatttataa gctttctaac cgggactctg 180
gggtcccaga cagattcagc ggcagtgggt caggcactga tttcacactg aaaatcagca 240
gggtggaggc tgaggatgtt ggggtttatt actgcatgca agctacacac tggccttgga 300
cgttcggcca agggaccaag gtggaaatca aa 332

<210> 253
<211> 116
<212> PRT
<213> Homo sapiens

<400> 253

Glu Val Gln Leu Leu Glu Ser Gly Gly Gly Leu Val Gln Pro Gly Gly
1               5                   10                  15

Ser Leu Arg Val Ser Cys Ala Ala Ser Gly Phe Thr Phe Ser Asn Ser
            20                  25                  30

Gly Met Ser Trp Val Arg Gln Ala Pro Gly Lys Gly Leu Glu Trp Val
        35                  40                  45

Ser Gly Ile Gly Gly Gly Gly Gly Ser Ala Tyr Tyr Ala Asp Ser Val
    50                  55                  60

```
Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Lys Gly Val Thr Ser Phe Asp Tyr Trp Gly Gln Gly Ile Leu Val
            100                 105                 110

Thr Val Ser Ser
        115


<210>  254
<211>  118
<212>  PRT
<213>  Homo sapiens

<400>  254

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asp
            20                  25                  30

Tyr Met Ser Trp Val Arg Gln Ala Pro Gly Lys Gly Leu Glu Trp Val
        35                  40                  45

Ser Val Met Tyr Ser Gly Gly Ser Thr Tyr Tyr Ala Asp Ala Val Lys
    50                  55                  60

Asp Arg Phe Thr Ile Ser Arg Asp Asn Ser Lys Asn Ile Leu Tyr Leu
65                  70                  75                  80

Gln Met Asn Ser Leu Arg Ala Glu Asp Thr Ala Val Tyr Tyr Cys Ala
                85                  90                  95

Arg Asp Pro Gly Ile Arg Asn Gly Met Gly Val Trp Gly Gln Gly Thr
            100                 105                 110
```

```
Thr Val Thr Val Ser Ser
        115


<210>  255
<211>  121
<212>  PRT
<213>  Homo sapiens

<400>  255

Glu Val Gln Leu Leu Glu Ser Gly Gly Ala Leu Val Gln Pro Gly Gly
1               5                   10                  15


Ser Leu Arg Leu Ser Cys Ala Ala Ser Gly Phe Thr Phe Thr Ser Phe
            20                  25                  30


Ala Met Gly Trp Val Arg Gln Ala Pro Gly Lys Gly Leu Glu Trp Val
        35                  40                  45


Ser Ala Val Thr Gly Ser Gly Tyr Tyr Lys Asn Tyr Ala Asp Ser Val
    50                  55                  60


Lys Gly Arg Phe Thr Ile Ser Arg Asp Asn Ser Asp Asn Thr Leu Tyr
65                  70                  75                  80


Leu Gln Met Asn Ser Leu Arg Gly Asp Asp Thr Ala Leu Tyr Tyr Cys
                85                  90                  95


Ala Lys Ala His Arg Gly Asp Trp Asn Asn Phe Phe Asp Tyr Trp Gly
            100                 105                 110


Gln Gly Thr Leu Val Thr Val Ser Ser
        115                 120


<210>  256
<211>  115
<212>  PRT
<213>  Homo sapiens

<400>  256
```

Gln Val Gln Leu Gln Glu Ser Gly Pro Gly Leu Val Lys Pro Ser Glu
1 5 10 15

Thr Leu Ser Leu Thr Cys Ser Val Ser Ala Asp Ser Phe Ser Pro Tyr
20 25 30

Lys Trp Ser Trp Ile Arg Gln Pro Pro Gly Lys Gly Leu Glu Trp Ile
35 40 45

Gly Tyr Ile Tyr Ser Ser Gly Asn Thr Asn Tyr Asn Pro Pro Leu Lys
50 55 60

Ser Arg Val Thr Ile Ser Leu Asp Thr Ser Lys Asn Gln Val Ser Leu
65 70 75 80

Arg Leu Ser Ser Val Ala Ala Ala Asp Thr Ala Met Tyr Tyr Cys Ala
85 90 95

Arg Glu Trp Ser Gly Phe Asp Phe Trp Gly Gln Gly Thr Met Val Thr
100 105 110

Val Ser Ser
115

<210> 257
<211> 115
<212> PRT
<213> Homo sapiens

<400> 257

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Asn Tyr
20 25 30

Trp Met Ser Trp Val Arg Gln Ala Pro Gly Lys Gly Leu Glu Trp Val
35 40 45

Ala Asn Ile Lys Gln Asp Gly Arg Glu Thr Tyr Tyr Val Asp Ser Val
    50                  55                  60

Lys Gly Arg Phe Thr Ile Ser Arg Asp Asn Ala Lys Asn Ser Val Ser
65                  70                  75                  80

Leu Gln Met Ser Ser Leu Arg Ala Glu Asp Thr Ala Val Tyr Tyr Cys
                85                  90                  95

Ala Arg Gly Gln Trp Leu Ala Phe Arg Gly Gln Gly Thr Leu Val Thr
            100                 105                 110

Val Ser Ser
        115

<210>  258
<211>  116
<212>  PRT
<213>  Homo sapiens

<400>  258

Glu Val Gln Leu Val Glu Ser Gly Gly Gly Leu Val Gln Ile Gly Gly
1               5                   10                  15

Ser Leu Arg Leu Ser Cys Ala Ala Ser Gly Phe Thr Phe Ser Thr Tyr
            20                  25                  30

Trp Met Ser Trp Val Arg Gln Ala Pro Gly Lys Gly Leu Glu Cys Val
        35                  40                  45

Ala Ser Ile Lys Glu Asp Gly Ser Glu Arg Tyr Tyr Val Asp Ser Val
    50                  55                  60

Lys Gly Arg Phe Thr Ile Ser Arg Asp Asn Ala Lys Asn Ser Leu His
65                  70                  75                  80

Leu Gln Met Asp Ser Leu Arg Ala Ala Asp Thr Ala Val Tyr Phe Cys

```
                85                  90                  95

Ala Arg Gly Arg Asn Asn Phe Arg His Trp Gly Gln Gly Thr Leu Val
            100                 105                 110

Thr Val Ser Ser
        115


<210>  259
<211>  126
<212>  PRT
<213>  Homo sapiens

<400>  259

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Trp Thr Asp Asp Thr Val Tyr Ala Asp Ser Val Lys
    50                  55                  60

Gly Arg Phe Thr Ile Ser Arg Asp Val Ser Lys Asn Met Val His Leu
65                  70                  75                  80

Gln Met Ser Ser Leu Arg Val Glu Asp Thr Ala Val Tyr Tyr Cys Ala
                85                  90                  95

Arg Glu Leu Gly Val Phe His Ser Gly Gly Asp Gln Trp Leu Gly Pro
            100                 105                 110

Leu Asp Cys Trp Gly Gln Gly Thr Leu Val Thr Val Ser Ser
        115                 120                 125
```

<210> 260
<211> 120
<212> PRT
<213> Homo sapiens

<400> 260

```
Glu Val Gln Leu Val Glu Ser Gly Gly Gly Leu Val Gln Pro Gly Gln
1               5                   10                  15

Ser Leu Arg Leu Ser Cys Thr Val Ser Gly Phe Ser Val Glu Asp His
            20                  25                  30

Gly Leu Asn Trp Val Arg Gln Ala Pro Gly Lys Gly Leu Glu Trp Val
        35                  40                  45

Gly Phe Ile Arg Arg Lys Ser Ser Gly Gly Thr Glu Tyr Ala Ala Ser
    50                  55                  60

Val Lys Gly Arg Phe Thr Ile Ser Arg Asp Asp Ser Lys Ser Ala Val
65                  70                  75                  80

Tyr Leu Gln Met Asn Ser Leu Lys Met Glu Asp Thr Gly Val Tyr Tyr
                85                  90                  95

Cys Leu Arg Trp Thr Gly Gly Val Ser Phe Gly Ala Tyr Trp Gly Gln
            100                 105                 110

Gly Thr Leu Val Thr Val Ser Ser
        115                 120
```

<210> 261
<211> 116
<212> PRT
<213> Homo sapiens

<400> 261

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Thr Ser Trp
            20                  25                  30

Met His Trp Val Arg Gln Ala Pro Gly Lys Gly Leu Val Trp Val Ser
        35                  40                  45

His Ile Asn Thr Asp Gly Ser Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Tyr Tyr His Ser Val Asp Tyr Trp Gly Gln Gly Thr Leu Val
            100                 105                 110

Thr Val Ser Ser
        115


<210>  262
<211>  117
<212>  PRT
<213>  Homo sapiens

<400>  262

Gln Val Gln Leu Gln Glu Ser Gly Pro Gly Met Val Lys Pro Ser Glu
1               5                   10                  15

Thr Leu Ser Leu Ile Cys Ser Val Ser Gly Ala Ser Val Ser Arg Asp
            20                  25                  30

His Trp Ser Trp Ile Arg Gln Ser Pro Gly Lys Gly Leu Glu Trp Ile
        35                  40                  45

Val Tyr Ile Tyr Asn Ser Glu Ser Ile Glu Tyr Asn Pro Ser Leu Lys
    50                  55                  60
```

```
Ser Arg Val Thr Ile Ser Val Asp Thr Ser Lys Asn Gln Val Ser Leu
65                  70                  75                  80

Thr Val Thr Ser Val Thr Ala Ala Asp Thr Ala Phe Tyr Tyr Cys Ala
                85                  90                  95

Arg Gly Pro Asp Ala His Lys Thr Gly Tyr Trp Gly Pro Gly Thr Leu
            100                 105                 110

Val Thr Val Ser Ser
        115


<210>  263
<211>  117
<212>  PRT
<213>  Homo sapiens

<400>  263

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Trp Met Tyr Trp Val Arg Gln Val Pro Gly Lys Gly Leu Val Cys Val
        35                  40                  45

Ser Arg Ile Asn Arg Asp Gly Ser Ile Thr Leu Tyr Ala Asp Ser Val
    50                  55                  60

Arg Gly Arg Phe Thr Ile Ser Arg Asp Asn Ala Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Asp Ser Tyr Thr Ser Pro Asp Tyr Trp Gly Gln Gly Thr Leu
            100                 105                 110
```

```
Val Thr Val Ser Ser
        115


<210>  264
<211>  120
<212>  PRT
<213>  Homo sapiens

<400>  264

Glu Val Gln Leu Val Glu Ser Gly Gly Gly Leu Val Lys Pro Gly Glu
1               5                   10                  15


Ser Leu Arg Leu Ser Cys Ala Thr Ser Gly Leu Thr Phe Ser Asn Val
            20                  25                  30


Trp Met Ser Trp Val Arg Gln Ala Pro Gly Lys Gly Leu Glu Trp Val
        35                  40                  45


Gly Arg Leu Lys Asn Lys Pro Asp Gly Gly Thr Thr Asp Tyr Ala Ala
    50                  55                  60


Pro Val Lys Gly Arg Phe Thr Ile Ser Arg Asp Asp Ser Lys Thr Thr
65                  70                  75                  80


Leu Tyr Leu Glu Met Asn Ser Leu Lys Val Glu Asp Thr Ala Val Tyr
                85                  90                  95


Tyr Cys Thr Thr Asp Asn Gly Val Lys Ala Phe Asp Ile Trp Gly Gln
            100                 105                 110


Gly Thr Met Val Thr Val Ser Ser
        115                 120


<210>  265
<211>  118
<212>  PRT
<213>  Homo sapiens
```

<400> 265

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Trp Met His Trp Val Arg Gln Thr Pro Glu Lys Gly Leu Val Trp Val
35 40 45

Ser Arg Ile His Pro Asp Gly Ser Asn Thr Ala Tyr Ala Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Val Glu Asp Thr Ala Phe Tyr Tyr Cys
85 90 95

Thr Arg Gly Gly Ser Gly Ala Thr Ile Asn Tyr Trp Gly Gln Gly Ile
100 105 110

Leu Val Thr Val Ser Ser
115

<210> 266
<211> 124
<212> PRT
<213> Homo sapiens

<400> 266

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Gly Gly
20 25 30

Thr Tyr Ser Trp Thr Trp Ile Arg Gln Pro Ala Gly Lys Gly Leu Glu 35 40 45

Trp Ile Gly Arg Ile Phe Ala Ser Gly Ser Thr Asn Tyr Asn Ser Ser
50 55 60

Leu Lys Ser Arg Val Thr Ile Leu Val Asp Thr Ser Lys Asn Leu Phe
65 70 75 80

Ser Leu Ser Leu Ser Ser Val Thr Ala Ala Asp Thr Ala Met Tyr Tyr
85 90 95

Cys Ala Arg Asp Arg Ala Gly Ile Asp Gly Tyr Asn Tyr Tyr Phe Asp
100 105 110

Tyr Trp Gly Gln Gly Thr Leu Val Thr Val Ser Ser
115 120

<210> 267
<211> 119
<212> PRT
<213> Homo sapiens

<400> 267

Val Gln Leu Val Gln Ser Gly Ala Glu Val Lys Lys Pro Gly Ala Ser
1 5 10 15

Val Lys Val Ser Cys Lys Thr Ser Gly Tyr Thr Leu Thr Ser Tyr Tyr
20 25 30

Met His Trp Val Arg Gln Ala Pro Gly Gln Gly Leu Glu Trp Leu Gly
35 40 45

Val Ile Arg Pro Thr Asp Ala Ser Thr Arg Ser Ala Gln Lys Phe Gln
50 55 60

Gly Arg Ile Thr Met Thr Arg Asp Thr Ser Thr Ser Thr Leu Tyr Met
65 70 75 80

```
Glu Leu Ser Ser Leu Arg Ser Glu Asp Thr Ala Val Tyr Tyr Cys Ala
                85                  90                  95

Arg Glu Val Ala Ala Glu Gly Lys Ala Phe Asp Tyr Trp Gly Gln Gly
            100                 105                 110

Thr Leu Val Thr Val Ser Ser
        115
```

```
<210>  268
<211>  116
<212>  PRT
<213>  Homo sapiens

<400>  268

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Gly Lys Ile Lys Glu Asp Gly Ser Glu Lys Tyr Tyr Val Asp Ser Val
    50                  55                  60

Lys Gly Arg Phe Ala Ile Ser Arg Asp Asn Ala Lys Asn Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gln Ser Tyr Pro Gly Ile Trp Gly Gln Gly Thr Met Val
            100                 105                 110

Thr Val Ser Ser
        115
```

```
<210>  269
<211>  121
<212>  PRT
<213>  Homo sapiens

<400>  269

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Asn Tyr
            20                  25                  30

Tyr Trp Gly Trp Ile Arg Gln Pro Pro Gly Glu Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Gly Arg Ala Tyr Ser Ser Gly Tyr Tyr Tyr Leu Ile Asp Tyr Trp Gly
            100                 105                 110

Gln Gly Thr Leu Val Thr Val Ser Ser
        115                 120


<210>  270
<211>  107
<212>  PRT
<213>  Homo sapiens

<400>  270

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Thr Tyr Leu
            20                  25                  30

Ala Trp Tyr Gln Gln Lys Pro Gly Gln Ala Pro Arg Leu Leu Phe Tyr
        35                  40                  45

Gly Thr Ser Ser Arg Ala Thr Gly Ile Pro Asp Arg Phe Ser Gly Ser
    50                  55                  60

Gly Ser Gly Thr Asp Phe Thr Leu Thr Ile Ser Arg Val Glu Pro Glu
65                  70                  75                  80

Asp Phe Ala Val Tyr Tyr Cys Gln Gln Phe Gly Ser Ser Pro Pro Asp
                85                  90                  95

Thr Phe Gly Gly Gly Thr Lys Val Glu Ile Lys
            100                 105


<210>  271
<211>  110
<212>  PRT
<213>  Homo sapiens

<400>  271

Val Met Thr Gln Ser Pro Leu Ser Leu Pro Val Thr Leu Gly Gln Pro
1               5                   10                  15

Ala Ser Ile Ser Cys Arg Ala Ser Gln Gly Leu Glu His Ser Asp Gly
            20                  25                  30

Asn Thr Tyr Leu Ser Trp Phe Gln Gln Arg Pro Gly Arg Ser Pro Arg
        35                  40                  45

Arg Leu Ile Tyr Lys Val Ser Asn Arg Asp Ser Gly Val Pro Asp Arg
    50                  55                  60

Phe Ser Gly Ser Gly Ser Gly Thr Asp Phe Thr Leu Glu Ile Thr Arg
65                  70                  75                  80
```

```
Val Glu Ala Glu Asp Val Gly Val Tyr Tyr Cys Met Gln Val Thr His
                85                  90                  95

Trp Pro Arg Thr Phe Gly Gln Gly Thr Lys Val Glu Ile Lys
            100                 105                 110

<210>  272
<211>  107
<212>  PRT
<213>  Homo sapiens

<400>  272

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Pro His
            20                  25                  30

Leu Ala Trp Tyr Gln Gln Lys Pro Gly Gln Ser Pro Arg Leu Leu Ile
        35                  40                  45

Tyr Asp Ala Ser Asn Arg Ala Thr Gly Ile Pro Ala Arg Phe Ser Gly
    50                  55                  60

Ser Glu Ser Gly Thr Asp Phe Thr Leu Ser Ile Ser Ser Leu Glu Pro
65                  70                  75                  80

Glu Asp Phe Ala Val Tyr Tyr Cys Gln Gln Ser Gly Asp Trp Pro Leu
                85                  90                  95

Thr Phe Gly Gly Gly Thr Lys Val Glu Ile Lys
            100                 105

<210>  273
<211>  108
<212>  PRT
<213>  Homo sapiens
```

<400> 273

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Tyr Ser Ile
            20                  25                  30

Tyr Phe Ala Trp Tyr Gln Gln Lys Pro Gly Gln Ala Pro Arg Pro Leu
        35                  40                  45

Ile Tyr Gly Val Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Arg Thr Phe Gly Gln Gly Thr Lys Val Glu Ile Lys
            100                 105
```

<210> 274
<211> 110
<212> PRT
<213> Homo sapiens

<400> 274

```
Val Met Thr Gln Ser Pro Leu Ser Leu Pro Val Thr Leu Gly Gln Pro
1               5                   10                  15

Ala Ser Ile Ser Cys Arg Ser Ser Arg Ser Leu Val Tyr Ser Asp Gly
            20                  25                  30

Gly Thr Tyr Leu Asn Trp Phe Gln Gln Arg Pro Gly Gln Ser Pro Arg
        35                  40                  45

Arg Leu Ile Trp His Val Ser Asn Arg Asp Ser Gly Val Pro Asp Arg
```

```
    50                  55                  60

Phe Ser Gly Ser Gly Ser Gly Thr Asp Phe Thr Leu Lys Ile Ser Arg
65                  70                  75                  80

Val Glu Ala Glu Asp Val Gly Val Tyr Tyr Cys Met Gln Gly Thr His
                85                  90                  95

Trp Pro Tyr Thr Phe Gly Gln Gly Thr Lys Val Glu Ile Lys
            100                 105                 110


<210>  275
<211>  107
<212>  PRT
<213>  Homo sapiens

<400>  275

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Arg Lys Leu
            20                  25                  30

Leu Asn Trp Tyr Gln Gln Arg Pro Gly Lys Ala Pro Asn Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr His Phe Ser Phe Thr Ile Thr Ser Leu Gln Pro
65                  70                  75                  80

Glu Asp Ile Ala Thr Tyr Tyr Cys Gln Gln Phe Glu Ser Phe Pro Arg
                85                  90                  95

Thr Phe Gly Pro Gly Thr Lys Val Asp Ile Lys
            100                 105
```

```
<210>  276
<211>  109
<212>  PRT
<213>  Homo sapiens

<400>  276

Glu Ile Val Met Thr Gln Ser Pro Ala Thr Leu Ser Val Ser Pro Gly
1               5                   10                  15


Glu Thr Ala Thr Leu Ser Cys Arg Ala Ser Gln Ser Val Asn Ser Phe
            20                  25                  30


Leu Ala Trp Tyr Gln Gln Lys Pro Gly Gln Ala Pro Arg Leu Leu Ile
        35                  40                  45


Tyr Ala Ala Ser Thr Arg Ala Thr Gly Val Pro Ala Arg Phe Ser Gly
    50                  55                  60


Ser Gly Ser Gly Thr Glu Phe Thr Leu Thr Ile Ser Ser Leu Gln Ser
65                  70                  75                  80


Glu Asp Phe Ala Val Tyr Tyr Cys His Gln Tyr Lys Asn Trp Pro Pro
                85                  90                  95


Met Gly Thr Phe Gly Pro Gly Thr Lys Val Asp Ile Lys
            100                 105


<210>  277
<211>  106
<212>  PRT
<213>  Homo sapiens

<400>  277

Asp Ile Gln Met Thr Gln Ser Pro Ser Thr Leu Ser Ser Ser Val Gly
1               5                   10                  15


Asp Arg Val Thr Ile Thr Cys Arg Ala Ser Gln Asn Ile Gly Val Ser
            20                  25                  30
```

```
Leu Ala Trp Tyr Gln Gln Lys Pro Gly Lys Ala Pro Asn Leu Leu Ile
        35                  40                  45

Tyr Lys Ala Ser Tyr Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ile Tyr Leu Thr
                85                  90                  95

Phe Gly Gln Gly Thr Lys Val Glu Ile Lys
            100                 105


<210>  278
<211>  110
<212>  PRT
<213>  Homo sapiens

<400>  278

Val Met Thr Gln Ser Pro Leu Ser Leu Pro Val Thr Leu Gly Gln Pro
1               5                   10                  15

Ala Ser Ile Ser Cys Arg Ser Ser Gln Ser Leu Ala His Ser Asp Gly
            20                  25                  30

Asn Thr Tyr Leu Asn Trp Phe Gln Gln Arg Pro Gly Gln Ser Pro Arg
        35                  40                  45

Arg Leu Ile Tyr Lys Val Ser Asn Arg Asp Ser Gly Val Pro Asp Arg
    50                  55                  60

Phe Ser Gly Ser Gly Ser Gly Thr Asp Phe Thr Leu Lys Ile Ser Arg
65                  70                  75                  80

Val Glu Ala Glu Asp Val Gly Val Tyr Tyr Cys Met Gln Gly Thr His
                85                  90                  95
```

```
Trp Pro Tyr Thr Phe Gly Gln Gly Thr Lys Val Glu Ile Lys
            100                 105                 110


<210>  279
<211>  113
<212>  PRT
<213>  Homo sapiens

<400>  279

Asp Ile Val Met Thr Gln Ser Pro Asp Ser Leu Ala Val Ser Leu Gly
1               5                   10                  15


Glu Arg Ala Thr Ile Asn Cys Lys Ser Ser Gln Ser Val Leu Tyr Ser
            20                  25                  30


Pro Asn Asn Lys Asn Tyr Leu Ala Trp Phe Gln Gln Lys Pro Gly Gln
        35                  40                  45


Pro Pro Lys Leu Leu Ile Tyr Trp Ala Ser Ile Arg Asp Ser Gly Val
    50                  55                  60


Pro Asp Arg Phe Ser Gly Ser Gly Ser Gly Thr Asp Phe Thr Leu Thr
65                  70                  75                  80


Val Ser Ser Leu Gln Ala Asp Asp Val Ala Val Tyr Tyr Cys Gln Gln
                85                  90                  95


Tyr Ala Ala Thr Pro Trp Thr Phe Gly Gln Gly Thr Lys Val Glu Ile
            100                 105                 110


Lys



<210>  280
<211>  110
<212>  PRT
<213>  Homo sapiens

<400>  280
```

```
Val Met Thr Gln Ser Pro Leu Ser Leu Pro Val Thr Leu Gly Gln Pro
1               5                   10                  15

Ala Ser Ile Ser Cys Ser Ser Ser Gln Ser Leu Val Tyr Ser Asp Gly
            20                  25                  30

Asn Thr Tyr Leu Ser Trp Phe Gln Gln Arg Pro Gly Gln Ser Pro Arg
        35                  40                  45

Arg Leu Ile Tyr Lys Val Ser Asn Arg Asp Ser Gly Val Pro Asp Arg
    50                  55                  60

Phe Ser Gly Ser Gly Ser Gly Thr Asp Phe Thr Leu Arg Ile Ser Arg
65                  70                  75                  80

Val Glu Ala Glu Asp Val Gly Val Tyr Tyr Cys Met Gln Gly Ser His
                85                  90                  95

Trp Pro Leu Thr Phe Gly Gly Gly Thr Lys Val Glu Ile Lys
            100                 105                 110


<210>  281
<211>  113
<212>  PRT
<213>  Homo sapiens

<400>  281

Asp Ile Val Met Thr Gln Ser Pro Asp Ser Leu Ala Val Ser Leu Gly
1               5                   10                  15

Glu Arg Ala Thr Ile Asn Cys Lys Ser Ser Leu Ser Val Leu Ser Ser
            20                  25                  30

Ser Asn Asn Glu Asn Tyr Leu Ala Trp Tyr Gln Gln Lys Pro Gly Gln
        35                  40                  45

Pro Pro Lys Leu Leu Ile Tyr Trp Ala Ser Thr Arg Gly Ser Gly Val
    50                  55                  60
```

Pro Gly Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys His Gln
85 90 95

Tyr Tyr Thr Thr Pro Phe Ala Phe Gly Pro Gly Thr Lys Val Asp Ile
100 105 110

Lys

<210> 282
<211> 107
<212> PRT
<213> Homo sapiens

<400> 282

Asp Ile Gln Met Thr Gln Ser Pro Ser Ser Leu Ser Ala Ser Val Gly
1 5 10 15

Asp Ser Val Thr Ile Thr Cys Arg Ala Ser Gln Ser Ile Ser Ser Tyr
20 25 30

Leu Asn Trp Tyr His Gln Lys Pro Gly Lys Ala Pro Lys Leu Leu Ile
35 40 45

Tyr Gly Ala Ser Thr Leu Gln Ser Gly Val Pro Ser Arg Phe Gly Gly
50 55 60

Ser Gly Ser Gly Thr Asp Phe Thr Leu Thr Ile Ser Ser Leu Gln Pro
65 70 75 80

Asp Asp Phe Ala Thr Tyr Tyr Cys Gln Gln Ser His Ser Ser Pro Leu
85 90 95

Thr Phe Gly Gly Gly Thr Lys Val Glu Ile Lys

```
            100                 105


<210>  283
<211>  106
<212>  PRT
<213>  Homo sapiens

<400>  283

Asp Ile Gln Met Thr Gln Ser Pro Ser Thr Leu Ser Ala Ser Val Gly
1               5                   10                  15


Asp Arg Val Thr Ile Thr Cys Arg Ala Ser Arg Ser Leu Gly Ser Trp
            20                  25                  30


Leu Ala Trp Tyr Gln Gln Ser Pro Gly Lys Ala Pro Lys Leu Leu Ile
        35                  40                  45


Tyr Lys Ala Ser Thr Leu Glu Ser Gly Val Pro Ser Arg Phe Ser Gly
    50                  55                  60


Ser Gly Ser Gly Thr Glu Phe Thr Leu Thr Ile Ser Ser Leu Gln Pro
65                  70                  75                  80


Asp Asp Phe Ala Thr Tyr Tyr Cys Gln Gln Tyr Tyr Ser Phe Tyr Thr
                85                  90                  95


Phe Gly Gln Gly Thr Lys Val Glu Ile Lys
            100                 105


<210>  284
<211>  113
<212>  PRT
<213>  Homo sapiens

<400>  284

Asp Ile Val Met Thr Gln Ser Ala Asp Ser Leu Ala Val Ser Leu Gly
1               5                   10                  15


Glu Arg Ala Thr Ile Asn Cys Lys Ser Ser Gln Ser Leu Phe Tyr Ser
```

```
            20                  25                  30

Ser Asn Lys Lys Asn Tyr Leu Ala Trp Tyr Gln Gln Lys Pro Gly Gln
        35                  40                  45

Pro Pro Lys Leu Ile Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Thr Ser Leu Arg Ala Glu Asp Val Ala Val Tyr Tyr Cys Gln Gln
                85                  90                  95

Tyr Tyr Thr Pro Pro Leu Thr Phe Gly Gly Gly Thr Lys Val Glu Ile
            100                 105                 110

Lys


<210>  285
<211>  107
<212>  PRT
<213>  Homo sapiens

<400>  285

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Gly Asp
            20                  25                  30

Leu Val Trp Tyr Gln Gln Lys Pro Gly Gln Ala Pro Arg Leu Leu Ile
        35                  40                  45

Tyr Gly Ala Thr Thr Arg Ala Ser Gly Val Pro Ala Arg Phe Ser Gly
    50                  55                  60
```

```
Ser Gly Ser Gly Thr Glu Phe Thr Leu Thr Ile Ser Ser Leu Gln Ser
65                  70                  75                  80

Glu Asp Phe Ala Ile Tyr Tyr Cys Gln Gln Tyr Asn Asn Trp Pro Arg
                85                  90                  95

Thr Phe Gly Gln Gly Thr Lys Val Glu Ile Lys
            100                 105


<210>  286
<211>  107
<212>  PRT
<213>  Homo sapiens

<400>  286

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Asn Asn
            20                  25                  30

Leu Ala Trp Phe Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr His Cys Gln His Tyr His Asn Trp Pro Pro
                85                  90                  95

Thr Phe Gly Gln Gly Thr Lys Val Glu Ile Lys
            100                 105


<210>  287
<211>  122
<212>  PRT
```

<213> Homo sapiens

<400> 287

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn His
            20                  25                  30

Gly Met His Trp Leu Arg Gln Thr Pro Gly Lys Gly Leu Glu Trp Val
        35                  40                  45

Ala Val Ile Ser Tyr Asp Gly Ser Thr Lys Tyr Tyr Ala Asp Ser Val
    50                  55                  60

Lys Gly Arg Cys Thr Leu Ser Arg Asp Asn Ser Lys Glu Thr Val Phe
65                  70                  75                  80

Leu Gln Met Asn Ser Leu Arg Pro Glu Asp Thr Ala Val Tyr Tyr Cys
                85                  90                  95

Ala Lys Gly Cys Ser Asn Gly Gly Asn Cys Phe Leu Ile Asp Tyr Trp
            100                 105                 110

Gly Pro Gly Thr Leu Val Thr Val Ser Ser
        115                 120
```

<210> 288
<211> 123
<212> PRT
<213> Homo sapiens

<400> 288

```
Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Asp Phe Ser Ile Tyr
            20                  25                  30
```

```
Gly Met Asn Trp Val Arg Gln Ala Pro Gly Lys Gly Leu Glu Trp Val
        35                  40                  45

Ser Val Ile Ser Gly Asp Gly Thr Ile Ile Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Val Asn Ser Val Arg Ala Glu Asp Thr Ala Val Tyr Tyr Cys
                85                  90                  95

Ala Lys Gly Gly Tyr Tyr Glu Ser Gly Thr Met Arg Ala Phe Asp Ile
            100                 105                 110

Trp Gly Gln Gly Thr Met Val Thr Val Ser Ser
        115                 120


<210>  289
<211>  116
<212>  PRT
<213>  Homo sapiens

<400>  289

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Ser Met Ser Trp Val Arg Gln Ala Pro Gly Lys Gly Leu Glu Trp Val
        35                  40                  45

Ala Ser Ile Lys Pro Glu Gly Ser Glu Lys Phe Tyr Val Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Gly Glu Asp Thr Ala Val Tyr Tyr Cys
                85                  90                  95

Ala Arg Gly Glu Ser Asn Phe Arg Tyr Trp His Gln Gly Thr Leu Val
            100                 105                 110

Thr Val Ser Ser
        115

<210>  290
<211>  119
<212>  PRT
<213>  Homo sapiens

<400>  290

Glu Val Gln Leu Val Glu Ser Gly Gly Ala Leu Val Gln Pro Gly Gly
1               5                   10                  15

Ser Leu Arg Leu Ser Cys Ala Ala Ser Gly Phe Ile Phe Ser Asn Ser
            20                  25                  30

Trp Met Gly Trp Phe Arg Gln Ala Pro Gly Lys Arg Pro Glu Phe Val
        35                  40                  45

Ala Asn Ile Lys Pro Asp Gly Ser Glu Lys Phe His Val Asp Ser Val
    50                  55                  60

Lys Gly Arg Phe Thr Ile Ser Arg Asp Asn Ala Glu Asn Ser Leu Tyr
65                  70                  75                  80

Leu Leu Met Asn Ser Leu Arg Ala Glu Asp Thr Ala Val Tyr Tyr Cys
                85                  90                  95

Ala Arg Asp Ser Thr Ser Pro Ala Arg Phe Gly Tyr Trp Gly Gln Gly
            100                 105                 110

Thr Leu Val Thr Val Ser Ser
```

115

<210> 291
<211> 118
<212> PRT
<213> Homo sapiens

<400> 291

```
Glu Val Gln Leu Val Glu Thr Gly Gly Gly Leu Ile Gln Pro Gly Gly
1               5                   10                  15


Ser Leu Arg Leu Ser Cys Ala Ala Ser Gly Leu Asn Val Asn Ser Tyr
            20                  25                  30


Tyr Met Asn Trp Val Arg Gln Ala Pro Gly Lys Gly Leu Glu Trp Val
        35                  40                  45


Ser Val Ile Tyr Ser Gly Gly Gly Thr Asn Tyr Ala Asp Ser Val Arg
    50                  55                  60


Gly Arg Phe Ile Ile Ser Arg Asp Asn Ser Arg Asn Ala Leu Tyr Leu
65                  70                  75                  80


Gln Met Asn Ser Leu Arg Ala Glu Asp Thr Ala Val Tyr Tyr Cys Ala
                85                  90                  95


Thr Gly Gly Met Thr Ser Ser Trp Tyr Gly Tyr Trp Gly Gln Gly Thr
            100                 105                 110


Leu Val Thr Val Ser Ser
        115
```

<210> 292
<211> 124
<212> PRT
<213> Homo sapiens

<400> 292

```
Val Gln Leu Val Gln Ser Gly Ala Glu Val Lys Lys Pro Gly Ala Ser
```

```
1               5                   10                  15

Val Lys Val Ser Cys Lys Ala Ser Glu Tyr Thr Phe Ile Asn Tyr Leu
            20                  25                  30

Val Phe Trp Val Arg Gln Ala Pro Gly Gln Gly Leu Glu Trp Met Gly
        35                  40                  45

Glu Met Asn Pro Thr Arg Gly Ser Thr Ser Tyr Ala Gln Lys Phe Gln
    50                  55                  60

Gly Arg Val Thr Met Thr Arg Asp Thr Ser Thr Ser Thr Val Tyr Met
65                  70                  75                  80

Glu Leu Ser Ser Leu Arg Ser Asp Asp Thr Ala Val Tyr Tyr Cys Ser
                85                  90                  95

Met Gly Pro Pro Tyr Cys Thr Gly Gly Ser Cys Tyr Ser Ala Cys Asp
            100                 105                 110

Phe Trp Gly Pro Gly Thr Leu Val Thr Val Ser Ser
        115                 120

<210>  293
<211>  124
<212>  PRT
<213>  Homo sapiens

<400>  293

Glu Val Gln Leu Val Glu Ser Gly Gly Gly Leu Met Lys Pro Gly Gly
1               5                   10                  15

Ser Leu Arg Leu Ser Cys Ala Val Ser Gly Phe Thr Phe Thr Asn Ala
            20                  25                  30

Trp Leu Ser Trp Val Arg Gln Pro Pro Gly Lys Gly Leu Glu Trp Val
        35                  40                  45
```

```
Gly Arg Ala Tyr Ser Ser Ser Gly Gly Trp Thr Met Asp Tyr Ser Ser
    50                  55                  60

Pro Val Arg Gly Arg Phe Thr Ile Thr Arg Asp Asp Ser Lys Asn Thr
65                  70                  75                  80

Leu Tyr Leu Gln Met Asn Asn Leu Lys Thr Glu Asp Thr Ala Val Tyr
                85                  90                  95

Tyr Cys Thr Thr Asp Ile Gly Lys Gly Trp Tyr Thr His Tyr Pro Asp
            100                 105                 110

Leu Trp Gly Gln Gly Thr Leu Val Thr Val Ser Ser
        115                 120


<210>  294
<211>  121
<212>  PRT
<213>  Homo sapiens

<400>  294

Gln Val Gln Leu Val Glu Ser Gly Gly Gly Val Val Gln Pro Gly Lys
1               5                   10                  15

Ser Leu Arg Leu Ser Cys Val Ala Ser Gly Phe Thr Leu Ser Thr Cys
            20                  25                  30

Gly Met His Trp Val Arg Gln Ala Pro Gly Lys Gly Leu Glu Trp Val
        35                  40                  45

Ala Val Thr Thr Tyr Asp Gly Asp Arg Lys Tyr Asn Val Asp Ser Val
    50                  55                  60

Lys Gly Arg Phe Thr Ile Ser Arg Asp Asn Ser Lys Asn Thr Val Tyr
65                  70                  75                  80

Leu Gln Met Asp Gly Leu Lys Ala Glu Asp Thr Ala Val Tyr His Cys
                85                  90                  95
```

```
Val Lys Glu Tyr Ser Trp Gly Tyr Tyr Arg Thr Ala Asp Tyr Trp Gly
            100                 105                 110

Gln Gly Thr Leu Val Thr Val Ser Ser
        115                 120


<210>  295
<211>  117
<212>  PRT
<213>  Homo sapiens

<400>  295

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Thr Tyr
            20                  25                  30

Trp Met His Trp Val Arg Gln Pro Pro Gly Lys Gly Leu Val Trp Val
        35                  40                  45

Ser Arg Ile Asn Pro Asp Gly Ser Ser Thr Asn Tyr Ala Asp Ser Val
    50                  55                  60

Asn Gly Arg Phe Thr Ile Ser Arg Asp Asn Ala Lys Asn Thr Leu Tyr
65                  70                  75                  80

Leu Glu Met Asn Ser Leu Arg Val Glu Asp Thr Ala Leu Tyr Tyr Cys
                85                  90                  95

Ala Arg Ser Pro Gly Gly Tyr Phe Asp Tyr Trp Gly His Ser Thr Leu
            100                 105                 110

Val Thr Val Ser Ser
        115


<210>  296
<211>  116
```

<212> PRT
<213> Homo sapiens

<400> 296

Glu Val Gln Leu Val Glu Ser Gly Gly Gly Leu Val Lys Pro Gly Gly
1               5                   10                  15

Ser Leu Thr Leu Ser Cys Ala Val Ser Gly Phe Thr Phe Ser Thr Gly
            20                  25                  30

Trp Met Ser Trp Val Arg Gln Ala Pro Gly Lys Gly Leu Asp Trp Val
        35                  40                  45

Gly Arg Ile Lys Ser Lys Thr Ala Gly Gly Thr Thr Asp Tyr Ala Ala
    50                  55                  60

Pro Val Lys Asp Arg Phe Thr Ile Ser Arg Asp Asp Ser Lys Asn Thr
65                  70                  75                  80

Leu Tyr Leu Gln Leu Ser Ser Leu Lys Thr Glu Asp Thr Ala Val Tyr
                85                  90                  95

Tyr Cys Thr Thr Asp Asp Leu Lys Asn Trp Gly Gln Gly Thr Leu Val
            100                 105                 110

Thr Val Ser Ser
        115

<210> 297
<211> 129
<212> PRT
<213> Homo sapiens

<400> 297

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Ser Met Asn Trp Val Arg Gln Val Pro Gly Lys Gly Leu Glu Trp Val
        35                  40                  45

Ser Tyr Thr Ser Thr Lys Ser Asp Ile Lys Tyr Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Gly Arg Asp Cys Tyr Gly Gly Asn Cys Val Ile Tyr Phe His
            100                 105                 110

Tyr Tyr Gly Leu Asp Val Trp Gly Gln Gly Thr Thr Val Thr Val Ser
        115                 120                 125

Ser



<210>  298
<211>  121
<212>  PRT
<213>  Homo sapiens

<400>  298

Gln Val Gln Leu Val Glu Ser Gly Gly Gly Val Val Gln Pro Gly Gly
1               5                   10                  15

Ser Leu Arg Leu Ser Cys Val Val Ser Gly Phe Thr Leu Ser Ser Cys
            20                  25                  30

Gly Met His Trp Val Arg Gln Ser Pro Gly Lys Gly Leu Glu Trp Leu
        35                  40                  45

Ser Val Ser Thr Tyr Asp Gly Asn Gln Lys Tyr Tyr Ala Ala Ser Val
```

```
    50                  55                  60

Lys Gly Arg Phe Leu Ile Ser Arg Asp Thr Ser Lys Asn Thr Val Tyr
65                  70                  75                  80

Leu His Met Asn Ser Leu Thr Ala Glu Asp Thr Ala Leu Tyr Tyr Cys
                85                  90                  95

Val Lys Glu Ser Ala Thr Gly Trp Tyr Arg Thr Ala Asp Tyr Trp Gly
            100                 105                 110

Gln Gly Thr Leu Val Thr Val Ser Ser
        115                 120

<210>  299
<211>  122
<212>  PRT
<213>  Homo sapiens

<400>  299

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ile
            20                  25                  30

Phe Met Ser Trp Val Arg Gln Ala Pro Gly Gln Gly Leu Glu Trp Val
        35                  40                  45

Ser Val Ile Tyr Thr Asp Gly Lys Thr Tyr Tyr Ala His Ser Val Glu
    50                  55                  60

Gly Arg Phe Thr Ile Ser Arg Asp Asp Ser Lys Asn Met Val Tyr Leu
65                  70                  75                  80

Gln Leu Ser Ser Leu Arg Thr Glu Asp Thr Ala Val Tyr Tyr Cys Ala
                85                  90                  95
```

```
Arg Asp Ile Pro Thr Thr Phe Gly Ile Gly Glu Ala Phe Asp Ile Trp
            100                 105                 110

Gly Gln Gly Thr Met Val Thr Val Ser Ser
        115                 120


<210>  300
<211>  115
<212>  PRT
<213>  Homo sapiens

<400>  300

Val Gln Leu Val Gln Ser Gly Ala Glu Val Lys Lys Pro Gly Ala Ser
1               5                   10                  15

Val Lys Leu Ser Cys Lys Thr Ser Gly Tyr Ser Phe Thr Ser Asn Tyr
            20                  25                  30

Leu His Trp Val Arg Gln Ala Pro Gly Gln Gly Leu Glu Trp Met Gly
        35                  40                  45

Met Val Tyr Pro Asn Asp Gly Thr Thr Thr Tyr Ala Gln Lys Phe Gln
    50                  55                  60

Gly Arg Val Thr Met Thr Ser Glu Thr Ser Thr Thr Thr Ile Tyr Met
65                  70                  75                  80

Asp Leu Ser Gly Leu Thr Ser Glu Asp Thr Ala Ile Tyr Tyr Cys Ala
                85                  90                  95

Arg Asp Asp Ser Ala Phe Asp Tyr Trp Gly Gln Gly Thr Leu Val Thr
            100                 105                 110

Val Ser Ser
        115


<210>  301
<211>  121
<212>  PRT
```

<213> Homo sapiens

<400> 301

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Ile Phe Ser Ser Asn
            20                  25                  30

Gly Met His Trp Val Arg Gln Ala Pro Gly Lys Gly Leu Glu Trp Val
        35                  40                  45

Ala Val Ile Ser Ser Asp Gly Ser Arg Arg Tyr Tyr Ala Asp Ser Met
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Asp Asp Thr Ala Val Tyr Tyr Cys
                85                  90                  95

Ala Lys Gly Cys Ser Gly Glu Asn Cys Phe Tyr Met Asp Asp Trp Gly
            100                 105                 110

Lys Gly Thr Thr Val Thr Val Ser Ser
        115                 120
```

<210> 302
<211> 128
<212> PRT
<213> Homo sapiens

<400> 302

```
Val Gln Leu Val Gln Ser Gly Ala Glu Val Lys Lys Pro Gly Ala Ser
1               5                   10                  15

Leu Lys Val Ser Cys Lys Ala Ser Gly Tyr Thr Phe Arg Gln Asn Tyr
            20                  25                  30
```

```
Phe His Trp Val Arg Gln Ala Pro Gly Gln Gly Leu Glu Trp Met Gly
        35                  40                  45

Val Ile Asn Pro Ser Asp Gly Ser Thr Lys Phe Ala Gln Lys Phe Gln
    50                  55                  60

Gly Arg Val Ser Met Thr Arg Asp Thr Ser Thr Ser Thr Val Tyr Met
65                  70                  75                  80

Asp Leu Ser Ser Leu Thr Ser Glu Asp Thr Ala Val Tyr Tyr Cys Thr
                85                  90                  95

Arg Glu Ile Gly Ala Val Val Val Asp Ala Thr Ser Leu Gly Trp Leu
            100                 105                 110

Gly Tyr Phe Asp Tyr Trp Gly Gln Gly Thr Leu Val Thr Val Ser Ser
        115                 120                 125


<210>  303
<211>  115
<212>  PRT
<213>  Homo sapiens

<400>  303

Glu Val Gln Leu Val Glu Ser Gly Gly Gly Leu Val Gln Pro Gly Gly
1               5                   10                  15

Ser Leu Ser Leu Ser Cys Glu Ala Ser Gly Leu Thr Phe Ser Gly Tyr
            20                  25                  30

Trp Met Asn Trp Val Arg Gln Ala Pro Gly Lys Gly Leu Glu Trp Val
        35                  40                  45

Ala Asn Ile Asn Pro Glu Gly Ser Glu Arg Arg Tyr Val Glu Ser Val
    50                  55                  60

Gln Gly Arg Phe Thr Val Ser Arg Asp Asn Pro Lys Asn Thr Leu Tyr
65                  70                  75                  80
```

```
Leu Gln Met Asn Ser Leu Arg Val Glu Asp Thr Ala Leu Tyr Tyr Cys
                85                  90                  95

Ala Gly Trp Gly Arg Thr Gln Asp Trp Gly Gln Gly Ala Leu Val Thr
            100                 105                 110

Val Ser Ser
        115


<210>  304
<211>  121
<212>  PRT
<213>  Homo sapiens

<400>  304

Gln Val Gln Leu Val Glu Ser Gly Gly Gly Val Val Gln Pro Gly Arg
1               5                   10                  15

Ser Leu Arg Leu Ser Cys Ala Ala Ser Gly Leu Thr Phe Ser Asn Tyr
            20                  25                  30

Gly Met His Trp Val Arg Gln Ala Pro Gly Lys Gly Leu Glu Trp Val
        35                  40                  45

Ala Val Val Ser Ala Arg Gly Gly Thr Thr Tyr Tyr Ala Asp Ser Val
    50                  55                  60

Lys Gly Arg Phe Thr Ile Ser Arg Asp Asn Ser Lys Asn Thr Met Ser
65                  70                  75                  80

Leu Gln Met Asn Gly Leu Arg Pro Asp Asp Thr Ala Val Tyr Phe Cys
                85                  90                  95

Thr Lys Glu Gly Ala Pro Pro Gly Lys Tyr Ala Phe Asp Ile Trp Gly
            100                 105                 110

Gln Gly Thr Met Val Thr Val Ser Ser
```

```
        115                 120


<210>  305
<211>  120
<212>  PRT
<213>  Homo sapiens

<400>  305

Glu Val Gln Leu Val Glu Ser Gly Gly Gly Leu Val Gln Pro Gly Gly
1               5                   10                  15


Ser Leu Arg Leu Ser Cys Ala Ala Ser Gly Phe Thr Phe Ser Asp Tyr
            20                  25                  30


Arg Met Asp Trp Val Arg Gln Ala Pro Gly Arg Gly Leu Glu Trp Ile
        35                  40                  45


Ala Arg Ile Arg His Arg Asp Ala Gly Tyr Ser Thr Glu Tyr Ala Ala
    50                  55                  60


Ser Val Arg Gly Arg Phe Thr Val Ser Arg Asp Asp Ser Gln Ser Thr
65                  70                  75                  80


Leu Tyr Leu Gln Met Asn Ser Leu Lys Ala Asp Asp Thr Ala Val Tyr
                85                  90                  95


Ile Cys Leu Lys Asp Ser Ser Gln Tyr Ser Phe Asp Ala Trp Gly Gln
            100                 105                 110


Gly Thr Met Val Thr Val Ser Ser
        115                 120


<210>  306
<211>  113
<212>  PRT
<213>  Homo sapiens

<400>  306

Asp Ile Val Met Thr Gln Ser Pro Asp Ser Leu Ala Val Ser Leu Gly
```

1 5 10 15

Glu Arg Ala Thr Ile Asn Cys Lys Ser Ser Gln Ser Ile Leu Ser Arg
20 25 30

Ser Asn Asn Lys Asn Tyr Leu Ala Trp Tyr Gln Gln Lys Pro Gly Gln
35 40 45

Pro Pro Lys Leu Leu Leu Tyr Trp Ala Ser Thr Arg Glu Ser Gly Val
50 55 60

Pro Asp Arg Phe Ser Val Ser Gly Ser Gly Ser Asp Phe Thr Leu Thr
65 70 75 80

Ile Ser Ser Leu Gln Ala Glu Asp Val Ala Val Tyr Tyr Cys Gln Gln
85 90 95

Tyr Tyr Asn Ala Pro Leu Thr Phe Gly Gly Gly Thr Lys Val Glu Ile
100 105 110

Lys

<210> 307
<211> 107
<212> PRT
<213> Homo sapiens

<400> 307

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Thr Val Ser Arg Tyr
20 25 30

Leu Ala Trp Tyr Gln Gln Lys Pro Gly Gln Ala Pro Arg Leu Leu Ile
35 40 45

```
Tyr Ala Ala Ser Asn Arg Ala Thr Gly Ile Pro Thr Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Ser Asn Trp Pro Ala
                85                  90                  95

Thr Phe Gly Gly Gly Thr Lys Val Glu Ile Lys
            100                 105


<210>  308
<211>  107
<212>  PRT
<213>  Homo sapiens

<400>  308

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Arg Asp Arg
            20                  25                  30

Leu Asn Trp Tyr Gln Gln Lys Pro Gly Lys Ala Pro Asn Leu Leu Ile
        35                  40                  45

Tyr Asp Ala Ser Ser Leu Glu Thr Gly Val Pro Ser Arg Phe Arg Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Val Ser Phe Pro Arg
                85                  90                  95

Thr Phe Gly Pro Gly Thr Lys Val Asp Ile Lys
            100                 105
```

<210> 309
<211> 110
<212> PRT
<213> Homo sapiens

<400> 309

```
Glu Ile Val Leu Thr Gln Ser Pro Gly Ile Leu Ser Leu Ser Pro Gly
1               5                   10                  15

Glu Arg Ala Thr Leu Ser Cys Arg Ala Ser Gln Ser Val Ser Ser Arg
            20                  25                  30

Ser Leu Ser Trp Tyr Gln Gln Arg Pro Gly Leu Ala Pro Arg Leu Leu
        35                  40                  45

Ile Tyr Ala Ala Ser Ser Arg Ala Ala Val Thr Pro Asp Arg Phe Thr
    50                  55                  60

Ala Ser Gly Ser Gly Thr Asp Phe Thr Leu Thr Ile Ser Ser Leu Glu
65                  70                  75                  80

Pro Glu Asp Phe Ala Val Tyr Tyr Cys Gln His Tyr Gly Thr Ser Pro
                85                  90                  95

Pro Arg Tyr Thr Phe Gly Gln Gly Thr Lys Val Glu Ile Lys
            100                 105                 110
```

<210> 310
<211> 113
<212> PRT
<213> Homo sapiens

<400> 310

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu His Ser
            20                  25                  30
```

```
Ser Asn Asn Lys Asn Tyr Phe Ala Trp Tyr Gln Gln Lys Pro Gly Gln
        35                  40                  45

Pro Pro Lys Leu Leu Ile His Trp Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Thr Ile Tyr Tyr Cys Gln Gln
                85                  90                  95

Tyr Tyr Ser Thr Pro Tyr Thr Phe Gly Gln Gly Thr Lys Val Glu Ile
            100                 105                 110

Lys



<210>  311
<211>  109
<212>  PRT
<213>  Homo sapiens

<400>  311

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Pro Ser Leu Asp Ser Ala
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Val Thr Gly Ile Pro Asp Arg Phe Ser
    50                  55                  60

Gly Ser Ala Ser Gly Thr Asp Phe Thr Leu Thr Ile Ser Arg Leu Glu
65                  70                  75                  80
```

```
Pro Glu Asp Phe Ala Val Tyr Tyr Cys Gln Arg Tyr Gly Asn Ser Pro
                85                  90                  95

Pro Tyr Thr Phe Gly Gln Gly Thr Lys Val Glu Ile Lys
            100                 105


<210>  312
<211>  113
<212>  PRT
<213>  Homo sapiens

<400>  312

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Tyr Ser
            20                  25                  30

Ser Ser Asn Lys Asn Tyr Leu Ala Trp Phe Gln Gln Lys Pro Gly Gln
        35                  40                  45

Ala Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Thr Glu Asp Val Ala Val Tyr Tyr Cys Leu Gln
                85                  90                  95

Tyr Arg Ser Ala Pro Phe Thr Phe Gly Gly Gly Thr Lys Val Glu Ile
            100                 105                 110

Lys


<210>  313
```

```
<211>  107
<212>  PRT
<213>  Homo sapiens

<400>  313

Asp Ile Gln Met Thr Gln Ser Pro Ser Thr Gln Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Ala Val Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Thr Tyr Pro Trp
                85                  90                  95

Thr Phe Gly Pro Gly Thr Lys Val Glu Ile Lys
            100                 105


<210>  314
<211>  107
<212>  PRT
<213>  Homo sapiens

<400>  314

Glu Ile Val Met Thr Gln Ser Pro Ala Ser Leu Ser Val Ser Pro Gly
1               5                   10                  15

Glu Thr Ala Thr Leu Ser Cys Arg Ala Ser Gln Ser Val Gly Ser Thr
            20                  25                  30

Leu Ala Trp Tyr Gln Gln Lys Pro Gly Gln Ala Pro Arg Leu Leu Ile
```

```
        35                  40                  45

Tyr Asn Val Phe Thr Arg Ala Ala Gly Val Pro Ala Arg Phe Ser Gly
    50                  55                  60

Ser Gly Ser Arg Thr Glu Phe Thr Leu Thr Ile Ser Ser Leu Gln Ser
65                  70                  75                  80

Glu Asp Phe Ala Val Tyr Tyr Cys Gln Gln Tyr Ser Thr Trp Leu Trp
                85                  90                  95

Thr Phe Gly Gln Gly Thr Lys Val Glu Ile Lys
            100                 105


<210>  315
<211>  107
<212>  PRT
<213>  Homo sapiens

<400>  315

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ala Ser Leu His Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Arg Ile Pro Tyr
                85                  90                  95
```

```
Ser Phe Gly Pro Gly Thr Lys Val Glu Ile Lys
            100                 105


<210>  316
<211>  112
<212>  PRT
<213>  Homo sapiens

<400>  316

Asp Ile Val Met Thr Gln Ser Pro Leu Ser Leu Ser Val Thr Pro Gly
1               5                   10                  15


Glu Pro Ala Ser Ile Ser Cys Arg Ser Ser Gln Ser Leu Leu Gln Gly
            20                  25                  30


Asn Gly His Asn Tyr Leu Asp Trp Tyr Leu Gln Lys Pro Gly Gln Ser
        35                  40                  45


Pro Gln Leu Leu Ile Tyr Leu Gly Ser Ile Arg Ala Ser Gly Val Pro
    50                  55                  60


Asp Arg Phe Ser Gly Ser Gly Ser Gly Thr Asp Phe Ile Leu Lys Ile
65                  70                  75                  80


Ser Arg Val Glu Ala Glu Asp Val Gly Val Tyr Tyr Cys Met Arg Ala
                85                  90                  95


Leu Gln Thr Pro Tyr Thr Phe Gly Gln Gly Thr Lys Val Glu Ile Lys
            100                 105                 110


<210>  317
<211>  107
<212>  PRT
<213>  Homo sapiens

<400>  317

Asp Ile Gln Met Thr Gln Ser Pro Ser Thr Leu Ser Ala Ser Val Gly
1               5                   10                  15
```

```
Asp Arg Val Thr Leu Thr Cys Arg Ala Ser Glu Thr Leu Asn Asn Trp
            20                  25                  30

Leu Ala Trp Phe Gln Gln Lys Pro Gly Lys Ala Pro Thr Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Asp Phe Ala Leu Thr Ile Ser Ser Leu Gln Pro
65                  70                  75                  80

Asp Asp Phe Ala Thr Tyr Tyr Cys His Gln Tyr Asn Lys Tyr Pro Trp
                85                  90                  95

Thr Phe Gly Gln Gly Thr Lys Val Glu Ile Lys
            100                 105


<210>  318
<211>  106
<212>  PRT
<213>  Homo sapiens

<400>  318

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Trp
            20                  25                  30

Leu Ala Trp Tyr Gln Gln Lys Ala Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

```
Asp Asp Phe Ala Thr Tyr Tyr Cys Gln Gln Tyr Tyr Ser Trp Gly Thr
                85                  90                  95

Phe Gly Gln Gly Thr Lys Val Glu Ile Lys
            100                 105

<210>  319
<211>  112
<212>  PRT
<213>  Homo sapiens

<400>  319

Asp Ile Val Met Thr Gln Thr Pro Leu Ser Leu Pro Val Thr Leu Gly
1               5                   10                  15

Gln Pro Ala Ser Ile Ser Cys Ile Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Gln Ser Thr Trp Thr Leu Gly Gln Gly Thr Lys Val Glu Ile Lys
            100                 105                 110

<210>  320
<211>  113
<212>  PRT
<213>  Homo sapiens

<400>  320
```

```
Asp Ile Val Met Thr Gln Ser Pro Asp Ser Leu Ala Val Pro Leu Gly
1               5                   10                  15

Glu Arg Ala Thr Ile Asn Cys Thr Ser Ser Gln Thr Val Leu Ser Ser
            20                  25                  30

Ser Asn Asn Lys Asn Tyr Leu Val Trp Tyr Gln Gln Lys Pro Gly Gln
        35                  40                  45

Pro Pro Lys Leu Leu Leu Tyr Trp Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Cys Tyr Asn Ala Pro Leu Thr Phe Gly Arg Gly Thr Lys Val Glu Ile
            100                 105                 110

Lys


<210>  321
<211>  108
<212>  PRT
<213>  Homo sapiens

<400>  321

Glu Ile Val Met Thr Gln Ser Pro Ala Thr Leu Ser Val Phe Pro Gly
1               5                   10                  15

Glu Gly Val Thr Leu Ser Cys Arg Ala Ser Gln Ser Ile Ser Asn Asn
            20                  25                  30

Leu Ala Trp Tyr Gln Gln Lys Pro Gly Gln Ala Pro Arg Leu Leu Met
        35                  40                  45
```

```
Tyr Asp Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Val Thr Phe Gly Gln Gly Thr Lys Val Glu Ile Lys
            100                 105


<210>  322
<211>  110
<212>  PRT
<213>  Homo sapiens

<400>  322

Val Met Thr Gln Ser Pro Leu Ser Leu Pro Val Thr Leu Gly Gln Ser
1               5                   10                  15

Ala Ser Val Ser Cys Arg Ser Ser Gln Ser Leu Gly Pro Ser Asp Gly
            20                  25                  30

Ser Thr Arg Leu Asp Trp Phe Gln Gln Arg Pro Gly Gln Ser Pro Arg
        35                  40                  45

Arg Leu Ile Tyr Ala Val Ser Asn Arg Asp Ser Gly Val Pro Asp Arg
    50                  55                  60

Phe Ser Gly Ser Gly Ser Gly Ser Asp Phe Thr Leu Arg Ile Ser Arg
65                  70                  75                  80

Val Glu Ala Glu Asp Val Gly Val Tyr Tyr Cys Met Gln Tyr Thr Tyr
                85                  90                  95

Trp Pro His Thr Phe Gly Gln Gly Thr Lys Val Glu Ile Lys
```

100 105 110

<210> 323
<211> 109
<212> PRT
<213> Homo sapiens

<400> 323

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Ser
20 25 30

Leu Ala Trp Tyr Gln Gln Lys Pro Gly Gln Ala Pro Arg Leu Leu Ile
35 40 45

Tyr Asp Ala Ser Lys Arg Ala Thr Asp Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln His Arg Gly Glu Trp Pro Pro
85 90 95

Gly Ala Thr Phe Gly Pro Gly Thr Lys Val Asp Ile Lys
100 105

<210> 324
<211> 107
<212> PRT
<213> Homo sapiens

<400> 324

Asp Ile Gln Leu Thr Gln Ser Pro Ser Phe Leu Ser Ala Ser Val Gly
1 5 10 15

Asp Arg Val Thr Ile Thr Cys Arg Ala Ser Gln Gly Ile Asp Thr Arg

```
            20                  25                  30

Leu Ile Trp Tyr Gln Gln Lys Pro Gly Glu Ala Pro Lys Leu Leu Ile
        35                  40                  45

Tyr Glu Ala Ser Thr Leu Gln Ser Gly Ala Pro Ser Arg Phe Ser Gly
    50                  55                  60

Ser Gly Phe Gly Thr Glu Phe Thr Leu Thr Ile Ser Ser Leu Gln Pro
65                  70                  75                  80

Glu Asp Phe Ala Thr Tyr Tyr Cys Gln Gln Phe Lys Gly Tyr Pro Leu
                85                  90                  95

Thr Phe Gly Gly Gly Thr Lys Val Glu Ile Lys
            100                 105


<210>  325
<211>  115
<212>  PRT
<213>  Homo sapiens

<400>  325

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser His
            20                  25                  30

Tyr Trp Ser Trp Ile Arg Gln Pro Pro Ala Lys Gly Leu Glu Trp Ile
        35                  40                  45

Gly Tyr Ile Tyr His Ser Gly Met Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80
```

```
Lys Leu Ser Ser Val Thr Ala Ala Asp Thr Ala Val Tyr Tyr Cys Ala
                85                  90                  95

Arg Gly Asp Gly Tyr Asn Phe Phe Trp Gly Gln Gly Thr Leu Val Thr
            100                 105                 110

Val Ser Ser
        115


<210>  326
<211>  125
<212>  PRT
<213>  Homo sapiens

<400>  326

Gln Val Gln Leu Val Glu Ser Gly Gly Gly Val Val Gln Pro Gly Gly
1               5                   10                  15

Ser Leu Arg Leu Ser Cys Ala Ala Ser Gly Leu Thr Phe Ser Asn Gln
            20                  25                  30

Asp Phe His Trp Val Arg Gln Ala Pro Gly Lys Gly Leu Glu Trp Val
        35                  40                  45

Ala Phe Ile Arg Tyr Asp Gly Gly Phe Lys Asn Tyr Ala Asp Ser Val
    50                  55                  60

Lys Gly Arg Phe Thr Ile Ser Arg Asp Asn Ser Gln Lys Met Leu Tyr
65                  70                  75                  80

Leu Gln Met Asp Ser Leu Arg Val Glu Asp Thr Ala Val Tyr Tyr Cys
                85                  90                  95

Ala Lys Cys Gly Ala Glu Asp Ser Thr Thr Val Trp Leu Asn Trp Phe
            100                 105                 110

Asp Pro Trp Gly Gln Gly Thr Leu Val Thr Val Ser Ser
        115                 120                 125
```

<210> 327
<211> 120
<212> PRT
<213> Homo sapiens

<400> 327

```
Glu Val Gln Leu Leu Glu Ser Gly Gly Gly Leu Val Glu Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Asp Ser Gly Gly Ser Thr Tyr Tyr Ala Asp Ser Val
    50                  55                  60

Lys Gly Arg Phe Thr Ile Ser Arg Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asn Tyr Phe Gly Ser Gly Ser Pro Asp Tyr Trp Gly Gln
            100                 105                 110

Gly Thr Leu Val Thr Val Ser Ser
        115                 120
```

<210> 328
<211> 115
<212> PRT
<213> Homo sapiens

<400> 328

```
Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Ala Ser Ile Ser Ser His
            20                  25                  30

Tyr Trp Ser Trp Ile Arg Gln Pro Pro Gly Lys Gly Leu Glu Trp Ile
        35                  40                  45

Gly Tyr Ile Tyr His Ser Gly Ile Thr Asn Tyr Asn Pro Ser Leu Lys
    50                  55                  60

Ser Arg Val Thr Ile Ser Ile Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Arg Gly Asp Gly Tyr Asn Phe Tyr Trp Gly Gln Gly Thr Leu Val Thr
            100                 105                 110

Val Ser Ser
        115

<210>  329
<211>  126
<212>  PRT
<213>  Homo sapiens

<400>  329

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Thr Trp Val Arg Gln Ala Pro Gly Lys Gly Leu Glu Trp Ile
        35                  40                  45

Ser Gly Ile Cys Cys Asn Gly Gly Cys Ser Gly Tyr Ala Asp Ser Val
    50                  55                  60
```

```
Lys Gly Arg Phe Thr Ile Ser Arg Asp Asn Ala Lys Lys Ser Leu Phe
65                  70                  75                  80

Leu Val Met Asn Ser Leu Arg Ala Glu Asp Thr Ala Leu Tyr Tyr Cys
                85                  90                  95

Val Arg Val Ala Val Pro Ala Ala Thr Tyr Thr Arg Gly Asn Asp Ala
            100                 105                 110

Phe Asp Ile Trp Gly Gln Gly Thr Met Val Thr Val Ser Ser
        115                 120                 125


<210>  330
<211>  119
<212>  PRT
<213>  Homo sapiens

<400>  330

Glu Val Gln Leu Val Glu Ser Gly Gly Gly Leu Val Glu Pro Gly Gly
1               5                   10                  15

Ser Leu Arg Leu Ser Cys Ala Val Ser Gly Phe Thr Phe Thr Asp Ala
            20                  25                  30

Trp Met Thr Trp Val Arg Gln Ala Pro Gly Lys Gly Leu Asp Trp Val
        35                  40                  45

Gly His Val Lys Ser Lys Tyr Asp Gly Ala Thr Thr Glu Tyr Ala Ala
    50                  55                  60

Pro Val Gln Gly Arg Phe Thr Ile Ser Arg Asp Asp Ser Lys Lys Thr
65                  70                  75                  80

Ile Tyr Leu Gln Met Asn Ser Leu Asn Thr Glu Asp Thr Gly Val Tyr
                85                  90                  95

Phe Cys Thr Thr Ala His Gly Pro Val Gly Asp His Trp Gly Gln Gly
```

```
                100                 105                 110

Thr Leu Val Thr Val Ser Ser
        115


<210>  331
<211>  126
<212>  PRT
<213>  Homo sapiens

<400>  331

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Asp Thr Ser
            20                  25                  30

Trp Met Thr Trp Val Arg Gln Ala Pro Gly Lys Gly Leu Glu Trp Val
        35                  40                  45

Ala Thr Ile Asn Gln Gly Gly Ser Asp Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Gly Cys Ser Ser Thr Arg Cys His Thr Thr Pro Gly
            100                 105                 110

Phe Asp Tyr Trp Gly Gln Gly Ala Leu Val Thr Val Ser Ser
        115                 120                 125


<210>  332
<211>  117
<212>  PRT
<213>  Homo sapiens
```

<400> 332

```
Gln Leu Gln Glu Ser Gly Pro Gly Leu Val Lys Pro Ser Glu Thr Leu
1               5                   10                  15

Ser Leu Thr Cys Thr Val Ser Gly Ser Ser Ile Ser Ser Ser Ser Tyr
            20                  25                  30

Tyr Trp Gly Trp Val Arg Gln Ser Pro Gly Lys Gly Leu Glu Trp Ile
        35                  40                  45

Gly Ser Ile Tyr His Ser Gly Thr Ile Tyr Tyr Asn Pro Ser Leu Arg
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Ser Leu Ser Gly Thr Asn Ala Phe Asp Ile Trp Gly Gln Gly Thr Met
            100                 105                 110

Val Thr Val Ser Ser
        115
```

<210> 333
<211> 120
<212> PRT
<213> Homo sapiens

<400> 333

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30
```

```
Asp Met Ser Trp Val Arg Leu Ala Pro Gly Lys Gly Pro Glu Trp Val
        35                  40                  45

Ser Ala Leu Gly Ala Gly Asp Ala Trp Thr His Tyr Ala Asn Ser Val
    50                  55                  60

Arg Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Pro Arg Gly Tyr Ser Tyr Gly Tyr Phe Asp Tyr Trp Gly Gln
            100                 105                 110

Gly Thr Leu Val Thr Val Ser Ser
        115                 120

<210>  334
<211>  117
<212>  PRT
<213>  Homo sapiens

<400>  334

Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Ser Thr Tyr
            20                  25                  30

Trp Met Thr Trp Val Arg Gln Ala Pro Gly Lys Gly Leu Glu Trp Val
        35                  40                  45

Ala Asn Ile Asn Gln Asp Gly Ser Glu Lys Gln Tyr Val Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Val Glu Asp Thr Ala Ile Tyr Tyr Cys
                85                  90                  95

Ala Arg Pro Pro Ala Arg Arg Leu Asp Tyr Trp Gly Gln Gly Ser Leu
            100                 105                 110

Val Thr Val Ser Ser
        115


<210>  335
<211>  116
<212>  PRT
<213>  Homo sapiens

<400>  335

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Phe Ser Asp Tyr
            20                  25                  30

Trp Met His Trp Val Arg Gln Ala Pro Gly Lys Gly Leu Val Trp Val
        35                  40                  45

Ser Arg Ile Asn Thr Asp Gly Ser Thr Thr Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Gly His Glu Ala Trp Gly Gln Gly Thr Leu Val
            100                 105                 110

Thr Val Ser Ser
        115
```

<210> 336
<211> 117
<212> PRT
<213> Homo sapiens

<400> 336

```
Val Gln Leu Val Gln Ser Gly Ala Glu Val Lys Lys Pro Gly Ala Ser
1               5                   10                  15

Val Arg Val Ser Cys Lys Ala Ser Gly Tyr Thr Phe Thr Asn Tyr Trp
            20                  25                  30

Ile His Trp Val Arg Gln Ala Pro Gly Gln Gly Leu Glu Trp Met Gly
        35                  40                  45

Met Ile Ala Pro Lys Glu Gly Tyr Thr Phe Tyr Ala Gln Gln Leu Gln
    50                  55                  60

Gly Arg Val Thr Val Thr Arg Asp Thr Ser Thr Ser Ala Val Tyr Met
65                  70                  75                  80

Glu Leu Asn Ser Leu Arg Ser Glu Asp Thr Ala Val Tyr Phe Cys Ala
                85                  90                  95

Arg Asp Ile Pro His Ala Asn Leu Asp Tyr Trp Gly Gln Gly Thr Leu
            100                 105                 110

Val Thr Val Ser Ser
        115
```

<210> 337
<211> 121
<212> PRT
<213> Homo sapiens

<400> 337

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asp Tyr
            20                  25                  30

Thr Met Asn Trp Ala Arg Gln Ala Pro Gly Lys Gly Leu Glu Trp Val
        35                  40                  45

Ser Ala Ile Arg Glu Ser Gly Asp Ser Thr Tyr Tyr Ala Asp Ser Val
    50                  55                  60

Thr Gly Arg Phe Thr Ile Ser Arg Asp Asn Ser Arg Asn Thr Leu Tyr
65                  70                  75                  80

Leu His Met Asn Ser Leu Arg Ala Glu Asp Thr Ala Met Tyr Phe Cys
                85                  90                  95

Val Lys Asp Arg Val Pro Pro Gly Asp Val Pro Gly Asp Phe Trp Gly
            100                 105                 110

Pro Gly Thr Leu Val Thr Val Ser Ser
        115                 120

<210>  338
<211>  107
<212>  PRT
<213>  Homo sapiens

<400>  338

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asp Met Thr His Ser
            20                  25                  30

Leu Ala Trp Tyr Gln Gln Lys Pro Gly Lys Ala Pro Asn Leu Leu Ile
        35                  40                  45

Tyr Asn Ala Tyr Thr Leu Gln Ser Gly Val Pro Ser Arg Phe Ser Gly
```

```
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ile Asn Ser Tyr Pro Arg
                85                  90                  95

Thr Phe Gly Gln Gly Thr Lys Val Glu Ile Lys
            100                 105


<210>  339
<211>  107
<212>  PRT
<213>  Homo sapiens

<400>  339

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Asn Ile Gly Thr Ala
            20                  25                  30

Leu Ala Trp Tyr Gln Gln Lys Pro Gly Gln Ala Pro Arg Leu Ile Ile
        35                  40                  45

Tyr Glu Thr Ser Asn Arg Ala Thr Asp Val Pro Ala Arg Phe Ser Gly
    50                  55                  60

Ser Gly Ser Gly Thr Asp Phe Thr Leu Thr Ile Ser Ser Leu Glu Arg
65                  70                  75                  80

Glu Asp Phe Ala Leu Tyr Tyr Cys Gln Gln Arg Ala Asp Trp Pro Leu
                85                  90                  95

Thr Phe Gly Gly Gly Thr Lys Val Glu Ile Lys
            100                 105
```

<210> 340
<211> 108
<212> PRT
<213> Homo sapiens

<400> 340

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Arg Pro Gly Gln Ala Pro Arg Leu Val Ile
        35                  40                  45

Tyr Ala Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Leu Gln Cys Ser Asn Trp Pro Met
                85                  90                  95

Tyr Thr Phe Gly Gln Gly Thr Lys Val Glu Ile Lys
            100                 105
```

<210> 341
<211> 107
<212> PRT
<213> Homo sapiens

<400> 341

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asp Ile Thr Asp Ser
            20                  25                  30
```

```
Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Thr Thr Tyr Tyr Cys Gln Gln Ile Asn Ser Tyr Pro Arg
                85                  90                  95

Thr Phe Gly Gln Gly Thr Lys Val Glu Ile Lys
            100                 105


<210>  342
<211>  107
<212>  PRT
<213>  Homo sapiens

<400>  342

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ser Tyr Tyr Cys Leu Gln His Ser Ser Phe Pro Trp
                85                  90                  95
```

```
Thr Phe Gly Gln Gly Thr Lys Val Glu Ile Lys
            100                 105


<210>  343
<211>  114
<212>  PRT
<213>  Homo sapiens

<400>  343

Asp Ile Val Met Thr Gln Ser Pro Asp Ser Leu Ala Val Ser Leu Gly
1               5                   10                  15


Glu Arg Ala Ala Ile Asn Cys Lys Ser Ser Gln Ser Val Leu Asp Ser
            20                  25                  30


Ser Asn Met Lys Arg Tyr Leu Ala Trp Tyr Gln Leu Lys Ala Gly Gln
        35                  40                  45


Pro Pro Arg Leu Leu Ile Tyr Leu Ala Ser Thr Arg Glu Ser Gly Val
    50                  55                  60


Pro Asp Arg Phe Ser Gly Ser Gly Ser Gly Thr Asp Phe Asn Leu Thr
65                  70                  75                  80


Ile Ser Ser Leu Gln Ala Glu Asp Val Ala Val Tyr Tyr Cys Gln Gln
                85                  90                  95


Tyr Tyr Thr Thr Pro Ser Ile Thr Phe Gly Gln Gly Thr Arg Leu Glu
            100                 105                 110


Ile Lys



<210>  344
<211>  114
<212>  PRT
<213>  Homo sapiens

<400>  344
```

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Met Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Pro Ile Thr Phe Gly Gln Gly Thr Arg Leu Glu
            100                 105                 110

Ile Lys


<210>  345
<211>  106
<212>  PRT
<213>  Homo sapiens

<400>  345

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ile Tyr
            20                  25                  30

Leu Ala Trp Tyr Gln Gln Lys Pro Gly Gln Ala Pro Arg Leu Leu Ile
        35                  40                  45
```

```
Tyr Asp Ser Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ser Gly Arg Thr
                85                  90                  95

Phe Gly Gln Gly Thr Lys Val Glu Ile Lys
            100                 105


<210>  346
<211>  108
<212>  PRT
<213>  Homo sapiens

<400>  346

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Thr Asn Asn
            20                  25                  30

Tyr Leu Ala Trp Tyr Gln His Lys Pro Gly Leu Ala Pro Arg Leu Leu
        35                  40                  45

Ile Phe Asp Ala Ser Ile Arg Ala Thr Gly Ile Pro Asp Arg Phe Ser
    50                  55                  60

Gly Ser Gly Ser Gly Ala Asp Phe Thr Leu Thr Ile Ser Arg Leu Glu
65                  70                  75                  80

Pro Glu Asp Phe Thr Phe Tyr Tyr Cys Gln Gln Tyr Gly Ile Ser Pro
                85                  90                  95

Arg Thr Phe Gly Gln Gly Thr Lys Val Glu Ile Lys
```

```
            100                 105


<210>  347
<211>  112
<212>  PRT
<213>  Homo sapiens

<400>  347

Asp Ile Val Met Thr Gln Thr Pro Leu Ser Leu Ser Val Thr Pro Gly
1               5                   10                  15


Gln Pro Ala Ser Ile Ser Cys Lys Ser Ser Gln Ser Leu Leu Asp Ser
            20                  25                  30


Asp Gly Arg Thr Tyr Phe Phe Trp Tyr Leu Gln Lys Pro Gly Gln Ser
        35                  40                  45


Pro Gln Leu Leu Ile Tyr Glu Val Ser Asn Arg Phe Ser Gly Val Pro
    50                  55                  60


Asp Arg Phe Ser Gly Ser Gly Ser Gly Thr Asp Phe Thr Leu Lys Ile
65                  70                  75                  80


Ser Arg Val Glu Ser Glu Asp Val Gly Val Tyr Tyr Cys Met Gln Gly
                85                  90                  95


Thr His His Pro Trp Thr Phe Gly Gln Gly Thr Lys Val Glu Ile Lys
            100                 105                 110


<210>  348
<211>  113
<212>  PRT
<213>  Homo sapiens

<400>  348

Asp Ile Val Met Thr Gln Ser Pro Asp Ser Leu Ala Val Ser Leu Gly
1               5                   10                  15


Glu Arg Ala Thr Val Asn Cys Lys Ser Ser Gln Ser Val Leu Tyr Ser
```

```
            20                  25                  30

Ser Asn Ser Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys


<210>  349
<211>  107
<212>  PRT
<213>  Homo sapiens

<400>  349

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asn Asp
            20                  25                  30

Leu Gly Trp Tyr Gln His Glu Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60
```

```
Ser Ala Ser Gly Thr Glu Phe Thr Leu Thr Ile Thr Ser Leu Gln Pro
65                  70                  75                  80

Glu Asp Phe Ala Thr Tyr Tyr Cys Leu Gln His Thr Thr Phe Pro Trp
                85                  90                  95

Thr Phe Gly Gln Gly Thr Lys Val Glu Ile Lys
            100                 105

<210>  350
<211>  108
<212>  PRT
<213>  Homo sapiens

<400>  350

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser His
            20                  25                  30

Phe Ala Trp Tyr Gln Gln Lys Pro Gly Gln Ala Pro Arg Leu Leu Ile
        35                  40                  45

Tyr Gly Ala Ser Asn Arg Ala Pro Gly Ile Pro Pro Arg Phe Ser Ala
    50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Arg Arg Thr Trp Pro Pro
                85                  90                  95

Leu Thr Phe Gly Gln Gly Thr Arg Leu Glu Ile Lys
            100                 105

<210>  351
<211>  119
<212>  PRT
```

<213> Homo sapiens

<400> 351

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Ser Phe Ser Gly His
            20                  25                  30

Glu Met Asn Trp Val Arg Gln Pro Pro Gly Lys Gly Leu Glu Trp Val
        35                  40                  45

Ser His Ile Gly Ser Gly Gly Asp Tyr Ile Gly Tyr Ala Asp Ser Val
    50                  55                  60

Lys Gly Arg Phe Thr Val Ser Arg Asp Asn Ala Lys Asn Leu Leu Tyr
65                  70                  75                  80

Leu Gln Met Asn Ser Leu Arg Ala Asp Asp Thr Ala Val Tyr Tyr Cys
                85                  90                  95

Ala Thr Leu Leu Leu Arg Asp Asn Gln Leu Asp Val Trp Gly Gln Gly
            100                 105                 110

Thr Thr Val Thr Val Ser Ser
        115
```

<210> 352
<211> 121
<212> PRT
<213> Homo sapiens

<400> 352

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Ser Cys
            20                  25                  30
```

```
Gly Met His Trp Ile Arg Gln Ala Pro Gly Lys Gly Leu Glu Trp Val
        35                  40                  45

Ala Val Ile Thr Tyr Asp Gly Arg Ser His Phe Asn Ala Asp Ala Val
    50                  55                  60

Lys Gly Arg Phe Thr Ile Ser Arg Asp Arg Ser Met Asn Thr Val Ser
65                  70                  75                  80

Leu Gln Met Asp Ser Leu Arg Pro Glu Asp Thr Ala Val Tyr Tyr Cys
                85                  90                  95

Val Lys Glu Gln Gly Phe Gly Tyr Tyr Arg Thr Ala Asp Tyr Trp Gly
            100                 105                 110

Gln Gly Thr Leu Val Thr Val Ser Ser
        115                 120

<210>  353
<211>  114
<212>  PRT
<213>  Homo sapiens

<400>  353

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Ser Ser Asp
            20                  25                  30

His Trp Ser Trp Ile Arg Gln Pro Pro Gly Lys Gly Leu Glu Trp Ile
        35                  40                  45

Gly Asn Val Tyr Tyr Ser Gly Arg Thr Tyr Tyr Asn Pro Ser Phe Lys
    50                  55                  60

Ser Arg Val Thr Ile Ser Val Ala Thr Ser Lys Asn Gln Phe Ser Leu
65                  70                  75                  80
```

```
Lys Val Thr Ser Val Thr Ala Ala Asp Thr Ala Ile Tyr Tyr Cys Ala
                85                  90                  95

Arg Arg Asn Asp Phe Asn Ile Trp Gly Gln Gly Thr Met Val Thr Val
            100                 105                 110

Ser Ser



<210>  354
<211>  123
<212>  PRT
<213>  Homo sapiens

<400>  354

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ala Val Ser Trp Val Arg Gln Ala Pro Gly Lys Gly Leu Glu Trp Val
        35                  40                  45

Ser Ala Val Ser Gly Asn Gly Asp Ser Thr Tyr Tyr Ala Asp Pro Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ser Ile Trp Trp Gly Thr Ser Val Gln Tyr Pro Leu Val Leu Asp Tyr
            100                 105                 110

Trp Gly Leu Gly Thr Leu Val Thr Val Ser Ser
```

115 120

<210> 355
<211> 121
<212> PRT
<213> Homo sapiens

<400> 355

Gln Val Gln Leu Val Glu Ser Gly Gly Gly Val Val Gln Pro Gly Arg
1 5 10 15

Ser Leu Arg Leu Leu Cys Ala Ala Ser Gly Phe Thr Leu Ser Thr Cys
20 25 30

Gly Met His Trp Ile Arg Gln Thr Pro Gly Lys Gly Leu Glu Trp Val
35 40 45

Ala Val Lys Thr Tyr Asp Gly Arg Glu Glu Phe Tyr Ala Asp Ser Val
50 55 60

Lys Gly Arg Phe Thr Ile Ser Arg Asp Glu Ser Met Asn Thr Leu Ser
65 70 75 80

Leu Gln Met Asn Ser Leu Arg Pro Glu Asp Thr Ala Val Tyr Tyr Cys
85 90 95

Val Lys Glu Gln Asp Tyr Gly Tyr Tyr Arg Thr Ala Asp His Trp Gly
100 105 110

Gln Gly Thr Leu Val Thr Val Ser Ser
115 120

<210> 356
<211> 117
<212> PRT
<213> Homo sapiens

<400> 356

Gln Val Gln Leu Gln Glu Ala Gly Pro Gly Leu Val Lys Pro Ser Gln 1 5 10 15

Thr Leu Ser Leu Thr Cys Thr Val Ser Gly Gly Ser Ile Ser Ser Gly
20 25 30

Gly Tyr Tyr Trp Ser Trp Ile Arg Gln His Pro Gly Lys Gly Leu Glu
35 40 45

Trp Ile Gly Tyr Ile Tyr Tyr Ser Gly Ser Thr Tyr Tyr Asn Pro Ser
50 55 60

Leu Lys Ser Arg Val Thr Ile Ser Val Asp Thr Ser Lys Asn Gln Tyr
65 70 75 80

Ser Leu Lys Leu Ser Ser Val Thr Ala Ala Asp Thr Ala Val Tyr Tyr
85 90 95

Cys Ala Arg Gly His Gly Phe Asn Ala Tyr Trp Gly Gln Gly Thr Leu
100 105 110

Val Thr Val Ser Ser
115

<210> 357
<211> 122
<212> PRT
<213> Homo sapiens

<400> 357

Glu Val Gln Leu Val Glu Ser Gly Gly Gly Leu Val Lys Pro Gly Glu
1 5 10 15

Ser Leu Arg Leu Ser Cys Ala Thr Ser Gly Val Asn Phe Asn Ile Ala
20 25 30

Trp Met Thr Trp Val Arg Gln Ala Pro Gly Lys Gly Leu Glu Trp Val
35 40 45

```
Gly Arg Ile Lys Ser Lys Ile Gly Gly Gly Thr Thr Asp Tyr Ala Ala
    50                  55                  60

Pro Val Lys Gly Arg Phe Thr Met Ser Ile Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Val Arg Asn Met Ala Asp Leu Ser Leu Asn His Trp
            100                 105                 110

Gly Gln Gly Thr Leu Val Thr Val Ser Ser
        115                 120


<210>  358
<211>  118
<212>  PRT
<213>  Homo sapiens

<400>  358

Glu Val Gln Leu Val Glu Ser Gly Gly Gly Leu Val Gln Pro Gly Ala
1               5                   10                  15

Ser Leu Thr Leu Ser Cys Val Val Ser Gly Phe Thr Phe Ile Gly Thr
            20                  25                  30

Glu Met Thr Trp Ile Arg Gln Ala Pro Gly Lys Gly Leu Glu Gly Leu
        35                  40                  45

Ser Tyr Ile Ser Gly Ser Gly Gly Thr Thr Tyr Tyr Ala Glu Ser Val
    50                  55                  60

Arg Gly Arg Phe Thr Ile Ser Arg Asp Asn Ala Lys Lys Ser Leu Phe
65                  70                  75                  80

Leu Gln Met Thr Ser Leu Thr Ala Glu Asp Thr Ala Val Tyr Tyr Cys
                85                  90                  95
```

```
Ala Thr Gly Asn Arg Gly Ser Leu Pro Arg Arg Trp Gly Gln Gly Thr
            100                 105                 110

Leu Val Thr Val Ser Ser
        115


<210>  359
<211>  118
<212>  PRT
<213>  Homo sapiens

<400>  359

Glu Val Gln Leu Val Glu Phe Gly Gly Gly Leu Val Gln Pro Gly Gly
1               5                   10                  15

Ser Leu Arg Leu Ser Cys Val Ala Ser Gly Phe Thr Phe Ser Ser Ser
            20                  25                  30

Trp Met Ser Trp Val Arg Gln Ala Pro Gly Lys Gly Leu Glu Cys Val
        35                  40                  45

Gly Asn Ile Lys Pro Asp Ala Ser Leu Val Ser Tyr Val Asp Ser Val
    50                  55                  60

Lys Gly Arg Val Thr Ile Ser Arg Asp Asn Ala Lys Asn Ser Leu Phe
65                  70                  75                  80

Leu Asp Met Ser Ser Leu Arg Val Glu Asp Thr Ala Val Tyr Tyr Cys
                85                  90                  95

Val Arg Asp Gly Trp Asp Thr Phe Phe Asp Ser Trp Gly Gln Gly Thr
            100                 105                 110

Leu Val Thr Val Ser Ser
        115


<210>  360
<211>  113
```

<212> PRT
<213> Homo sapiens

<400> 360

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Arg Trp Val Arg Gln Ser Pro Gly Lys Gly Leu Val Trp Val
        35                  40                  45

Ser His Ile Asn Pro Asp Gly Ser Phe Thr Asn Tyr Ala Asp Ser Val
    50                  55                  60

Lys Gly Arg Phe Thr Ile Ser Arg Asp Asn Thr Lys Asn Thr Leu Tyr
65                  70                  75                  80

Leu Gln Met Asn Ser Leu Arg Ala Glu Asp Thr Ala Val Tyr Tyr Cys
                85                  90                  95

Val Asn Phe Gln Leu Gly Trp Gly Gln Gly Thr Leu Val Thr Val Ser
            100                 105                 110

Ser
```

<210> 361
<211> 123
<212> PRT
<213> Homo sapiens

<400> 361

```
Gln Val Gln Leu Val Glu Ser Gly Gly Gly Val Val Gln Pro Gly Arg
1               5                   10                  15

Ser Leu Lys Leu Ser Cys Ala Val Ala Gly Phe Thr Phe Arg Thr Tyr
            20                  25                  30
```

```
Ala Met His Trp Val Arg Gln Ala Pro Gly Arg Gly Leu Glu Trp Val
        35                  40                  45

Ala Leu Ile Ser Asn Asp Gly Thr Lys Lys Tyr Ser Ala Asp Ser Val
    50                  55                  60

Arg Gly His Phe Thr Ile Ser Arg Asp Asn Ser Lys Asp Thr Leu Tyr
65                  70                  75                  80

Leu Gln Met Asn Ser Leu Arg Pro Asp Asp Thr Ala Val Tyr Tyr Cys
                85                  90                  95

Ala Arg Ala Glu Tyr Cys Ser Pro Gly Asp Cys Phe Leu Ile Asp Thr
            100                 105                 110

Trp Gly Gln Gly Thr Leu Val Thr Val Ser Ser
        115                 120

<210>  362
<211>  119
<212>  PRT
<213>  Homo sapiens

<400>  362

Gln Val Gln Leu Val Glu Ser Gly Gly Gly Val Val Gln Pro Gly Arg
1               5                   10                  15

Ser Leu Arg Leu Ser Cys Ala Val Ser Gly Phe Thr Phe Ser Arg Tyr
            20                  25                  30

Gly Met His Trp Val Arg Gln Ala Pro Gly Lys Gly Leu Glu Trp Val
        35                  40                  45

Val Val Ile Trp His Asp Gly Ser Asn Thr Tyr Tyr Ala Asp Ser Val
    50                  55                  60

Lys Gly Arg Phe Thr Ile Ser Arg Asp Asp Ser Lys Asn Thr Val Tyr
```

```
65                  70                  75                  80

Leu Gln Met Asn Ser Leu Arg Val Glu Asp Thr Ala Met Tyr Tyr Cys
                85                  90                  95

Leu Arg Gly Asn Pro Pro Ser Ser Pro Thr Asp Tyr Trp Gly Gln Gly
            100                 105                 110

Thr Leu Val Thr Val Ser Ser
        115


<210>  363
<211>  119
<212>  PRT
<213>  Homo sapiens

<400>  363

Glu Val Gln Leu Leu Glu Ser Gly Gly Gly Leu Val Gln Pro Gly Gly
1               5                   10                  15

Ser Leu Arg Leu Ser Cys Glu Val Ser Gly Phe Ile Phe Ser Asn Tyr
            20                  25                  30

Ala Met Thr Trp Val Arg Gln Ala Pro Gly Lys Gly Leu Gln Trp Val
        35                  40                  45

Ser Ala Ile Gly Thr Ser Gly Gly Asp Thr His Tyr Ala Asp Ser Val
    50                  55                  60

Lys Gly Arg Phe Thr Ile Ser Arg His Asn Ser Gln Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Val Val Tyr Ser Arg Pro Pro Met Asp Val Trp Gly Gln Gly
            100                 105                 110
```

```
Thr Thr Val Thr Val Ser Ser
        115


<210>  364
<211>  118
<212>  PRT
<213>  Homo sapiens

<400>  364

Glu Val Gln Leu Val Glu Ser Gly Gly Gly Leu Val Gln Pro Gly Gly
1               5                   10                  15


Ser Leu Arg Leu Ser Cys Ala Ala Ser Gly Phe Thr Phe Ser Asn Arg
            20                  25                  30


Trp Met Ser Trp Val Arg Gln Ala Pro Gly Lys Gly Leu Glu Trp Val
        35                  40                  45


Ala Asn Ile Asn Glu Asp Gly Ser Gln Lys His Tyr Val Asp Ser Val
    50                  55                  60


Arg Gly Arg Phe Thr Ile Ser Arg Asp Asn Ala Lys Asn Ser Leu Ser
65                  70                  75                  80


Leu Gln Met Asp Ser Leu Arg Val Glu Asp Thr Ala Val Tyr Tyr Cys
                85                  90                  95


Ala Arg Ala Ser Arg Glu Thr Gly Glu Pro Tyr Trp Gly Gln Gly Thr
            100                 105                 110


Leu Val Thr Val Ser Ser
        115


<210>  365
<211>  109
<212>  PRT
<213>  Homo sapiens

<400>  365
```

```
Val Met Thr Gln Ser Pro Leu Ser Leu Pro Val Thr Leu Gly Gln Ser
1               5                   10                  15

Ala Ser Ile Ser Cys Arg Ser Ser Arg Ser Leu Val Phe Ser Asp Gly
            20                  25                  30

Asn Thr Tyr Leu Asn Trp Phe Gln Gln Arg Pro Gly Arg Ser Pro Arg
        35                  40                  45

Arg Leu Ile Tyr Lys Val Ser Lys Arg Asp Ser Gly Val Pro Asp Arg
    50                  55                  60

Phe Ser Gly Ser Gly Ser Asp Thr Asp Phe Thr Leu Lys Ile Ser Arg
65                  70                  75                  80

Val Glu Ala Glu Asp Val Gly Val Tyr Tyr Cys Met Gln Gly Thr His
                85                  90                  95

Trp Arg Thr Phe Gly Gln Gly Thr Lys Val Glu Ile Lys
            100                 105


<210>  366
<211>  107
<212>  PRT
<213>  Homo sapiens

<400>  366

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Ser Trp
            20                  25                  30

Leu Ala Trp Tyr Gln Arg Lys Pro Gly Lys Thr Pro Lys Leu Leu Ile
        35                  40                  45

Tyr Glu Ala Ser Ser Leu Glu Ser Gly Val Pro Ser Arg Phe Ser Gly
    50                  55                  60
```

```
Ser Arg Ser Gly Thr Glu Phe Thr Leu Thr Ile Ser Ser Leu Gln Ala
65                  70                  75                  80

Asp Asp Phe Ala Thr Tyr Tyr Cys His Gln Tyr Asp Lys Tyr Pro Trp
                85                  90                  95

Thr Phe Gly Gln Gly Thr Lys Val Glu Ile Lys
            100                 105


<210>  367
<211>  108
<212>  PRT
<213>  Homo sapiens

<400>  367

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Asn Asn
            20                  25                  30

Tyr Leu Val Trp His Gln Gln Lys Pro Gly Gln Ala Pro Arg Leu Leu
        35                  40                  45

Ile Ser Asp Ala Ser Asn Arg Ala Thr Gly Ile Pro Asp Arg Phe Ser
    50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105


<210>  368
<211>  108
```

<212> PRT
<213> Homo sapiens

<400> 368

```
Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Ile Gly Ser Ser
            20                  25                  30

Leu Ala Trp Tyr Leu Gln Lys Pro Gly Gln Ala Pro Arg Val Leu Ile
        35                  40                  45

Tyr Gly Ala Ser Thr Arg Thr Pro Gly Thr Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Leu Ala Ile Tyr Tyr Cys Gln Gln Tyr Ser Lys Trp Pro Pro
                85                  90                  95

Ile Thr Phe Gly Gln Gly Thr Arg Leu Glu Ile Lys
            100                 105
```

<210> 369
<211> 107
<212> PRT
<213> Homo sapiens

<400> 369

```
Asp Ile Gln Met Thr Gln Ser Pro Ser Ile Leu Ser Ala Ser Val Gly
1               5                   10                  15

Asp Arg Val Thr Ile Asn Cys Arg Ala Ser Gln Ser Ile Asn Ala Trp
            20                  25                  30

Leu Ala Trp Tyr Gln Gln Lys Pro Gly Lys Ala Pro Lys Phe Leu Ile
        35                  40                  45
```

```
Tyr Lys Ala Ser Ser Leu Glu Ser Gly Val Ser Ser Arg Phe Ser Gly
    50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Asp Lys Tyr Pro Trp
                85                  90                  95

Thr Phe Gly Arg Gly Thr Lys Val Glu Ile Lys
            100                 105


<210>  370
<211>  108
<212>  PRT
<213>  Homo sapiens

<400>  370

Glu Ile Val Leu Thr Gln Ser Pro Gly Thr Leu Ser Phe Ser Pro Gly
1               5                   10                  15

Asp Arg Ala Thr Leu Ser Cys Arg Ala Ser Gln Ser Val Ser Ser Ser
            20                  25                  30

Ser Leu Ala Trp Tyr Gln Gln Arg Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Arg Thr Phe Gly Gln Gly Thr Lys Val Glu Ile Lys
```

```
            100                 105


<210>  371
<211>  108
<212>  PRT
<213>  Homo sapiens

<400>  371

Glu Ile Val Leu Thr Gln Ser Pro Gly Thr Leu Ser Leu Ser Pro Gly
1               5                   10                  15


Glu Arg Ala Thr Leu Ser Cys Arg Ala Ser Gln Ser Val Ser Ser Thr
            20                  25                  30


Tyr Leu Asn Trp Tyr Gln Gln Lys Pro Gly Gln Ala Pro Arg Leu Leu
        35                  40                  45


Ile Tyr Gly Ala Ser Thr Arg Ala Thr Gly Ile Pro Asp Arg Phe Ser
    50                  55                  60


Gly Ser Gly Ser Gly Ala Asp Phe Thr Leu Thr Ile Ser Arg Leu Glu
65                  70                  75                  80


Pro Glu Asp Phe Ala Val Tyr Tyr Cys Gln Gln Tyr Asp Asp Ser Arg
                85                  90                  95


Trp Thr Phe Gly Gln Gly Thr Lys Val Glu Ile Lys
            100                 105


<210>  372
<211>  112
<212>  PRT
<213>  Homo sapiens

<400>  372

Asp Ile Val Met Thr Gln Ser Pro Leu Ser Leu Pro Val Thr Pro Gly
1               5                   10                  15


Glu Pro Ala Ser Ile Ser Cys Arg Ser Gly Gln Ser Leu Leu Tyr Ser
```

```
            20                  25                  30

Asp Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Glu Ser Gly Thr Asp Phe Thr Leu Lys Ile
65                  70                  75                  80

Ser Arg Val Glu Ala Gly Asp Val Gly Ile Tyr Tyr Cys Met Gln Ala
                85                  90                  95

Leu Arg Ser Pro Tyr Thr Phe Gly Gln Gly Thr Lys Val Glu Ile Lys
            100                 105                 110

<210>  373
<211>  110
<212>  PRT
<213>  Homo sapiens

<400>  373

Val Met Thr Gln Ser Pro Leu Ser Leu Pro Val Thr Leu Gly Gln Pro
1               5                   10                  15

Ala Ser Ile Ser Cys Arg Ser Ser Gln Ser Pro Val Tyr Ser Asp Gly
            20                  25                  30

Asn Thr Tyr Leu Asn Trp Phe Gln Gln Arg Pro Gly Gln Ser Pro Arg
        35                  40                  45

Arg Leu Ile Tyr Lys Val Ser Asn Arg Asp Ser Gly Val Pro Asp Arg
    50                  55                  60

Phe Ser Gly Ser Gly Ser Gly Thr Asp Phe Thr Leu Asn Ile Ser Gly
65                  70                  75                  80
```

```
Val Glu Ala Glu Asp Val Gly Val Tyr Tyr Cys Met Gln Gly Arg Tyr
                85                  90                  95

Trp Pro Tyr Thr Phe Gly Gln Gly Thr Lys Val Glu Ile Lys
            100                 105                 110

<210>  374
<211>  108
<212>  PRT
<213>  Homo sapiens

<400>  374

Glu Ile Val Leu Thr Gln Ser Pro Gly Thr Leu Ser Phe Ser Pro Gly
1               5                   10                  15

Asp Arg Ala Thr Leu Ser Cys Arg Ala Ser Gln Ser Val Ser Ser Ser
            20                  25                  30

Ala Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Arg Thr Phe Gly Gln Gly Thr Lys Val Glu Ile Lys
            100                 105

<210>  375
<211>  109
<212>  PRT
<213>  Homo sapiens

<400>  375
```

```
Val Met Thr Gln Ser Pro Leu Ser Leu Pro Val Thr Leu Gly Gln Ser
1               5                   10                  15

Ala Ser Ile Ser Cys Arg Ser Ser Arg Ser Leu Val Phe Ser Asp Gly
            20                  25                  30

Asn Thr Tyr Leu Asn Trp Phe Gln Gln Arg Pro Gly Arg Ser Pro Arg
        35                  40                  45

Arg Leu Ile Tyr Lys Val Ser Lys Arg Asp Ser Gly Val Pro Asp Arg
    50                  55                  60

Phe Ser Gly Ser Gly Ser Asp Thr Asp Phe Thr Leu Lys Ile Ser Arg
65                  70                  75                  80

Val Glu Ala Glu Asp Val Gly Val Tyr Tyr Cys Met Gln Gly Thr His
                85                  90                  95

Trp Arg Thr Phe Gly Gln Gly Thr Lys Val Glu Ile Lys
            100                 105


<210>  376
<211>  107
<212>  PRT
<213>  Homo sapiens

<400>  376

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Gly Ile Asn Asn Tyr
            20                  25                  30

Leu Ala Trp Phe Gln Gln Lys Pro Gly Lys Ala Pro Lys Thr Leu Ile
        35                  40                  45

Tyr Ser Thr Ser Thr Leu Gln Ser Gly Val Pro Ser Lys Phe Ser Gly
    50                  55                  60
```

```
Ser Gly Ser Gly Thr Val Phe Thr Leu Thr Ile Ser Asn Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210>  377
<211>  107
<212>  PRT
<213>  Homo sapiens

<400>  377

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Tyr
            20                  25                  30

Leu Asn Trp Phe Gln Gln Lys Pro Gly Lys Ala Pro Arg Leu Leu Ile
        35                  40                  45

Tyr Ala Ala Ser Ser Leu Gln Ser Gly Val Pro Ser Arg Phe Ser Gly
    50                  55                  60

Ser Gly Ser Val Thr Asp Phe Thr Leu Thr Ile Ser Ser Leu Gln Pro
65                  70                  75                  80

Glu Asp Phe Ala Thr Tyr Phe Cys Gln Gln Ser Tyr Ser Thr Pro Trp
                85                  90                  95

Thr Phe Gly Gln Gly Thr Lys Val Glu Ile Lys
            100                 105

<210>  378
<211>  110
```

```
<212>  PRT
<213>  Homo sapiens

<400>  378

Val Met Thr Gln Ser Pro Phe Ser Leu Pro Val Thr Leu Gly Gln Pro
1               5                   10                  15

Ala Ser Ile Ser Cys Arg Ser Ser Gln Ser Leu Val Tyr Ser Asp Gly
            20                  25                  30

Asn Thr Tyr Leu Asn Trp Phe Gln Gln Arg Pro Gly Gln Ser Pro Arg
        35                  40                  45

Arg Leu Ile Tyr Lys Leu Ser Asn Arg Asp Ser Gly Val Pro Asp Arg
    50                  55                  60

Phe Ser Gly Ser Gly Ser Gly Thr Asp Phe Thr Leu Lys Ile Ser Arg
65                  70                  75                  80

Val Glu Ala Glu Asp Val Gly Val Tyr Tyr Cys Met Gln Ala Thr His
                85                  90                  95

Trp Pro Trp Thr Phe Gly Gln Gly Thr Lys Val Glu Ile Lys
            100                 105                 110
```